US012774474B2

(12) United States Patent
Van Der Sanden et al.

(10) Patent No.: US 12,774,474 B2
(45) Date of Patent: Oct. 27, 2026

(54) MODIFIED AAV CAPSID PROTEINS FOR TREATMENT OF ARTHRITIC DISEASE

(71) Applicants: MEIRAGTX GENE REGULATION LIMITED, London (GB); University of Heidelberg, Heidelberg (DE)

(72) Inventors: Sabine Maria Gertrude Van Der Sanden, Amsterdam (NL); Susanne Anna Snoek, Heiloo (NL); Niels Broekstra, Nieuwkoop (NL); Jonathan Douglas Finn, Melrose, MA (US); Dirk Grimm, Heidelberg (DE); Kathleen Börner, Schriesheim (DE)

(73) Assignees: MeiraGTx Gene Regulation Limited, London (GB); University of Heidelberg, Heidelberg (DE)

( * ) Notice: Subject to any disclaimer, the term of this patent is extended or adjusted under 35 U.S.C. 154(b) by 1066 days.

(21) Appl. No.: 17/627,364

(22) PCT Filed: Jul. 15, 2020

(86) PCT No.: PCT/IB2020/056635
§ 371 (c)(1),
(2) Date: Jan. 14, 2022

(87) PCT Pub. No.: WO2021/009684
PCT Pub. Date: Jan. 21, 2021

(65) Prior Publication Data

US 2022/0267797 A1 Aug. 25, 2022

(30) Foreign Application Priority Data

Jul. 15, 2019 (NL) ..................................... 2023505

(51) Int. Cl.

| | |
|---|---|
| ***C12N 15/86*** | (2006.01) |
| ***A61K 38/16*** | (2006.01) |
| ***A61K 45/06*** | (2006.01) |
| ***A61P 19/02*** | (2006.01) |
| ***C07K 14/005*** | (2006.01) |
| *A61K 48/00* | (2006.01) |

(52) U.S. Cl.
CPC ............ *C12N 15/86* (2013.01); *A61K 38/162* (2013.01); *A61K 45/06* (2013.01); *A61P 19/02* (2018.01); *C07K 14/005* (2013.01); *A61K 48/00* (2013.01); *C12N 2750/14122* (2013.01); *C12N 2750/14143* (2013.01); *C12N 2750/14145* (2013.01); *C12N 2750/14171* (2013.01)

(58) Field of Classification Search
None
See application file for complete search history.

(56) References Cited

U.S. PATENT DOCUMENTS

| | | | |
|---|---|---|---|
| 10,287,318 | B2 | 5/2019 | Körbelin et al. |
| 10,876,134 | B2 | 12/2020 | Kielian et al. |
| 11,499,141 | B2 | 11/2022 | Strings-Ufombah et al. |
| 2007/0104687 | A1 | 5/2007 | Tak et al. |
| 2015/0057189 | A1 | 2/2015 | Kay et al. |
| 2017/0304466 | A1 | 10/2017 | Finn et al. |
| 2022/0267797 | A1 | 8/2022 | Van Der Sanden et al. |

FOREIGN PATENT DOCUMENTS

| | | | | |
|---|---|---|---|---|
| AU | 2010201278 B2 | 11/2012 | | |
| CN | 104107438 A | 10/2014 | | |
| DE | 102013215817 A1 * | 2/2015 | | ................ A61P 9/12 |
| DE | 10 2014 207498 A1 | 10/2015 | | |
| EP | 3492597 A2 | 6/2019 | | |
| JP | 2017531652 A | 10/2017 | | |
| WO | 2005021768 A1 | 3/2005 | | |
| WO | 2008145401 A2 | 12/2008 | | |
| WO | 2013174460 A1 | 11/2013 | | |
| WO | WO-2013174760 A1 * | 11/2013 | | ........... C07K 14/005 |
| WO | 2016100575 A1 | 6/2016 | | |
| WO | WO-2016086227 A2 * | 6/2016 | | ............. C12N 15/86 |
| WO | 2017123934 A1 | 7/2017 | | |
| WO | 2018035451 A1 | 2/2018 | | |
| WO | 2018106956 A2 | 6/2018 | | |
| WO | 2018189244 A1 | 10/2018 | | |
| WO | 2019043630 A1 | 3/2019 | | |
| WO | 2019141765 A1 | 7/2019 | | |

OTHER PUBLICATIONS

Voet et al., Biochemistry, John Wiley and Sons, 1990, p. 126-129 (Year: 1990).*
Rudinger, J., Peptide Hormones. Palgrave, London, 1976. 1-7. (Year: 1976).*
Ngo, J. Thomas, Joe Marks, and Martin Karplus., The protein folding problem and tertiary structure prediction. Boston, MA: Birkhäuser Boston, 1994. 433-506. (Year: 1994).*
Mease, Philip J., et al. Annals of the rheumatic diseases 68.8 (2009): 1247-1254. (Year: 2009).*
Chtarto, Abdelwahed, et al. PLoS One 8.1 (2013): e53156. (Year: 2013).*
Lin, Phoebe. Clinical Ophthalmology (2015): 1697-1702. (Year: 2015).*
Aalbers, Caroline J., et al. Human gene therapy 28.2 (2017): 168-178. (Year: 2017).*
Khoury, M. et al., "Inflammation-Inducible Anti-TNF Gene Expression Mediated by Intra-Articular Injection of Serotype 5 Andeno-associated Virus Reduces Arthritis"; The Journal of Gene Medicine (2007); vol. 9; pp. 596-604.

(Continued)

*Primary Examiner* — Maria G Leavitt
*Assistant Examiner* — Brendan Thomas Tinsley
(74) *Attorney, Agent, or Firm* — Fox Rothschild LLP

(57) ABSTRACT

The invention relates to recombinant adeno-associated virus (rAAV) virions for gene therapy, wherein the rAAV virions comprise a novel capsid protein. In particular, the invention relates to the use of such virions in gene therapy for the treatment of an arthritic disease, such as for example rheumatoid arthritis, or symptoms thereof, preferably by intraarticular administration.

17 Claims, 14 Drawing Sheets

Specification includes a Sequence Listing.

(56) References Cited

OTHER PUBLICATIONS

Aalbers, C. J. et al., "Preclinical Potency and Biodistribution Studies of an AAV 5 Vector Expressing Human Interferon-Beta (ART-I02) for Local Treatment of Patients with Rheumatoid Arthritis"; PLOS ONE (2015); vol. 106; 17 pgs.
Vervoordeldonk, M. J., et al., "Interferon [beta] for Rheumatoid Arthritis: New Clothes for an Old Kid on the Block". Annals of the Rheumatic Diseases (2009), vol. 68:2, pp. 157-158.
Bevaart, L. et al., "Safety, Biodistribution, and Efficacy of an AAV-5 Vector Encoding Human Interferon-Beta (ART-I02) Delivered via Intra-Articular Injection in Rhesus Monkeys with Collagen-Induced Arthritis", Human Gene Therapy. Clinical Development (2015), vol. 26:2, pp. 103-112.
Kuzmin, D. A., et al., "The Clinical Landscape for AAV Gene Therapies", Nature Reviews Drug Discovery (2021), vol. 20:3, pp. 173-174. (with 16 Supplementary pgs).
Aalbers, C.J. et al., "Preclinical Potency and Biodistribution Studies of an AAV 5 Vector Expressing Human Interferon-beta (ART-I02) for Local Treatment of Patients with Rheumatoid Arthritis", PLoS ONE (2015), vol. 10:6, pp. e0130612.—12 pgs.
Li, W. et al., "Intra-Articular Delivery of AAV vectors Encoding PD-L 1 Attenuates Joint Inflammation and Tissue Damage an A Mouse Model of Rheumatoid Arthritis", Frontiers in Immunology (2023), vol. 14, 16 pgs.
Luo, T. et al., "An AAV-Based NF-KB-Targeting Gene Therapy (rAAV-DMP-miR533) to Inflammatory Diseases", Journal of Inflammation Research (2022), vol. 15, pp. 3447-3466.
Berkhout, L. C. et al., "Dynamics of Circulating TN F During Adalimumab Treatment Using a Drug-Tolerant TN F Assay", Science Translational Medicine (2019), vol. 11:477, 11 pgs.
Seol, D. et al., "Intra-Articular Adeno-Associated Virus-Mediated Proteoglycan 4 Gene Therapy for Preventing Posttraumatic Osteoarthritis", Human Gene Therapy (2022), vol. 33:9-10, pp. 529-540.
Moss, K. L. "Sustained Interleukin-10 Transgene Expression Following Intra-Articular AAV5-IL-10 Administration to Horses", Human Gene Therapy (2020), vol. 31 (1-2), pp. 110-118.
Watson Levings, R. S. et al. Gene Therapy for Osteoarthritis: Pharmacokinetics of Intra-Articular Self- Complementary V Adena-Associated Virus Interleukin-1 Receptor Antagonist Delivery in an Equine Model. Human Gene Therapy. Clinical Development, 29(2), 90-100. (Year: 2018).
Watson Levings, R. S. et al. "Self-Complementary Adeno-Associated Virus-Mediated Interleukin-1 Receptor Antagonist Gene Delivery for the Treatment of Osteoarthritis: Test of Efficacy in an Equine Model", Human Gene Therapy. Clinical Development (2018), vol. 29:2, pp. 101-112.
Chakrabarti, S. et al. Intraarticular Adeno-Associated Virus Serotype AAV-PHP.S-Mediated Chemogenetic Targeting of Knee-Innervating Dorsal Root Ganglion Neurons Alleviates Inflammatory Pain in Mice, Arthritis & Rheumatology (2020), vol. 72:10, pp. 1749-1758.
Vrouwe, J. P. M. et al. "Administration of an Adeno-Associated Viral Vector Expressing Interferon-beta in Patients with Inflammatory Hand Arthritis, Results of a Phase I/II Study", Osteoarthritis and Cartilage (2022), vol. 30, pp. 52-60.
Muller, O.J. et al., "Random Peptide Libraries Displayed on Adeno-Associated Virus to Select for Targeted GeneTherapy Vectors", Nature Biotechnology (2003), vol. 21:9, pp. 1040-1046.
Pasero, G., et al., "A short Story of Anti-Rheumatic Therapy. VIII. The Immunodepressants", Reumatismo (2012), Mar. 19;64(1):44-54. doi: 10.4081/reumatismo.2012.44.
Kozlowski M., et al., "Adeno-Associated Viral Delivery of a Metabolically Regulated Insulin Transgene to Hepatocytes", Mol Cell Endocrinol. (2007) vol. 273, pp. 6-15.
Lau, et al., "In Vivo Genome Editing in Animals Using AAV-CRISPR System: Applications to Translational Research of Human Disease", .F1OOOResearch (2017), 20 pgs.
Adriaansen J., et al. "Enhanced Gene Transfer to Arthritic Joints Using Adeno-Associated Virus Type 5: Implications for Intra-Articular Gene Therapy", Ann Rheum Dis. (2005), vol. 64, pp. 1677-1684.
Apparailly, F., et al. Adeno-Associated Virus Pseudotype 5 Vector Improves Gene Transfer in Arthritic joints. Hum Joints Gene Ther. (2005), vol. 16{4), pp. 426-434.
Zincarelli, C., et al. "Analysis of AAV Serotypes 1-9 Mediated Gene Expression and Tropism in Mice after systemic after Systemic Injection", Mol. Ther. (2008); vol. 16:6, pp. 1073-1080.

* cited by examiner

```
CLUSTAL format alignment by MAFFT FFT-NS-i (v7.215)


AAV1P4          -gqsgndvrs--anaqaa
AAV9A2          -gqrgnysrg--vdaqaa
AAVrh10A2       -gqrgnysrg--vdaqaa
AAV7A6          -gqrgnearv--reaq--
AAV7A6+         -gqrgnearv--reaqaa
AAV10A6         -gqrgnearv--reaqaa
AAV2P2          qgqsgcdcrgdcfca---
AAV-DJ-QR-P2    qgqrgcdcrgdcfca---
AAV2P2+         qgqsgcdcrgdcfcaqaa
AAV-DJ-QR-P2+   qgqrgcdcrgdcfcaqaa
                 ** *   *     *
```

Fig. 5

```
CLUSTAL multiple sequence alignment by MUSCLE (3.8)


AAV2P2                QGQSGCDCRG-DCFCA---
AAV2P2+               QGQSGCDCRG-DCFCAQAA
AAV-DJ-QR-P2          QGQRGCDCRG-DCFCA---
AAV-DJ-QR-P2+         QGQRGCDCRG-DCFCAQAA
AAV1P4                -GQSGNDVRSANAQAA---
AAV9A2                -GQRGNYSRGVDAQAA---
AAVrh10A2             -GQRGNYSRGVDAQAA---
AAV7A6                -GQRGNEARVREAQ-----
AAV7A6+               -GQRGNEARVREAQAA---
AAV10A6               -GQRGNEARVREAQAA---
                       ** *   *   :.
```

Fig. 6

```
CLUSTAL format alignment by MAFFT FFT-NS-i (v7.215)


insertP4          -gqsgndvrs--anaqaa
insertA2          -gqrgnysrg--vdaqaa
insertA6          -gqrgnearv--reaqaa
insertP2          qgqsgcdcrgdcfcaqaa
insertQR-P2       qgqrgcdcrgdcfcaqaa
                   ** *   *     ****
```

```
CLUSTAL multiple sequence alignment by MUSCLE (3.8)


insertP2         QGQSGCDCRGDCFCAQAA
insertQR-P2      QGQRGCDCRGDCFCAQAA
insertP4         -GQSGNDVRSA--NAQAA
insertA2         -GQRGNYSRGV--DAQAA
insertA6         -GQRGNEARVR--EAQAA
                  ** *    *    ****
```

MODIFIED AAV CAPSID PROTEINS FOR TREATMENT OF ARTHRITIC DISEASE

CROSS-REFERENCE TO RELATED APPLICATIONS

This application is a national stage patent application of International Patent Application No. PCT/IB2020/056635, filed on Jul. 15, 2020, which claims priority to Dutch Application No. 2023505, filed on Jul. 15, 2019; both of which are hereby incorporated by reference in their entireties.

REFERENCE TO A SEQUENCE LISTING

This application contains a Sequence Listing, which has been submitted electronically in txt format and is hereby incorporated by reference in its entirety. Said txt copy, created on Jun. 30, 2025, is named SeqList2-162027-50001_ST25.txt and is 122,066 bytes in size.

FIELD OF THE INVENTION

The invention relates to the field of recombinant adeno-associated virus (rAAV) based gene therapy, in particular to the use of a mutant capsid rAAV in the treatment or prevention of an arthritic disease.

BACKGROUND OF THE INVENTION

Recombinant adeno-associated virus (rAAV) vectors have demonstrated excellent safety and efficacy profiles for the delivery of genes in humans in vivo. Therefore, rAAV vectors have been extensively used for in vivo gene therapy and have been shown safe and effective in pre-clinical models as well as in clinical trials. rAAV vectors have been successful in a number of gene therapy clinical trials for a range of diseases including haemophilia B, haemophilia A, cystic fibrosis, alpha-1 anti-trypsin deficiency, spinal muscular atrophy (SMA), Parkinson disease, Duchenne muscular dystrophy and Leber's congenital amaurosis (Selot et al., Current Pharmaceutical Biotechnology, 2013, 14, 1072-1082). Alipogene tiparvovec (Glybera®, uniQure) has been granted marketing authorization in Europe as a gene therapy for the treatment of lipoprotein lipase deficiency (LPLD). Subsequently, gene therapy drug approval was granted for herpes-virus based Talimogene laherparepvec for the treatment of skin cancer (T-Vec, Imlygic®, Amgen) and for ex vivo stem cell retroviral-based gene therapy Strimvelis for the treatment of ADA-SCID (GSK).

rAAV vector-based gene therapy has also been applied in rheumatoid arthritis (RA), which is a chronic inflammatory disease that affects ~1% of the population. The pathology of RA extends throughout the synovial joint. The localized nature of the joint makes in vivo gene therapy very attractive. Therapies providing anti-inflammatory proteins aimed at shifting the balance in RA towards an anti-inflammatory state have been applied.

Much work has focused on the development of AAV capsid proteins with desired properties. Such properties can include higher transduction efficiency, tissue/organ tropism, de-targeting of non-desired tissues/organs, or avoidance of pre-existing neutralizing antibodies.

There is, however, still a need in the art to further improve rAAV gene therapy vectors. In particular, there is a need to improve the use of rAAV gene therapy vectors in arthritic disease and, more precisely, to improve the efficiency of delivering genetic material to the targeted tissue, such as the synovial joint or specific cell types within the synovial joint, preferably to fibroblast-like synoviocytes (FLS).

SUMMARY OF THE INVENTION

In some aspects, the invention relates to the following numbered embodiments:

Embodiment 1. A recombinant adeno-associated virus (rAAV) virion comprising a modified capsid protein and a promoter operably linked to a nucleotide sequence encoding a gene product of interest, wherein the rAAV virion is for use in treating or preventing an arthritic disease or for use in treating or preventing symptoms associated with an arthritic disease, wherein the modified capsid protein comprises in the C-terminal part of the protein an amino acid sequence Z, residues of which are exposed on the surface of the capsid protein, preferably wherein the product of interest is an immunosuppressant.

Embodiment 2. An rAAV virion for use according to embodiment 1, wherein the amino acid sequence Z:

a. comprises or consists of a sequence of amino acid residues of the formula I:

(SEQ ID NO: 23)

$$y\text{-}G\text{-}Q\text{-}x\text{-}G\text{-}(x)_3\text{-}R\text{-}(x)_3\text{-}y\text{-}A\text{-}Q\text{-}A\text{-}A$$

wherein x represents a single amino acid residue and wherein y represents 0, 1 or 2 amino acid residues; and b. is present at a location corresponding to a position 100-200, preferably 120-180, more preferably 130-170, more preferably 140-160 amino acid residues from the C terminus of a wild-type AAV capsid protein.

Embodiment 3. An rAAV virion for use according to embodiment 1 or 2, wherein the gene product of interest is an IL-6 inhibitor.

Embodiment 4. An rAAV virion for use according to embodiment 1 or 2, wherein the gene product of interest is an TNFα inhibitor.

Embodiment 5. An rAAV virion for use according to embodiment 1 or 2, wherein the gene product of interest is an IL-1 inhibitor.

Embodiment 6. An rAAV virion for use according to embodiment 3, wherein the IL-6 inhibitor is selected from the group consisting of an IL-6 receptor antagonist, a humanised anti-IL-6 monoclonal antibody, a chimeric anti-IL-6 monoclonal antibody, a humanized rabbit anti-IL-6 monoclonal antibody and a soluble IL-6 receptor, preferably wherein at least one of i) the IL-6 receptor antagonist is at least one of tocilizumab and sarilumab;

ii) the humanised anti-IL-6 monoclonal antibody is at least one of olokizumab and sirukumab;

iii) the chimeric anti-IL-6 monoclonal antibody is siltuximab; and iv) the humanized rabbit anti-IL-6 monoclonal antibody is clazakizumab.

Embodiment 7. An rAAV virion for use according to embodiment 4, wherein the TNFα inhibitor is selected from the group consisting of etanercept, infliximab, adalimumab, certilizumab pegol and golimumab, preferably wherein the TNFα inhibitor is etanercept.

Embodiment 8. An rAAV virion for use according to embodiment 5, wherein the IL-1 inhibitor is selected from the group consisting of
- i) an IL-1 receptor antagonist, preferably a human IL-1 receptor antagonist, preferably the human IL-1 receptor antagonist anakinra;
- ii) an anti-IL-1 monoclonal antibody, preferably a human anti-IL-1 monoclonal antibody, preferably the human IL-1 monoclonal antibody canakinumab or gevokizumab
- iii) a human dimeric anti-IL-1 fusion protein, preferably the human dimeric anti-IL-1 fusion protein rilonacept; and
- iv) a human dual variable domain anti-IL-1 immunoglobulin, preferably the human dual variable domain anti-IL-1 immunoglobulin lutikizumab.

Embodiment 9. An rAAV virion for use according to any one of the preceding embodiments, wherein the promoter is a constitutive promoter or an inducible promoter, preferably the promoter is an NFκB responsive promoter, preferably an NFκB responsive CMV promoter, preferably an NFκB responsive minimal CMV promoter.

Embodiment 10. An rAAV virion for use according to any one of the preceding embodiments, wherein the sequence Z is comprised in the modified capsid protein at a location represented by the formula II:

(SEQ ID NO: 27)
EEEIxxxxPVATExxGxxxxNxQy-Z-(x)$_n$LPGMVWQxRDVYLQGPIW
AKIPHTDG

- a. wherein Z, x and y are as defined in embodiment 2; and
- b. wherein n is 5, 6, 7, 8, 9, 10, 11, 12, 13, 14 or 15.

Embodiment 11. An rAAV virion for use according to any one of the preceding embodiments, wherein the capsid protein comprises an amino acid sequence selected from the group consisting of:
- i) an amino acid sequence having at least 70% sequence identity with an amino acid sequence having SEQ ID NO: 1 and wherein amino acids at positions 588-602 of SEQ ID NO: 1 have at least 80% sequence identity with SEQ ID NO: 11,
- ii) an amino acid sequence having at least 70% sequence identity with an amino acid sequence having SEQ ID NO: 2 and wherein amino acids at positions 585-602 of SEQ ID NO: 2 have at least 80% sequence identity with SEQ ID NO: 10,
- iii) an amino acid sequence having at least 70% sequence identity with an amino acid sequence having SEQ ID NO: 3 and wherein amino acids at positions 587-601 of SEQ ID NO: 3 have at least 80% sequence identity with SEQ ID NO: 9,
- iv) an amino acid sequence having at least 70% sequence identity with an amino acid sequence having SEQ ID NO: 4 and wherein amino acids at positions 586-600 of SEQ ID NO: 4 have at least 80% sequence identity with SEQ ID NO: 8,
- v) an amino acid sequence having at least 70% sequence identity with an amino acid sequence having SEQ ID NO: 5 and wherein amino acids at positions 588-602 of SEQ ID NO: 5 have at least 80% sequence identity with SEQ ID NO: 9,
- vi) an amino acid sequence having at least 70% sequence identity with an amino acid sequence having SEQ ID NO: 6 and wherein amino acids at positions 588-602 of SEQ ID NO: 6 have at least 80% sequence identity with SEQ ID NO: 8, and
- vii) an amino acid sequence having at least 70% sequence identity with an amino acid sequence having SEQ ID NO: 7 and wherein amino acids at positions 587-604 of SEQ ID NO: 7 have at least 80% sequence identity with SEQ ID NO: 12, wherein the modified capsid protein provides for an at least two-fold increase in expression, preferably in human FLS cells, in comparison to an unmodified capsid protein with an amino acid sequence selected from the group consisting of SEQ ID NO: 13-19, when tested under the same conditions, wherein preferably the unmodified capsid protein has the amino acid sequence SEQ ID NO: 19 or has the same serotype as the modified capsid protein.

Embodiment 12. An rAAV virion for use according to any one of the preceding embodiments, wherein the capsid protein comprises or consists of an amino acid sequence selected from the group consisting of SEQ ID NO:1-7, preferably wherein the capsid protein comprises or consists of SEQ ID NO: 4 or SEQ ID NO: 6.

Embodiment 13. An rAAV composition for use in treating or preventing an arthritic disease or for use in treating or preventing symptoms associated with an arthritic disease, wherein the rAAV composition comprises an rAAV virion as defined in any one of embodiments 1-12 and a pharmaceutically acceptable carrier.

Embodiment 14. An rAAV composition and an immunosuppressant for use in treating or preventing an arthritic disease or for use in treating or preventing symptoms associated with an arthritic disease, wherein the rAAV composition is as defined in embodiment 13 and wherein the treatment or prevention comprises the administration of the rAAV composition and the administration of the 5 immunosuppressant to an individual.

Embodiment 15. An rAAV virion for use according to any one of embodiments 1-12, an rAAV composition for use according to embodiment 13, or an rAAV composition and an immunosuppressant for use according to embodiment 14, wherein the arthritic disease is selected from the group consisting of rheumatoid arthritis (RA), juvenile rheumatoid arthritis, osteoarthritis (OA), gout, pseudogout, spondyloarthritis (SpA), psoriatic arthritis, ankylosing spondylitis, septic arthritis, arthritis, juvenile idiopathic arthritis, blunt trauma, joint replacement and Still's disease.

Embodiment 16. An rAAV virion for use according to any one of embodiment 1-12 or an rAAV composition for use according to embodiment 13, wherein the rAAV virion and/or the rAAV composition is administered systemically and/or locally.

Embodiment 17. An rAAV composition and an immunosuppressant for use according to embodiment 14, wherein at least one of the rAAV composition and the immunosuppressant is administered locally.

Embodiment 18. An rAAV virion or an rAAV composition for use according to embodiment 16 and/or an rAAV composition and an immunosuppressant for use according to embodiment 17, wherein the local administration is intraarticular administration.

DETAILED DESCRIPTION OF THE INVENTION

The inventors have discovered that a recombinant adeno-associated virus (rAAV) virion comprising a modified capsid protein is surprisingly efficient at transducing cells, and in particular efficient at transducing cells of the synovial joint.

Primary target cells in the joint in the treatment of arthritic diseases, such as for example rheumatoid arthritis include, but are not limited to, fibroblast-like synoviocytes (FLS), cartilage cells, chondrocytes and chondroblasts. The aim of the present invention is to provide for capsid proteins which are improved in one or more of the following properties: i) higher expression levels in the joint tissue, in particular in FLS; ii) improved joint tissue tropism, in particular improved tropism for FLS;

and/or iii) improved de-targeting from non-desired tissues/organs upon rAAV administration as compared to capsid proteins known in the art. In particular, these properties of the rAAV virion comprising a modified capsid protein of the invention are improved as compared to unmodified capsid proteins, preferably the wild-type capsid protein of the same serotype as the modified capsid protein and/or AAV5 capsid proteins. It has been previously established that AAV5 capsid gives rise to the highest FLS expression levels when compared with other AAV serotypes (Adriaansen et al. (2005) Ann Rheum Dis 64:1677-1684; Apparailly et al. (2005) Hum. Gene Ther. 16:426-434). As it is the capsid that confers the tissue/cell tropism properties, the modified capsids described in this invention have the property of enhanced FLS transduction potential preferably when compared with unmodified AAV5. In particular, it is preferred that the capsid proteins of the present invention provide higher expression levels in synovial tissue, in particular in FLS, preferably upon intraarticular administration, as compared to unmodified capsid proteins (that is, the same capsid protein without the modification that is to be tested, preferably of the same serotype as the modified capsid proteins), preferably wild-type unmodified capsid proteins (preferably of the same serotype as the modified capsid proteins), more preferably unmodified AAV5 or wtAAV5 capsid proteins.

Hence, in a first aspect, the invention pertains to an rAAV virion comprising a modified capsid protein. The rAAV virion as defined herein is particularly useful for use in gene therapy.

As used herein, "gene therapy" is the insertion of nucleic acid sequences (such as for example a transgene (also referred to as a nucleotide sequence encoding a gene product of interest) as defined herein below) into an individual's cells and/or tissues to treat or prevent a disease or disorder or to treat or prevent the symptoms of a disease or disorder.

AAV can infect both dividing and quiescent cells and infection occurs by interaction of the capsid proteins with a cell-membrane receptor, followed by endocytosis of the AAV virion. AAV belongs to the genus Dependovirus, which in turn belongs to the subfamily of the Parvovirinae, also referred to as parvoviruses, which are capable of infecting vertebrates. Parvovirinae belong to a family of small DNA animal viruses, i.e. the Parvoviridae family. As may be deduced from the name of their genus, members of the Dependovirus are unique in that they usually require coinfection with a helper virus such as adenovirus or herpes virus for productive infection in cell culture. The genus Dependovirus includes AAV, which normally infects humans, and related viruses that infect other warm-blooded animals (e.g., bovine, canine, equine, and ovine adeno-associated viruses). Further information on parvoviruses and other members of the Parvoviridae is described in Kenneth I. Berns, "Parvoviridae: The Viruses and Their Replication," Chapter 69 in Fields Virology (3d Ed. 1996). For convenience, the present invention is further exemplified and described herein by reference to AAV. It is however understood that the invention is not limited to AAV but may equally be applied to other parvoviruses.

The genomic organization of all known AAV serotypes is very similar. The genome of AAV is a linear, single-stranded DNA molecule that is less than about 5,000 nucleotides (nt) in length. Inverted terminal repeats (ITRs) flank the unique coding nucleotide sequences for the non-structural replication (Rep) proteins and the structural (VP) proteins. The VP proteins (VP1, -2 and -3) form the capsid or protein shell with the help of the assembly-activating protein (AAP) (for some serotypes), which is encoded in an alternative open reading frame overlapping with that of VP2/VP3. The terminal nucleotides are self-complementary and are organized so that an energetically stable intramolecular duplex forming a T-shaped hairpin may be formed. The size of the terminal nucleotides is serotype-dependent. For example, in the case of AAV2, of the terminal 145 nt, 125 nt are self-complementary and the remaining 20 nt remain single-stranded. These hairpin structures function as an origin for viral DNA replication, serving as primers for the cellular DNA polymerase complex. Following wild-type AAV (wtAAV) infection in mammalian cells the Rep proteins (i.e. Rep78 and Rep52) are expressed from mRNAs transcribed by the p5 promoter and the p19 promoter, respectively. Both Rep proteins have a function in the replication of the viral genome. A splicing event in the Rep ORF results in the expression of actually four Rep proteins (i.e. Rep78, Rep68, Rep52 and Rep40). However, it has been shown that the Rep78 and Rep52 proteins, encoded by the unspliced mRNAs, in mammalian cells are sufficient for AAV vector production. Production of wtAAV or rAAV in mammalian cells moreover relies on a combination of alternate usage of two splice acceptor sites and the suboptimal utilization of an ACG initiation codon for VP2, which ensures proper expression of all three capsid proteins in an approximate 1:1:10 ratio (VP1:VP2:VP3).

An "rAAV virion" (also referred to as an "rAAV vector" or an "rAAV transgene vector" herein) as used herein means an AAV capsid comprising a non-native nucleic acid sequence. Such a sequence in rAAV is generally flanked by ITR sequences, preferably from wtAAV, and preferably encodes a gene product of interest, such as for example a transgene or homology arms. Said differently, an rAAV virion means an rAAV genome, comprising (i) a nucleotide sequence encoding a gene product of interest and (ii) at least one AAV ITR sequence, encapsidated by capsid proteins. An rAAV genome may have one or preferably all wtAAV genes deleted, but may still comprise functional ITR nucleic acid sequences. Preferably, the rAAV virion does not comprise any nucleotide sequences encoding viral proteins, such as the rep (replication) or cap (capsid) genes of AAV. Thus, an rAAV virion is distinguished from a wtAAV virion, since all or a part of the viral genome has been replaced with a nucleotide sequence encoding a gene product of interest, which is a non-native nucleic acid with respect to the AAV nucleic acid sequence as further defined herein.

In a preferred embodiment, an rAAV virion comprising a modified capsid protein of the invention is for use in treating or preventing an arthritic disease or for use in treating or preventing symptoms associated with an arthritic disease. The medical use (e.g. gene therapy for treatment or prevention of (symptoms associated with) arthritic disease) herein described is formulated as an rAAV virion according to the invention for use as a medicament for prevention or treatment of the disease(s) and/or disorder(s) defined herein, but could equally be formulated as (i) a method of prevention or treatment of the disease(s) and/or disorder(s) defined herein or symptoms thereof comprising administering a sufficient or an effective amount of an rAAV virion according to the invention to a subject in need thereof, as (ii) an rAAV virion according to the invention for use in the preparation of a medicament to prevent or treat the disease(s) and/or disorder(s) defined herein, or as (iii) use of an rAAV virion according to the invention for the prevention or treatment of the disease(s) and/or disorder(s) defined herein. Such medical uses are all envisaged by the present invention. Preferably, the modified capsid protein comprises in the C-terminal part of the protein an amino acid sequence Z, residues of which are exposed on the surface of the capsid protein.

As used herein, the terms "treat", "treatment", or "treating" refer to application or administration of an rAAV virion of the invention to a subject who has an arthritic disease, wherein the object is to cure, partially or completely reverse, alleviate, ameliorate, inhibit, delay, suppress, slow down or stop the progression or severity of an arthritic disease, or of the symptoms associated with the arthritic disease. The term "treating" includes reducing or alleviating at least one adverse effect or symptom of the arthritic disease. Treatment is generally "effective" if one or more symptoms or clinical markers are reduced. Alternatively, treatment is "effective" if the progression of the arthritic disease is reduced or halted. That is, "treatment" includes not just the improvement of symptoms or markers, but also a cessation or at least slowing of progress or worsening of symptoms that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. The term "treatment" of an arthritic disease also includes providing relief from the symptoms or side-effects of the arthritic disease (including palliative treatment). As used herein, the term "prevent", "prevention", or "preventative" (also referred to as prophylactic) refer to application or administration of an rAAV virion according to the invention to a subject who has a predisposition toward an arthritic disease, with the purpose to delay or prevent onset of, alleviate, ameliorate, relieve, inhibit progression of, reduce severity of, and/or reduce incidence of one or more symptoms or features of a future arthritic disease. Thus, an rAAV virion according to the invention may be administered to a subject who does not exhibit signs of an arthritic disease and/or to a subject who exhibits only early signs of an arthritic disease, preferably for the purpose of decreasing the risk of developing pathology associated with the arthritic disease.

The term "cure" or "curing" as used herein means to completely alleviate one or more, preferably all of the symptoms or features of an arthritic disease. The term "delay" or "delaying" as used herein means to delay onset of and/or inhibit progression of and/or reduce severity of one or more of the symptoms or features of the arthritic disease.

In a preferred embodiment, the modified capsid protein of the invention provides for an at least two-fold increase in expression in comparison to an unmodified capsid protein, when tested under the same conditions. Preferably, the unmodified capsid protein, is a capsid protein of the same serotype as the modified capsid protein, but without the modification that is to be tested. More preferably, the unmodified capsid protein is a wild-type (wt) capsid protein of the same serotype as the modified capsid protein, wherein the wt capsid protein preferably has an amino acid sequence selected from the group consisting of SEQ ID NO: 13-19. Alternatively, it is preferred that the unmodified capsid protein has an amino acid sequence selected from the group consisting of SEQ ID NO: 13-19. Most preferably, the unmodified capsid protein has the amino acid sequence as shown in SEQ ID NO: 19. The preferred unmodified capsid proteins may depend on the tissue that is to be targeted by the rAAV virion. For example, an rAAV with AAV5 capsid proteins appears to be a virion of choice for FLS cells (Apparailly et al. (2005) Human Gene Therapy 16 (4): 426-434; Adriaansen et al. (2005) Ann. Rheum. Dis. 64 (12): 1677-1684) and therefore—irrespective of the original serotype of the rAAV mutant virions—the rAAV control virion preferably comprises AAV5 capsid proteins, more preferably wild-type AAV5 (wtAAV5) capsid protein, more preferably the AAV5 capsid protein has the amino acid sequence shown in SEQ ID NO:19, even more preferably the rAAV control virion is an rAAV5 virion. An rAAV control virion is an rAAV virion comprising unmodified capsid proteins as defined herein instead of modified capsid proteins. In a preferred embodiment, the rAAV virion (comprising modified capsid proteins) provides for higher expression upon in vitro transduction in Fibroblast Like Synoviocytes from rheumatoid arthritis patients (RA-FLS) and/or HEK293, preferably HEK293T, cells as compared to the same rAAV virion with unmodified capsid proteins as defined herein instead of modified capsid proteins, using a method as described in the Examples. In other words, apart from the capsid proteins, the rAAV virion and the rAAV control virion preferably are identical. Preferably, transduction efficiency is detected in an in vitro transduction assay: by measuring expression levels of a reporter gene encoded by the transgene, such as GFP, YFP and/or Luciferase. In a preferred embodiment, the test to determine the expression is an in vitro transduction assay as described in Example 2/3. Briefly, RA-FLS (isolated as described in van de Sande M G et al., (2011) Ann Rheum Dis 70:423-427) are plated at 2500 cells/well or HEK293T cells (human embryonic kidney cells) are plated at 40,000 cells/well in a 96-well plate (DMEM-GlutaMAX-I (Gibco, ref. 31966-021), 10% FBS (heat inactivated (HI) Bovine Serum Gold, Gibco ref. A15-151), 100 µg/ml Penicillin/100 µg/ml Streptomycin (Sigma-Aldrich, ref. P0781; 37° C./5% $CO_2$). After 24 hours, supernatant is removed and replaced by medium (DMEM-glutaMAX-I (Gibco, ref. 31966-021), 0.001% pluronic F68 (Sigma, ref. p5559)) containing the rAAV mutant virions or the rAAV control virions—all expressing yellow fluorescent protein (yFP) and/or luciferase under control of a cytomegalovirus (CMV) promoter—at a multiplicity of infection (MOI) of 10,000, 20,000 and 100,000. Crude lysates (i.e. non-purified supernatants of cells transfected with all plasmids needed for rAAV production and containing reporter-expressing virions) or purified AAV (preferably based on Iodixanol purification or cesium chloride (CsCl) density gradient purification) can be used. Four hours after transduction, medium (DMEM-GlutaMAX-I, 10% FBS 100 U/ml penicillin, 100 µg/ml streptomycin) containing doxorubicin (Sigma, ref. D1515; final concentration 0.4 µM), FBS (final concentration 1%), is added. After 48 h hours (HEK293T) or 4-6 days (RA-FLS), cells are assayed for the percentage of cells expressing YFP or luciferase by fluorescence microscopy or FLOW cytometry. Preferably, the in vitro transduction assay is performed multiple times with FLS isolated from different patients, such as for example FLS isolated from 2, 3, 4, 5, 6, 7, 8, 9, 10 or more patients.

A "serotype" is traditionally defined on the basis of a lack of cross-reactivity between antibodies to one virus as compared to another virus. Such cross-reactivity differences are usually due to differences in capsid protein sequences/antigenic determinants (e.g., due to VP1, VP2, and/or VP3 sequence differences of AAV serotypes). Under the traditional definition, a serotype means that the virus of interest has been tested against serum specific for all existing and characterized serotypes for neutralizing activity and no antibodies have been found that neutralize the virus of interest. As more naturally occurring virus isolates are discovered and capsid mutants generated, there may or may not be serological differences with any of the currently existing serotypes. Thus, in cases where the new AAV has no serological difference, this new AAV would be a subgroup or variant of the corresponding serotype. In many cases, serology testing for neutralizing activity has yet to be performed on mutant viruses with capsid sequence modifications to determine if they are of another serotype according to the traditional definition of serotype. Accordingly, for the sake of convenience and to avoid repetition, the term "serotype" broadly refers to both serologically distinct viruses (e.g., AAV) as well as viruses (e.g., AAV) that are not serologically distinct that may be within a subgroup or a variant of a given serotype.

"Transduction" refers to the transfer of a transgene into a recipient host cell by a viral vector. Transduction of a target cell by an rAAV virion of the invention leads to transfer of the transgene contained in that rAAV virion into the transduced cell. "Host cell" or "target cell" refers to the cell into which the DNA delivery takes place, such as the synoviocytes or synovial cells of an individual, or such as isolated FLS cells from patients or HEK293T cells in case of the in vitro transduction assay. AAV vectors are able to transduce both dividing and non-dividing cells. In a cell comprising a gene product of interest, such as for example GFP, the gene product of interest has been introduced/transferred/transduced by rAAV "transduction" of the cell. A cell into which the transgene has been introduced is referred to as a "transduced" cell.

The recipient host cell wherein the transgene is transduced preferably is a cell that is affected by the disease that is to be treated, such as for example synovial cells, more specifically FLS, macrophages, monocytes, neutrophils, osteoblasts, osteoclasts, chondrocytes, T-lymphocytes, dendritic cells, plasma cells, mast cells, B lymphocytes in case of an arthritic disease. The "synovium" or "synovial tissue" or "synovial cells" as used herein refers to the cellular lining covering the non-cartilaginous surfaces of the synovial joints, as further described in Tak (2000, Examination of the synovium and synovial fluid. In: Firestein G S, Panyani G S, Wollheim F A editors. Rheumatoid Arthritis. New York: Oxford Univ. Press, Inc. 55-68) and incorporated herein by reference. The synovium consists of the intimal lining layer (or synovial lining layer) and the synovial sublining (subsynovium), which merges with the joint capsule. The intimal lining layer comprises intimal macrophages (or macrophage-like synoviocytes or type A synoviocytes) and FLS (or type B synoviocytes). "Synovium" may therefore be replaced by, or is synonymous with, "synovial tissue". A synovial cell can include any cell present in the synovium including FLS and macrophage-like synoviocytes. A synoviocyte cell may also be a neutrophil, T, B cells and/or connective tissue cells, which may all be present in the synovium.

"Fibroblast-like synoviocytes" (FLS) are cells of mesenchymal origin that display many characteristics that are in common with fibroblasts, such as expression of specific proteins, such as for example several types of collagens. However, FLS also secrete proteins that are normally absent in other fibroblast lineages, such as for example lubricin. In addition, FLS express molecules that are important for the mediation of cell adhesion, such as cadherin-11, VCAM-1, several integrins and their receptors. Specific for FLS is the expression of CD55 and this protein is therefore typically used to identify FLS in the synovium by immunohistochemistry. FLS represent a specialized cell type located inside joints in the synovium, whose cells play a crucial role in the pathogenesis of chronic inflammatory diseases, such as rheumatoid arthritis (RA). The term "rheumatoid synovium" or "rheumatoid synovial cells" or "rheumatoid synovial tissue" refers to the inflamed synovium of the joints of an individual suffering from RA. The rheumatoid synovium is characterized by intimal lining hyperplasia and by accumulation of FLS, T-cells, plasma cells, macrophages, B-cells, natural killer cells and dendritic cells in the synovial sublining. These accumulated cells are comprised in the definition of rheumatoid synovial cells. During the progression of RA, the synovial tissue becomes a place where constant inflammatory processes take place, which can eventually lead to cartilage damage and joint destruction and deformation. FLS that are present in the synovium during RA have been reported to display an altered phenotype compared to the FLS present in normal tissues. For example, the FLS in rheumatoid synovium lose "contact inhibition", i.e., they lose the property to arrest their growth when more cells come into contact with each other. In addition, they lose the dependency to grow on adhesive surfaces. As a result, the number of FLS in the diseased synovium increases. The inflammation is further enhanced by the production of several pro-inflammatory signaling molecules, particularly interleukins IL-6 and IL-8, prostanoids and matrix metalloproteinases (MMPs).

Alternatively, or in combination with another embodiment, in a further preferred embodiment of the present invention, an rAAV virion comprising a modified capsid protein according to the invention provides for an at least two-fold increase in expression of a gene product of interest in human FLS in comparison to an rAAV virion comprising an unmodified capsid protein as defined herein, preferably to the unmodified capsid protein with an amino acid sequence selected from the group consisting of SEQ ID NO: 13-19, when tested under the same conditions, wherein preferably the unmodified capsid protein has the same serotype as the modified capsid protein or has the amino acid sequence shown in SEQ ID NO: 19.

More preferably, the rAAV virion of the invention results in increased expression levels of a gene product of interest upon in vitro transduction as described above by at least 2-, 3-, 4-, 5-, 6-, 7-, 8-, 9-, 10-, 15-, 20-, 25-, 30-, 35-, 40-, 50-fold increased expression levels in human FLS cells as compared to an rAAV control virion.

Also preferred, and/or in addition to the above, the rAAV virion provides for increased expression upon in vivo administration to the air pouch synovium (APS) mouse model (adapted from Edwards et al (1981) J Pathol 134: 147-156 as described in Example 4) as compared to an rAAV control virion, preferably as compared to an rAAV virion comprising wtAAV5 capsid proteins, provided that the rAAV is otherwise identical (apart from its capsid protein(s)). Preferably, expression of the gene product of interest is at least 2-, 3-, 4-, 5-, 6-, 7-, 8-, 9-, 10-, 15-, 20-, 25-, 30-, 35-fold increased using an rAAV comprising the mutant capsid proteins of the method of the invention. An exemplary method is provided in the Examples.

Also preferred, or in addition to the above, the rAAV virion comprising a modified capsid protein provides for similar or lower neutralizing antibody (nAb) titers as compared with the same rAAV virion comprising unmodified, preferably wild-type, AAV capsid protein of the same serotype. WtAAV5 capsids are known to have an attractive nAb profile, and therefore, similar or lower nAb titers of rAAV comprising a modified capsid protein according to the present invention as compared to wtAAV5 is preferred.

Alternatively, the in vitro transduction assay could be performed similarly as described above, but in a cell type/cell line different from FLS, depending on the cell type that is to be targeted, such as for example, in cells selected from the group consisting of primary hepatocytes, liver cell lines, e.g. HuH, HepG2, HepA1-6, heart cells, skeletal muscle cells, lung cells such as the cell line A549, CNS cells, eye cells, gastrointestinal tract cells, bone marrow cells and blood cells, such as the cell line THP-1. This also may require a different AAV serotype as preferred control, depending on the tropism of the wild-type capsid proteins. In general, a control vector preferably comprises wild-type capsid proteins that naturally target to the tissue of choice. As the skilled person will appreciate, this may also depend on mode of administration: locally or systemically. For example AAV2, which has been the most extensively examined AAV, presents tropism towards skeletal muscle cells, neurons, vascular smooth muscle cells and hepatocytes; AAV6 presents tropism towards airway epithelial cells; AAV7 presents tropism towards skeletal muscle cells; AAV8 presents tropism towards hepatocytes; AAV1 and AAV5 present tropism towards vascular endothelial cells. Upon systemic administration, AAV 1-3 and 5-9 have tropism towards the liver, with high protein levels observed with AAV9, 8, 7, 6, 1 and to a lesser extent 5 and 2; heart is transduced by AAV4, 6, 7, 8 and 9; thoracic expression is seen for AAV4 and 6 (Zincarelli et al (2008) Molecular Therapy 16 (6): 1073-1080).

Without wishing to be bound by any theory, we believe that the increased expression achieved by the rAAV virions comprising a modified capsid protein of the invention as compared to rAAV control virions is caused by an improved transduction of the rAAV into the cell, possibly by altered tropism, resulting in (i) an increased number of cells within the cell population being transduced, and/or (ii) an increased level of expression per cell, for example, due to better virion uptake and/or intracellular processing.

Another advantage of the rAAV virion with a modified capsid protein according to the invention could preferably be other improvements such as possible avoidance of pre-existing neutralizing antibodies.

In a preferred embodiment of the present invention, the modified capsid protein comprises an amino acid sequence Z, preferably amino acid sequence Z is comprised in the C-terminal part of the protein. Preferably, sequence Z is 12-18 amino acid residues in length (herein also referred to as "loop region" and as "insert"). In a preferred embodiment, sequence Z is located in the C-terminal part of the capsid protein, preferably at a location corresponding to a position at 100-200, preferably 120-180, more preferably 130-170, more preferably 140-160, most preferably about 150 amino acids from the C-terminus of the wild-type capsid protein, such as for example shown in SEQ ID NO's: 13-19. Residues of amino acid sequence Z are preferably exposed on the surface of the capsid protein, such as for example at least 2, 3, 4, 5, 6, 7, 8, 9, 10, 11, 12, 13, 14, 15, 16, 17 or 18 residues are exposed on the surface of the capsid protein (a so-called "loop"). In a preferred embodiment, the sequence Z is 14-18 amino acid residues in length, more preferably, 15, 16, 17 or 18 residues in length, most preferably, 15, 17 or 18 amino acid residues in length. Sequence Z may replace some amino acid residues as compared to the unmodified, such as the wild-type, capsid protein sequence. Preferably, the insert replaces 3, 4, 5, 6, 7, 8, 9 or 10 amino acid residues, more preferably 6 or 7 amino acid residues of the same sequence but without the insert, preferably of the unmodified, more preferably of the wild-type sequence. Apart from the sequence Z/insert, thus in the framework, the capsid protein may comprise further modifications, such as amino acid substitutions (for example conservative amino acid substitutions) or the framework capsid protein may be as the wild-type amino acid sequence. The framework AAV wherein the insert is comprised can be of any serotype, such as for example AAV1, AAV2, AAV3, AAV4, AAV5, AAV6, AAV7, AAV8, AAV9, AAV10, AAV11, AAVrh10 or AAVDJ. Preferably, the framework AAV wherein the sequence Z is comprised is selected from the group consisting of AAV1, AAV2, AAV7, AAV9, AAVrh10, AAVDJ, more preferably from the unmodified capsid proteins having an amino acid sequence as shown in any one of SEQ ID NO: 13-19. The insert according to the invention is preferably comprised in the C-terminal part of the capsid protein, preferably at a location corresponding to 100-200, preferably 120-180, more preferably 130-170, more preferably 140-160, most preferably approximately 150 amino acid residues from the C-terminus of the wild-type capsid protein, such as for example shown in SEQ ID NO's: 13-19, wherein the location of the insert is represented by formula II:

(SEQ ID NO: 27)

$$\text{EEEIxxxxPVATExxGxxxxNxQy-Z-(x)}_n\text{LPGMVWQxRDVYLQGPIWA}$$
$$\text{KIPHTDG}$$

wherein x represents a single amino acid residue, wherein y represents 0, 1 or 2 amino acid residue(s) (which thus may be absent), and wherein n is 5, 6, 7, 8, 9, 10, 11, 12, 13, 14 or 15, preferably 8, 9 or 10 or wherein the location of the insert is represented by a sequence having at least 90, 93, 95, 96, 97, 98 or 99% sequence identity with formula II. Preferably, the last three amino acid residues preceding the N-terminal end of sequence Z of the invention are NLQ, NHQ or NFQ. Preferably, y represents 0 or 2 amino acid residues. In some cases, y represents 2 amino acid residues, thus two additional amino acid residues, preferably two serine residues, may be present between the NxQ motif and the insert of the invention. This is preferably the case where the NxQ motif is NFQ, for example if the AAV capsid is an AAV1 capsid sequence as represented in SEQ ID NO: 1. The skilled person will be able to determine these motifs and this region where the insert is located, also if it harbors some variations, such as amino acid substitutions or deletions, which are also encompassed in the scope of the present invention.

In a preferred embodiment, based on the alignments shown in FIGS. 4 and 5, the insert (sequence Z) comprises or consists of a sequence of the formula: $x_1$-G-Q-$x_2$-G-$x_3$-$x_4$-$x_5$-R-$x_6$-$x_7$-$x_8$-$x_9$-$x_{10}$-$x_{11}$-$x_{12}$-$x_{13}$-$x_{14}$-$x_{15}$ (SEQ ID NO: 24), wherein $x_1$ is Q or none, $x_2$ is S or R, $x_3$ is N or C, $x_4$ is D, Y or E, $x_5$ is C, V, S or A, $x_6$ is G, S or V, $x_7$ is none, A, V or R, $x_8$ is D, N or E, $x_9$ is C or A, $x_{10}$ is F or Q, $x_{11}$ is none, C or A, $x_{12}$ is none or A, $x_{13}$ is none or Q, $x_{14}$ is none or A and $x_{15}$ is none or A. Alternatively, the insert (sequence Z) comprises or consists of a sequence of the formula:

$y_1$-G-Q-$y_2$-G-$y_3$-$y_4$-$y_5$-R-$y_6$-$y_7$-$y_8$-$y_9$-$y_{10}$-A-$y_{11}$-$y_{12}$-$y_{13}$ (SEQ ID NO: 25), wherein $y_1$ is Q or none, $y_2$ is S or R, $y_3$ is N or C, $y_4$ is D, Y or E, $y_5$ is C, V, S or A, $y_6$ is G, S or V, $y_7$ is none or D, $y_8$ is none or C, $y_9$ is A, V, R or F, $y_{10}$ is N, D, E or C, $y_{11}$ is none or Q, $y_{12}$ is none or A, $y_{13}$ is none or A. In yet another alternative, in the most preferred embodiment, based on the alignments shown in FIGS. 6 and 7, the insert (sequence Z) comprises or consists of a sequence of the general formula I:

(SEQ ID NO: 23)
y-G-Q-x-G-$(x)_3$-R-$(x)_3$-y-A-Q-A-A wherein x represents a single amino acid residue and wherein y represents 0, 1 or 2 amino acid residues (which thus may be absent). Preferably, (i) if at the N-terminus y represents 0 amino acids, then the other y within formula I represents 0 amino acid residues or (ii) if at the N-terminus y represents 1 amino acid residue, then the other y within formula I represents 2 amino acid residues. More preferably, the insert (sequence Z) comprises or consists of a sequence of the more specific formula:

(SEQ ID NO: 26)
$z_0$-G-Q-$z_1$-G-$z_2$-$z_3$-$z_4$-R-$z_5$-$z_6$-$z_7$-$z_8$-$z_9$-A-Q-A-A wherein $z_0$ is none or Q, $z_1$ is R or S, $z_2$ is C or N, $z_3$ is D, E or Y, $z_4$ is C, A, S or V, $z_5$ is G, V or S, $z_6$ is d or none, $z_7$ is C or none, $z_8$ is F, R, V or A, $z_9$ is C, D, N or E. More preferably, if $z_0$ is none, then also $z_6$ and $z_7$ both represent none.

More preferably, sequence Z/insert comprises or consists of an amino acid sequence that has at least 80, 85, 87, 90, 91, 92, 93, 94, 95, 96, 97, 98 or 99%, most preferably 100% sequence identity with any one of the amino acid sequences selected from the group consisting of SEQ ID NOs: 8-12. It is preferred that sequence Z/insert comprises or consists of an amino acid sequence represented by any one of the formulae above and that has at least 80, 85, 87, 90, 91, 92, 93, 94, 95, 96, 97, 98 or 99%, most preferably 100% sequence identity with any one of the amino acid sequences selected from the group consisting of SEQ ID NOs: 8-12.

In mammalian cells, expression of the three AAV capsid proteins (VP1, VP2 and VP3) in the correct stoichiometry relies on a combination of alternate usage of two splice acceptor sites and the suboptimal utilization of a ACG initiation codon for VP2 that is not accurately reproduced by insect cells. Correct stoichiometry is important for infectivity of the AAV particles. For production of the three AAV capsid proteins in insect cells in the correct stoichiometry, it is common in the art to use a construct that is transcribed into a single polycistronic messenger that is able to express all three VP proteins without requiring splicing. In order to achieve this, the VP1 protein could be under control of a suboptimal translation initiation codon instead of ATG. Examples of such a suboptimal translation initiation codon are ACG, TTG, CTG and GTG (Urabe et al. (2002) Human Gene Therapy 13:1935-1943; US20030148506; US20040197895; WO 2007/046703). Alternatively, in the production of rAAV in insect cells a nucleic acid cassette can be used for expressing VP1, VP2 and VP3 proteins, where these proteins are encoded by a nucleic acid sequence comprising overlapping open reading frames (ORFs) as described in European patent No. 2,061,891 B1, where a VP expression cassette is disclosed that comprises an intron comprising a promoter prior to the VP2 ACG initiation codon. The modified capsid protein of the invention is defined with respect to the protein sequence of the VP1 capsid protein. However, since sequence Z/insert is located in the C-terminal part of the VP1 protein, it is included in the invention that also VP2 and VP3 proteins harbor the sequence Z/insert and thus are modified (irrespective of the method of production of rAAV, such as for example in insect cells or in mammalian cells).

Alternatively, or in combination with another embodiment, in a further preferred embodiment of the present invention, the modified capsid protein according to the invention comprises or consists of an amino acid sequence selected from the group consisting of: i) an amino acid sequence having at least 70, 75, 80, 85, 87, 90, 91, 92, 93, 94, 95, 96, 97, 98, 99%, most preferably having 100% sequence identity with an amino acid sequence having SEQ ID NO: 1 and wherein amino acids at positions 588-602 of SEQ ID NO: 1 have at least 80, 85, 87, 90, 91, 92, 93, 94, 95, 96, 97, 98, 99%, most preferably having 100% sequence identity with SEQ ID NO: 11, ii) an amino acid sequence having at least 70, 75, 80, 85, 87, 90, 91, 92, 93, 94, 95, 96, 97, 98, 99%, most preferably having 100% sequence identity with an amino acid sequence having SEQ ID NO: 2 and wherein amino acids at positions 585-602 of SEQ ID NO: 2 have at least 80, 85, 87, 90, 91, 92, 93, 94, 95, 96, 97, 98, 99%, most preferably having 100% sequence identity with SEQ ID NO: 10, iii) an amino acid sequence having at least 70, 75, 80, 85, 87, 90, 91, 92, 93, 94, 95, 96, 97, 98, 99%, most preferably having 100% sequence identity with an amino acid sequence having SEQ ID NO: 3 and wherein amino acids at positions 587-601 of SEQ ID NO: 3 have at least 80, 85, 87, 90, 91, 92, 93, 94, 95, 96, 97, 98, 99%, most preferably having 100% sequence identity with SEQ ID NO: 9, iv) an amino acid sequence having at least 70, 75, 80, 85, 87, 90, 91, 92, 93, 94, 95, 96, 97, 98, 99%, most preferably having 100% sequence identity with an amino acid sequence having SEQ ID NO: 4 and wherein amino acids at positions 586-600 of SEQ ID NO: 4 have at least 80, 85, 87, 90, 91, 92, 93, 94, 95, 96, 97, 98, 99%, most preferably having 100% sequence identity with SEQ ID NO: 8, v) an amino acid sequence having at least 70, 75, 80, 85, 87, 90, 91, 92, 93, 94, 95, 96, 97, 98, 99%, most preferably having 100% sequence identity with an amino acid sequence having SEQ ID NO: 5 and wherein amino acids at positions 588-602 of SEQ ID NO: 5 have at least 80, 85, 87, 90, 91, 92, 93, 94, 95, 96, 97, 98, 99%, most preferably having 100% sequence identity with SEQ ID NO: 9, vi) an amino acid sequence having at least 70, 75, 80, 85, 87, 90, 91, 92, 93, 94, 95, 96, 97, 98, 99%, most preferably having 100% sequence identity with an amino acid sequence having SEQ ID NO: 6 and wherein amino acids at positions 588-602 of SEQ ID NO: 6 have at least 80, 85, 87, 90, 91, 92, 93, 94, 95, 96, 97, 98, 99%, most preferably having 100% sequence identity with SEQ ID NO: 8, and vii) an amino acid sequence having at least 70, 75, 80, 85, 87, 90, 91, 92, 93, 94, 95, 96, 97, 98, 99%, most preferably having 100% sequence identity with an amino acid sequence having SEQ ID NO: 7 and wherein amino acids at positions 587-604 of SEQ ID NO: 7 have at least 80, 85, 87, 90, 91, 92, 93, 94, 95, 96, 97, 98, 99%, most preferably having 100% sequence identity with SEQ ID NO: 12. Preferably, the framework AAV capsid protein wherein the insert is comprised, has the amino acid sequence of a wild-type AAV capsid, such as for example of AAV5, AAV1, AAV2, AAV7, AAV9, AAVrh10 or AAVDJ or an amino acid sequence comprising conservative amino acid substitutions. More preferably, the framework AAV capsid protein wherein the insert is comprised, has the amino acid sequence of a wtAAV5 capsid or an amino acid sequence comprising conservative amino acid substitutions.

"Sequence identity" is herein defined as a relationship between two or more amino acid (polypeptide or protein) sequences or two or more nucleic acid (polynucleotide) sequences, as determined by comparing the sequences. In a preferred embodiment, sequence identity is calculated based on the full length of two given SEQ ID NO or on part thereof. Part thereof preferably means at least 10, 20, 30, 40, 50, 60, 70, 80, 90%, or 100% of both SEQ ID NO. In the art, "identity" also means the degree of sequence relatedness between amino acid or nucleic acid sequences, as the case may be, as determined by the match between strings of such sequences. Unless otherwise indicated herein, identity or similarity with a given SEQ ID NO means identity or similarity based on the full length of said sequence (i.e. over its whole length or as a whole).

"Similarity" between two amino acid sequences is determined by comparing the amino acid sequence and its conserved amino acid substitutes of one polypeptide to the sequence of a second polypeptide. "Identity" and "similarity" can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heine, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48:1073 (1988)).

Preferred methods to determine identity are designed to give the largest match between the sequences tested. Methods to determine identity and similarity are codified in publicly available computer programs. Preferred computer program methods to determine identity and similarity between two sequences include e.g., the GCG program package (Devereux, J., et al., Nucleic Acids Research 12 (1): 387 (1984)), BestFit, BLASTP, BLASTN, and FASTA (Altschul, S. F. et al., J. Mol. Biol. 215:403-410 (1990)). The BLAST X program is publicly available from NCBI and other sources (BLAST Manual, Altschul, S. et al., NCBI NLM NIH Bethesda, MD 20894; Altschul, S. et al., J. Mol. Biol. 215:403-410 (1990)). The well-known Smith Waterman algorithm may also be used to determine identity.

Preferred parameters for polypeptide sequence comparison include the following Algorithm: Needleman and Wunsch, J. Mol. Biol. 48:443-453 (1970); Comparison matrix: BLOSSUM62 from Hentikoff and Hentikoff, Proc. Natl. Acad. Sci. USA. 89:10915-10919 (1992); Gap Penalty: 12; and Gap Length Penalty: 4. Such a program is publicly available as the "Ogap" program from Genetics Computer Group, located in Madison, WI. The aforementioned parameters are the default parameters for amino acid comparisons (along with no penalty for end gaps).

Preferred parameters for nucleic acid comparison include the following Algorithm: Needleman and Wunsch, J. Mol. Biol. 48:443-453 (1970); Comparison matrix: matches=+10, mismatch=0; Gap Penalty: 50; Gap Length Penalty: 3. Available as the Gap program from Genetics Computer Group, located in Madison, Wis. Given above are the default parameters for nucleic acid comparisons.

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acid substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to Ser; Arg to Lys; Asn to Gln or His; Asp to Glu; Cys to Ser or Ala; Gln to Asn; Glu to Asp; Gly to Pro; His to Asn or Gin; Ile to Leu or Val; Leu to Ile or Val; Lys to Arg; Gln or Glu; Met to Leu or Ile; Phe to Met, Leu or Tyr; Ser to Thr; Thr to Ser; Trp to Tyr; Tyr to Trp or Phe; and, Val to Ile or Leu.

Alternatively, or in combination with another embodiment, in a further preferred embodiment of the present invention, the capsid protein comprises or consists of an amino acid sequence selected from the group consisting of SEQ ID NO:1-7, more preferably from the group consisting of SEQ ID NO: 1, 2, 3, 4, 6 and 7, even more preferably from the group consisting of SEQ ID NO: 3, 4 and 6, still more preferably from the group consisting of SEQ ID NO: 4 and 6, most preferably SEQ ID NO:4.

The rAAV virion of the invention may comprise a single type of modified capsid protein, preferably a single type of modified capsid protein as defined herein. Hence in an embodiment, the rAAV virion of the invention comprises modified capsid proteins, wherein each modified capsid protein has the same or substantially the same amino acid sequence. Alternatively, the rAAV virion of the invention may comprise different types of modified capsid proteins. As a non-limiting example, the AAV virion of the invention may comprise 1, 2, 3, 4, 5, 6, 7, 8, 9, 10 or more types of modified capsid proteins. The rAAV virion of the invention may further comprise one or wild type capsid proteins, in combination with a single type or different types of modified capsid proteins.

In preferred embodiments, the capsid protein is a modified capsid protein as defined herein.

In preferred embodiments, the capsid protein comprises in the C-terminal part of the protein an amino acid sequence Z, residues of which are exposed on the surface of the capsid protein. Preferably amino acid sequence Z a. comprises or consists of a sequence of amino acid residues of the formula I:

$$y\text{-}G\text{-}Q\text{-}x\text{-}G\text{-}(x)_3\text{-}R\text{-}(x)_3\text{-}y\text{-}A\text{-}Q\text{-}A\text{-}A$$

wherein x represents a single amino acid residue and wherein y represents 0, 1 or 2 amino acid residues; and b. is present at a location corresponding to a position 100-200, preferably 120-180, more preferably 130-170, more preferably 140-160 amino acid residues from the C terminus of a wild-type AAV capsid protein.

Preferably, the rAAV virion of the invention comprises an modified capsid protein as defined herein for use in treating or preventing an arthritic disease or for use in treating or preventing symptoms associated with an arthritic disease.

In preferred embodiments, the modified capsid protein comprises or consists of an amino acid sequence having SEQ ID NO: 1 (AAV1 P4). Preferably, the modified capsid protein has at least about 70%, 75%, 80%, 85%, 90%, 95%, 96%, 97%, 98%, 99% or 100% sequence identity with SEQ ID NO: 1. Preferably amino acids at positions 588-602 of SEQ ID NO: 1 have at least 80% sequence identity with SEQ ID NO: 11. Preferably, the rAAV virion of the invention comprises an AAV1 P4 modified capsid protein for use in treating or preventing an arthritic disease or for use in treating or preventing symptoms associated with an arthritic disease.

In preferred embodiments, the modified capsid protein comprises or consists of an amino acid sequence having SEQ ID NO: 2 (AAV2 P2). Preferably, the modified capsid protein has at least about 70%, 75%, 80%, 85%, 90%, 95%, 96%, 97%, 98%, 99% or 100% sequence identity with SEQ ID NO: 2. Preferably amino acids at positions 585-602 of SEQ ID NO: 2 have at least 80% sequence identity with SEQ ID NO: 10. Preferably, the rAAV virion of the invention comprises an AAV2 P2 modified capsid protein for use in treating or preventing an arthritic disease or for use in treating or preventing symptoms associated with an arthritic disease.

In preferred embodiments, the modified capsid protein comprises or consists of an amino acid sequence having SEQ ID NO: 3 (AAV7 A6). Preferably, the modified capsid protein has at least about 70%, 75%, 80%, 85%, 90%, 95%, 96%, 97%, 98%, 99% or 100% sequence identity with SEQ ID NO: 3. Preferably amino acids at positions 587-601 of SEQ ID NO: 3 have at least 80% sequence identity with SEQ ID NO: 9. Preferably, the rAAV virion of the invention comprises an AAV7 A6 modified capsid protein for use in treating or preventing an arthritic disease or for use in treating or preventing symptoms associated with an arthritic disease.

In preferred embodiments, the modified capsid protein comprises or consists of an amino acid sequence having SEQ ID NO: 4 (AAV9 A2). Preferably, the modified capsid protein has at least about 70%, 75%, 80%, 85%, 90%, 95%, 96%, 97%, 98%, 99% or 100% sequence identity with SEQ ID NO: 4. Preferably amino acids at positions 586-600 of SEQ ID NO: 4 have at least 80% sequence identity with SEQ ID NO: 8. Preferably, the rAAV virion of the invention comprises an AAV9 A2 modified capsid protein for use in treating or preventing an arthritic disease or for use in treating or preventing symptoms associated with an arthritic disease.

In preferred embodiments, the modified capsid protein comprises or consists of an amino acid sequence having SEQ ID NO: 5 (AAVrh10 A6). Preferably, the modified capsid protein has at least about 70%, 75%, 80%, 85%, 90%, 95%, 96%, 97%, 98%, 99% or 100% sequence identity with SEQ ID NO: 5. Preferably amino acids at positions 588-602 of SEQ ID NO: 5 have at least 80% sequence identity with SEQ ID NO: 9. Preferably, the rAAV virion of the invention comprises an AAVrh10 A6 modified capsid protein for use in treating or preventing an arthritic disease or for use in treating or preventing symptoms associated with an arthritic disease.

In preferred embodiments, the modified capsid protein comprises or consists of an amino acid sequence having SEQ ID NO: 6 (AAVrh10 A2). Preferably, the modified capsid protein has at least about 70%, 75%, 80%, 85%, 90%, 95%, 96%, 97%, 98%, 99% or 100% sequence identity with SEQ ID NO: 6. Preferably amino acids at positions 588-602 of SEQ ID NO: 6 have at least 80% sequence identity with SEQ ID NO: 8. Preferably, the rAAV virion of the invention comprises an AAVrh10 A2 modified capsid protein for use in treating or preventing an arthritic disease or for use in treating or preventing symptoms associated with an arthritic disease.

In preferred embodiments, the modified capsid protein comprises or consists of an amino acid sequence having SEQ ID NO: 7 (AAV-DJ-QR-P2). Preferably, the modified capsid protein has at least about 70%, 75%, 80%, 85%, 90%, 95%, 96%, 97%, 98%, 99% or 100% sequence identity with SEQ ID NO: 7. Preferably amino acids at positions 587-604 of SEQ ID NO: 7 have at least 80% sequence identity with SEQ ID NO: 12. Preferably, the rAAV virion of the invention comprises an AAV-DJ-QR-P2 modified capsid protein for use in treating or preventing an arthritic disease or for use in treating or preventing symptoms associated with an arthritic disease.

Functional ITR sequences are necessary for the replication, rescue and packaging of rAAV virions. The ITR sequences may be wild-type sequences or may have at least 80%, 85%, 90%, 95%, or 100% sequence identity with wild-type sequences or may be altered by, for example, insertion, mutation, deletion or substitution of nucleotides, as long as they remain functional. In this context, functionality refers to the ability to directly package the genome into the capsid shell and then allow for expression in the host cell to be transduced or target cell. Typically, the ITRs of the wild-type AAV genome are retained in the rAAV-vector. The ITRs can be cloned from the AAV viral genome or excised from a vector comprising the AAV ITRs. The ITR nucleotide sequences can be either ligated at either end to a transgene as defined herein using standard molecular biology techniques, or the wild-type AAV sequence between the ITRs can be replaced with the desired nucleotide sequence. The rAAV-vector preferably comprises at least the nucleotide sequences of the ITR regions of one of the AAV serotypes, or nucleotide sequences substantially identical thereto, and at least one nucleotide sequence encoding a therapeutic protein (under control of a suitable regulatory element) inserted between the two ITRs. The majority of currently used rAAV-vectors use the ITR sequences from AAV serotype 2. Most preferred ITRs present in an rAAV-vector are of the AAV2 serotype. Other preferred ITRs are of the AAV1, AAV3, AAV5 or AAV6 serotype (Grimm et al. (2006) J Virol 80 (1): 426-439). An rAAV genome can comprise single-stranded or double-stranded (self-complementary) DNA. The single-stranded nucleic acid molecule is either sense or antisense strand, as both polarities are equally capable of packaging into AAV capsids. Single-stranded rAAV-vectors may utilize the wild-type AAV serotype 2 (AAV2) ITR sequences, and double-stranded (self-complementary) rAAV-vectors may utilize a modified version of the ITRs. Alternatively, in an embodiment, a double-stranded vector comprises one ITR, which ITR is from AAV4. The rAAV-vector may further comprise a marker or reporter gene, such as a gene for example encoding an antibiotic resistance gene, a fluorescent protein (e.g., gfp) or a gene encoding a chemically, enzymatically or otherwise detectable and/or selectable product (e.g., lacZ, alkaline phosphatase (AP), SEAP, Luc, Neo, Bla, etc.) known in the art.

The rAAV-vector, including any possible combination of AAV serotype capsid and AAV genome ITRs, is produced using methods known in the art, for example using a mammalian rAAV production system or an insect cell rAAV production system. Methods known in the art are for example described in Pan et al. (J. of Virology (1999) 73:3410-3417), Clark et al. (Human Gene Therapy (1999) 10:1031-1039), Wang et al. (Methods Mol. Biol. (2011) 807:361-404), Grimm (Methods (2002) 28 (2): 146-157), and the insect cell system based on Urabe et al (Human Gene Therapy (2002) 13:1935-1943), Kohlbrenner et al (Molecular Therapy (2005) 12 (6): 1217-1225), International Patent publication WO 2007/046703, International Patent publication WO 2007/148971, International Patent publication WO 2009/014445, International Patent publication WO 2009/104964, International Patent publication WO 2009/154452, International Patent publication WO 2011/112089, International Patent publication WO 2013/036118, U.S. Pat. No. 6,723,551 B, which are incorporated herein by reference. In short, the methods generally may involve (a) the introduction of the rAAV genome construct into a host cell, (b) the introduction of an AAV helper construct into the host cell, wherein the helper construct comprises the viral functions missing from the wild-type rAAV genome and (c) introducing a helper virus construct into the host cell. All functions for rAAV vector replication and packaging need to be present, to achieve replication and packaging of the rAAV genome into rAAV vectors. The introduction into the host cell can be carried out using standard molecular biology techniques and can be simultaneously or sequentially. Finally, the host cells are cultured to produce rAAV vectors which are then purified using standard techniques such as CsCl gradients (Xiao et al. 1996, J. Virol. 70:8098-8108) or Iodixanol purification. The purified rAAV vector is then typically ready for use in the methods. High titers of more than $10^{12}$ particles per ml and high purity (free of detectable helper and wild-type viruses) can be achieved (see for example Clark et al. supra and Flotte et al. 1995, Gene Ther. 2:29-37). The total size of the transgene inserted into the rAAV vector between the ITR regions is generally smaller than 5 kilobases (kb) in size.

In the context of the present invention a capsid protein shell may be of a different serotype than the rAAV-genome, comprising (i) a nucleotide sequence encoding a gene product of interested and (ii) at least one AAV ITR sequence. An rAAV-genome of the invention may thus be encapsidated by a capsid protein shell of the present invention, i.e. the icosahedral capsid, which comprises capsid proteins (VP1, VP2, and/or VP3) according to the present invention, e.g., mutants of AAV capsid proteins according to the invention, whereas the ITRs sequences contained in that rAAV-vector may be any of the AAV serotypes described above, including for example AAV2 or AAV5. In an embodiment, the rAAV genome or ITRs present in the rAAV virion are derived from AAV serotype 2 or AAV serotype 5 or AAV serotype 8. The complete genome of AAV5 and other AAV serotypes has been sequenced (Chiorini et al. 1999, J. of Virology Vol. 73, No. 2, p1309-1319) and the nucleotide sequence of AAV5 is available in GenBank (Accession No. AF085716). The ITR nucleotide sequences of AAV2 and AAV5 are thus readily available to a skilled person. The complete genome of AAV2 is available in NCBI (NCBI Reference Sequence NC_001401.2). They can be either cloned or made by chemical synthesis as known in the art, using for example an oligonucleotide synthesizer as supplied e.g., by Applied Biosystems Inc. (Fosters, CA, USA) or by standard molecular biology techniques.

Alternatively, or in combination with another embodiment, in a further preferred embodiment of the present invention, the rAAV vector comprises a nucleotide sequence encoding a gene product of interest.

The term "transgene" is used to refer to a polynucleotide that can be introduced into a cell or organism. A transgene includes any polynucleotide, such as a gene that encodes a polypeptide or protein, a polynucleotide that is transcribed into an inhibitory polynucleotide, or a polynucleotide that is not transcribed (e.g., lacks an expression control element, such as a promoter that drives transcription). A transgene of the invention may comprise at least two nucleotide sequences each being different or encoding different therapeutic molecules. The at least two different nucleotide sequences may be linked by an IRES (internal ribosome entry site) element, providing a bicistronic transcript under control of a single promoter. Suitable IRES elements are described in e.g., Hsieh et al. (1995, Biochem. Biophys. Res. Commun. 214:910-917). Furthermore, the at least two different nucleotide sequences encoding different (therapeutic) polypeptides or proteins may be linked by a viral 2A sequence to allow for efficient expression of both transgenes from a single promoter. Examples of 2A sequences include those from foot and mouth disease virus, equine rhinitis A virus, Thosea asigna virus and porcine teschovirus-1 (Kim et al., PLOS One (2011) 6 (4): e18556). A transgene is preferably inserted within the rAAV genome or between ITR sequences. A transgene may also be an expression construct comprising an expression regulatory element such as a promoter or transcription regulatory sequence operably linked to a coding sequence and a 3' termination sequence. The transgene can be a functional mutant allele that replaces or supplements a defective one. Gene therapy also includes insertion of transgenes that are inhibitory in nature, i.e., that inhibit, decrease or reduce expression, activity or function of an endogenous or exogenous gene or protein, such as an undesirable or aberrant (e.g., pathogenic) gene or protein. Such transgenes may be exogenous. An exogenous molecule or sequence is understood to be a molecule or sequence not normally occurring in the cell, tissue and/or individual to be treated. Both acquired and congenital diseases are amenable to gene therapy.

"Gene" or "coding sequence" refers to a DNA or RNA region which "encodes" a particular protein. A coding sequence is transcribed (DNA) and translated (RNA) into a polypeptide when placed under the control of an appropriate regulatory region, such as a promoter. A gene may comprise several operably linked fragments, such as a promoter, a 5' leader sequence, an intron, a coding sequence and a 3' non-translated sequence, comprising a polyadenylation site or a signal sequence. A chimeric or recombinant gene is a gene not normally found in nature, such as a gene in which for example the promoter is not associated in nature with part or all of the transcribed DNA region. "Expression of a gene" refers to the process wherein a gene is transcribed into an RNA and/or translated into an active protein.

As used herein, the term "promoter" or "transcription regulatory sequence" refers to a nucleic acid fragment that functions to control the transcription of one or more coding sequences, and is located upstream with respect to the direction of transcription of the transcription initiation site of the coding sequence, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active in most tissues under most physiological and developmental conditions. An "inducible" promoter is a promoter that is physiologically or developmentally regulated, e.g., by the application of a chemical inducer. A "tissue specific" promoter is preferentially active in specific types of tissues or cells. The selection of an appropriate promoter sequence generally depends upon the host cell selected for the expression of a DNA segment. A transgene may be operably linked to a promoter that allows for efficient systemic expression or allows for tissue specific expression.

Promoters

In preferred embodiments the expression of a transgene encoding a gene product of interest, preferably a gene product of interest as defined herein, is operably linked to a promoter. Hence preferably the rAAV virion of the invention comprises a promoter sequence. Preferably, the promoter is selected from the group consisting of a constitutive promoter, inducible promoter, tissue specific promoter, promoters which confer expression in cells of the joint, CMV promoter, CAG (cytomegalovirus early enhancer/chicken β-actin) promoter, EF1α promoter, SV40 promoter, CBA (chicken beta-actin) promoter, liver-specific promoter, NFκB responsive (inducible) promoter, promoter of an inflammatory modulator gene, IL1β promoter, IL-6 (HGF) promoter, IL8 (CXCL8) promoter, CXCL10 promoter, MMP3 promoter, MMP2 promoter, ICAM1 promoter, MMP13 promoter, ADAMTS4 promoter, ADAMDEC1 promoter, COL1A1 promoter, MMP12 promoter, RUNX2 promoter, ADAMTS5 promoter, COX2 (PTGS2) promoter, TNFα (TNF) promoter, VEGF (VEGFA) promoter, (Basic) FGF (FGF2) promoter and TGF-β (TGB1) promoter.

Preferably, the promoter is selected from the group consisting of NFκB responsive (inducible) minimal CMV promoter, promoter of a pro-inflammatory cytokine gene, minimized promoter of a pro-inflammatory cytokine gene, a promoter which confers expression in cells of the arthritic joint, a promoter which confers expression in connective tissue cells, a promoter which confers expression in synovial cells, a promoter which confers expression in sub-synovial cells, a promoter which confers expression in intimal macrophages, a promoter which confers expression in FLS, a promoter which confers expression in cartilage cells, a promoter which confers expression in chondrocytes, a promoter which confers expression in chondroblasts, a promoter which confers expression in adipocytes, a promoter which confers expression in osteoclasts, a promoter which confers expression in T-cells, human alpha-1 anti-trypsin (hAAT) promoter and TBG (thyroxine-binding globulin) promoter.

Preferably, the promoter is selected from the group consisting of an NFκB responsive (inducible) minimal CMV promoter, a CMV promoter, an EF1α promoter, a CAG promoter, a MMP13 promoter, an IL-6 promoter and an IL8 promoter, preferably an NFκB responsive (inducible) minimal CMV promoter. Preferably, the NFκB responsive (inducible) CMV promoter is a promoter as described in Khoury et al. 2007, J Gene Med, 9:596-604.

In preferred embodiments the expression of a transgene, preferably a transgene as defined herein, is controlled by a constitutive promoter.

In preferred embodiments the expression of a transgene, preferably a transgene as defined herein, is controlled by an inducible promoter.

In preferred embodiments the expression of a transgene, preferably a transgene as defined herein, is controlled by a tissue specific promoter.

In preferred embodiments the expression of a transgene, preferably a transgene as defined herein, is controlled by a promoter which confers expression in cells of the joint, preferably the arthritic joint. A preferred promoter confers expression in at least one of connective tissue cells, synovial cells, sub-synovial cells, intimal macrophages, FLS, cartilage cells, chondrocytes, chondroblasts, adipocytes, osteoclasts and T-cells, preferably the promoter confers expression in cells of the FLS.

In preferred embodiments the expression of a transgene, preferably a transgene as defined herein, is controlled by a CMV promoter.

In preferred embodiments the expression of a transgene, preferably a transgene as defined herein, is controlled by a CAG (cytomegalovirus early enhancer/chicken β-actin) promoter.

In preferred embodiments the expression of a transgene, preferably a transgene as defined herein, is controlled by an EF1α promoter.

In preferred embodiments the expression of a transgene, preferably a transgene as defined herein, is controlled by an SV40 promoter.

In preferred embodiments the expression of a transgene, preferably a transgene as defined herein, is controlled by a CBA (chicken beta-actin) promoter.

In preferred embodiments the expression of a transgene, preferably a transgene as defined herein, is controlled by a liver-specific promoter. A preferred liver-specific promoter is at least one of human alpha-1 anti-trypsin (hAAT) promoter and TBG (thyroxine-binding globulin) promoter.

In preferred embodiments the expression of a transgene, preferably a transgene as defined herein, is controlled by an NFκB responsive (inducible) promoter. A preferred NFκB responsive (inducible) promoter is an NFκB responsive (inducible) CMV promoter, preferably an NFκB responsive (inducible) minimal CMV promoter. Preferably, the NFκB responsive (inducible) CMV promoter is a promoter as described in Khoury et al. 2007, J Gene Med, 9:596-604.

In preferred embodiments the expression of a transgene, preferably a transgene as defined herein, is controlled by a promoter of an inflammatory modulator, preferably a promoter of a pro-inflammatory cytokine gene. Preferably the promoter of a pro-inflammatory cytokine gene is a minimized promoter of a pro-inflammatory cytokine gene.

In preferred embodiments the expression of a transgene, preferably a transgene as defined herein, is controlled by a IL1β promoter.

In preferred embodiments the expression of a transgene, preferably a transgene as defined herein, is controlled by an IL-6 (HGF) promoter.

In preferred embodiments the expression of a transgene, preferably a transgene as defined herein, is controlled by an IL8 (CXCL8) promoter.

In preferred embodiments the expression of a transgene, preferably a transgene as defined herein, is controlled by an CXCL10 promoter.

In preferred embodiments the expression of a transgene, preferably a transgene as defined herein, is controlled by an MMP3 promoter.

In preferred embodiments the expression of a transgene, preferably a transgene as defined herein, is controlled by an MMP2 promoter.

In preferred embodiments the expression of a transgene, preferably a transgene as defined herein, is controlled by an ICAM1 promoter.

In preferred embodiments the expression of a transgene, preferably a transgene as defined herein, is controlled by an MMP13 promoter.

In preferred embodiments the expression of a transgene, preferably a transgene as defined herein, is controlled by an ADAMTS4 promoter.

In preferred embodiments the expression of a transgene, preferably a transgene as defined herein, is controlled by an ADAMDEC1 promoter.

In preferred embodiments the expression of a transgene, preferably a transgene as defined herein, is controlled by a COL1A1 promoter.

In preferred embodiments the expression of a transgene, preferably a transgene as defined herein, is controlled by an MMP12 promoter.

In preferred embodiments the expression of a transgene, preferably a transgene as defined herein, is controlled by a RUNX2 promoter.

In preferred embodiments the expression of a transgene, preferably a transgene as defined herein, is controlled by an ADAMTS5 promoter.

In preferred embodiments the expression of a transgene, preferably a transgene as defined herein, is controlled by a COX2 (PTGS2) promoter.

In preferred embodiments the expression of a transgene, preferably a transgene as defined herein, is controlled by a TNF$\alpha$ (TNF) promoter.

In preferred embodiments the expression of a transgene, preferably a transgene as defined herein, is controlled by a VEGF (VEGFA) promoter.

In preferred embodiments the expression of a transgene, preferably a transgene as defined herein, is controlled by a (basic) FGF (FGF2) promoter.

In preferred embodiments the expression of a transgene, preferably a transgene as defined herein, is controlled by a TGF-$\beta$ (TGB1) promoter.

In preferred embodiments, the promoter within the rAAV virion is not a steroid-inducible promoter. Preferably, the promoter within the rAAV virion is not a dexamethasone-inducible promoter.

In preferred embodiments, the modified capsid protein is a modified capsid protein as defined herein. Preferably the rAAV virion comprising a modified capsid protein as defined herein further comprises a promoter controlling the expression of a transgene. Preferably, the promoter is a promoter as defined herein above.

In preferred embodiments, the modified capsid protein comprises in the C-terminal part of the protein an amino acid sequence Z, residues of which are exposed on the surface of the capsid protein. Preferably amino acid sequence Z a. comprises or consists of a sequence of amino acid residues of the formula I:

$$\text{y-G-Q-x-G-(x)}_3\text{-R-(x)}_3\text{-y-A-Q-A-A}$$

wherein x represents a single amino acid residue and wherein y represents 0, 1 or 2 amino acid residues; and b. is present at a location corresponding to a position 100-200, preferably 120-180, more preferably 130-170, more preferably 140-160 amino acid residues from the C terminus of a wild-type AAV capsid protein. Preferably the rAAV virion comprising a modified capsid protein as defined herein further comprises a promoter controlling the expression of a transgene. Preferably, the promoter is a promoter as defined herein above.

In preferred embodiments, the modified capsid protein comprises or consists of an amino acid sequence having SEQ ID NO: 1 (AAV1 P4). Preferably, the modified capsid protein has at least about 70%, 75%, 80%, 85%, 90%, 95%, 96%, 97%, 98%, 99% or 100% sequence identity with SEQ ID NO: 1. Preferably amino acids at positions 588-602 of SEQ ID NO: 1 have at least 80% sequence identity with SEQ ID NO: 11. Preferably the rAAV virion comprising an AAV1 P4 modified capsid protein further comprises a promoter controlling the expression of a transgene. Preferably, the promoter is a promoter as defined herein above.

In preferred embodiments, the modified capsid protein comprises or consists of an amino acid sequence having SEQ ID NO: 2 (AAV2 P2). Preferably, the modified capsid protein has at least about 70%, 75%, 80%, 85%, 90%, 95%, 96%, 97%, 98%, 99% or 100% sequence identity with SEQ ID NO: 2. Preferably amino acids at positions 585-602 of SEQ ID NO: 2 have at least 80% sequence identity with SEQ ID NO: 10. Preferably the rAAV virion comprising an AAV2 P2 modified capsid protein further comprises a promoter controlling the expression of a transgene. Preferably, the promoter is a promoter as defined herein above.

In preferred embodiments, the modified capsid protein comprises or consists of an amino acid sequence having SEQ ID NO: 3 (AAV7 A6). Preferably, the modified capsid protein has at least about 70%, 75%, 80%, 85%, 90%, 95%, 96%, 97%, 98%, 99% or 100% sequence identity with SEQ ID NO: 3. Preferably amino acids at positions 587-601 of SEQ ID NO: 3 have at least 80% sequence identity with SEQ ID NO: 9. Preferably the rAAV virion comprising an AAV7 A6 modified capsid protein further comprises a promoter controlling the expression of a transgene. Preferably, the promoter is a promoter as defined herein above.

In preferred embodiments, the modified capsid protein comprises or consists of an amino acid sequence having SEQ ID NO: 4 (AAV9 A2). Preferably, the modified capsid protein has at least about 70%, 75%, 80%, 85%, 90%, 95%, 96%, 97%, 98%, 99% or 100% sequence identity with SEQ ID NO: 4. Preferably amino acids at positions 586-600 of SEQ ID NO: 4 have at least 80% sequence identity with SEQ ID NO: 8. Preferably the rAAV virion comprising an AAV9 A2 modified capsid protein further comprises a promoter controlling the expression of a transgene. Preferably, the promoter is a promoter as defined herein above.

In preferred embodiments, the modified capsid protein comprises or consists of an amino acid sequence having SEQ ID NO: 5 (AAVrh10 A6). Preferably, the modified capsid protein has at least about 70%, 75%, 80%, 85%, 90%, 95%, 96%, 97%, 98%, 99% or 100% sequence identity with SEQ ID NO: 5. Preferably amino acids at positions 588-602 of SEQ ID NO: 5 have at least 80% sequence identity with SEQ ID NO: 9. Preferably the rAAV virion comprising an AAVrh10 A6 modified capsid protein further comprises a promoter controlling the expression of a transgene. Preferably, the promoter is a promoter as defined herein above.

In preferred embodiments, the modified capsid protein comprises or consists of an amino acid sequence having SEQ ID NO: 6 (AAVrh10 A2). Preferably, the modified capsid protein has at least about 70%, 75%, 80%, 85%, 90%, 95%, 96%, 97%, 98%, 99% or 100% sequence identity with SEQ ID NO: 6. Preferably amino acids at positions 588-602 of SEQ ID NO: 6 have at least 80% sequence identity with SEQ ID NO: 8. Preferably the rAAV virion comprising an AAVrh10 A2 modified capsid protein further comprises a promoter controlling the expression of a transgene. Preferably, the promoter is a promoter as defined herein above.

In preferred embodiments, the modified capsid protein comprises or consists of an amino acid sequence having SEQ ID NO: 7 (AAV-DJ-QR-P2). Preferably, the modified capsid protein has at least about 70%, 75%, 80%, 85%, 90%, 95%, 96%, 97%, 98%, 99% or 100% sequence identity with SEQ ID NO: 7. Preferably amino acids at positions 587-604 of SEQ ID NO: 7 have at least 80% sequence identity with SEQ ID NO: 12. Preferably the rAAV virion comprising an AAV-DJ-QR-P2 modified capsid protein further comprises a promoter controlling the expression of a transgene. Preferably, the promoter is a promoter as defined herein above.

The term "controlling the expression" and "operably linked" can be used interchangeably herein. As used herein, the term "operably linked" refers to a linkage of polynucleotide (or polypeptide) elements in a functional relationship. A nucleic acid is "operably linked" when it is placed into a functional relationship with another nucleic acid sequence. For instance, a transcription regulatory sequence is operably linked to a coding sequence if it affects the transcription of the coding sequence. "Operably linked" means that the DNA sequences being linked are typically contiguous and, where necessary to join two protein-encoding regions, contiguous and in reading frame.

Gene Product of Interest

A transgene as defined herein preferably encodes a gene product of interest as defined herein. A "gene product of interest" can be a "therapeutic polypeptide" or "therapeutic protein" which are to be understood herein as a polypeptide or protein that can have a beneficial effect on an individual, preferably said individual is a human, more preferably said human suffers from a disease. Such therapeutic polypeptide may be selected from, but is not limited to, the group consisting of an enzyme, a co-factor, a cytokine, an antibody, a growth factor, a hormone and an anti-inflammatory protein.

Alternatively, or in combination with another embodiment, in a further preferred embodiment of the present invention, the nucleotide sequence encoding a gene product of interest is located between two AAV ITR sequences. Alternatively said, the nucleotide sequence encoding the gene product of interest is flanked by two AAV ITR sequences, i.e., one ITR on either end of the nucleotide sequence encoding the gene product of interest.

Alternatively, or in combination with another embodiment, in a further preferred embodiment of the present invention, the gene product of interest treats, prevents or suppresses symptoms associated with an arthritic disease.

It is understood herein that the gene product of interest may include biosimilars of said gene product of interest.

In preferred embodiments, the gene product of interest is an immunosuppressant.

In preferred embodiments, the gene product of interest is selected from the group consisting of ANP32A, Nrf2, IL-6 inhibitor, soluble IL-6 receptor, IL-6 receptor antagonist, humanised anti-IL-6 monoclonal antibody, chimeric anti-IL-6 monoclonal antibody, humanized rabbit anti-IL-6 monoclonal antibody, interleukin1 (IL-1) inhibitor, tumor necrosis factor alpha (TNFα) inhibitor, IL-1 receptor antagonist, soluble IL-1 receptor, IL-17 inhibitor, IL-12/IL-23 inhibitor, T-cell costimulation inhibitor, B cell depleting and inhibiting agents, IL-15 inhibitor, IL-22 inhibitor, inhibitor of GM-CSF, insulin-like growth factor (IGF-1), fibroblast-growth factor (FGF), receptor activator of nuclear factor kappa-B ligand (RANKL) inhibitor, complement 5a inhibitor, bone morphogenetic protein family member (BMPs), transforming growth factor-beta (TGF-β), growth differentiation factor family member (GDFs), interleukin-18 inhibitor, IL-2 inhibitor, soluble TNFα (sTNFα) receptor p55, sTNFα receptor p75, sTNFα receptors fused with an IgG, inhibitors of TNFα receptor p55, inhibitors of sTNFα receptor p75, dominant negative IκB-kinase (dn-IKK-β), interleukin-4 (IL-4), interleukin-10 (IL-10), interleukin-13 (IL-13), IL-33 inhibitor, CCL17-inhibitor, interferon beta (IFN-β), tissue inhibitor of MMP family member (TIMPs), plasminogen-activator inhibitor (PAIs), serine protease inhibitor (serpins), signaling molecules/transcription factors, extracellular matrix components, vasoactive intestinal peptide (VIP), Cluster of Differentiation 39 (CD39), Cluster of Differentiation 73 (CD73) and Superoxide dismutase (SOD).

In preferred embodiments, the gene product of interest is selected from the group consisting of tocilizumab, sarilumab, olokizumab, sirukumab, Siltuximab, Clazakizumab, anakinra, canakinumab, rilonacept, gevokizumab and lutikizumab, etanercept, infliximab, adalimumab, certilizumab pegol, golimumab, secukinumab, brodalumab, ixekizumab, ustekinumab, risankizumab, guselkumab, tildrakizumab, abatacept, rituximab, belimumab, ianalumab, tabalumab, AMG-714, Fezakunimab, lenzilumab, namilumab, rhFGF-18/sprifermin, denosumab, C5aR-151, Tadekinig alfa/IL-18 binding protein, basiliximab, daclizumab, F8IL10/Dekavil, SMAD, Sox9, IkB, collagen, cartilage oligomeric matrix protein (COMP), proteoglycans and elastin.

In preferred embodiments, the gene product of interest is etanercept. Preferably, etanercept is encoded by the sequence of SEQ ID NO: 28. The etanercept protein may comprise a signal peptide, e.g. the protein may have an amino acid sequence of SEQ ID NO: 29 and after the signal peptide is cleaved the protein may have an amino acid sequence of SEQ ID NO: 30.

In preferred embodiments, the gene product of interest is ANP32A.

In preferred embodiments, the gene product of interest is Nrf2.

In preferred embodiments, the gene product of interest is an IL-6 inhibitor.

In preferred embodiments, the gene product of interest is a soluble IL-6 receptor.

In preferred embodiments, the gene product of interest is an IL-6 receptor antagonist. Preferably the IL-6 receptor antagonist is at least one of tocilizumab and sarilumab.

In preferred embodiments, the gene product of interest is a humanised anti-IL-6 monoclonal antibody. Preferably, the humanised anti-IL-6 monoclonal antibody is at least one of olokizumab and sirukumab.

In preferred embodiments, the gene product of interest is a chimeric anti-IL-6 monoclonal antibody. Preferably, the chimeric anti-IL-6 monoclonal antibody is siltuximab.

In preferred embodiments, the gene product of interest is a humanized rabbit anti-IL-6 monoclonal antibody. Preferably, the humanized rabbit anti-IL-6 monoclonal antibody is clazakizumab.

In preferred embodiments, the gene product of interest is a interleukin1 (IL-1) inhibitor. Preferably the interleukin1 (IL-1) inhibitor is selected from the group consisting of anakinra, canakinumab, rilonacept, gevokizumab and lutikizumab. Preferably the IL-1 inhibitor is selected from the group consisting of i) an IL-1 receptor antagonist, preferably a human IL-1 receptor antagonist, preferably the human IL-1 receptor antagonist anakinra; ii) an anti-IL-1 monoclonal antibody, preferably a human anti-IL-1 monoclonal antibody, preferably the human IL-1 monoclonal antibody canakinumab or gevokizumab, iii) a human dimeric anti-IL-1 fusion protein, preferably the human dimeric anti-IL-1 fusion protein rilonacept; and iv) a human dual variable domain anti-IL-1 immunoglobulin, preferably the human dual variable domain anti-IL-1 immunoglobulin lutikizumab.

In preferred embodiments, the gene product of interest is a tumor necrosis factor alpha (TNFα) inhibitor. Preferably, the tumor necrosis factor alpha (TNFα) inhibitor is selected from the group consisting of etanercept, infliximab, adalimumab, certilizumab pegol and golimumab. Preferably, the TNFα inhibitor is etanercept. Preferably the gene product of interest is etanercept.

In preferred embodiments, the gene product of interest is an IL-1 receptor antagonist.

In preferred embodiments, the gene product of interest is a soluble IL-1 receptor.

In preferred embodiments, the gene product of interest is an IL-17 inhibitor. Preferably, the IL-17 inhibitor is selected from the group consisting of secukinumab, brodalumab and ixekizumab.

In preferred embodiments, the gene product of interest is an IL-12/IL-23 inhibitor. Preferably the IL-12/IL-23 inhibitor is selected from the group consisting of ustekinumab, risankizumab, guselkumab and tildrakizumab.

In preferred embodiments, the gene product of interest is a T-cell costimulation inhibitor. Preferably, the T-cell costimulation inhibitor is abatacept.

In preferred embodiments, the gene product of interest is a B cell depleting and inhibiting agent. Preferably the B cell depleting and inhibiting agent is selected from the group consisting of rituximab, belimumab, ianalumab and tabalumab.

In preferred embodiments, the gene product of interest is an IL-15 inhibitor. Preferably the IL-15 inhibitor is AMG-714.

In preferred embodiments, the gene product of interest is an IL-22 inhibitor. Preferably the IL-22 inhibitor is fezakunimab.

In preferred embodiments, the gene product of interest is an inhibitor of GM-CSF.

Preferably the inhibitor of GM-CSF is at least one of lenzilumab and namilumab.

In preferred embodiments, the gene product of interest is an insulin-like growth factor (IGF-1).

In preferred embodiments, the gene product of interest is a fibroblast-growth factor (FGF). Preferably the fibroblast-growth factor (FGF) is rhFGF-18/sprifermin.

In preferred embodiments, the gene product of interest is a receptor activator of nuclear factor kappa-B ligand (RANKL) inhibitor. Preferably the RANKL inhibitor is denosumab.

In preferred embodiments, the gene product of interest is a complement 5a inhibitor. Preferably the complement 5a inhibitor is C5aR-151.

In preferred embodiments, the gene product of interest is a bone morphogenetic protein family member (BMPs).

In preferred embodiments, the gene product of interest is a transforming growth factor-beta (TGF-β).

In preferred embodiments, the gene product of interest is a growth differentiation factor family member (GDFs).

In preferred embodiments, the gene product of interest is an interleukin-18 inhibitor. Preferably the interleukin-18 inhibitor is Tadekinig alfa/IL-18 binding protein.

In preferred embodiments, the gene product of interest is an IL-2 inhibitor. Preferably the IL-2 inhibitor is at least one of basiliximab and daclizumab.

In preferred embodiments, the gene product of interest is a soluble TNFα (sTNFα) receptor p55.

In preferred embodiments, the gene product of interest is a sTNFα receptor p75.

In preferred embodiments, the gene product of interest is a sTNFα receptor fused with an IgG.

In preferred embodiments, the gene product of interest is an inhibitor of TNFα receptor p55.

In preferred embodiments, the gene product of interest is an inhibitor of sTNFα receptor p75.

In preferred embodiments, the gene product of interest is a dominant negative IκB-kinase (dn-IKK-β).

In preferred embodiments, the gene product of interest is an interleukin-4 (IL-4).

In preferred embodiments, the gene product of interest is an interleukin-10 (IL-10). Preferably the IL-10 is F8IL10/Dekavil.

In preferred embodiments, the gene product of interest is an interleukin-13 (IL-13).

In preferred embodiments, the gene product of interest is an IL-33 inhibitor.

In preferred embodiments, the gene product of interest is a CCL17-inhibitor.

In preferred embodiments, the gene product of interest is an interferon beta (IFN-β).

In preferred embodiments, the gene product of interest is a tissue inhibitor of MMP family member (TIMPs).

In preferred embodiments, the gene product of interest is a plasminogen-activator inhibitor (PAIs).

In preferred embodiments, the gene product of interest is a serine protease inhibitor (serpins).

In preferred embodiments, the gene product of interest is a signaling molecule/transcription factor. Preferably the signaling molecule/transcription factor is selected from the group consisting of SMAD, Sox9 and IkB.

In preferred embodiments, the gene product of interest is an extracellular matrix component. Preferably the extracellular matrix component is selected from the group consisting of collagen, cartilage oligomeric matrix protein (COMP), proteoglycans and elastin.

In preferred embodiments, the gene product of interest is a vasoactive intestinal peptide (VIP).

In preferred embodiments, the gene product of interest is a Cluster of Differentiation 39 (CD39).

In preferred embodiments, the gene product of interest is a Cluster of Differentiation 73 (CD73).

In preferred embodiments, the gene product of interest is a Superoxide dismutase (SOD).

In preferred embodiments, the gene product of interest is a sequence-specific nuclease (complex) for functional genome editing. Functional genome editing systems for use in all embodiments of the invention are known to the person skilled in the art and include: Transcription Activator-Like Effector Nucleases (TALENs, Gaj et al. (2013) Trends Biotechnol. 31 (7): 397-405), zinc-finger nucleases (ZFNs, Gaj et al. (2013) supra), meganucleases such as I-SceI (Arnould et al. (2007) J Mol Biol 371 (1): 49-65; Takeuchi et al. (2011) PNAS USA 108 (32): 13077-13082), RNA-guided endonuclease systems like CRISPR/Cas (Mali et al. (2013) Nat methods 10 (10): 957-963; Mali et al. (2013) Nat Biotechnol 31 (9): 833-838; Cong et al. (2013) Science 339 (6121): 819-823) and CRISPR/Cpf1 (Zetsche et al. (2015) Cell 163 (3): 759-771), triplex-forming molecules, synthetic polyamides and designer zinc-finger proteins (Uil et al. (2003) Nucleic Acids Res 31 (21): 6064-6078). Functional genome editing systems employ nucleases which create site-specific double-strand breaks at desired locations in the genome. The induced double-strand breaks are repaired through nonhomologous end-joining or homologous recombination. As a result, targeted mutations are obtained. It is advantageous to replace a defective gene (causing a disease or disorder) with a normal allele at its natural location by any of these methods, because it does not require that the full coding sequences and regulatory sequences are included in the rAAV virion when only a small portion of the gene needs to be altered. Expression of the partially replaced gene is also thought to be more consistent with normal cell biology than full genes that are carried by virions. The preferred gene editing system is CRISPR (comprising CRISPR/Cpf1 and CRISPR-Cas), because it is quicker and cheaper than other methods. A major advantage is also that CRISPR can be easily repurposed to target different DNA sequences using the CRISPR single guide RNAs. Thus, alternatively, or in combination with another embodiment, in a further preferred embodiment of the present invention, the rAAV genome comprises at least one of: (i) a polynucleotide comprising a sequence encoding at least one guide RNA (gRNA); wherein the guide RNA is substantially complementary—preferably complementary—to a target polynucleotide sequence(s) in a genome; and (ii) a polynucleotide comprising a sequence encoding a nuclease; wherein the nuclease forms a ribonuclease complex with the guide RNA, and wherein the ribonuclease complex makes site-specific double-stranded DNA breaks in the genome.

In preferred embodiments, the modified capsid protein is a modified capsid protein as defined herein. Preferably the rAAV virion comprising the modified capsid protein as defined herein further comprises a transgene encoding a gene product of interest. Preferably, the gene product of interest is a gene product of interest as defined herein above.

In preferred embodiments, the modified capsid protein comprises in the C-terminal part of the protein an amino acid sequence Z, residues of which are exposed on the surface of the capsid protein. Preferably amino acid sequence Z a. comprises or consists of a sequence of amino acid residues of the formula I:

$$y\text{-}G\text{-}Q\text{-}x\text{-}G\text{-}(x)_3\text{-}R\text{-}(x)_3\text{-}y\text{-}A\text{-}Q\text{-}A\text{-}A$$

wherein x represents a single amino acid residue and wherein y represents 0, 1 or 2 amino acid residues; and b. is present at a location corresponding to a position 100-200, preferably 120-180, more preferably 130-170, more preferably 140-160 amino acid residues from the C terminus of a wild-type AAV capsid protein. Preferably the rAAV virion comprising the modified capsid protein as defined herein further comprises a transgene encoding a gene product of interest. Preferably, the gene product of interest is a gene product of interest as defined herein above.

In preferred embodiments, the modified capsid protein comprises or consists of an amino acid sequence having SEQ ID NO: 1 (AAV1 P4). Preferably, the modified capsid protein has at least about 70%, 75%, 80%, 85%, 90%, 95%, 96%, 97%, 98%, 99% or 100% sequence identity with SEQ ID NO: 1. Preferably amino acids at positions 588-602 of SEQ ID NO: 1 have at least 80% sequence identity with SEQ ID NO: 11. Preferably the rAAV virion comprising an AAV1 P4 modified capsid protein further comprises a transgene encoding a gene product of interest. Preferably, the gene product of interest is a gene product of interest as defined herein above.

In preferred embodiments, the modified capsid protein comprises or consists of an amino acid sequence having SEQ ID NO: 2 (AAV2 P2). Preferably, the modified capsid protein has at least about 70%, 75%, 80%, 85%, 90%, 95%, 96%, 97%, 98%, 99% or 100% sequence identity with SEQ ID NO: 2. Preferably amino acids at positions 585-602 of SEQ ID NO: 2 have at least 80% sequence identity with SEQ ID NO: 10. Preferably the rAAV virion comprising an AAV2 P2 modified capsid protein further comprises a transgene encoding a gene product of interest. Preferably, the gene product of interest is a gene product of interest as defined herein above.

In preferred embodiments, the modified capsid protein comprises or consists of an amino acid sequence having SEQ ID NO: 3 (AAV7 A6). Preferably, the modified capsid protein has at least about 70%, 75%, 80%, 85%, 90%, 95%, 96%, 97%, 98%, 99% or 100% sequence identity with SEQ ID NO: 3. Preferably amino acids at positions 587-601 of SEQ ID NO: 3 have at least 80% sequence identity with SEQ ID NO: 9. Preferably the rAAV virion comprising an AAV7 A6 modified capsid protein further comprises a transgene encoding a gene product of interest. Preferably, the gene product of interest is a gene product of interest as defined herein above.

In preferred embodiments, the modified capsid protein comprises or consists of an amino acid sequence having SEQ ID NO: 4 (AAV9 A2). Preferably, the modified capsid protein has at least about 70%, 75%, 80%, 85%, 90%, 95%, 96%, 97%, 98%, 99% or 100% sequence identity with SEQ ID NO: 4. Preferably amino acids at positions 586-600 of SEQ ID NO: 4 have at least 80% sequence identity with SEQ ID NO: 8. Preferably the rAAV virion comprising an AAV9 A2 modified capsid protein further comprises a transgene encoding a gene product of interest. Preferably, the gene product of interest is a gene product of interest as defined herein above.

In preferred embodiments, the modified capsid protein comprises or consists of an amino acid sequence having SEQ ID NO: 5 (AAVrh10 A6). Preferably, the modified capsid protein has at least about 70%, 75%, 80%, 85%, 90%, 95%, 96%, 97%, 98%, 99% or 100% sequence identity with SEQ ID NO: 5. Preferably amino acids at positions 588-602 of SEQ ID NO: 5 have at least 80% sequence identity with SEQ ID NO: 9. Preferably the rAAV virion comprising an AAVrh10 A6 modified capsid protein further comprises a transgene encoding a gene product of interest. Preferably, the gene product of interest is a gene product of interest as defined herein above.

In preferred embodiments, the modified capsid protein comprises or consists of an amino acid sequence having SEQ ID NO: 6 (AAVrh10 A2). Preferably, the modified capsid protein has at least about 70%, 75%, 80%, 85%, 90%, 95%, 96%, 97%, 98%, 99% or 100% sequence identity with SEQ ID NO: 6. Preferably amino acids at positions 588-602 of SEQ ID NO: 6 have at least 80% sequence identity with SEQ ID NO: 8. Preferably the rAAV virion comprising an AAVrh10 A2 modified capsid protein further comprises a transgene encoding a gene product of interest. Preferably, the gene product of interest is a gene product of interest as defined herein above.

In preferred embodiments, the modified capsid protein comprises or consists of an amino acid sequence having SEQ ID NO: 7 (AAV-DJ-QR-P2). Preferably, the modified capsid protein has at least about 70%, 75%, 80%, 85%, 90%, 95%, 96%, 97%, 98%, 99% or 100% sequence identity with SEQ ID NO: 7. Preferably amino acids at positions 587-604 of SEQ ID NO: 7 have at least 80% sequence identity with SEQ ID NO: 12. Preferably the rAAV virion comprising an AAV-DJ-QR-P2 modified capsid protein further comprises a transgene encoding a gene product of interest. Preferably, the gene product of interest is a gene product of interest as defined herein above.

In preferred embodiments, the modified capsid protein comprises in the C-terminal part of the protein an amino acid sequence Z, residues of which are exposed on the surface of the capsid protein. Preferably amino acid sequence Z; a) comprises or consists of a sequence of amino acid residues of the formula I: y-G-Q-x-G-$(x)_3$-R-$(x)_3$-y-A-Q-A-A wherein x represents a single amino acid residue and wherein y represents 0, 1 or 2 amino acid residues; and b) is present at a location corresponding to a position 100-200, preferably 120-180, more preferably 130-170, more preferably 140-160 amino acid residues from the C terminus of a wild-type AAV capsid protein. Preferably the rAAV virion comprising a modified capsid protein as defined herein further comprises a constitutive promoter controlling the expression of a transgene, preferably a transgene as defined herein.

In preferred embodiments, the modified capsid protein comprises in the C-terminal part of the protein an amino acid sequence Z, residues of which are exposed on the surface of the capsid protein. Preferably amino acid sequence Z; a) comprises or consists of a sequence of amino acid residues of the formula I: y-G-Q-x-G-$(x)_3$-R-$(x)_3$-y-A-Q-A-A wherein x represents a single amino acid residue and wherein y represents 0, 1 or 2 amino acid residues; and b) is present at a location corresponding to a position 100-200, preferably 120-180, more preferably 130-170, more preferably 140-160 amino acid residues from the C terminus of a wild-type AAV capsid protein. Preferably the rAAV virion comprising a modified capsid protein as defined herein further comprises a tissue-specific promoter, which promoter controls the expression of a transgene, preferably a transgene as defined herein.

In preferred embodiments, the modified capsid protein comprises in the C-terminal part of the protein an amino acid sequence Z, residues of which are exposed on the surface of the capsid protein. Preferably amino acid sequence Z; a) comprises or consists of a sequence of amino acid residues of the formula I: y-G-Q-x-G-$(x)_3$-R-$(x)_3$-y-A-Q-A-A wherein x represents a single amino acid residue and wherein y represents 0, 1 or 2 amino acid residues; and b) is present at a location corresponding to a position 100-200, preferably 120-180, more preferably 130-170, more preferably 140-160 amino acid residues from the C terminus of a wild-type AAV capsid protein. Preferably the rAAV virion comprising a modified capsid protein as defined herein further comprises a CMV promoter controlling the expression of a transgene, preferably a transgene as defined herein.

In preferred embodiments, the modified capsid protein comprises in the C-terminal part of the protein an amino acid sequence Z, residues of which are exposed on the surface of the capsid protein. Preferably amino acid sequence Z; a) comprises or consists of a sequence of amino acid residues of the formula I: y-G-Q-x-G-$(x)_3$-R-$(x)_3$-y-A-Q-A-A wherein x represents a single amino acid residue and wherein y represents 0, 1 or 2 amino acid residues; and b) is present at a location corresponding to a position 100-200, preferably 120-180, more preferably 130-170, more preferably 140-160 amino acid residues from the C terminus of a wild-type AAV capsid protein. Preferably the rAAV virion comprising a modified capsid protein as defined herein further comprises a CBA (chicken beta-actin) promoter controlling the expression of a transgene, preferably a transgene as defined herein.

In preferred embodiments, the modified capsid protein comprises in the C-terminal part of the protein an amino acid sequence Z, residues of which are exposed on the surface of the capsid protein. Preferably amino acid sequence Z; a) comprises or consists of a sequence of amino acid residues of the formula I: y-G-Q-x-G-$(x)_3$-R-$(x)_3$-y-A-Q-A-A wherein x represents a single amino acid residue and wherein y represents 0, 1 or 2 amino acid residues; and b) is present at a location corresponding to a position 100-200, preferably 120-180, more preferably 130-170, more preferably 140-160 amino acid residues from the C terminus of a wild-type AAV capsid protein. Preferably the rAAV virion comprising a modified capsid protein as defined herein further comprises an EF1α promoter controlling the expression of a transgene, preferably a transgene as defined herein.

In preferred embodiments, the modified capsid protein comprises in the C-terminal part of the protein an amino acid sequence Z, residues of which are exposed on the surface of the capsid protein. Preferably amino acid sequence Z; a) comprises or consists of a sequence of amino acid residues of the formula I: y-G-Q-x-G-$(x)_3$-R-$(x)_3$-y-A-Q-A-A wherein x represents a single amino acid residue and wherein y represents 0, 1 or 2 amino acid residues; and b) is present at a location corresponding to a position 100-200, preferably 120-180, more preferably 130-170, more preferably 140-160 amino acid residues from the C terminus of a wild-type AAV capsid protein. Preferably the rAAV virion comprising a modified capsid protein as defined herein further comprises a TGF-β (TGB1) promoter controlling the expression of a transgene, preferably a transgene as defined herein.

In preferred embodiments, the modified capsid protein comprises in the C-terminal part of the protein an amino acid sequence Z, residues of which are exposed on the surface of the capsid protein. Preferably amino acid sequence Z; a) comprises or consists of a sequence of amino acid residues of the formula I: y-G-Q-x-G-$(x)_3$-R-$(x)_3$-y-A-Q-A-A wherein x represents a single amino acid residue and wherein y represents 0, 1 or 2 amino acid residues; and b) is present at a location corresponding to a position 100-200, preferably 120-180, more preferably 130-170, more preferably 140-160 amino acid residues from the C terminus of a wild-type AAV capsid protein. Preferably the rAAV virion comprising a modified capsid protein as defined herein further comprises an IL1β promoter controlling the expression of a transgene, preferably a transgene as defined herein.

In preferred embodiments, the modified capsid protein comprises in the C-terminal part of the protein an amino acid sequence Z, residues of which are exposed on the surface of the capsid protein. Preferably amino acid sequence Z; a) comprises or consists of a sequence of amino acid residues of the formula I: y-G-Q-x-G-$(x)_3$-R-$(x)_3$-y-A-Q-A-A wherein x represents a single amino acid residue and wherein y represents 0, 1 or 2 amino acid residues; and b) is present at a location corresponding to a position 100-200, preferably 120-180, more preferably 130-170, more preferably 140-160 amino acid residues from the C terminus of a wild-type AAV capsid protein. Preferably the rAAV virion comprising a modified capsid protein as defined herein further comprises an IL8 (CXCL8) promoter controlling the expression of a transgene, preferably a transgene as defined herein.

In preferred embodiments, the modified capsid protein comprises in the C-terminal part of the protein an amino acid sequence Z, residues of which are exposed on the surface of the capsid protein. Preferably amino acid sequence Z; a) comprises or consists of a sequence of amino acid residues of the formula I: y-G-Q-x-G-$(x)_3$-R-$(x)_3$-y-A-Q-A-A wherein x represents a single amino acid residue and wherein y represents 0, 1 or 2 amino acid residues; and b) is present at a location corresponding to a position 100-200, preferably 120-180, more preferably 130-170, more preferably 140-160 amino acid residues from the C terminus of a wild-type AAV capsid protein. Preferably the rAAV virion comprising a modified capsid protein as defined herein further comprises an MMP3 promoter controlling the expression of a transgene, preferably a transgene as defined herein.

In preferred embodiments, the modified capsid protein comprises in the C-terminal part of the protein an amino acid sequence Z, residues of which are exposed on the surface of the capsid protein. Preferably amino acid sequence Z; a) comprises or consists of a sequence of amino acid residues of the formula I: y-G-Q-x-G-$(x)_3$-R-$(x)_3$-y-A-Q-A-A wherein x represents a single amino acid residue and wherein y represents 0, 1 or 2 amino acid residues; and b) is present at a location corresponding to a position 100-200, preferably 120-180, more preferably 130-170, more preferably 140-160 amino acid residues from the C terminus of a wild-type AAV capsid protein. Preferably the rAAV virion comprising a modified capsid protein as defined herein further comprises an ICAM1 promoter promoter controlling the expression of a transgene, preferably a transgene as defined herein.

In preferred embodiments, the modified capsid protein comprises in the C-terminal part of the protein an amino acid sequence Z, residues of which are exposed on the surface of the capsid protein. Preferably amino acid sequence Z; a) comprises or consists of a sequence of amino acid residues of the formula I: y-G-Q-x-G-$(x)_3$-R-$(x)_3$-y-A-Q-A-A wherein x represents a single amino acid residue and wherein y represents 0, 1 or 2 amino acid residues; and b) is present at a location corresponding to a position 100-200, preferably 120-180, more preferably 130-170, more preferably 140-160 amino acid residues from the C terminus of a wild-type AAV capsid protein. Preferably the rAAV virion comprising a modified capsid protein as defined herein further comprises an ADAMTS4 promoter controlling the expression of a transgene, preferably a transgene as defined herein.

In preferred embodiments, the modified capsid protein comprises in the C-terminal part of the protein an amino acid sequence Z, residues of which are exposed on the surface of the capsid protein. Preferably amino acid sequence Z; a) comprises or consists of a sequence of amino acid residues of the formula I: y-G-Q-x-G-$(x)_3$-R-$(x)_3$-y-A-Q-A-A wherein x represents a single amino acid residue and wherein y represents 0, 1 or 2 amino acid residues; and b) is present at a location corresponding to a position 100-200, preferably 120-180, more preferably 130-170, more preferably 140-160 amino acid residues from the C terminus of a wild-type AAV capsid protein. Preferably the rAAV virion comprising a modified capsid protein as defined herein further comprises a COL1A1 promoter controlling the expression of a transgene, preferably a transgene as defined herein.

In preferred embodiments, the modified capsid protein comprises in the C-terminal part of the protein an amino acid sequence Z, residues of which are exposed on the surface of the capsid protein. Preferably amino acid sequence Z; a) comprises or consists of a sequence of amino acid residues of the formula I: y-G-Q-x-G-$(x)_3$-R-$(x)_3$-y-A-Q-A-A wherein x represents a single amino acid residue and wherein y represents 0, 1 or 2 amino acid residues; and b) is present at a location corresponding to a position 100-200, preferably 120-180, more preferably 130-170, more preferably 140-160 amino acid residues from the C terminus of a wild-type AAV capsid protein. Preferably the rAAV virion comprising a modified capsid protein as defined herein further comprises an RUNX2 promoter controlling the expression of a transgene, preferably a transgene as defined herein.

In preferred embodiments, the modified capsid protein comprises in the C-terminal part of the protein an amino acid sequence Z, residues of which are exposed on the surface of the capsid protein. Preferably amino acid sequence Z; a) comprises or consists of a sequence of amino acid residues of the formula I: y-G-Q-x-G-$(x)_3$-R-$(x)_3$-y-A-Q-A-A wherein x represents a single amino acid residue and wherein y represents 0, 1 or 2 amino acid residues; and b) is present at a location corresponding to a position 100-200, preferably 120-180, more preferably 130-170, more preferably 140-160 amino acid residues from the C terminus of a wild-type AAV capsid protein. Preferably the rAAV virion comprising a modified capsid protein as defined herein further comprises a COX2 (PTGS2) promoter controlling the expression of a transgene, preferably a transgene as defined herein.

In preferred embodiments, the modified capsid protein comprises in the C-terminal part of the protein an amino acid sequence Z, residues of which are exposed on the surface of the capsid protein. Preferably amino acid sequence Z; a) comprises or consists of a sequence of amino acid residues of the formula I: y-G-Q-x-G-$(x)_3$-R-$(x)_3$-y-A-Q-A-A wherein x represents a single amino acid residue and wherein y represents 0, 1 or 2 amino acid residues; and b) is present at a location corresponding to a position 100-200, preferably 120-180, more preferably 130-170, more preferably 140-160 amino acid residues from the C terminus of a wild-type AAV capsid protein. Preferably the rAAV virion comprising a modified capsid protein as defined herein further comprises a VEGF (VEGFA) promoter controlling the expression of a transgene, preferably a transgene as defined herein.

In preferred embodiments, the modified capsid protein comprises or consists of an amino acid sequence having SEQ ID NO: 1 (AAV1 P4). Preferably, the modified capsid protein has at least about 70%, 75%, 80%, 85%, 90%, 95%, 96%, 97%, 98%, 99% or 100% sequence identity with SEQ ID NO: 1. Preferably amino acids at positions 588-602 of SEQ ID NO: 1 have at least 80% sequence identity with SEQ ID NO: 11. Preferably the rAAV virion comprising a modified capsid protein as defined herein further comprises a constitutive promoter controlling the expression of a transgene, preferably a transgene as defined herein.

In preferred embodiments, the modified capsid protein comprises or consists of an amino acid sequence having SEQ ID NO: 1 (AAV1 P4). Preferably, the modified capsid protein has at least about 70%, 75%, 80%, 85%, 90%, 95%, 96%, 97%, 98%, 99% or 100% sequence identity with SEQ ID NO: 1. Preferably amino acids at positions 588-602 of SEQ ID NO: 1 have at least 80% sequence identity with SEQ ID NO: 11. Preferably the rAAV virion comprising a modified capsid protein as defined herein further comprises a tissue-specific promoter, which promoter controls the expression of a transgene, preferably a transgene as defined herein.

In preferred embodiments, the modified capsid protein comprises or consists of an amino acid sequence having SEQ ID NO: 1 (AAV1 P4). Preferably, the modified capsid protein has at least about 70%, 75%, 80%, 85%, 90%, 95%, 96%, 97%, 98%, 99% or 100% sequence identity with SEQ ID NO: 1. Preferably amino acids at positions 588-602 of SEQ ID NO: 1 have at least 80% sequence identity with SEQ ID NO: 11. Preferably the rAAV virion comprising a modified capsid protein as defined herein further comprises a CMV promoter controlling the expression of a transgene, preferably a transgene as defined herein.

In preferred embodiments, the modified capsid protein comprises or consists of an amino acid sequence having SEQ ID NO: 1 (AAV1 P4). Preferably, the modified capsid protein has at least about 70%, 75%, 80%, 85%, 90%, 95%, 96%, 97%, 98%, 99% or 100% sequence identity with SEQ ID NO: 1. Preferably amino acids at positions 588-602 of SEQ ID NO: 1 have at least 80% sequence identity with SEQ ID NO: 11. Preferably the rAAV virion comprising a modified capsid protein as defined herein further comprises a CBA (chicken beta-actin) promoter controlling the expression of a transgene, preferably a transgene as defined herein.

In preferred embodiments, the modified capsid protein comprises or consists of an amino acid sequence having SEQ ID NO: 1 (AAV1 P4). Preferably, the modified capsid protein has at least about 70%, 75%, 80%, 85%, 90%, 95%, 96%, 97%, 98%, 99% or 100% sequence identity with SEQ ID NO: 1. Preferably amino acids at positions 588-602 of SEQ ID NO: 1 have at least 80% sequence identity with SEQ ID NO: 11. Preferably the rAAV virion comprising a modified capsid protein as defined herein further comprises an EF1α promoter controlling the expression of a transgene, preferably a transgene as defined herein.

In preferred embodiments, the modified capsid protein comprises or consists of an amino acid sequence having SEQ ID NO: 1 (AAV1 P4). Preferably, the modified capsid protein has at least about 70%, 75%, 80%, 85%, 90%, 95%, 96%, 97%, 98%, 99% or 100% sequence identity with SEQ ID NO: 1. Preferably amino acids at positions 588-602 of SEQ ID NO: 1 have at least 80% sequence identity with SEQ ID NO: 11. Preferably the rAAV virion comprising a modified capsid protein as defined herein further comprises a TGF-β (TGB1) promoter controlling the expression of a transgene, preferably a transgene as defined herein.

In preferred embodiments, the modified capsid protein comprises or consists of an amino acid sequence having SEQ ID NO: 1 (AAV1 P4). Preferably, the modified capsid protein has at least about 70%, 75%, 80%, 85%, 90%, 95%, 96%, 97%, 98%, 99% or 100% sequence identity with SEQ ID NO: 1. Preferably amino acids at positions 588-602 of SEQ ID NO: 1 have at least 80% sequence identity with SEQ ID NO: 11. Preferably the rAAV virion comprising a modified capsid protein as defined herein further comprises an IL1β promoter controlling the expression of a transgene, preferably a transgene as defined herein.

In preferred embodiments, the modified capsid protein comprises or consists of an amino acid sequence having SEQ ID NO: 1 (AAV1 P4). Preferably, the modified capsid protein has at least about 70%, 75%, 80%, 85%, 90%, 95%, 96%, 97%, 98%, 99% or 100% sequence identity with SEQ ID NO: 1. Preferably amino acids at positions 588-602 of SEQ ID NO: 1 have at least 80% sequence identity with SEQ ID NO: 11. Preferably the rAAV virion comprising a modified capsid protein as defined herein further comprises an IL8 (CXCL8) promoter controlling the expression of a transgene, preferably a transgene as defined herein.

In preferred embodiments, the modified capsid protein comprises or consists of an amino acid sequence having SEQ ID NO: 1 (AAV1 P4). Preferably, the modified capsid protein has at least about 70%, 75%, 80%, 85%, 90%, 95%, 96%, 97%, 98%, 99% or 100% sequence identity with SEQ ID NO: 1. Preferably amino acids at positions 588-602 of SEQ ID NO: 1 have at least 80% sequence identity with SEQ ID NO: 11. Preferably the rAAV virion comprising a modified capsid protein as defined herein further comprises an MMP3 promoter controlling the expression of a transgene, preferably a transgene as defined herein.

In preferred embodiments, the modified capsid protein comprises or consists of an amino acid sequence having SEQ ID NO: 1 (AAV1 P4). Preferably, the modified capsid protein has at least about 70%, 75%, 80%, 85%, 90%, 95%, 96%, 97%, 98%, 99% or 100% sequence identity with SEQ ID NO: 1. Preferably amino acids at positions 588-602 of SEQ ID NO: 1 have at least 80% sequence identity with SEQ ID NO: 11. Preferably the rAAV virion comprising a modified capsid protein as defined herein further comprises an ICAM1 promoter controlling the expression of a transgene, preferably a transgene as defined herein.

In preferred embodiments, the modified capsid protein comprises or consists of an amino acid sequence having SEQ ID NO: 1 (AAV1 P4). Preferably, the modified capsid protein has at least about 70%, 75%, 80%, 85%, 90%, 95%, 96%, 97%, 98%, 99% or 100% sequence identity with SEQ ID NO: 1. Preferably amino acids at positions 588-602 of SEQ ID NO: 1 have at least 80% sequence identity with SEQ ID NO: 11. Preferably the rAAV virion comprising a modified capsid protein as defined herein further comprises an ADAMTS4 promoter controlling the expression of a transgene, preferably a transgene as defined herein.

In preferred embodiments, the modified capsid protein comprises or consists of an amino acid sequence having SEQ ID NO: 1 (AAV1 P4). Preferably, the modified capsid protein has at least about 70%, 75%, 80%, 85%, 90%, 95%, 96%, 97%, 98%, 99% or 100% sequence identity with SEQ ID NO: 1. Preferably amino acids at positions 588-602 of SEQ ID NO: 1 have at least 80% sequence identity with SEQ ID NO: 11. Preferably the rAAV virion comprising a modified capsid protein as defined herein further comprises an COL1A1 promoter controlling the expression of a transgene, preferably a transgene as defined herein.

In preferred embodiments, the modified capsid protein comprises in the C-terminal part of the protein. In preferred embodiments, the modified capsid protein comprises or consists of an amino acid sequence having SEQ ID NO: 1 (AAV1 P4). Preferably, the modified capsid protein has at least about 70%, 75%, 80%, 85%, 90%, 95%, 96%, 97%, 98%, 99% or 100% sequence identity with SEQ ID NO: 1. Preferably amino acids at positions 588-602 of SEQ ID NO: 1 have at least 80% sequence identity with SEQ ID NO: 11. Preferably the rAAV virion comprising a modified capsid protein as defined herein further comprises an RUNX2 promoter controlling the expression of a transgene, preferably a transgene as defined herein.

In preferred embodiments, the modified capsid protein comprises or consists of an amino acid sequence having SEQ ID NO: 1 (AAV1 P4). Preferably, the modified capsid protein has at least about 70%, 75%, 80%, 85%, 90%, 95%, 96%, 97%, 98%, 99% or 100% sequence identity with SEQ ID NO: 1. Preferably amino acids at positions 588-602 of SEQ ID NO: 1 have at least 80% sequence identity with SEQ ID NO: 11. Preferably the rAAV virion comprising a modified capsid protein as defined herein further comprises an COX2 (PTGS2) promoter controlling the expression of a transgene, preferably a transgene as defined herein.

In preferred embodiments, the modified capsid protein comprises or consists of an amino acid sequence having SEQ ID NO: 1 (AAV1 P4). Preferably, the modified capsid protein has at least about 70%, 75%, 80%, 85%, 90%, 95%, 96%, 97%, 98%, 99% or 100% sequence identity with SEQ ID NO: 1. Preferably amino acids at positions 588-602 of SEQ ID NO: 1 have at least 80% sequence identity with SEQ ID NO: 11. Preferably the rAAV virion comprising a modified capsid protein as defined herein further comprises a VEGF (VEGFA) promoter controlling the expression of a transgene, preferably a transgene as defined herein.

In preferred embodiments, the modified capsid protein comprises or consists of an amino acid sequence having SEQ ID NO: 2 (AAV2 P2). Preferably, the modified capsid protein has at least about 70%, 75%, 80%, 85%, 90%, 95%, 96%, 97%, 98%, 99% or 100% sequence identity with SEQ ID NO: 2. Preferably amino acids at positions 585-602 of SEQ ID NO: 2 have at least 80% sequence identity with SEQ ID NO: 10. Preferably the rAAV virion comprising a modified capsid protein as defined herein further comprises a constitutive promoter controlling the expression of a transgene, preferably a transgene as defined herein.

In preferred embodiments, the modified capsid protein comprises or consists of an amino acid sequence having SEQ ID NO: 2 (AAV2 P2). Preferably, the modified capsid protein has at least about 70%, 75%, 80%, 85%, 90%, 95%, 96%, 97%, 98%, 99% or 100% sequence identity with SEQ ID NO: 2. Preferably amino acids at positions 585-602 of SEQ ID NO: 2 have at least 80% sequence identity with SEQ ID NO: 10. Preferably the rAAV virion comprising a modified capsid protein as defined herein further comprises a tissue-specific promoter, which promoter controls the expression of a transgene, preferably a transgene as defined herein.

In preferred embodiments, the modified capsid protein comprises or consists of an amino acid sequence having SEQ ID NO: 2 (AAV2 P2). Preferably, the modified capsid protein has at least about 70%, 75%, 80%, 85%, 90%, 95%, 96%, 97%, 98%, 99% or 100% sequence identity with SEQ ID NO: 2. Preferably amino acids at positions 585-602 of SEQ ID NO: 2 have at least 80% sequence identity with SEQ ID NO: 10. Preferably the rAAV virion comprising a modified capsid protein as defined herein further comprises a CMV promoter controlling the expression of a transgene, preferably a transgene as defined herein.

In preferred embodiments, the modified capsid protein comprises or consists of an amino acid sequence having SEQ ID NO: 2 (AAV2 P2). Preferably, the modified capsid protein has at least about 70%, 75%, 80%, 85%, 90%, 95%, 96%, 97%, 98%, 99% or 100% sequence identity with SEQ ID NO: 2. Preferably amino acids at positions 585-602 of SEQ ID NO: 2 have at least 80% sequence identity with SEQ ID NO: 10. Preferably the rAAV virion comprising a modified capsid protein as defined herein further comprises a CBA (chicken beta-actin) promoter controlling the expression of a transgene, preferably a transgene as defined herein.

In preferred embodiments, the modified capsid protein comprises or consists of an amino acid sequence having SEQ ID NO: 2 (AAV2 P2). Preferably, the modified capsid protein has at least about 70%, 75%, 80%, 85%, 90%, 95%, 96%, 97%, 98%, 99% or 100% sequence identity with SEQ ID NO: 2. Preferably amino acids at positions 585-602 of SEQ ID NO: 2 have at least 80% sequence identity with SEQ ID NO: 10. Preferably the rAAV virion comprising a modified capsid protein as defined herein further comprises an EF1α promoter controlling the expression of a transgene, preferably a transgene as defined herein.

In preferred embodiments, the modified capsid protein comprises or consists of an amino acid sequence having SEQ ID NO: 2 (AAV2 P2). Preferably, the modified capsid protein has at least about 70%, 75%, 80%, 85%, 90%, 95%, 96%, 97%, 98%, 99% or 100% sequence identity with SEQ ID NO: 2. Preferably amino acids at positions 585-602 of SEQ ID NO: 2 have at least 80% sequence identity with SEQ ID NO: 10. Preferably the rAAV virion comprising a modified capsid protein as defined herein further comprises a TGF-β (TGB1) promoter controlling the expression of a transgene, preferably a transgene as defined herein.

In preferred embodiments, the modified capsid protein comprises or consists of an amino acid sequence having SEQ ID NO: 2 (AAV2 P2). Preferably, the modified capsid protein has at least about 70%, 75%, 80%, 85%, 90%, 95%, 96%, 97%, 98%, 99% or 100% sequence identity with SEQ ID NO: 2. Preferably amino acids at positions 585-602 of SEQ ID NO: 2 have at least 80% sequence identity with SEQ ID NO: 10. Preferably the rAAV virion comprising a modified capsid protein as defined herein further comprises an IL1β promoter controlling the expression of a transgene, preferably a transgene as defined herein.

In preferred embodiments, the modified capsid protein comprises or consists of an amino acid sequence having SEQ ID NO: 2 (AAV2 P2). Preferably, the modified capsid protein has at least about 70%, 75%, 80%, 85%, 90%, 95%, 96%, 97%, 98%, 99% or 100% sequence identity with SEQ ID NO: 2. Preferably amino acids at positions 585-602 of SEQ ID NO: 2 have at least 80% sequence identity with SEQ ID NO: 10. Preferably the rAAV virion comprising a modified capsid protein as defined herein further comprises an IL8 (CXCL8) promoter controlling the expression of a transgene, preferably a transgene as defined herein.

In preferred embodiments, the modified capsid protein comprises or consists of an amino acid sequence having SEQ ID NO: 2 (AAV2 P2). Preferably, the modified capsid protein has at least about 70%, 75%, 80%, 85%, 90%, 95%, 96%, 97%, 98%, 99% or 100% sequence identity with SEQ ID NO: 2. Preferably amino acids at positions 585-602 of SEQ ID NO: 2 have at least 80% sequence identity with SEQ ID NO: 10. Preferably the rAAV virion comprising a modified capsid protein as defined herein further comprises an MMP3 promoter controlling the expression of a transgene, preferably a transgene as defined herein.

In preferred embodiments, the modified capsid protein comprises or consists of an amino acid sequence having SEQ ID NO: 2 (AAV2 P2). Preferably, the modified capsid protein has at least about 70%, 75%, 80%, 85%, 90%, 95%, 96%, 97%, 98%, 99% or 100% sequence identity with SEQ ID NO: 2. Preferably amino acids at positions 585-602 of SEQ ID NO: 2 have at least 80% sequence identity with SEQ ID NO: 10. Preferably the rAAV virion comprising a modified capsid protein as defined herein further comprises an ICAM1 promoter controlling the expression of a transgene, preferably a transgene as defined herein.

In preferred embodiments, the modified capsid protein comprises or consists of an amino acid sequence having SEQ ID NO: 2 (AAV2 P2). Preferably, the modified capsid protein has at least about 70%, 75%, 80%, 85%, 90%, 95%, 96%, 97%, 98%, 99% or 100% sequence identity with SEQ ID NO: 2. Preferably amino acids at positions 585-602 of SEQ ID NO: 2 have at least 80% sequence identity with SEQ ID NO: 10. Preferably the rAAV virion comprising a modified capsid protein as defined herein further comprises an ADAMTS4 promoter controlling the expression of a transgene, preferably a transgene as defined herein.

In preferred embodiments, the modified capsid protein comprises or consists of an amino acid sequence having SEQ ID NO: 2 (AAV2 P2). Preferably, the modified capsid protein has at least about 70%, 75%, 80%, 85%, 90%, 95%, 96%, 97%, 98%, 99% or 100% sequence identity with SEQ ID NO: 2. Preferably amino acids at positions 585-602 of SEQ ID NO: 2 have at least 80% sequence identity with SEQ ID NO: 10. Preferably the rAAV virion comprising a modified capsid protein as defined herein further comprises a COL1A1 promoter controlling the expression of a transgene, preferably a transgene as defined herein.

In preferred embodiments, the modified capsid protein comprises or consists of an amino acid sequence having SEQ ID NO: 2 (AAV2 P2). Preferably, the modified capsid protein has at least about 70%, 75%, 80%, 85%, 90%, 95%, 96%, 97%, 98%, 99% or 100% sequence identity with SEQ ID NO: 2. Preferably amino acids at positions 585-602 of SEQ ID NO: 2 have at least 80% sequence identity with SEQ ID NO: 10. Preferably the rAAV virion comprising a modified capsid protein as defined herein further comprises an RUNX2 promoter controlling the expression of a transgene, preferably a transgene as defined herein.

In preferred embodiments, the modified capsid protein comprises or consists of an amino acid sequence having SEQ ID NO: 2 (AAV2 P2). Preferably, the modified capsid protein has at least about 70%, 75%, 80%, 85%, 90%, 95%, 96%, 97%, 98%, 99% or 100% sequence identity with SEQ ID NO: 2. Preferably amino acids at positions 585-602 of SEQ ID NO: 2 have at least 80% sequence identity with SEQ ID NO: 10. Preferably the rAAV virion comprising a modified capsid protein as defined herein further comprises at an COX2 (PTGS2) promoter controlling the in preferred embodiments, the modified capsid protein comprises or consists of an amino acid sequence having SEQ ID NO: 2 (AAV2 P2). Preferably, the modified capsid protein has at least about 70%, 75%, 80%, 85%, 90%, 95%, 96%, 97%, 98%, 99% or 100% sequence identity with SEQ ID NO: 2. Preferably amino acids at positions 585-602 of SEQ ID NO: 2 have at least 80% sequence identity with SEQ ID NO: 10. Preferably the rAAV virion comprising a modified capsid protein as defined herein further comprises a VEGF (VEGFA) promoter controlling the expression of a transgene, preferably a transgene as defined herein.

In preferred embodiments, the modified capsid protein comprises or consists of an amino acid sequence having SEQ ID NO: 3 (AAV7 A6). Preferably, the modified capsid protein has at least about 70%, 75%, 80%, 85%, 90%, 95%, 96%, 97%, 98%, 99% or 100% sequence identity with SEQ ID NO: 3. Preferably amino acids at positions 587-601 of SEQ ID NO: 3 have at least 80% sequence identity with SEQ ID NO: 9. Preferably the rAAV virion comprising a modified capsid protein as defined herein further comprises a constitutive promoter controlling the expression of a transgene, preferably a transgene as defined herein.

In preferred embodiments, the modified capsid protein comprises or consists of an amino acid sequence having SEQ ID NO: 3 (AAV7 A6). Preferably, the modified capsid protein has at least about 70%, 75%, 80%, 85%, 90%, 95%, 96%, 97%, 98%, 99% or 100% sequence identity with SEQ ID NO: 3. Preferably amino acids at positions 587-601 of SEQ ID NO: 3 have at least 80% sequence identity with SEQ ID NO: 9. Preferably the rAAV virion comprising a modified capsid protein as defined herein further comprises a tissue-specific promoter, which promoter controls the expression of a transgene, preferably a transgene as defined herein.

In preferred embodiments, the modified capsid protein comprises or consists of an amino acid sequence having SEQ ID NO: 3 (AAV7 A6). Preferably, the modified capsid protein has at least about 70%, 75%, 80%, 85%, 90%, 95%, 96%, 97%, 98%, 99% or 100% sequence identity with SEQ ID NO: 3. Preferably amino acids at positions 587-601 of SEQ ID NO: 3 have at least 80% sequence identity with SEQ ID NO: 9. Preferably the rAAV virion comprising a modified capsid protein as defined herein further comprises at a CMV promoter controlling the expression of a transgene, preferably a transgene as defined herein.

In preferred embodiments, the modified capsid protein comprises or consists of an amino acid sequence having SEQ ID NO: 3 (AAV7 A6). Preferably, the modified capsid protein has at least about 70%, 75%, 80%, 85%, 90%, 95%, 96%, 97%, 98%, 99% or 100% sequence identity with SEQ ID NO: 3. Preferably amino acids at positions 587-601 of SEQ ID NO: 3 have at least 80% sequence identity with SEQ ID NO: 9. Preferably the rAAV virion comprising a modified capsid protein as defined herein further comprises a CBA (chicken beta-actin) promoter controlling the expression of a transgene, preferably a transgene as defined herein.

In preferred embodiments, the modified capsid protein comprises or consists of an amino acid sequence having SEQ ID NO: 3 (AAV7 A6). Preferably, the modified capsid protein has at least about 70%, 75%, 80%, 85%, 90%, 95%, 96%, 97%, 98%, 99% or 100% sequence identity with SEQ ID NO: 3. Preferably amino acids at positions 587-601 of SEQ ID NO: 3 have at least 80% sequence identity with SEQ ID NO: 9. Preferably the rAAV virion comprising a modified capsid protein as defined herein further comprises an EF1α promoter controlling the expression of a transgene, preferably a transgene as defined herein.

In preferred embodiments, the modified capsid protein comprises or consists of an amino acid sequence having SEQ ID NO: 3 (AAV7 A6). Preferably, the modified capsid protein has at least about 70%, 75%, 80%, 85%, 90%, 95%, 96%, 97%, 98%, 99% or 100% sequence identity with SEQ ID NO: 3. Preferably amino acids at positions 587-601 of SEQ ID NO: 3 have at least 80% sequence identity with SEQ ID NO: 9. Preferably the rAAV virion comprising a modified capsid protein as defined herein further comprises a TGF-β (TGB1) promoter controlling the expression of a transgene, preferably a transgene as defined herein.

In preferred embodiments, the modified capsid protein comprises or consists of an amino acid sequence having SEQ ID NO: 3 (AAV7 A6). Preferably, the modified capsid protein has at least about 70%, 75%, 80%, 85%, 90%, 95%, 96%, 97%, 98%, 99% or 100% sequence identity with SEQ ID NO: 3. Preferably amino acids at positions 587-601 of SEQ ID NO: 3 have at least 80% sequence identity with SEQ ID NO: 9. Preferably the rAAV virion comprising a modified capsid protein as defined herein further comprises an IL1β promoter controlling the expression of a transgene, preferably a transgene as defined herein.

In preferred embodiments, the modified capsid protein comprises or consists of an amino acid sequence having SEQ ID NO: 3 (AAV7 A6). Preferably, the modified capsid protein has at least about 70%, 75%, 80%, 85%, 90%, 95%, 96%, 97%, 98%, 99% or 100% sequence identity with SEQ ID NO: 3. Preferably amino acids at positions 587-601 of SEQ ID NO: 3 have at least 80% sequence identity with SEQ ID NO: 9. Preferably the rAAV virion comprising a modified capsid protein as defined herein further comprises an IL8 (CXCL8) promoter controlling the expression of a transgene, preferably a transgene as defined herein.

In preferred embodiments, the modified capsid protein comprises or consists of an amino acid sequence having SEQ ID NO: 3 (AAV7 A6). Preferably, the modified capsid protein has at least about 70%, 75%, 80%, 85%, 90%, 95%, 96%, 97%, 98%, 99% or 100% sequence identity with SEQ ID NO: 3. Preferably amino acids at positions 587-601 of SEQ ID NO: 3 have at least 80% sequence identity with SEQ ID NO: 9. Preferably the rAAV virion comprising a modified capsid protein as defined herein further comprises an MMP3 promoter controlling the expression of a transgene, preferably a transgene as defined herein.

In preferred embodiments, the modified capsid protein comprises or consists of an amino acid sequence having SEQ ID NO: 3 (AAV7 A6). Preferably, the modified capsid protein has at least about 70%, 75%, 80%, 85%, 90%, 95%, 96%, 97%, 98%, 99% or 100% sequence identity with SEQ ID NO: 3. Preferably amino acids at positions 587-601 of SEQ ID NO: 3 have at least 80% sequence identity with SEQ ID NO: 9. Preferably the rAAV virion comprising a modified capsid protein as defined herein further comprises an ICAM1 promoter controlling the expression of a transgene, preferably a transgene as defined herein.

In preferred embodiments, the modified capsid protein comprises or consists of an amino acid sequence having SEQ ID NO: 3 (AAV7 A6). Preferably, the modified capsid protein has at least about 70%, 75%, 80%, 85%, 90%, 95%, 96%, 97%, 98%, 99% or 100% sequence identity with SEQ ID NO: 3. Preferably amino acids at positions 587-601 of SEQ ID NO: 3 have at least 80% sequence identity with SEQ ID NO: 9. Preferably the rAAV virion comprising a modified capsid protein as defined herein further comprises an ADAMTS4 promoter controlling the expression of a transgene, preferably a transgene as defined herein.

In preferred embodiments, the modified capsid protein comprises or consists of an amino acid sequence having SEQ ID NO: 3 (AAV7 A6). Preferably, the modified capsid protein has at least about 70%, 75%, 80%, 85%, 90%, 95%, 96%, 97%, 98%, 99% or 100% sequence identity with SEQ ID NO: 3. Preferably amino acids at positions 587-601 of SEQ ID NO: 3 have at least 80% sequence identity with SEQ ID NO: 9. Preferably the rAAV virion comprising a modified capsid protein as defined herein further comprises at a COL1A1 promoter controlling the expression of a transgene, preferably a transgene as defined herein.

In preferred embodiments, the modified capsid protein comprises or consists of an amino acid sequence having SEQ ID NO: 3 (AAV7 A6). Preferably, the modified capsid protein has at least about 70%, 75%, 80%, 85%, 90%, 95%, 96%, 97%, 98%, 99% or 100% sequence identity with SEQ ID NO: 3. Preferably amino acids at positions 587-601 of SEQ ID NO: 3 have at least 80% sequence identity with SEQ ID NO: 9. Preferably the rAAV virion comprising a modified capsid protein as defined herein further comprises an RUNX2 promoter controlling the expression of a transgene, preferably a transgene as defined herein.

In preferred embodiments, the modified capsid protein comprises or consists of an amino acid sequence having SEQ ID NO: 3 (AAV7 A6). Preferably, the modified capsid protein has at least about 70%, 75%, 80%, 85%, 90%, 95%, 96%, 97%, 98%, 99% or 100% sequence identity with SEQ ID NO: 3. Preferably amino acids at positions 587-601 of SEQ ID NO: 3 have at least 80% sequence identity with SEQ ID NO: 9. Preferably the rAAV virion comprising a modified capsid protein as defined herein further comprises an COX2 (PTGS2) promoter controlling the expression of a transgene, preferably a transgene as defined herein.

In preferred embodiments, the modified capsid protein comprises or consists of an amino acid sequence having SEQ ID NO: 3 (AAV7 A6). Preferably, the modified capsid protein has at least about 70%, 75%, 80%, 85%, 90%, 95%, 96%, 97%, 98%, 99% or 100% sequence identity with SEQ ID NO: 3. Preferably amino acids at positions 587-601 of SEQ ID NO: 3 have at least 80% sequence identity with SEQ ID NO: 9. Preferably the rAAV virion comprising a modified capsid protein as defined herein further comprises a VEGF (VEGFA) promoter controlling the expression of a transgene, preferably a transgene as defined herein.

In preferred embodiments, the modified capsid protein comprises or consists of an amino acid sequence having SEQ ID NO: 4 (AAV9 A2). Preferably, the modified capsid protein has at least about 70%, 75%, 80%, 85%, 90%, 95%, 96%, 97%, 98%, 99% or 100% sequence identity with SEQ ID NO: 4. Preferably amino acids at positions 586-600 of SEQ ID NO: 4 have at least 80% sequence identity with SEQ ID NO: 8. Preferably the rAAV virion comprising a modified capsid protein as defined herein further comprises constitutive promoter controlling the expression of a transgene, preferably a transgene as defined herein.

In preferred embodiments, the modified capsid protein comprises or consists of an amino acid sequence having SEQ ID NO: 4 (AAV9 A2). Preferably, the modified capsid protein has at least about 70%, 75%, 80%, 85%, 90%, 95%, 96%, 97%, 98%, 99% or 100% sequence identity with SEQ ID NO: 4. Preferably amino acids at positions 586-600 of SEQ ID NO: 4 have at least 80% sequence identity with SEQ ID NO: 8. Preferably the rAAV virion comprising a modified capsid protein as defined herein further comprises a tissue-specific promoter, which promoter controls the expression of a transgene, preferably a transgene as defined herein.

In preferred embodiments, the modified capsid protein comprises or consists of an amino acid sequence having SEQ ID NO: 4 (AAV9 A2). Preferably, the modified capsid protein has at least about 70%, 75%, 80%, 85%, 90%, 95%, 96%, 97%, 98%, 99% or 100% sequence identity with SEQ ID NO: 4. Preferably amino acids at positions 586-600 of SEQ ID NO: 4 have at least 80% sequence identity with SEQ ID NO: 8. Preferably the rAAV virion comprising a modified capsid protein as defined herein further comprises a CMV promoter controlling the expression of a transgene, preferably a transgene as defined herein.

In preferred embodiments, the modified capsid protein comprises or consists of an amino acid sequence having SEQ ID NO: 4 (AAV9 A2). Preferably, the modified capsid protein has at least about 70%, 75%, 80%, 85%, 90%, 95%, 96%, 97%, 98%, 99% or 100% sequence identity with SEQ ID NO: 4. Preferably amino acids at positions 586-600 of SEQ ID NO: 4 have at least 80% sequence identity with SEQ ID NO: 8. Preferably the rAAV virion comprising a modified capsid protein as defined herein further comprises a CBA (chicken beta-actin) promoter controlling the expression of a transgene, preferably a transgene as defined herein.

In preferred embodiments, the modified capsid protein comprises or consists of an amino acid sequence having SEQ ID NO: 4 (AAV9 A2). Preferably, the modified capsid protein has at least about 70%, 75%, 80%, 85%, 90%, 95%, 96%, 97%, 98%, 99% or 100% sequence identity with SEQ ID NO: 4. Preferably amino acids at positions 586-600 of SEQ ID NO: 4 have at least 80% sequence identity with SEQ ID NO: 8. Preferably the rAAV virion comprising a modified capsid protein as defined herein further comprises an EF1α promoter controlling the expression of a transgene, preferably a transgene as defined herein.

In preferred embodiments, the modified capsid protein comprises or consists of an amino acid sequence having SEQ ID NO: 4 (AAV9 A2). Preferably, the modified capsid protein has at least about 70%, 75%, 80%, 85%, 90%, 95%, 96%, 97%, 98%, 99% or 100% sequence identity with SEQ ID NO: 4. Preferably amino acids at positions 586-600 of SEQ ID NO: 4 have at least 80% sequence identity with SEQ ID NO: 8. Preferably the rAAV virion comprising a modified capsid protein as defined herein further comprises a TGF-β (TGB1) promoter controlling the expression of a transgene, preferably a transgene as defined herein.

In preferred embodiments, the modified capsid protein comprises or consists of an amino acid sequence having SEQ ID NO: 4 (AAV9 A2). Preferably, the modified capsid protein has at least about 70%, 75%, 80%, 85%, 90%, 95%, 96%, 97%, 98%, 99% or 100% sequence identity with SEQ ID NO: 4. Preferably amino acids at positions 586-600 of SEQ ID NO: 4 have at least 80% sequence identity with SEQ ID NO: 8. Preferably the rAAV virion comprising a modified capsid protein as defined herein further comprises an IL1β promoter controlling the expression of a transgene, preferably a transgene as defined herein.

In preferred embodiments, the modified capsid protein comprises or consists of an amino acid sequence having SEQ ID NO: 4 (AAV9 A2). Preferably, the modified capsid protein has at least about 70%, 75%, 80%, 85%, 90%, 95%, 96%, 97%, 98%, 99% or 100% sequence identity with SEQ ID NO: 4. Preferably amino acids at positions 586-600 of SEQ ID NO: 4 have at least 80% sequence identity with SEQ ID NO: 8. Preferably the rAAV virion comprising a modified capsid protein as defined herein further comprises an IL8 (CXCL8) promoter controlling the expression of a transgene, preferably a transgene as defined herein.

In preferred embodiments, the modified capsid protein comprises or consists of an amino acid sequence having SEQ ID NO: 4 (AAV9 A2). Preferably, the modified capsid protein has at least about 70%, 75%, 80%, 85%, 90%, 95%, 96%, 97%, 98%, 99% or 100% sequence identity with SEQ ID NO: 4. Preferably amino acids at positions 586-600 of SEQ ID NO: 4 have at least 80% sequence identity with SEQ ID NO: 8. Preferably the rAAV virion comprising a modified capsid protein as defined herein further comprises an MMP3 promoter controlling the expression of a transgene, preferably a transgene as defined herein.

In preferred embodiments, the modified capsid protein comprises or consists of an amino acid sequence having SEQ ID NO: 4 (AAV9 A2). Preferably, the modified capsid protein has at least about 70%, 75%, 80%, 85%, 90%, 95%, 96%, 97%, 98%, 99% or 100% sequence identity with SEQ ID NO: 4. Preferably amino acids at positions 586-600 of SEQ ID NO: 4 have at least 80% sequence identity with SEQ ID NO: 8. Preferably the rAAV virion comprising a modified capsid protein as defined herein further comprises an ICAM1 promoter controlling the expression of a transgene, preferably a transgene as defined herein.

In preferred embodiments, the modified capsid protein comprises or consists of an amino acid sequence having SEQ ID NO: 4 (AAV9 A2). Preferably, the modified capsid protein has at least about 70%, 75%, 80%, 85%, 90%, 95%, 96%, 97%, 98%, 99% or 100% sequence identity with SEQ ID NO: 4. Preferably amino acids at positions 586-600 of SEQ ID NO: 4 have at least 80% sequence identity with SEQ ID NO: 8. Preferably the rAAV virion comprising a modified capsid protein as defined herein further comprises an ADAMTS4 promoter controlling the expression of a transgene, preferably a transgene as defined herein.

In preferred embodiments, the modified capsid protein comprises or consists of an amino acid sequence having SEQ ID NO: 4 (AAV9 A2). Preferably, the modified capsid protein has at least about 70%, 75%, 80%, 85%, 90%, 95%, 96%, 97%, 98%, 99% or 100% sequence identity with SEQ ID NO: 4. Preferably amino acids at positions 586-600 of SEQ ID NO: 4 have at least 80% sequence identity with SEQ ID NO: 8. Preferably the rAAV virion comprising a modified capsid protein as defined herein further comprises a COL1A1 promoter controlling the expression of a transgene, preferably a transgene as defined herein.

In preferred embodiments, the modified capsid protein comprises or consists of an amino acid sequence having SEQ ID NO: 4 (AAV9 A2). Preferably, the modified capsid protein has at least about 70%, 75%, 80%, 85%, 90%, 95%, 96%, 97%, 98%, 99% or 100% sequence identity with SEQ ID NO: 4. Preferably amino acids at positions 586-600 of SEQ ID NO: 4 have at least 80% sequence identity with SEQ ID NO: 8. Preferably the rAAV virion comprising a modified capsid protein as defined herein further comprises an RUNX2 promoter controlling the expression of a transgene, preferably a transgene as defined herein.

In preferred embodiments, the modified capsid protein comprises or consists of an amino acid sequence having SEQ ID NO: 4 (AAV9 A2). Preferably, the modified capsid protein has at least about 70%, 75%, 80%, 85%, 90%, 95%, 96%, 97%, 98%, 99% or 100% sequence identity with SEQ ID NO: 4. Preferably amino acids at positions 586-600 of SEQ ID NO: 4 have at least 80% sequence identity with SEQ ID NO: 8. Preferably the rAAV virion comprising a modified capsid protein as defined herein further comprises an COX2 (PTGS2) promoter controlling the expression of a transgene, preferably a transgene as defined herein.

In preferred embodiments, the modified capsid protein comprises or consists of an amino acid sequence having SEQ ID NO: 4 (AAV9 A2). Preferably, the modified capsid protein has at least about 70%, 75%, 80%, 85%, 90%, 95%, 96%, 97%, 98%, 99% or 100% sequence identity with SEQ ID NO: 4. Preferably amino acids at positions 586-600 of SEQ ID NO: 4 have at least 80% sequence identity with SEQ ID NO: 8. Preferably the rAAV virion comprising a modified capsid protein as defined herein further comprises a VEGF (VEGFA) promoter controlling the expression of a transgene, preferably a transgene as defined herein.

In preferred embodiments, the modified capsid protein comprises or consists of an amino acid sequence having SEQ ID NO: 5 (AAVrh10 A6). Preferably, the modified capsid protein has at least about 70%, 75%, 80%, 85%, 90%, 95%, 96%, 97%, 98%, 99% or 100% sequence identity with SEQ ID NO: 5. Preferably amino acids at positions 588-602 of SEQ ID NO: 5 have at least 80% sequence identity with SEQ ID NO: 9. Preferably the rAAV virion comprising a modified capsid protein as defined herein further comprises a constitutive promoter controlling the expression of a transgene, preferably a transgene as defined herein.

In preferred embodiments, the modified capsid protein comprises or consists of an amino acid sequence having SEQ ID NO: 5 (AAVrh10 A6). Preferably, the modified capsid protein has at least about 70%, 75%, 80%, 85%, 90%, 95%, 96%, 97%, 98%, 99% or 100% sequence identity with SEQ ID NO: 5. Preferably amino acids at positions 588-602 of SEQ ID NO: 5 have at least 80% sequence identity with SEQ ID NO: 9. Preferably the rAAV virion comprising a modified capsid protein as defined herein further comprises a tissue-specific promoter, which promoter controls the expression of a transgene, preferably a transgene as defined herein.

In preferred embodiments, the modified capsid protein comprises or consists of an amino acid sequence having SEQ ID NO: 5 (AAVrh10 A6). Preferably, the modified capsid protein has at least about 70%, 75%, 80%, 85%, 90%, 95%, 96%, 97%, 98%, 99% or 100% sequence identity with SEQ ID NO: 5. Preferably amino acids at positions 588-602 of SEQ ID NO: 5 have at least 80% sequence identity with SEQ ID NO: 9. Preferably the rAAV virion comprising a modified capsid protein as defined herein further comprises a CMV promoter controlling the expression of a transgene, preferably a transgene as defined herein.

In preferred embodiments, the modified capsid protein comprises or consists of an amino acid sequence having SEQ ID NO: 5 (AAVrh10 A6). Preferably, the modified capsid protein has at least about 70%, 75%, 80%, 85%, 90%, 95%, 96%, 97%, 98%, 99% or 100% sequence identity with SEQ ID NO: 5. Preferably amino acids at positions 588-602 of SEQ ID NO: 5 have at least 80% sequence identity with SEQ ID NO: 9. Preferably the rAAV virion comprising a modified capsid protein as defined herein further comprises a CBA (chicken beta-actin) promoter controlling the expression of a transgene, preferably a transgene as defined herein.

In preferred embodiments, the modified capsid protein comprises or consists of an amino acid sequence having SEQ ID NO: 5 (AAVrh10 A6). Preferably, the modified capsid protein has at least about 70%, 75%, 80%, 85%, 90%, 95%, 96%, 97%, 98%, 99% or 100% sequence identity with SEQ ID NO: 5. Preferably amino acids at positions 588-602 of SEQ ID NO: 5 have at least 80% sequence identity with SEQ ID NO: 9. Preferably the rAAV virion comprising a modified capsid protein as defined herein further comprises an EF1α promoter controlling the expression of a transgene, preferably a transgene as defined herein.

In preferred embodiments, the modified capsid protein comprises or consists of an amino acid sequence having SEQ ID NO: 5 (AAVrh10 A6). Preferably, the modified capsid protein has at least about 70%, 75%, 80%, 85%, 90%, 95%, 96%, 97%, 98%, 99% or 100% sequence identity with SEQ ID NO: 5. Preferably amino acids at positions 588-602 of SEQ ID NO: 5 have at least 80% sequence identity with SEQ ID NO: 9. Preferably the rAAV virion comprising a modified capsid protein as defined herein further comprises a TGF-β (TGB1) promoter controlling the expression of a transgene, preferably a transgene as defined herein.

In preferred embodiments, the modified capsid protein comprises or consists of an amino acid sequence having SEQ ID NO: 5 (AAVrh10 A6). Preferably, the modified capsid protein has at least about 70%, 75%, 80%, 85%, 90%, 95%, 96%, 97%, 98%, 99% or 100% sequence identity with SEQ ID NO: 5. Preferably amino acids at positions 588-602 of SEQ ID NO: 5 have at least 80% sequence identity with SEQ ID NO: 9. Preferably the rAAV virion comprising a modified capsid protein as defined herein further comprises an IL1β promoter controlling the expression of a transgene, preferably a transgene as defined herein.

In preferred embodiments, the modified capsid protein comprises or consists of an amino acid sequence having SEQ ID NO: 5 (AAVrh10 A6). Preferably, the modified capsid protein has at least about 70%, 75%, 80%, 85%, 90%, 95%, 96%, 97%, 98%, 99% or 100% sequence identity with SEQ ID NO: 5. Preferably amino acids at positions 588-602 of SEQ ID NO: 5 have at least 80% sequence identity with SEQ ID NO: 9. Preferably the rAAV virion comprising a modified capsid protein as defined herein further comprises an IL8 (CXCL8) promoter controlling the expression of a transgene, preferably a transgene as defined herein.

In preferred embodiments, the modified capsid protein comprises or consists of an amino acid sequence having SEQ ID NO: 5 (AAVrh10 A6). Preferably, the modified capsid protein has at least about 70%, 75%, 80%, 85%, 90%, 95%, 96%, 97%, 98%, 99% or 100% sequence identity with SEQ ID NO: 5. Preferably amino acids at positions 588-602 of SEQ ID NO: 5 have at least 80% sequence identity with SEQ ID NO: 9. Preferably the rAAV virion comprising a modified capsid protein as defined herein further comprises an MMP3 promoter controlling the expression of a transgene, preferably a transgene as defined herein.

In preferred embodiments, the modified capsid protein comprises or consists of an amino acid sequence having SEQ ID NO: 5 (AAVrh10 A6). Preferably, the modified capsid protein has at least about 70%, 75%, 80%, 85%, 90%, 95%, 96%, 97%, 98%, 99% or 100% sequence identity with SEQ ID NO: 5. Preferably amino acids at positions 588-602 of SEQ ID NO: 5 have at least 80% sequence identity with SEQ ID NO: 9. Preferably the rAAV virion comprising a modified capsid protein as defined herein further comprises an ICAM1 promoter controlling the expression of a transgene, preferably a transgene as defined herein.

In preferred embodiments, the modified capsid protein comprises or consists of an amino acid sequence having SEQ ID NO: 5 (AAVrh10 A6). Preferably, the modified capsid protein has at least about 70%, 75%, 80%, 85%, 90%, 95%, 96%, 97%, 98%, 99% or 100% sequence identity with SEQ ID NO: 5. Preferably amino acids at positions 588-602 of SEQ ID NO: 5 have at least 80% sequence identity with SEQ ID NO: 9. Preferably the rAAV virion comprising a modified capsid protein as defined herein further comprises an ADAMTS4 promoter controlling the expression of a transgene, preferably a transgene as defined herein.

In preferred embodiments, the modified capsid protein comprises or consists of an amino acid sequence having SEQ ID NO: 5 (AAVrh10 A6). Preferably, the modified capsid protein has at least about 70%, 75%, 80%, 85%, 90%, 95%, 96%, 97%, 98%, 99% or 100% sequence identity with SEQ ID NO: 5. Preferably amino acids at positions 588-602 of SEQ ID NO: 5 have at least 80% sequence identity with SEQ ID NO: 9. Preferably the rAAV virion comprising a modified capsid protein as defined herein further comprises a COL1A1 promoter controlling the expression of a transgene, preferably a transgene as defined herein.

In preferred embodiments, the modified capsid protein comprises or consists of an amino acid sequence having SEQ ID NO: 5 (AAVrh10 A6). Preferably, the modified capsid protein has at least about 70%, 75%, 80%, 85%, 90%, 95%, 96%, 97%, 98%, 99% or 100% sequence identity with SEQ ID NO: 5. Preferably amino acids at positions 588-602 of SEQ ID NO: 5 have at least 80% sequence identity with SEQ ID NO: 9. Preferably the rAAV virion comprising a modified capsid protein as defined herein further comprises an RUNX2 promoter controlling the expression of a transgene, preferably a transgene as defined herein.

In preferred embodiments, the modified capsid protein comprises or consists of an amino acid sequence having SEQ ID NO: 5 (AAVrh10 A6). Preferably, the modified capsid protein has at least about 70%, 75%, 80%, 85%, 90%, 95%, 96%, 97%, 98%, 99% or 100% sequence identity with SEQ ID NO: 5. Preferably amino acids at positions 588-602 of SEQ ID NO: 5 have at least 80% sequence identity with SEQ ID NO: 9. Preferably the rAAV virion comprising a modified capsid protein as defined herein further comprises an COX2 (PTGS2) promoter controlling the expression of a transgene, preferably a transgene as defined herein.

In preferred embodiments, the modified capsid protein comprises or consists of an amino acid sequence having SEQ ID NO: 5 (AAVrh10 A6). Preferably, the modified capsid protein has at least about 70%, 75%, 80%, 85%, 90%, 95%, 96%, 97%, 98%, 99% or 100% sequence identity with SEQ ID NO: 5. Preferably amino acids at positions 588-602 of SEQ ID NO: 5 have at least 80% sequence identity with SEQ ID NO: 9. Preferably the rAAV virion comprising a modified capsid protein as defined herein further comprises a VEGF (VEGFA) promoter controlling the expression of a transgene, preferably a transgene as defined herein.

In preferred embodiments, the modified capsid protein comprises or consists of an amino acid sequence having SEQ ID NO: 6 (AAVrh10 A2). Preferably, the modified capsid protein has at least about 70%, 75%, 80%, 85%, 90%, 95%, 96%, 97%, 98%, 99% or 100% sequence identity with SEQ ID NO: 6. Preferably amino acids at positions 588-602 of SEQ ID NO: 6 have at least 80% sequence identity with SEQ ID NO: 8. Preferably the rAAV virion comprising a modified capsid protein as defined herein further comprises constitutive promoter controlling the expression of a transgene, preferably a transgene as defined herein.

In preferred embodiments, the modified capsid protein comprises or consists of an amino acid sequence having SEQ ID NO: 6 (AAVrh10 A2). Preferably, the modified capsid protein has at least about 70%, 75%, 80%, 85%, 90%, 95%, 96%, 97%, 98%, 99% or 100% sequence identity with SEQ ID NO: 6. Preferably amino acids at positions 588-602 of SEQ ID NO: 6 have at least 80% sequence identity with SEQ ID NO: 8. Preferably the rAAV virion comprising a modified capsid protein as defined herein further comprises a tissue-specific promoter, which promoter controls the expression of a transgene, preferably a transgene as defined herein.

In preferred embodiments, the modified capsid protein comprises or consists of an amino acid sequence having SEQ ID NO: 6 (AAVrh10 A2). Preferably, the modified capsid protein has at least about 70%, 75%, 80%, 85%, 90%, 95%, 96%, 97%, 98%, 99% or 100% sequence identity with SEQ ID NO: 6. Preferably amino acids at positions 588-602 of SEQ ID NO: 6 have at least 80% sequence identity with SEQ ID NO: 8. Preferably the rAAV virion comprising a modified capsid protein as defined herein further comprises a CMV promoter controlling the expression of a transgene, preferably a transgene as defined herein.

In preferred embodiments, the modified capsid protein comprises or consists of an amino acid sequence having SEQ ID NO: 6 (AAVrh10 A2). Preferably, the modified capsid protein has at least about 70%, 75%, 80%, 85%, 90%, 95%, 96%, 97%, 98%, 99% or 100% sequence identity with SEQ ID NO: 6. Preferably amino acids at positions 588-602 of SEQ ID NO: 6 have at least 80% sequence identity with SEQ ID NO: 8. Preferably the rAAV virion comprising a modified capsid protein as defined herein further comprises a CBA (chicken beta-actin) promoter controlling the expression of a transgene, preferably a transgene as defined herein.

In preferred embodiments, the modified capsid protein comprises or consists of an amino acid sequence having SEQ ID NO: 6 (AAVrh10 A2). Preferably, the modified capsid protein has at least about 70%, 75%, 80%, 85%, 90%, 95%, 96%, 97%, 98%, 99% or 100% sequence identity with SEQ ID NO: 6. Preferably amino acids at positions 588-602 of SEQ ID NO: 6 have at least 80% sequence identity with SEQ ID NO: 8. Preferably the rAAV virion comprising a modified capsid protein as defined herein further comprises an EF1α promoter controlling the expression of a transgene, preferably a transgene as defined herein.

In preferred embodiments, the modified capsid protein comprises or consists of an amino acid sequence having SEQ ID NO: 6 (AAVrh10 A2). Preferably, the modified capsid protein has at least about 70%, 75%, 80%, 85%, 90%, 95%, 96%, 97%, 98%, 99% or 100% sequence identity with SEQ ID NO: 6. Preferably amino acids at positions 588-602 of SEQ ID NO: 6 have at least 80% sequence identity with SEQ ID NO: 8. Preferably the rAAV virion comprising a modified capsid protein as defined herein further comprises a TGF-β (TGB1) promoter controlling the expression of a transgene, preferably a transgene as defined herein.

In preferred embodiments, the modified capsid protein comprises or consists of an amino acid sequence having SEQ ID NO: 6 (AAVrh10 A2). Preferably, the modified capsid protein has at least about 70%, 75%, 80%, 85%, 90%, 95%, 96%, 97%, 98%, 99% or 100% sequence identity with SEQ ID NO: 6. Preferably amino acids at positions 588-602 of SEQ ID NO: 6 have at least 80% sequence identity with SEQ ID NO: 8. Preferably the rAAV virion comprising a modified capsid protein as defined herein further comprises an IL1β promoter controlling the expression of a transgene, preferably a transgene as defined herein.

In preferred embodiments, the modified capsid protein comprises or consists of an amino acid sequence having SEQ ID NO: 6 (AAVrh10 A2). Preferably, the modified capsid protein has at least about 70%, 75%, 80%, 85%, 90%, 95%, 96%, 97%, 98%, 99% or 100% sequence identity with SEQ ID NO: 6. Preferably amino acids at positions 588-602 of SEQ ID NO: 6 have at least 80% sequence identity with SEQ ID NO: 8. Preferably the rAAV virion comprising a modified capsid protein as defined herein further comprises an IL8 (CXCL8) promoter controlling the expression of a transgene, preferably a transgene as defined herein.

In preferred embodiments, the modified capsid protein comprises or consists of an amino acid sequence having SEQ ID NO: 6 (AAVrh10 A2). Preferably, the modified capsid protein has at least about 70%, 75%, 80%, 85%, 90%, 95%, 96%, 97%, 98%, 99% or 100% sequence identity with SEQ ID NO: 6. Preferably amino acids at positions 588-602 of SEQ ID NO: 6 have at least 80% sequence identity with SEQ ID NO: 8. Preferably the rAAV virion comprising a modified capsid protein as defined herein further comprises an MMP3 promoter controlling the expression of a transgene, preferably a transgene as defined herein.

In preferred embodiments, the modified capsid protein comprises or consists of an amino acid sequence having SEQ ID NO: 6 (AAVrh10 A2). Preferably, the modified capsid protein has at least about 70%, 75%, 80%, 85%, 90%, 95%, 96%, 97%, 98%, 99% or 100% sequence identity with SEQ ID NO: 6. Preferably amino acids at positions 588-602 of SEQ ID NO: 6 have at least 80% sequence identity with SEQ ID NO: 8. Preferably the rAAV virion comprising a modified capsid protein as defined herein further comprises an ICAM1 promoter controlling the expression of a transgene, preferably a transgene as defined herein.

In preferred embodiments, the modified capsid protein comprises or consists of an amino acid sequence having SEQ ID NO: 6 (AAVrh10 A2). Preferably, the modified capsid protein has at least about 70%, 75%, 80%, 85%, 90%, 95%, 96%, 97%, 98%, 99% or 100% sequence identity with SEQ ID NO: 6. Preferably amino acids at positions 588-602 of SEQ ID NO: 6 have at least 80% sequence identity with SEQ ID NO: 8. Preferably the rAAV virion comprising a modified capsid protein as defined herein further comprises an ADAMTS4 promoter controlling the expression of a transgene, preferably a transgene as defined herein.

In preferred embodiments, the modified capsid protein comprises or consists of an amino acid sequence having SEQ ID NO: 6 (AAVrh10 A2). Preferably, the modified capsid protein has at least about 70%, 75%, 80%, 85%, 90%, 95%, 96%, 97%, 98%, 99% or 100% sequence identity with SEQ ID NO: 6. Preferably amino acids at positions 588-602 of SEQ ID NO: 6 have at least 80% sequence identity with SEQ ID NO: 8. Preferably the rAAV virion comprising a modified capsid protein as defined herein further comprises a COL1A1 promoter controlling the expression of a transgene, preferably a transgene as defined herein.

In preferred embodiments, the modified capsid protein comprises or consists of an amino acid sequence having SEQ ID NO: 6 (AAVrh10 A2). Preferably, the modified capsid protein has at least about 70%, 75%, 80%, 85%, 90%, 95%, 96%, 97%, 98%, 99% or 100% sequence identity with SEQ ID NO: 6. Preferably amino acids at positions 588-602 of SEQ ID NO: 6 have at least 80% sequence identity with SEQ ID NO: 8. Preferably the rAAV virion comprising a modified capsid protein as defined herein further comprises an RUNX2 promoter controlling the expression of a transgene, preferably a transgene as defined herein.

In preferred embodiments, the modified capsid protein comprises or consists of an amino acid sequence having SEQ ID NO: 6 (AAVrh10 A2). Preferably, the modified capsid protein has at least about 70%, 75%, 80%, 85%, 90%, 95%, 96%, 97%, 98%, 99% or 100% sequence identity with SEQ ID NO: 6. Preferably amino acids at positions 588-602 of SEQ ID NO: 6 have at least 80% sequence identity with SEQ ID NO: 8. Preferably the rAAV virion comprising a modified capsid protein as defined herein further comprises an COX2 (PTGS2) promoter controlling the expression of a transgene, preferably a transgene as defined herein.

In preferred embodiments, the modified capsid protein comprises or consists of an amino acid sequence having SEQ ID NO: 6 (AAVrh10 A2). Preferably, the modified capsid protein has at least about 70%, 75%, 80%, 85%, 90%, 95%, 96%, 97%, 98%, 99% or 100% sequence identity with SEQ ID NO: 6. Preferably amino acids at positions 588-602 of SEQ ID NO: 6 have at least 80% sequence identity with SEQ ID NO: 8. Preferably the rAAV virion comprising a modified capsid protein as defined herein further comprises a VEGF (VEGFA) promoter controlling the expression of a transgene, preferably a transgene as defined herein.

In preferred embodiments, the modified capsid protein comprises or consists of an amino acid sequence having SEQ ID NO: 7 (AAV-DJ-QR-P2). Preferably, the modified capsid protein has at least about 70%, 75%, 80%, 85%, 90%, 95%, 96%, 97%, 98%, 99% or 100% sequence identity with SEQ ID NO: 7. Preferably amino acids at positions 587-604 of SEQ ID NO: 7 have at least 80% sequence identity with SEQ ID NO: 12. Preferably the rAAV virion comprising a modified capsid protein as defined herein further comprises constitutive promoter controlling the expression of a transgene, preferably a transgene as defined herein.

In preferred embodiments, the modified capsid protein comprises or consists of an amino acid sequence having SEQ ID NO: 7 (AAV-DJ-QR-P2). Preferably, the modified capsid protein has at least about 70%, 75%, 80%, 85%, 90%, 95%, 96%, 97%, 98%, 99% or 100% sequence identity with SEQ ID NO: 7. Preferably amino acids at positions 587-604 of SEQ ID NO: 7 have at least 80% sequence identity with SEQ ID NO: 12. Preferably the rAAV virion comprising a modified capsid protein as defined herein further comprises a tissue-specific promoter, which promoter controls the expression of a transgene, preferably a transgene as defined herein.

In preferred embodiments, the modified capsid protein comprises or consists of an amino acid sequence having SEQ ID NO: 7 (AAV-DJ-QR-P2). Preferably, the modified capsid protein has at least about 70%, 75%, 80%, 85%, 90%, 95%, 96%, 97%, 98%, 99% or 100% sequence identity with SEQ ID NO: 7. Preferably amino acids at positions 587-604 of SEQ ID NO: 7 have at least 80% sequence identity with SEQ ID NO: 12. Preferably the rAAV virion comprising a modified capsid protein as defined herein further comprises a CMV promoter controlling the expression of a transgene, preferably a transgene as defined herein.

In preferred embodiments, the modified capsid protein comprises or consists of an amino acid sequence having SEQ ID NO: 7 (AAV-DJ-QR-P2). Preferably, the modified capsid protein has at least about 70%, 75%, 80%, 85%, 90%, 95%, 96%, 97%, 98%, 99% or 100% sequence identity with SEQ ID NO: 7. Preferably amino acids at positions 587-604 of SEQ ID NO: 7 have at least 80% sequence identity with SEQ ID NO: 12. Preferably the rAAV virion comprising a modified capsid protein as defined herein further comprises a CBA (chicken beta-actin) promoter controlling the expression of a transgene, preferably a transgene as defined herein.

In preferred embodiments, the modified capsid protein comprises or consists of an amino acid sequence having SEQ ID NO: 7 (AAV-DJ-QR-P2). Preferably, the modified capsid protein has at least about 70%, 75%, 80%, 85%, 90%, 95%, 96%, 97%, 98%, 99% or 100% sequence identity with SEQ ID NO: 7. Preferably amino acids at positions 587-604 of SEQ ID NO: 7 have at least 80% sequence identity with SEQ ID NO: 12. Preferably the rAAV virion comprising a modified capsid protein as defined herein further comprises an EF1α promoter controlling the expression of a transgene, preferably a transgene as defined herein.

In preferred embodiments, the modified capsid protein comprises or consists of an amino acid sequence having SEQ ID NO: 7 (AAV-DJ-QR-P2). Preferably, the modified capsid protein has at least about 70%, 75%, 80%, 85%, 90%, 95%, 96%, 97%, 98%, 99% or 100% sequence identity with SEQ ID NO: 7. Preferably amino acids at positions 587-604 of SEQ ID NO: 7 have at least 80% sequence identity with SEQ ID NO: 12. Preferably the rAAV virion comprising a modified capsid protein as defined herein further comprises a TGF-β (TGB1) promoter controlling the expression of a transgene, preferably a transgene as defined herein.

In preferred embodiments, the modified capsid protein comprises or consists of an amino acid sequence having SEQ ID NO: 7 (AAV-DJ-QR-P2). Preferably, the modified capsid protein has at least about 70%, 75%, 80%, 85%, 90%, 95%, 96%, 97%, 98%, 99% or 100% sequence identity with SEQ ID NO: 7. Preferably amino acids at positions 587-604 of SEQ ID NO: 7 have at least 80% sequence identity with SEQ ID NO: 12. Preferably the rAAV virion comprising a modified capsid protein as defined herein further comprises at an IL1β promoter controlling the expression of a transgene, preferably a transgene as defined herein.

In preferred embodiments, the modified capsid protein comprises or consists of an amino acid sequence having SEQ ID NO: 7 (AAV-DJ-QR-P2). Preferably, the modified capsid protein has at least about 70%, 75%, 80%, 85%, 90%, 95%, 96%, 97%, 98%, 99% or 100% sequence identity with SEQ ID NO: 7. Preferably amino acids at positions 587-604 of SEQ ID NO: 7 have at least 80% sequence identity with SEQ ID NO: 12. Preferably the rAAV virion comprising a modified capsid protein as defined herein further comprises an IL8 (CXCL8) promoter controlling the expression of a transgene, preferably a transgene as defined herein.

In preferred embodiments, the modified capsid protein comprises or consists of an amino acid sequence having SEQ ID NO: 7 (AAV-DJ-QR-P2). Preferably, the modified capsid protein has at least about 70%, 75%, 80%, 85%, 90%, 95%, 96%, 97%, 98%, 99% or 100% sequence identity with SEQ ID NO: 7. Preferably amino acids at positions 587-604 of SEQ ID NO: 7 have at least 80% sequence identity with SEQ ID NO: 12. Preferably the rAAV virion comprising a modified capsid protein as defined herein further comprises an MMP3 promoter controlling the expression of a transgene, preferably a transgene as defined herein.

In preferred embodiments, the modified capsid protein comprises or consists of an amino acid sequence having SEQ ID NO: 7 (AAV-DJ-QR-P2). Preferably, the modified capsid protein has at least about 70%, 75%, 80%, 85%, 90%, 95%, 96%, 97%, 98%, 99% or 100% sequence identity with SEQ ID NO: 7. Preferably amino acids at positions 587-604 of SEQ ID NO: 7 have at least 80% sequence identity with SEQ ID NO: 12. Preferably the rAAV virion comprising a modified capsid protein as defined herein further comprises an ICAM1 promoter controlling the expression of a transgene, preferably a transgene as defined herein.

In preferred embodiments, the modified capsid protein comprises or consists of an amino acid sequence having SEQ ID NO: 7 (AAV-DJ-QR-P2). Preferably, the modified capsid protein has at least about 70%, 75%, 80%, 85%, 90%, 95%, 96%, 97%, 98%, 99% or 100% sequence identity with SEQ ID NO: 7. Preferably amino acids at positions 587-604 of SEQ ID NO: 7 have at least 80% sequence identity with SEQ ID NO: 12. Preferably the rAAV virion comprising a modified capsid protein as defined herein further comprises an ADAMTS4 promoter controlling the expression of a transgene, preferably a transgene as defined herein.

In preferred embodiments, the modified capsid protein comprises or consists of an amino acid sequence having SEQ ID NO: 7 (AAV-DJ-QR-P2). Preferably, the modified capsid protein has at least about 70%, 75%, 80%, 85%, 90%, 95%, 96%, 97%, 98%, 99% or 100% sequence identity with SEQ ID NO: 7. Preferably amino acids at positions 587-604 of SEQ ID NO: 7 have at least 80% sequence identity with SEQ ID NO: 12. Preferably the rAAV virion comprising a modified capsid protein as defined herein further comprises a COL1A1 promoter controlling the expression of a transgene, preferably a transgene as defined herein.

In preferred embodiments, the modified capsid protein comprises or consists of an amino acid sequence having SEQ ID NO: 7 (AAV-DJ-QR-P2). Preferably, the modified capsid protein has at least about 70%, 75%, 80%, 85%, 90%, 95%, 96%, 97%, 98%, 99% or 100% sequence identity with SEQ ID NO: 7. Preferably amino acids at positions 587-604 of SEQ ID NO: 7 have at least 80% sequence identity with SEQ ID NO: 12. Preferably the rAAV virion comprising a modified capsid protein as defined herein further comprises an RUNX2 promoter controlling the expression of a transgene, preferably a transgene as defined herein.

In preferred embodiments, the modified capsid protein comprises or consists of an amino acid sequence having SEQ ID NO: 7 (AAV-DJ-QR-P2). Preferably, the modified capsid protein has at least about 70%, 75%, 80%, 85%, 90%, 95%, 96%, 97%, 98%, 99% or 100% sequence identity with SEQ ID NO: 7. Preferably amino acids at positions 587-604 of SEQ ID NO: 7 have at least 80% sequence identity with SEQ ID NO: 12. Preferably the rAAV virion comprising a modified capsid protein as defined herein further comprises an COX2 (PTGS2) promoter controlling the expression of a transgene, preferably a transgene as defined herein.

In preferred embodiments, the modified capsid protein comprises or consists of an amino acid sequence having SEQ ID NO: 7 (AAV-DJ-QR-P2). Preferably, the modified capsid protein has at least about 70%, 75%, 80%, 85%, 90%, 95%, 96%, 97%, 98%, 99% or 100% sequence identity with SEQ ID NO: 7. Preferably amino acids at positions 587-604 of SEQ ID NO: 7 have at least 80% sequence identity with SEQ ID NO: 12. Preferably the rAAV virion comprising a modified capsid protein as defined herein further comprises a VEGF (VEGFA) promoter controlling the expression of a transgene, preferably a transgene as defined herein.

In preferred embodiments, the modified capsid protein comprises in the C-terminal part of the protein an amino acid sequence Z, residues of which are exposed on the surface of the capsid protein. Preferably amino acid sequence Z; a) comprises or consists of a sequence of amino acid residues of the formula I: y-G-Q-x-G-$(x)_3$-R-$(x)_3$-y-A-Q-A-A wherein x represents a single amino acid residue and wherein y represents 0, 1 or 2 amino acid residues; and b) is present at a location corresponding to a position 100-200, preferably 120-180, more preferably 130-170, more preferably 140-160 amino acid residues from the C terminus of a wild-type AAV capsid protein. Preferably the rAAV virion comprising a modified capsid protein as defined herein further an inducible promoter controlling the expression of a transgene, preferably a transgene as defined herein.

In preferred embodiments, the modified capsid protein comprises in the C-terminal part of the protein an amino acid sequence Z, residues of which are exposed on the surface of the capsid protein. Preferably amino acid sequence Z; a) comprises or consists of a sequence of amino acid residues of the formula I: y-G-Q-x-G-$(x)_3$-R-$(x)_3$-y-A-Q-A-A wherein x represents a single amino acid residue and wherein y represents 0, 1 or 2 amino acid residues; and b) is present at a location corresponding to a position 100-200, preferably 120-180, more preferably 130-170, more preferably 140-160 amino acid residues from the C terminus of a wild-type AAV capsid protein. Preferably the rAAV virion comprising a modified capsid protein as defined herein further comprises a promoter which confers expression in cells of the joint, which promoter controls the expression of a transgene, preferably a transgene as defined herein. Preferably, the promoter which confers expression in cells of the joint, is a promoter that confers expression of cells in the arthritic joint. A preferred promoter confers expression in at least one of connective tissue cells, synovial cells, subsynovial cells, intimal macrophages, FLS, cartilage cells, chondrocytes, chondroblasts, adipocytes, osteoclasts and T-cells, preferably the promoter confers expression in cells of the FLS.

In preferred embodiments, the modified capsid protein comprises in the C-terminal part of the protein an amino acid sequence Z, residues of which are exposed on the surface of the capsid protein. Preferably amino acid sequence Z; a) comprises or consists of a sequence of amino acid residues of the formula I: y-G-Q-x-G-$(x)_3$-R-$(x)_3$-y-A-Q-A-A wherein x represents a single amino acid residue and wherein y represents 0, 1 or 2 amino acid residues; and b) is present at a location corresponding to a position 100-200, preferably 120-180, more preferably 130-170, more preferably 140-160 amino acid residues from the C terminus of a wild-type AAV capsid protein. Preferably the rAAV virion comprising a modified capsid protein as defined herein further a SV40 promoter controlling the expression of a transgene, preferably a transgene as defined herein.

In preferred embodiments, the modified capsid protein comprises in the C-terminal part of the protein an amino acid sequence Z, residues of which are exposed on the surface of the capsid protein. Preferably amino acid sequence Z; a) comprises or consists of a sequence of amino acid residues of the formula I: y-G-Q-x-G-$(x)_3$-R-$(x)_3$-y-A-Q-A-A wherein x represents a single amino acid residue and wherein y represents 0, 1 or 2 amino acid residues; and b) is present at a location corresponding to a position 100-200, preferably 120-180, more preferably 130-170, more preferably 140-160 amino acid residues from the C terminus of a wild-type AAV capsid protein. Preferably the rAAV virion comprising a modified capsid protein as defined herein further a CAG (cytomegalovirus early enhancer/chicken β-actin) promoter controlling the expression of a transgene, preferably a transgene as defined herein.

In preferred embodiments, the modified capsid protein comprises in the C-terminal part of the protein an amino acid sequence Z, residues of which are exposed on the surface of the capsid protein. Preferably amino acid sequence Z; a) comprises or consists of a sequence of amino acid residues of the formula I: y-G-Q-x-G-$(x)_3$-R-$(x)_3$-y-A-Q-A-A wherein x represents a single amino acid residue and wherein y represents 0, 1 or 2 amino acid residues; and b) is present at a location corresponding to a position 100-200, preferably 120-180, more preferably 130-170, more preferably 140-160 amino acid residues from the C terminus of a wild-type AAV capsid protein. Preferably the rAAV virion comprising a modified capsid protein as defined herein further comprises a liver-specific promoter controlling the expression of a transgene, preferably a transgene as defined herein. Preferably, the liver specific-promoter is a human alpha-1 anti-trypsin (hAAT) promoter.

In preferred embodiments, the modified capsid protein comprises in the C-terminal part of the protein an amino acid sequence Z, residues of which are exposed on the surface of the capsid protein. Preferably amino acid sequence Z; a) comprises or consists of a sequence of amino acid residues of the formula I: y-G-Q-x-G-$(x)_3$-R-$(x)_3$-y-A-Q-A-A wherein x represents a single amino acid residue and wherein y represents 0, 1 or 2 amino acid residues; and b) is present at a location corresponding to a position 100-200, preferably 120-180, more preferably 130-170, more preferably 140-160 amino acid residues from the C terminus of a wild-type AAV capsid protein. Preferably the rAAV virion comprising a modified capsid protein as defined herein further comprises a liver-specific promoter controlling the expression of a transgene, preferably a transgene as defined herein. Preferably, the liver specific-promoter is a TBG (thyroxine-binding globulin) promoter.

In preferred embodiments, the modified capsid protein comprises in the C-terminal part of the protein an amino acid sequence Z, residues of which are exposed on the surface of the capsid protein. Preferably amino acid sequence Z; a) comprises or consists of a sequence of amino acid residues of the formula I: y-G-Q-x-G-$(x)_3$-R-$(x)_3$-y-A-Q-A-A wherein x represents a single amino acid residue and wherein y represents 0, 1 or 2 amino acid residues; and b) is present at a location corresponding to a position 100-200, preferably 120-180, more preferably 130-170, more preferably 140-160 amino acid residues from the C terminus of a wild-type AAV capsid protein. Preferably the rAAV virion comprising a modified capsid protein as defined herein further comprises an NFκB responsive (inducible) promoter controlling the expression of a transgene, preferably a transgene as defined herein. Preferably, the NFκB responsive (inducible) promoter is an NFκB responsive (inducible) minimal CMV promoter. Preferably, the NFκB responsive (inducible) CMV promoter is a promoter as described in Khoury et al. 2007, J Gene Med, 9:596-604.

In preferred embodiments, the modified capsid protein comprises in the C-terminal part of the protein an amino acid sequence Z, residues of which are exposed on the surface of the capsid protein. Preferably amino acid sequence Z; a) comprises or consists of a sequence of amino acid residues of the formula I: y-G-Q-x-G-$(x)_3$-R-$(x)_3$-y-A-Q-A-A wherein x represents a single amino acid residue and wherein y represents 0, 1 or 2 amino acid residues; and b)

is present at a location corresponding to a position 100-200, preferably 120-180, more preferably 130-170, more preferably 140-160 amino acid residues from the C terminus of a wild-type AAV capsid protein. Preferably the rAAV virion comprising a modified capsid protein as defined herein further comprises a promoter of an inflammatory modulator controlling the expression of a transgene, preferably a transgene as defined herein. Preferably the promoter is a promoter of a pro-inflammatory cytokine gene. Preferably the promoter of a pro-inflammatory cytokine gene is a minimized promoter of a pro-inflammatory cytokine gene.

In preferred embodiments, the modified capsid protein comprises in the C-terminal part of the protein an amino acid sequence Z, residues of which are exposed on the surface of the capsid protein. Preferably amino acid sequence Z; a) comprises or consists of a sequence of amino acid residues of the formula I: y-G-Q-x-G-$(x)_3$-R-$(x)_3$-y-A-Q-A-A wherein x represents a single amino acid residue and wherein y represents 0, 1 or 2 amino acid residues; and b) is present at a location corresponding to a position 100-200, preferably 120-180, more preferably 130-170, more preferably 140-160 amino acid residues from the C terminus of a wild-type AAV capsid protein. Preferably the rAAV virion comprising a modified capsid protein as defined herein further comprises an IL-6 (HGF) promoter controlling the expression of a transgene, preferably a transgene as defined herein.

In preferred embodiments, the modified capsid protein comprises in the C-terminal part of the protein an amino acid sequence Z, residues of which are exposed on the surface of the capsid protein. Preferably amino acid sequence Z; a) comprises or consists of a sequence of amino acid residues of the formula I: y-G-Q-x-G-$(x)_3$-R-$(x)_3$-y-A-Q-A-A wherein x represents a single amino acid residue and wherein y represents 0, 1 or 2 amino acid residues; and b) is present at a location corresponding to a position 100-200, preferably 120-180, more preferably 130-170, more preferably 140-160 amino acid residues from the C terminus of a wild-type AAV capsid protein. Preferably the rAAV virion comprising a modified capsid protein as defined herein further comprises an CXCL10 promoter controlling the expression of a transgene, preferably a transgene as defined herein.

In preferred embodiments, the modified capsid protein comprises in the C-terminal part of the protein an amino acid sequence Z, residues of which are exposed on the surface of the capsid protein. Preferably amino acid sequence Z; a) comprises or consists of a sequence of amino acid residues of the formula I: y-G-Q-x-G-$(x)_3$-R-$(x)_3$-y-A-Q-A-A wherein x represents a single amino acid residue and wherein y represents 0, 1 or 2 amino acid residues; and b) is present at a location corresponding to a position 100-200, preferably 120-180, more preferably 130-170, more preferably 140-160 amino acid residues from the C terminus of a wild-type AAV capsid protein. Preferably the rAAV virion comprising a modified capsid protein as defined herein further comprises an MMP2 promoter controlling the expression of a transgene, preferably a transgene as defined herein.

In preferred embodiments, the modified capsid protein comprises in the C-terminal part of the protein an amino acid sequence Z, residues of which are exposed on the surface of the capsid protein. Preferably amino acid sequence Z; a) comprises or consists of a sequence of amino acid residues of the formula I: y-G-Q-x-G-$(x)_3$-R-$(x)_3$-y-A-Q-A-A wherein x represents a single amino acid residue and wherein y represents 0, 1 or 2 amino acid residues; and b)

is present at a location corresponding to a position 100-200, preferably 120-180, more preferably 130-170, more preferably 140-160 amino acid residues from the C terminus of a wild-type AAV capsid protein. Preferably the rAAV virion comprising a modified capsid protein as defined herein further comprises an MMP13 promoter controlling the expression of a transgene, preferably a transgene as defined herein.

In preferred embodiments, the modified capsid protein comprises in the C-terminal part of the protein an amino acid sequence Z, residues of which are exposed on the surface of the capsid protein. Preferably amino acid sequence Z; a) comprises or consists of a sequence of amino acid residues of the formula I: y-G-Q-x-G-$(x)_3$-R-$(x)_3$-y-A-Q-A-A wherein x represents a single amino acid residue and wherein y represents 0, 1 or 2 amino acid residues; and b) is present at a location corresponding to a position 100-200, preferably 120-180, more preferably 130-170, more preferably 140-160 amino acid residues from the C terminus of a wild-type AAV capsid protein. Preferably the rAAV virion comprising a modified capsid protein as defined herein further comprises an ADAMDEC1 promoter controlling the expression of a transgene, preferably a transgene as defined herein.

In preferred embodiments, the modified capsid protein comprises in the C-terminal part of the protein an amino acid sequence Z, residues of which are exposed on the surface of the capsid protein. Preferably amino acid sequence Z; a) comprises or consists of a sequence of amino acid residues of the formula I: y-G-Q-x-G-$(x)_3$-R-$(x)_3$-y-A-Q-A-A wherein x represents a single amino acid residue and wherein y represents 0, 1 or 2 amino acid residues; and b) is present at a location corresponding to a position 100-200, preferably 120-180, more preferably 130-170, more preferably 140-160 amino acid residues from the C terminus of a wild-type AAV capsid protein. Preferably the rAAV virion comprising a modified capsid protein as defined herein further comprises an MMP12 promoter controlling the expression of a transgene, preferably a transgene as defined herein.

In preferred embodiments, the modified capsid protein comprises in the C-terminal part of the protein an amino acid sequence Z, residues of which are exposed on the surface of the capsid protein. Preferably amino acid sequence Z; a) comprises or consists of a sequence of amino acid residues of the formula I: y-G-Q-x-G-$(x)_3$-R-$(x)_3$-y-A-Q-A-A wherein x represents a single amino acid residue and wherein y represents 0, 1 or 2 amino acid residues; and b) is present at a location corresponding to a position 100-200, preferably 120-180, more preferably 130-170, more preferably 140-160 amino acid residues from the C terminus of a wild-type AAV capsid protein. Preferably the rAAV virion comprising a modified capsid protein as defined herein further comprises an ADAMTS5 promoter controlling the expression of a transgene, preferably a transgene as defined herein.

In preferred embodiments, the modified capsid protein comprises in the C-terminal part of the protein an amino acid sequence Z, residues of which are exposed on the surface of the capsid protein. Preferably amino acid sequence Z; a) comprises or consists of a sequence of amino acid residues of the formula I: y-G-Q-x-G-$(x)_3$-R-$(x)_3$-y-A-Q-A-A wherein x represents a single amino acid residue and wherein y represents 0, 1 or 2 amino acid residues; and b) is present at a location corresponding to a position 100-200, preferably 120-180, more preferably 130-170, more preferably 140-160 amino acid residues from the C terminus of a wild-type AAV capsid protein. Preferably the rAAV virion comprising a modified capsid protein as defined herein further comprises an TNFα (TNF) promoter controlling the expression of a transgene, preferably a transgene as defined herein.

In preferred embodiments, the modified capsid protein comprises in the C-terminal part of the protein an amino acid sequence Z, residues of which are exposed on the surface of the capsid protein. Preferably amino acid sequence Z; a) comprises or consists of a sequence of amino acid residues of the formula I: y-G-Q-x-G-$(x)_3$-R-$(x)_3$-y-A-Q-A-A wherein x represents a single amino acid residue and wherein y represents 0, 1 or 2 amino acid residues; and b) is present at a location corresponding to a position 100-200, preferably 120-180, more preferably 130-170, more preferably 140-160 amino acid residues from the C terminus of a wild-type AAV capsid protein. Preferably the rAAV virion comprising a modified capsid protein as defined herein further comprises a (basic) FGF (FGF2) promoter controlling the expression of a transgene, preferably a transgene as defined herein.

In preferred embodiments, the modified capsid protein comprises or consists of an amino acid sequence having SEQ ID NO: 1 (AAV1 P4). Preferably, the modified capsid protein has at least about 70%, 75%, 80%, 85%, 90%, 95%, 96%, 97%, 98%, 99% or 100% sequence identity with SEQ ID NO: 1. Preferably amino acids at positions 588-602 of SEQ ID NO: 1 have at least 80% sequence identity with SEQ ID NO: 11. Preferably the rAAV virion comprising a modified capsid protein as defined herein further comprises an inducible promoter controlling the expression of a transgene, preferably a transgene as defined herein.

In preferred embodiments, the modified capsid protein comprises or consists of an amino acid sequence having SEQ ID NO: 1 (AAV1 P4). Preferably, the modified capsid protein has at least about 70%, 75%, 80%, 85%, 90%, 95%, 96%, 97%, 98%, 99% or 100% sequence identity with SEQ ID NO: 1. Preferably amino acids at positions 588-602 of SEQ ID NO: 1 have at least 80% sequence identity with SEQ ID NO: 11. Preferably the rAAV virion comprising a modified capsid protein as defined herein further comprises a promoter which confers expression in cells of the joint, which promoter controls the expression of a transgene, preferably a transgene as defined herein. Preferably, the promoter which confers expression in cells of the joint, is a promoter that confers expression of cells in the arthritic joint. A preferred promoter confers expression in at least one of connective tissue cells, synovial cells, sub-synovial cells, intimal macrophages, FLS, cartilage cells, chondrocytes, chondroblasts, adipocytes, osteoclasts and T-cells, preferably the promoter confers expression in cells of the FLS.

In preferred embodiments, the modified capsid protein comprises or consists of an amino acid sequence having SEQ ID NO: 1 (AAV1 P4). Preferably, the modified capsid protein has at least about 70%, 75%, 80%, 85%, 90%, 95%, 96%, 97%, 98%, 99% or 100% sequence identity with SEQ ID NO: 1. Preferably amino acids at positions 588-602 of SEQ ID NO: 1 have at least 80% sequence identity with SEQ ID NO: 11. Preferably the rAAV virion comprising a modified capsid protein as defined herein further comprises a SV40 promoter controlling the expression of a transgene, preferably a transgene as defined herein.

In preferred embodiments, the modified capsid protein comprises or consists of an amino acid sequence having SEQ ID NO: 1 (AAV1 P4). Preferably, the modified capsid protein has at least about 70%, 75%, 80%, 85%, 90%, 95%, 96%, 97%, 98%, 99% or 100% sequence identity with SEQ ID NO: 1. Preferably amino acids at positions 588-602 of SEQ ID NO: 1 have at least 80% sequence identity with SEQ ID NO: 11. Preferably the rAAV virion comprising a modified capsid protein as defined herein further comprises a CAG (cytomegalovirus early enhancer/chicken B-actin) promoter controlling the expression of a transgene, preferably a transgene as defined herein.

In preferred embodiments, the modified capsid protein comprises or consists of an amino acid sequence having SEQ ID NO: 1 (AAV1 P4). Preferably, the modified capsid protein has at least about 70%, 75%, 80%, 85%, 90%, 95%, 96%, 97%, 98%, 99% or 100% sequence identity with SEQ ID NO: 1. Preferably amino acids at positions 588-602 of SEQ ID NO: 1 have at least 80% sequence identity with SEQ ID NO: 11. Preferably the rAAV virion comprising a modified capsid protein as defined herein further comprises a liver-specific promoter controlling the expression of a transgene, preferably a transgene as defined herein. Preferably, the liver specific-promoter is a human alpha-1 antitrypsin (hAAT) promoter.

In preferred embodiments, the modified capsid protein comprises or consists of an amino acid sequence having SEQ ID NO: 1 (AAV1 P4). Preferably, the modified capsid protein has at least about 70%, 75%, 80%, 85%, 90%, 95%, 96%, 97%, 98%, 99% or 100% sequence identity with SEQ ID NO: 1. Preferably amino acids at positions 588-602 of SEQ ID NO: 1 have at least 80% sequence identity with SEQ ID NO: 11. Preferably the rAAV virion comprising a modified capsid protein as defined herein further comprises a liver-specific promoter controlling the expression of a transgene, preferably a transgene as defined herein. Preferably, the liver specific-promoter is a TBG (thyroxine-binding globulin) promoter.

In preferred embodiments, the modified capsid protein comprises or consists of an amino acid sequence having SEQ ID NO: 1 (AAV1 P4). Preferably, the modified capsid protein has at least about 70%, 75%, 80%, 85%, 90%, 95%, 96%, 97%, 98%, 99% or 100% sequence identity with SEQ ID NO: 1. Preferably amino acids at positions 588-602 of SEQ ID NO: 1 have at least 80% sequence identity with SEQ ID NO: 11. Preferably the rAAV virion comprising a modified capsid protein as defined herein further comprises an NFκB responsive (inducible) promoter controlling the expression of a transgene, preferably a transgene as defined herein. Preferably, the NFκB responsive (inducible) promoter is an NFκB responsive (inducible) minimal CMV promoter. Preferably, the NFκB responsive (inducible) CMV promoter is a promoter as described in Khoury et al. 2007, J Gene Med, 9:596-604.

In preferred embodiments, the modified capsid protein comprises or consists of an amino acid sequence having SEQ ID NO: 1 (AAV1 P4). Preferably, the modified capsid protein has at least about 70%, 75%, 80%, 85%, 90%, 95%, 96%, 97%, 98%, 99% or 100% sequence identity with SEQ ID NO: 1. Preferably amino acids at positions 588-602 of SEQ ID NO: 1 have at least 80% sequence identity with SEQ ID NO: 11. Preferably the rAAV virion comprising a modified capsid protein as defined herein further comprises a promoter of an inflammatory modulator controlling the expression of a transgene, preferably a transgene as defined herein. Preferably the promoter is a promoter of a pro-inflammatory cytokine gene. Preferably the promoter of a pro-inflammatory cytokine gene is a minimized promoter of a pro-inflammatory cytokine gene.

In preferred embodiments, the modified capsid protein comprises or consists of an amino acid sequence having SEQ ID NO: 1 (AAV1 P4). Preferably, the modified capsid protein has at least about 70%, 75%, 80%, 85%, 90%, 95%, 96%, 97%, 98%, 99% or 100% sequence identity with SEQ ID NO: 1. Preferably amino acids at positions 588-602 of SEQ ID NO: 1 have at least 80% sequence identity with SEQ ID NO: 11. Preferably the rAAV virion comprising a modified capsid protein as defined herein further comprises an IL-6 (HGF) promoter controlling the expression of a transgene, preferably a transgene as defined herein.

In preferred embodiments, the modified capsid protein comprises or consists of an amino acid sequence having SEQ ID NO: 1 (AAV1 P4). Preferably, the modified capsid protein has at least about 70%, 75%, 80%, 85%, 90%, 95%, 96%, 97%, 98%, 99% or 100% sequence identity with SEQ ID NO: 1. Preferably amino acids at positions 588-602 of SEQ ID NO: 1 have at least 80% sequence identity with SEQ ID NO: 11. Preferably the rAAV virion comprising a modified capsid protein as defined herein further comprises an CXCL10 promoter controlling the expression of a transgene, preferably a transgene as defined herein.

In preferred embodiments, the modified capsid protein comprises or consists of an amino acid sequence having SEQ ID NO: 1 (AAV1 P4). Preferably, the modified capsid protein has at least about 70%, 75%, 80%, 85%, 90%, 95%, 96%, 97%, 98%, 99% or 100% sequence identity with SEQ ID NO: 1. Preferably amino acids at positions 588-602 of SEQ ID NO: 1 have at least 80% sequence identity with SEQ ID NO: 11. Preferably the rAAV virion comprising a modified capsid protein as defined herein further comprises an MMP2 promoter controlling the expression of a transgene, preferably a transgene as defined herein.

In preferred embodiments, the modified capsid protein comprises or consists of an amino acid sequence having SEQ ID NO: 1 (AAV1 P4). Preferably, the modified capsid protein has at least about 70%, 75%, 80%, 85%, 90%, 95%, 96%, 97%, 98%, 99% or 100% sequence identity with SEQ ID NO: 1. Preferably amino acids at positions 588-602 of SEQ ID NO: 1 have at least 80% sequence identity with SEQ ID NO: 11. Preferably the rAAV virion comprising a modified capsid protein as defined herein further comprises an MMP13 promoter controlling the expression of a transgene, preferably a transgene as defined herein.

In preferred embodiments, the modified capsid protein comprises or consists of an amino acid sequence having SEQ ID NO: 1 (AAV1 P4). Preferably, the modified capsid protein has at least about 70%, 75%, 80%, 85%, 90%, 95%, 96%, 97%, 98%, 99% or 100% sequence identity with SEQ ID NO: 1. Preferably amino acids at positions 588-602 of SEQ ID NO: 1 have at least 80% sequence identity with SEQ ID NO: 11. Preferably the rAAV virion comprising a modified capsid protein as defined herein further comprises an ADAMDEC1 promoter controlling the expression of a transgene, preferably a transgene as defined herein.

In preferred embodiments, the modified capsid protein comprises or consists of an amino acid sequence having SEQ ID NO: 1 (AAV1 P4). Preferably, the modified capsid protein has at least about 70%, 75%, 80%, 85%, 90%, 95%, 96%, 97%, 98%, 99% or 100% sequence identity with SEQ ID NO: 1. Preferably amino acids at positions 588-602 of SEQ ID NO: 1 have at least 80% sequence identity with SEQ ID NO: 11. Preferably the rAAV virion comprising a modified capsid protein as defined herein further comprises an MMP12 promoter controlling the expression of a transgene, preferably a transgene as defined herein.

In preferred embodiments, the modified capsid protein comprises in the C-terminal part of the protein. In preferred embodiments, the modified capsid protein comprises or consists of an amino acid sequence having SEQ ID NO: 1

(AAV1 P4). Preferably, the modified capsid protein has at least about 70%, 75%, 80%, 85%, 90%, 95%, 96%, 97%, 98%, 99% or 100% sequence identity with SEQ ID NO: 1. Preferably amino acids at positions 588-602 of SEQ ID NO: 1 have at least 80% sequence identity with SEQ ID NO: 11. Preferably the rAAV virion comprising a modified capsid protein as defined herein further comprises an ADAMTS5 promoter controlling the expression of a transgene, preferably a transgene as defined herein.

In preferred embodiments, the modified capsid protein comprises or consists of an amino acid sequence having SEQ ID NO: 1 (AAV1 P4). Preferably, the modified capsid protein has at least about 70%, 75%, 80%, 85%, 90%, 95%, 96%, 97%, 98%, 99% or 100% sequence identity with SEQ ID NO: 1. Preferably amino acids at positions 588-602 of SEQ ID NO: 1 have at least 80% sequence identity with SEQ ID NO: 11. Preferably the rAAV virion comprising a modified capsid protein as defined herein further comprises an TNFα (TNF) promoter controlling the expression of a transgene, preferably a transgene as defined herein.

In preferred embodiments, the modified capsid protein comprises or consists of an amino acid sequence having SEQ ID NO: 1 (AAV1 P4). Preferably, the modified capsid protein has at least about 70%, 75%, 80%, 85%, 90%, 95%, 96%, 97%, 98%, 99% or 100% sequence identity with SEQ ID NO: 1. Preferably amino acids at positions 588-602 of SEQ ID NO: 1 have at least 80% sequence identity with SEQ ID NO: 11. Preferably the rAAV virion comprising a modified capsid protein as defined herein further comprises a (basic) FGF (FGF2) promoter controlling the expression of a transgene, preferably a transgene as defined herein.

In preferred embodiments, the modified capsid protein comprises or consists of an amino acid sequence having SEQ ID NO: 2 (AAV2 P2). Preferably, the modified capsid protein has at least about 70%, 75%, 80%, 85%, 90%, 95%, 96%, 97%, 98%, 99% or 100% sequence identity with SEQ ID NO: 2. Preferably amino acids at positions 585-602 of SEQ ID NO: 2 have at least 80% sequence identity with SEQ ID NO: 10. Preferably the rAAV virion comprising a modified capsid protein as defined herein further comprises an inducible promoter controlling the expression of a transgene, preferably a transgene as defined herein.

In preferred embodiments, the modified capsid protein comprises or consists of an amino acid sequence having SEQ ID NO: 2 (AAV2 P2). Preferably, the modified capsid protein has at least about 70%, 75%, 80%, 85%, 90%, 95%, 96%, 97%, 98%, 99% or 100% sequence identity with SEQ ID NO: 2. Preferably amino acids at positions 585-602 of SEQ ID NO: 2 have at least 80% sequence identity with SEQ ID NO: 10. Preferably the rAAV virion comprising a modified capsid protein as defined herein further comprises a promoter which confers expression in cells of the joint, which promoter controls the expression of a transgene, preferably a transgene as defined herein. Preferably, the promoter which confers expression in cells of the joint, is a promoter that confers expression of cells in the arthritic joint. A preferred promoter confers expression in at least one of connective tissue cells, synovial cells, sub-synovial cells, intimal macrophages, FLS, cartilage cells, chondrocytes, chondroblasts, adipocytes, osteoclasts and T-cells, preferably the promoter confers expression in cells of the FLS.

In preferred embodiments, the modified capsid protein comprises or consists of an amino acid sequence having SEQ ID NO: 2 (AAV2 P2). Preferably, the modified capsid protein has at least about 70%, 75%, 80%, 85%, 90%, 95%, 96%, 97%, 98%, 99% or 100% sequence identity with SEQ ID NO: 2. Preferably amino acids at positions 585-602 of SEQ ID NO: 2 have at least 80% sequence identity with SEQ ID NO: 10. Preferably the rAAV virion comprising a modified capsid protein as defined herein further comprises a SV40 promoter controlling the expression of a transgene, preferably a transgene as defined herein.

In preferred embodiments, the modified capsid protein comprises or consists of an amino acid sequence having SEQ ID NO: 2 (AAV2 P2). Preferably, the modified capsid protein has at least about 70%, 75%, 80%, 85%, 90%, 95%, 96%, 97%, 98%, 99% or 100% sequence identity with SEQ ID NO: 2. Preferably amino acids at positions 585-602 of SEQ ID NO: 2 have at least 80% sequence identity with SEQ ID NO: 10. Preferably the rAAV virion comprising a modified capsid protein as defined herein further comprises a CAG (cytomegalovirus early enhancer/chicken B-actin) promoter controlling the expression of a transgene, preferably a transgene as defined herein.

In preferred embodiments, the modified capsid protein comprises or consists of an amino acid sequence having SEQ ID NO: 2 (AAV2 P2). Preferably, the modified capsid protein has at least about 70%, 75%, 80%, 85%, 90%, 95%, 96%, 97%, 98%, 99% or 100% sequence identity with SEQ ID NO: 2. Preferably amino acids at positions 585-602 of SEQ ID NO: 2 have at least 80% sequence identity with SEQ ID NO: 10. Preferably the rAAV virion comprising a modified capsid protein as defined herein further comprises a liver-specific promoter controlling the expression of a transgene, preferably a transgene as defined herein. Preferably, the liver specific-promoter is human alpha-1 antitrypsin (hAAT) promoter.

In preferred embodiments, the modified capsid protein comprises or consists of an amino acid sequence having SEQ ID NO: 2 (AAV2 P2). Preferably, the modified capsid protein has at least about 70%, 75%, 80%, 85%, 90%, 95%, 96%, 97%, 98%, 99% or 100% sequence identity with SEQ ID NO: 2. Preferably amino acids at positions 585-602 of SEQ ID NO: 2 have at least 80% sequence identity with SEQ ID NO: 10. Preferably the rAAV virion comprising a modified capsid protein as defined herein further comprises a liver-specific promoter controlling the expression of a transgene, preferably a transgene as defined herein. Preferably, the liver specific-promoter is a TBG (thyroxine-binding globulin) promoter.

In preferred embodiments, the modified capsid protein comprises or consists of an amino acid sequence having SEQ ID NO: 2 (AAV2 P2). Preferably, the modified capsid protein has at least about 70%, 75%, 80%, 85%, 90%, 95%, 96%, 97%, 98%, 99% or 100% sequence identity with SEQ ID NO: 2. Preferably amino acids at positions 585-602 of SEQ ID NO: 2 have at least 80% sequence identity with SEQ ID NO: 10. Preferably the rAAV virion comprising a modified capsid protein as defined herein further comprises an NFκB responsive (inducible) promoter controlling the expression of a transgene, preferably a transgene as defined herein. Preferably, the NFκB responsive (inducible) promoter is an NFκB responsive (inducible) minimal CMV promoter. Preferably, the NFκB responsive (inducible) CMV promoter is a promoter as described in Khoury et al. 2007, J Gene Med, 9:596-604.

In preferred embodiments, the modified capsid protein comprises or consists of an amino acid sequence having SEQ ID NO: 2 (AAV2 P2). Preferably, the modified capsid protein has at least about 70%, 75%, 80%, 85%, 90%, 95%, 96%, 97%, 98%, 99% or 100% sequence identity with SEQ ID NO: 2. Preferably amino acids at positions 585-602 of SEQ ID NO: 2 have at least 80% sequence identity with SEQ ID NO: 10. Preferably the rAAV virion comprising a modified capsid protein as defined herein further comprises a promoter of an inflammatory modulator controlling the expression of a transgene, preferably a transgene as defined herein. Preferably the promoter is a promoter of a pro-inflammatory cytokine gene. Preferably the promoter of a pro-inflammatory cytokine gene is a minimized promoter of a pro-inflammatory cytokine gene.

In preferred embodiments, the modified capsid protein comprises or consists of an amino acid sequence having SEQ ID NO: 2 (AAV2 P2). Preferably, the modified capsid protein has at least about 70%, 75%, 80%, 85%, 90%, 95%, 96%, 97%, 98%, 99% or 100% sequence identity with SEQ ID NO: 2. Preferably amino acids at positions 585-602 of SEQ ID NO: 2 have at least 80% sequence identity with SEQ ID NO: 10. Preferably the rAAV virion comprising a modified capsid protein as defined herein further comprises at an IL-6 (HGF) promoter controlling the expression of a transgene, preferably a transgene as defined herein.

In preferred embodiments, the modified capsid protein comprises or consists of an amino acid sequence having SEQ ID NO: 2 (AAV2 P2). Preferably, the modified capsid protein has at least about 70%, 75%, 80%, 85%, 90%, 95%, 96%, 97%, 98%, 99% or 100% sequence identity with SEQ ID NO: 2. Preferably amino acids at positions 585-602 of SEQ ID NO: 2 have at least 80% sequence identity with SEQ ID NO: 10. Preferably the rAAV virion comprising a modified capsid protein as defined herein further comprises an CXCL10 promoter controlling the expression of a transgene, preferably a transgene as defined herein.

In preferred embodiments, the modified capsid protein comprises or consists of an amino acid sequence having SEQ ID NO: 2 (AAV2 P2). Preferably, the modified capsid protein has at least about 70%, 75%, 80%, 85%, 90%, 95%, 96%, 97%, 98%, 99% or 100% sequence identity with SEQ ID NO: 2. Preferably amino acids at positions 585-602 of SEQ ID NO: 2 have at least 80% sequence identity with SEQ ID NO: 10. Preferably the rAAV virion comprising a modified capsid protein as defined herein further comprises an MMP2 promoter controlling the expression of a transgene, preferably a transgene as defined herein.

In preferred embodiments, the modified capsid protein comprises or consists of an amino acid sequence having SEQ ID NO: 2 (AAV2 P2). Preferably, the modified capsid protein has at least about 70%, 75%, 80%, 85%, 90%, 95%, 96%, 97%, 98%, 99% or 100% sequence identity with SEQ ID NO: 2. Preferably amino acids at positions 585-602 of SEQ ID NO: 2 have at least 80% sequence identity with SEQ ID NO: 10. Preferably the rAAV virion comprising a modified capsid protein as defined herein further comprises an MMP13 promoter controlling the expression of a transgene, preferably a transgene as defined herein.

In preferred embodiments, the modified capsid protein comprises or consists of an amino acid sequence having SEQ ID NO: 2 (AAV2 P2). Preferably, the modified capsid protein has at least about 70%, 75%, 80%, 85%, 90%, 95%, 96%, 97%, 98%, 99% or 100% sequence identity with SEQ ID NO: 2. Preferably amino acids at positions 585-602 of SEQ ID NO: 2 have at least 80% sequence identity with SEQ ID NO: 10. Preferably the rAAV virion comprising a modified capsid protein as defined herein further comprises an ADAMDEC1 promoter controlling the expression of a transgene, preferably a transgene as defined herein.

In preferred embodiments, the modified capsid protein comprises or consists of an amino acid sequence having SEQ ID NO: 2 (AAV2 P2). Preferably, the modified capsid protein has at least about 70%, 75%, 80%, 85%, 90%, 95%, 96%, 97%, 98%, 99% or 100% sequence identity with SEQ ID NO: 2. Preferably amino acids at positions 585-602 of SEQ ID NO: 2 have at least 80% sequence identity with SEQ ID NO: 10. Preferably the rAAV virion comprising a modified capsid protein as defined herein further comprises an MMP12 promoter controlling the expression of a transgene, preferably a transgene as defined herein.

In preferred embodiments, the modified capsid protein comprises or consists of an amino acid sequence having SEQ ID NO: 2 (AAV2 P2). Preferably, the modified capsid protein has at least about 70%, 75%, 80%, 85%, 90%, 95%, 96%, 97%, 98%, 99% or 100% sequence identity with SEQ ID NO: 2. Preferably amino acids at positions 585-602 of SEQ ID NO: 2 have at least 80% sequence identity with SEQ ID NO: 10. Preferably the rAAV virion comprising a modified capsid protein as defined herein further comprises an ADAMTS5 promoter controlling the expression of a transgene, preferably a transgene as defined herein.

In preferred embodiments, the modified capsid protein comprises or consists of an amino acid sequence having SEQ ID NO: 2 (AAV2 P2). Preferably, the modified capsid protein has at least about 70%, 75%, 80%, 85%, 90%, 95%, 96%, 97%, 98%, 99% or 100% sequence identity with SEQ ID NO: 2. Preferably amino acids at positions 585-602 of SEQ ID NO: 2 have at least 80% sequence identity with SEQ ID NO: 10. Preferably the rAAV virion comprising a modified capsid protein as defined herein further comprises an TNFα (TNF) promoter controlling the in preferred embodiments, the modified capsid protein comprises or consists of an amino acid sequence having SEQ ID NO: 2 (AAV2 P2). Preferably, the modified capsid protein has at least about 70%, 75%, 80%, 85%, 90%, 95%, 96%, 97%, 98%, 99% or 100% sequence identity with SEQ ID NO: 2. Preferably amino acids at positions 585-602 of SEQ ID NO: 2 have at least 80% sequence identity with SEQ ID NO: 10. Preferably the rAAV virion comprising a modified capsid protein as defined herein further comprises a (basic) FGF (FGF2) promoter controlling the expression of a transgene, preferably a transgene as defined herein.

In preferred embodiments, the modified capsid protein comprises or consists of an amino acid sequence having SEQ ID NO: 3 (AAV7 A6). Preferably, the modified capsid protein has at least about 70%, 75%, 80%, 85%, 90%, 95%, 96%, 97%, 98%, 99% or 100% sequence identity with SEQ ID NO: 3. Preferably amino acids at positions 587-601 of SEQ ID NO: 3 have at least 80% sequence identity with SEQ ID NO: 9. Preferably the rAAV virion comprising a modified capsid protein as defined herein further comprises an inducible promoter controlling the expression of a transgene, preferably a transgene as defined herein.

In preferred embodiments, the modified capsid protein comprises or consists of an amino acid sequence having SEQ ID NO: 3 (AAV7 A6). Preferably, the modified capsid protein has at least about 70%, 75%, 80%, 85%, 90%, 95%, 96%, 97%, 98%, 99% or 100% sequence identity with SEQ ID NO: 3. Preferably amino acids at positions 587-601 of SEQ ID NO: 3 have at least 80% sequence identity with SEQ ID NO: 9. Preferably the rAAV virion comprising a modified capsid protein as defined herein further comprises a promoter which confers expression in cells of the joint, which promoter controls the expression of a transgene, preferably a transgene as defined herein. Preferably, the promoter which confers expression in cells of the joint, is a promoter that confers expression of cells in the arthritic joint. A preferred promoter confers expression in at least one of connective tissue cells, synovial cells, sub-synovial cells, intimal macrophages, FLS, cartilage cells, chondrocytes, chondroblasts, adipocytes, osteoclasts and T-cells, preferably the promoter confers expression in cells of the FLS.

In preferred embodiments, the modified capsid protein comprises or consists of an amino acid sequence having SEQ ID NO: 3 (AAV7 A6). Preferably, the modified capsid protein has at least about 70%, 75%, 80%, 85%, 90%, 95%, 96%, 97%, 98%, 99% or 100% sequence identity with SEQ ID NO: 3. Preferably amino acids at positions 587-601 of SEQ ID NO: 3 have at least 80% sequence identity with SEQ ID NO: 9. Preferably the rAAV virion comprising a modified capsid protein as defined herein further comprises a SV40 promoter controlling the expression of a transgene, preferably a transgene as defined herein.

In preferred embodiments, the modified capsid protein comprises or consists of an amino acid sequence having SEQ ID NO: 3 (AAV7 A6). Preferably, the modified capsid protein has at least about 70%, 75%, 80%, 85%, 90%, 95%, 96%, 97%, 98%, 99% or 100% sequence identity with SEQ ID NO: 3. Preferably amino acids at positions 587-601 of SEQ ID NO: 3 have at least 80% sequence identity with SEQ ID NO: 9. Preferably the rAAV virion comprising a modified capsid protein as defined herein further comprises a CAG (cytomegalovirus early enhancer/chicken β-actin) promoter controlling the expression of a transgene, preferably a transgene as defined herein.

In preferred embodiments, the modified capsid protein comprises or consists of an amino acid sequence having SEQ ID NO: 3 (AAV7 A6). Preferably, the modified capsid protein has at least about 70%, 75%, 80%, 85%, 90%, 95%, 96%, 97%, 98%, 99% or 100% sequence identity with SEQ ID NO: 3. Preferably amino acids at positions 587-601 of SEQ ID NO: 3 have at least 80% sequence identity with SEQ ID NO: 9. Preferably the rAAV virion comprising a modified capsid protein as defined herein further comprises at a liver-specific promoter controlling the expression of a transgene, preferably a transgene as defined herein. Preferably, the liver specific-promoter is a human alpha-1 antitrypsin (hAAT) promoter.

In preferred embodiments, the modified capsid protein comprises or consists of an amino acid sequence having SEQ ID NO: 3 (AAV7 A6). Preferably, the modified capsid protein has at least about 70%, 75%, 80%, 85%, 90%, 95%, 96%, 97%, 98%, 99% or 100% sequence identity with SEQ ID NO: 3. Preferably amino acids at positions 587-601 of SEQ ID NO: 3 have at least 80% sequence identity with SEQ ID NO: 9. Preferably the rAAV virion comprising a modified capsid protein as defined herein further comprises at a liver-specific promoter controlling the expression of a transgene, preferably a transgene as defined herein. Preferably, the liver specific-promoter is a TBG (thyroxine-binding globulin) promoter.

In preferred embodiments, the modified capsid protein comprises or consists of an amino acid sequence having SEQ ID NO: 3 (AAV7 A6). Preferably, the modified capsid protein has at least about 70%, 75%, 80%, 85%, 90%, 95%, 96%, 97%, 98%, 99% or 100% sequence identity with SEQ ID NO: 3. Preferably amino acids at positions 587-601 of SEQ ID NO: 3 have at least 80% sequence identity with SEQ ID NO: 9. Preferably the rAAV virion comprising a modified capsid protein as defined herein further comprises an NFκB responsive (inducible) promoter controlling the expression of a transgene, preferably a transgene as defined herein. Preferably, the NFκB responsive (inducible) promoter is an NFκB responsive (inducible) minimal CMV promoter. Preferably, the NFκB responsive (inducible) CMV promoter is a promoter as described in Khoury et al. 2007, J Gene Med, 9:596-604.

In preferred embodiments, the modified capsid protein comprises or consists of an amino acid sequence having SEQ ID NO: 3 (AAV7 A6). Preferably, the modified capsid protein has at least about 70%, 75%, 80%, 85%, 90%, 95%, 96%, 97%, 98%, 99% or 100% sequence identity with SEQ ID NO: 3. Preferably amino acids at positions 587-601 of SEQ ID NO: 3 have at least 80% sequence identity with SEQ ID NO: 9. Preferably the rAAV virion comprising a modified capsid protein as defined herein further comprises a promoter of an inflammatory modulator controlling the expression of a transgene, preferably a transgene as defined herein. Preferably the promoter is a promoter of a pro-inflammatory cytokine gene. Preferably the promoter of a pro-inflammatory cytokine gene is a minimized promoter of a pro-inflammatory cytokine gene.

In preferred embodiments, the modified capsid protein comprises or consists of an amino acid sequence having SEQ ID NO: 3 (AAV7 A6). Preferably, the modified capsid protein has at least about 70%, 75%, 80%, 85%, 90%, 95%, 96%, 97%, 98%, 99% or 100% sequence identity with SEQ ID NO: 3. Preferably amino acids at positions 587-601 of SEQ ID NO: 3 have at least 80% sequence identity with SEQ ID NO: 9. Preferably the rAAV virion comprising a modified capsid protein as defined herein further comprises an IL-6 (HGF) promoter controlling the expression of a transgene, preferably a transgene as defined herein.

In preferred embodiments, the modified capsid protein comprises or consists of an amino acid sequence having SEQ ID NO: 3 (AAV7 A6). Preferably, the modified capsid protein has at least about 70%, 75%, 80%, 85%, 90%, 95%, 96%, 97%, 98%, 99% or 100% sequence identity with SEQ ID NO: 3. Preferably amino acids at positions 587-601 of SEQ ID NO: 3 have at least 80% sequence identity with SEQ ID NO: 9. Preferably the rAAV virion comprising a modified capsid protein as defined herein further comprises an CXCL10 promoter controlling the expression of a transgene, preferably a transgene as defined herein.

In preferred embodiments, the modified capsid protein comprises or consists of an amino acid sequence having SEQ ID NO: 3 (AAV7 A6). Preferably, the modified capsid protein has at least about 70%, 75%, 80%, 85%, 90%, 95%, 96%, 97%, 98%, 99% or 100% sequence identity with SEQ ID NO: 3. Preferably amino acids at positions 587-601 of SEQ ID NO: 3 have at least 80% sequence identity with SEQ ID NO: 9. Preferably the rAAV virion comprising a modified capsid protein as defined herein further comprises an MMP2 promoter controlling the expression of a transgene, preferably a transgene as defined herein.

In preferred embodiments, the modified capsid protein comprises or consists of an amino acid sequence having SEQ ID NO: 3 (AAV7 A6). Preferably, the modified capsid protein has at least about 70%, 75%, 80%, 85%, 90%, 95%, 96%, 97%, 98%, 99% or 100% sequence identity with SEQ ID NO: 3. Preferably amino acids at positions 587-601 of SEQ ID NO: 3 have at least 80% sequence identity with SEQ ID NO: 9. Preferably the rAAV virion comprising a modified capsid protein as defined herein further comprises an MMP13 promoter controlling the expression of a transgene, preferably a transgene as defined herein.

In preferred embodiments, the modified capsid protein comprises or consists of an amino acid sequence having SEQ ID NO: 3 (AAV7 A6). Preferably, the modified capsid protein has at least about 70%, 75%, 80%, 85%, 90%, 95%, 96%, 97%, 98%, 99% or 100% sequence identity with SEQ ID NO: 3. Preferably amino acids at positions 587-601 of SEQ ID NO: 3 have at least 80% sequence identity with SEQ ID NO: 9. Preferably the rAAV virion comprising a modified capsid protein as defined herein further comprises an ADAMDEC1 promoter controlling the expression of a transgene, preferably a transgene as defined herein.

In preferred embodiments, the modified capsid protein comprises or consists of an amino acid sequence having SEQ ID NO: 3 (AAV7 A6). Preferably, the modified capsid protein has at least about 70%, 75%, 80%, 85%, 90%, 95%, 96%, 97%, 98%, 99% or 100% sequence identity with SEQ ID NO: 3. Preferably amino acids at positions 587-601 of SEQ ID NO: 3 have at least 80% sequence identity with SEQ ID NO: 9. Preferably the rAAV virion comprising a modified capsid protein as defined herein further comprises an MMP12 promoter controlling the expression of a transgene, preferably a transgene as defined herein.

In preferred embodiments, the modified capsid protein comprises or consists of an amino acid sequence having SEQ ID NO: 3 (AAV7 A6). Preferably, the modified capsid protein has at least about 70%, 75%, 80%, 85%, 90%, 95%, 96%, 97%, 98%, 99% or 100% sequence identity with SEQ ID NO: 3. Preferably amino acids at positions 587-601 of SEQ ID NO: 3 have at least 80% sequence identity with SEQ ID NO: 9. Preferably the rAAV virion comprising a modified capsid protein as defined herein further comprises an ADAMTS5 promoter controlling the expression of a transgene, preferably a transgene as defined herein.

In preferred embodiments, the modified capsid protein comprises or consists of an amino acid sequence having SEQ ID NO: 3 (AAV7 A6). Preferably, the modified capsid protein has at least about 70%, 75%, 80%, 85%, 90%, 95%, 96%, 97%, 98%, 99% or 100% sequence identity with SEQ ID NO: 3. Preferably amino acids at positions 587-601 of SEQ ID NO: 3 have at least 80% sequence identity with SEQ ID NO: 9. Preferably the rAAV virion comprising a modified capsid protein as defined herein further comprises an TNFα (TNF) promoter controlling the expression of a transgene, preferably a transgene as defined herein.

In preferred embodiments, the modified capsid protein comprises or consists of an amino acid sequence having SEQ ID NO: 3 (AAV7 A6). Preferably, the modified capsid protein has at least about 70%, 75%, 80%, 85%, 90%, 95%, 96%, 97%, 98%, 99% or 100% sequence identity with SEQ ID NO: 3. Preferably amino acids at positions 587-601 of SEQ ID NO: 3 have at least 80% sequence identity with SEQ ID NO: 9. Preferably the rAAV virion comprising a modified capsid protein as defined herein further comprises a (basic) FGF (FGF2) promoter controlling the expression of a transgene, preferably a transgene as defined herein.

In preferred embodiments, the modified capsid protein comprises or consists of an amino acid sequence having SEQ ID NO: 4 (AAV9 A2). Preferably, the modified capsid protein has at least about 70%, 75%, 80%, 85%, 90%, 95%, 96%, 97%, 98%, 99% or 100% sequence identity with SEQ ID NO: 4. Preferably amino acids at positions 586-600 of SEQ ID NO: 4 have at least 80% sequence identity with SEQ ID NO: 8. Preferably the rAAV virion comprising a modified capsid protein as defined herein further comprises an inducible promoter controlling the expression of a transgene, preferably a transgene as defined herein.

In preferred embodiments, the modified capsid protein comprises or consists of an amino acid sequence having SEQ ID NO: 4 (AAV9 A2). Preferably, the modified capsid protein has at least about 70%, 75%, 80%, 85%, 90%, 95%, 96%, 97%, 98%, 99% or 100% sequence identity with SEQ ID NO: 4. Preferably amino acids at positions 586-600 of SEQ ID NO: 4 have at least 80% sequence identity with SEQ ID NO: 8. Preferably the rAAV virion comprising a modified capsid protein as defined herein further comprises a promoter which confers expression in cells of the joint, which promoter controls the expression of a transgene, preferably a transgene as defined herein. Preferably, the promoter which confers expression in cells of the joint, is a promoter that confers expression of cells in the arthritic joint. A preferred promoter confers expression in at least one of connective tissue cells, synovial cells, sub-synovial cells, intimal macrophages, FLS, cartilage cells, chondrocytes, chondroblasts, adipocytes, osteoclasts and T-cells, preferably the promoter confers expression in cells of the FLS.

In preferred embodiments, the modified capsid protein comprises or consists of an amino acid sequence having SEQ ID NO: 4 (AAV9 A2). Preferably, the modified capsid protein has at least about 70%, 75%, 80%, 85%, 90%, 95%, 96%, 97%, 98%, 99% or 100% sequence identity with SEQ ID NO: 4. Preferably amino acids at positions 586-600 of SEQ ID NO: 4 have at least 80% sequence identity with SEQ ID NO: 8. Preferably the rAAV virion comprising a modified capsid protein as defined herein further comprises a SV40 promoter controlling the expression of a transgene, preferably a transgene as defined herein.

In preferred embodiments, the modified capsid protein comprises or consists of an amino acid sequence having SEQ ID NO: 4 (AAV9 A2). Preferably, the modified capsid protein has at least about 70%, 75%, 80%, 85%, 90%, 95%, 96%, 97%, 98%, 99% or 100% sequence identity with SEQ ID NO: 4. Preferably amino acids at positions 586-600 of SEQ ID NO: 4 have at least 80% sequence identity with SEQ ID NO: 8. Preferably the rAAV virion comprising a modified capsid protein as defined herein further comprises a CAG (cytomegalovirus early enhancer/chicken β-actin) promoter controlling the expression of a transgene, preferably a transgene as defined herein.

In preferred embodiments, the modified capsid protein comprises or consists of an amino acid sequence having SEQ ID NO: 4 (AAV9 A2). Preferably, the modified capsid protein has at least about 70%, 75%, 80%, 85%, 90%, 95%, 96%, 97%, 98%, 99% or 100% sequence identity with SEQ ID NO: 4. Preferably amino acids at positions 586-600 of SEQ ID NO: 4 have at least 80% sequence identity with SEQ ID NO: 8. Preferably the rAAV virion comprising a modified capsid protein as defined herein further comprises a liver-specific promoter controlling the expression of a transgene, preferably a transgene as defined herein. Preferably, the liver specific-promoter is a human alpha-1 antitrypsin (hAAT) promoter.

In preferred embodiments, the modified capsid protein comprises or consists of an amino acid sequence having SEQ ID NO: 4 (AAV9 A2). Preferably, the modified capsid protein has at least about 70%, 75%, 80%, 85%, 90%, 95%, 96%, 97%, 98%, 99% or 100% sequence identity with SEQ ID NO: 4. Preferably amino acids at positions 586-600 of SEQ ID NO: 4 have at least 80% sequence identity with SEQ ID NO: 8. Preferably the rAAV virion comprising a modified capsid protein as defined herein further comprises a liver-specific promoter controlling the expression of a transgene, preferably a transgene as defined herein. Preferably, the liver specific-promoter is a TBG (thyroxine-binding globulin) promoter.

In preferred embodiments, the modified capsid protein comprises or consists of an amino acid sequence having SEQ ID NO: 4 (AAV9 A2). Preferably, the modified capsid protein has at least about 70%, 75%, 80%, 85%, 90%, 95%, 96%, 97%, 98%, 99% or 100% sequence identity with SEQ ID NO: 4. Preferably amino acids at positions 586-600 of SEQ ID NO: 4 have at least 80% sequence identity with SEQ ID NO: 8. Preferably the rAAV virion comprising a modified capsid protein as defined herein further comprises an NFκB responsive (inducible) promoter controlling the expression of a transgene, preferably a transgene as defined herein. Preferably, the NFκB responsive (inducible) promoter is an NFκB responsive (inducible) minimal CMV promoter. Preferably, the NFκB responsive (inducible) CMV promoter is a promoter as described in Khoury et al. 2007, J Gene Med, 9:596-604.

In preferred embodiments, the modified capsid protein comprises or consists of an amino acid sequence having SEQ ID NO: 4 (AAV9 A2). Preferably, the modified capsid protein has at least about 70%, 75%, 80%, 85%, 90%, 95%, 96%, 97%, 98%, 99% or 100% sequence identity with SEQ ID NO: 4. Preferably amino acids at positions 586-600 of SEQ ID NO: 4 have at least 80% sequence identity with SEQ ID NO: 8. Preferably the rAAV virion comprising a modified capsid protein as defined herein further comprises a promoter of an inflammatory modulator controlling the expression of a transgene, preferably a transgene as defined herein. Preferably the promoter is a promoter of a pro-inflammatory cytokine gene. Preferably the promoter of a pro-inflammatory cytokine gene is a minimized promoter of a pro-inflammatory cytokine gene.

In preferred embodiments, the modified capsid protein comprises or consists of an amino acid sequence having SEQ ID NO: 4 (AAV9 A2). Preferably, the modified capsid protein has at least about 70%, 75%, 80%, 85%, 90%, 95%, 96%, 97%, 98%, 99% or 100% sequence identity with SEQ ID NO: 4. Preferably amino acids at positions 586-600 of SEQ ID NO: 4 have at least 80% sequence identity with SEQ ID NO: 8. Preferably the rAAV virion comprising a modified capsid protein as defined herein further comprises an IL-6 (HGF) promoter controlling the expression of a transgene, preferably a transgene as defined herein.

In preferred embodiments, the modified capsid protein comprises or consists of an amino acid sequence having SEQ ID NO: 4 (AAV9 A2). Preferably, the modified capsid protein has at least about 70%, 75%, 80%, 85%, 90%, 95%, 96%, 97%, 98%, 99% or 100% sequence identity with SEQ ID NO: 4. Preferably amino acids at positions 586-600 of SEQ ID NO: 4 have at least 80% sequence identity with SEQ ID NO: 8. Preferably the rAAV virion comprising a modified capsid protein as defined herein further comprises an CXCL10 promoter controlling the expression of a transgene, preferably a transgene as defined herein.

In preferred embodiments, the modified capsid protein comprises or consists of an amino acid sequence having SEQ ID NO: 4 (AAV9 A2). Preferably, the modified capsid protein has at least about 70%, 75%, 80%, 85%, 90%, 95%, 96%, 97%, 98%, 99% or 100% sequence identity with SEQ ID NO: 4. Preferably amino acids at positions 586-600 of SEQ ID NO: 4 have at least 80% sequence identity with SEQ ID NO: 8. Preferably the rAAV virion comprising a modified capsid protein as defined herein further comprises an MMP2 promoter controlling the expression of a transgene, preferably a transgene as defined herein.

In preferred embodiments, the modified capsid protein comprises or consists of an amino acid sequence having SEQ ID NO: 4 (AAV9 A2). Preferably, the modified capsid protein has at least about 70%, 75%, 80%, 85%, 90%, 95%, 96%, 97%, 98%, 99% or 100% sequence identity with SEQ ID NO: 4. Preferably amino acids at positions 586-600 of SEQ ID NO: 4 have at least 80% sequence identity with SEQ ID NO: 8. Preferably the rAAV virion comprising a modified capsid protein as defined herein further comprises an MMP13 promoter controlling the expression of a transgene, preferably a transgene as defined herein.

In preferred embodiments, the modified capsid protein comprises or consists of an amino acid sequence having SEQ ID NO: 4 (AAV9 A2). Preferably, the modified capsid protein has at least about 70%, 75%, 80%, 85%, 90%, 95%, 96%, 97%, 98%, 99% or 100% sequence identity with SEQ ID NO: 4. Preferably amino acids at positions 586-600 of SEQ ID NO: 4 have at least 80% sequence identity with SEQ ID NO: 8. Preferably the rAAV virion comprising a modified capsid protein as defined herein further comprises an ADAMDEC1 promoter controlling the expression of a transgene, preferably a transgene as defined herein.

In preferred embodiments, the modified capsid protein comprises or consists of an amino acid sequence having SEQ ID NO: 4 (AAV9 A2). Preferably, the modified capsid protein has at least about 70%, 75%, 80%, 85%, 90%, 95%, 96%, 97%, 98%, 99% or 100% sequence identity with SEQ ID NO: 4. Preferably amino acids at positions 586-600 of SEQ ID NO: 4 have at least 80% sequence identity with SEQ ID NO: 8. Preferably the rAAV virion comprising a modified capsid protein as defined herein further comprises an MMP12 promoter controlling the expression of a transgene, preferably a transgene as defined herein.

In preferred embodiments, the modified capsid protein comprises or consists of an amino acid sequence having SEQ ID NO: 4 (AAV9 A2). Preferably, the modified capsid protein has at least about 70%, 75%, 80%, 85%, 90%, 95%, 96%, 97%, 98%, 99% or 100% sequence identity with SEQ ID NO: 4. Preferably amino acids at positions 586-600 of SEQ ID NO: 4 have at least 80% sequence identity with SEQ ID NO: 8. Preferably the rAAV virion comprising a modified capsid protein as defined herein further comprises an ADAMTS5 promoter controlling the expression of a transgene, preferably a transgene as defined herein.

In preferred embodiments, the modified capsid protein comprises or consists of an amino acid sequence having SEQ ID NO: 4 (AAV9 A2). Preferably, the modified capsid protein has at least about 70%, 75%, 80%, 85%, 90%, 95%, 96%, 97%, 98%, 99% or 100% sequence identity with SEQ ID NO: 4. Preferably amino acids at positions 586-600 of SEQ ID NO: 4 have at least 80% sequence identity with SEQ ID NO: 8. Preferably the rAAV virion comprising a modified capsid protein as defined herein further comprises an TNFα (TNF) promoter controlling the expression of a transgene, preferably a transgene as defined herein.

In preferred embodiments, the modified capsid protein comprises or consists of an amino acid sequence having SEQ ID NO: 4 (AAV9 A2). Preferably, the modified capsid protein has at least about 70%, 75%, 80%, 85%, 90%, 95%, 96%, 97%, 98%, 99% or 100% sequence identity with SEQ ID NO: 4. Preferably amino acids at positions 586-600 of SEQ ID NO: 4 have at least 80% sequence identity with SEQ ID NO: 8. Preferably the rAAV virion comprising a modified capsid protein as defined herein further comprises a (basic) FGF (FGF2) promoter controlling the expression of a transgene, preferably a transgene as defined herein.

In preferred embodiments, the modified capsid protein comprises or consists of an amino acid sequence having SEQ ID NO: 5 (AAVrh10 A6). Preferably, the modified capsid protein has at least about 70%, 75%, 80%, 85%, 90%, 95%, 96%, 97%, 98%, 99% or 100% sequence identity with SEQ ID NO: 5. Preferably amino acids at positions 588-602 of SEQ ID NO: 5 have at least 80% sequence identity with SEQ ID NO: 9. Preferably the rAAV virion comprising a modified capsid protein as defined herein further comprises an inducible promoter controlling the expression of a transgene, preferably a transgene as defined herein.

In preferred embodiments, the modified capsid protein comprises or consists of an amino acid sequence having SEQ ID NO: 5 (AAVrh10 A6). Preferably, the modified capsid protein has at least about 70%, 75%, 80%, 85%, 90%, 95%, 96%, 97%, 98%, 99% or 100% sequence identity with SEQ ID NO: 5. Preferably amino acids at positions 588-602 of SEQ ID NO: 5 have at least 80% sequence identity with SEQ ID NO: 9. Preferably the rAAV virion comprising a modified capsid protein as defined herein further comprises a promoter which confers expression in cells of the joint, which promoter controls the expression of a transgene, preferably a transgene as defined herein. Preferably, the promoter which confers expression in cells of the joint, is a promoter that confers expression of cells in the arthritic joint. A preferred promoter confers expression in at least one of connective tissue cells, synovial cells, sub-synovial cells, intimal macrophages, FLS, cartilage cells, chondrocytes, chondroblasts, adipocytes, osteoclasts and T-cells, preferably the promoter confers expression in cells of the FLS.

In preferred embodiments, the modified capsid protein comprises or consists of an amino acid sequence having SEQ ID NO: 5 (AAVrh10 A6). Preferably, the modified capsid protein has at least about 70%, 75%, 80%, 85%, 90%, 95%, 96%, 97%, 98%, 99% or 100% sequence identity with SEQ ID NO: 5. Preferably amino acids at positions 588-602 of SEQ ID NO: 5 have at least 80% sequence identity with SEQ ID NO: 9. Preferably the rAAV virion comprising a modified capsid protein as defined herein further comprises a SV40 promoter controlling the expression of a transgene, preferably a transgene as defined herein.

In preferred embodiments, the modified capsid protein comprises or consists of an amino acid sequence having SEQ ID NO: 5 (AAVrh10 A6). Preferably, the modified capsid protein has at least about 70%, 75%, 80%, 85%, 90%, 95%, 96%, 97%, 98%, 99% or 100% sequence identity with SEQ ID NO: 5. Preferably amino acids at positions 588-602 of SEQ ID NO: 5 have at least 80% sequence identity with SEQ ID NO: 9. Preferably the rAAV virion comprising a modified capsid protein as defined herein further comprises a CAG (cytomegalovirus early enhancer/chicken β-actin) promoter controlling the expression of a transgene, preferably a transgene as defined herein.

In preferred embodiments, the modified capsid protein comprises or consists of an amino acid sequence having SEQ ID NO: 5 (AAVrh10 A6). Preferably, the modified capsid protein has at least about 70%, 75%, 80%, 85%, 90%, 95%, 96%, 97%, 98%, 99% or 100% sequence identity with SEQ ID NO: 5. Preferably amino acids at positions 588-602 of SEQ ID NO: 5 have at least 80% sequence identity with SEQ ID NO: 9. Preferably the rAAV virion comprising a modified capsid protein as defined herein further comprises a liver-specific promoter controlling the expression of a transgene, preferably a transgene as defined herein. Preferably, the liver specific-promoter is a human alpha-1 antitrypsin (hAAT) promoter.

In preferred embodiments, the modified capsid protein comprises or consists of an amino acid sequence having SEQ ID NO: 5 (AAVrh10 A6). Preferably, the modified capsid protein has at least about 70%, 75%, 80%, 85%, 90%, 95%, 96%, 97%, 98%, 99% or 100% sequence identity with SEQ ID NO: 5. Preferably amino acids at positions 588-602 of SEQ ID NO: 5 have at least 80% sequence identity with SEQ ID NO: 9. Preferably the rAAV virion comprising a modified capsid protein as defined herein further comprises a liver-specific promoter controlling the expression of a transgene, preferably a transgene as defined herein. Preferably, the liver specific-promoter is a TBG (thyroxine-binding globulin) promoter.

In preferred embodiments, the modified capsid protein comprises or consists of an amino acid sequence having SEQ ID NO: 5 (AAVrh10 A6). Preferably, the modified capsid protein has at least about 70%, 75%, 80%, 85%, 90%, 95%, 96%, 97%, 98%, 99% or 100% sequence identity with SEQ ID NO: 5. Preferably amino acids at positions 588-602 of SEQ ID NO: 5 have at least 80% sequence identity with SEQ ID NO: 9. Preferably the rAAV virion comprising a modified capsid protein as defined herein further comprises an NFκB responsive (inducible) promoter controlling the expression of a transgene, preferably a transgene as defined herein. Preferably, the NFκB responsive (inducible) promoter is an NFκB responsive (inducible) minimal CMV promoter. Preferably, the NFκB responsive (inducible) CMV promoter is a promoter as described in Khoury et al. 2007, J Gene Med, 9:596-604.

In preferred embodiments, the modified capsid protein comprises or consists of an amino acid sequence having SEQ ID NO: 5 (AAVrh10 A6). Preferably, the modified capsid protein has at least about 70%, 75%, 80%, 85%, 90%, 95%, 96%, 97%, 98%, 99% or 100% sequence identity with SEQ ID NO: 5. Preferably amino acids at positions 588-602 of SEQ ID NO: 5 have at least 80% sequence identity with SEQ ID NO: 9. Preferably the rAAV virion comprising a modified capsid protein as defined herein further comprises a promoter of an inflammatory modulator controlling the expression of a transgene, preferably a transgene as defined herein. Preferably the promoter is a promoter of a pro-inflammatory cytokine gene. Preferably the promoter of a pro-inflammatory cytokine gene is a minimized promoter of a pro-inflammatory cytokine gene.

In preferred embodiments, the modified capsid protein comprises or consists of an amino acid sequence having SEQ ID NO: 5 (AAVrh10 A6). Preferably, the modified capsid protein has at least about 70%, 75%, 80%, 85%, 90%, 95%, 96%, 97%, 98%, 99% or 100% sequence identity with SEQ ID NO: 5. Preferably amino acids at positions 588-602 of SEQ ID NO: 5 have at least 80% sequence identity with SEQ ID NO: 9. Preferably the rAAV virion comprising a modified capsid protein as defined herein further comprises at an IL-6 (HGF) promoter controlling the expression of a transgene, preferably a transgene as defined herein.

In preferred embodiments, the modified capsid protein comprises or consists of an amino acid sequence having SEQ ID NO: 5 (AAVrh10 A6). Preferably, the modified capsid protein has at least about 70%, 75%, 80%, 85%, 90%, 95%, 96%, 97%, 98%, 99% or 100% sequence identity with SEQ ID NO: 5. Preferably amino acids at positions 588-602 of SEQ ID NO: 5 have at least 80% sequence identity with SEQ ID NO: 9. Preferably the rAAV virion comprising a modified capsid protein as defined herein further comprises an CXCL10 promoter controlling the expression of a transgene, preferably a transgene as defined herein.

In preferred embodiments, the modified capsid protein comprises or consists of an amino acid sequence having SEQ ID NO: 5 (AAVrh10 A6). Preferably, the modified capsid protein has at least about 70%, 75%, 80%, 85%, 90%, 95%, 96%, 97%, 98%, 99% or 100% sequence identity with SEQ ID NO: 5. Preferably amino acids at positions 588-602 of SEQ ID NO: 5 have at least 80% sequence identity with SEQ ID NO: 9. Preferably the rAAV virion comprising a modified capsid protein as defined herein further comprises at an MMP2 promoter controlling the expression of a transgene, preferably a transgene as defined herein.

In preferred embodiments, the modified capsid protein comprises or consists of an amino acid sequence having SEQ ID NO: 5 (AAVrh10 A6). Preferably, the modified capsid protein has at least about 70%, 75%, 80%, 85%, 90%, 95%, 96%, 97%, 98%, 99% or 100% sequence identity with SEQ ID NO: 5. Preferably amino acids at positions 588-602 of SEQ ID NO: 5 have at least 80% sequence identity with SEQ ID NO: 9. Preferably the rAAV virion comprising a modified capsid protein as defined herein further comprises an MMP13 promoter controlling the expression of a transgene, preferably a transgene as defined herein.

In preferred embodiments, the modified capsid protein comprises or consists of an amino acid sequence having SEQ ID NO: 5 (AAVrh10 A6). Preferably, the modified capsid protein has at least about 70%, 75%, 80%, 85%, 90%, 95%, 96%, 97%, 98%, 99% or 100% sequence identity with SEQ ID NO: 5. Preferably amino acids at positions 588-602 of SEQ ID NO: 5 have at least 80% sequence identity with SEQ ID NO: 9. Preferably the rAAV virion comprising a modified capsid protein as defined herein further comprises an ADAMDEC1 promoter controlling the expression of a transgene, preferably a transgene as defined herein.

In preferred embodiments, the modified capsid protein comprises or consists of an amino acid sequence having SEQ ID NO: 5 (AAVrh10 A6). Preferably, the modified capsid protein has at least about 70%, 75%, 80%, 85%, 90%, 95%, 96%, 97%, 98%, 99% or 100% sequence identity with SEQ ID NO: 5. Preferably amino acids at positions 588-602 of SEQ ID NO: 5 have at least 80% sequence identity with SEQ ID NO: 9. Preferably the rAAV virion comprising a modified capsid protein as defined herein further comprises an MMP12 promoter controlling the expression of a transgene, preferably a transgene as defined herein.

In preferred embodiments, the modified capsid protein comprises or consists of an amino acid sequence having SEQ ID NO: 5 (AAVrh10 A6). Preferably, the modified capsid protein has at least about 70%, 75%, 80%, 85%, 90%, 95%, 96%, 97%, 98%, 99% or 100% sequence identity with SEQ ID NO: 5. Preferably amino acids at positions 588-602 of SEQ ID NO: 5 have at least 80% sequence identity with SEQ ID NO: 9. Preferably the rAAV virion comprising a modified capsid protein as defined herein further comprises an ADAMTS5 promoter controlling the expression of a transgene, preferably a transgene as defined herein.

In preferred embodiments, the modified capsid protein comprises or consists of an amino acid sequence having SEQ ID NO: 5 (AAVrh10 A6). Preferably, the modified capsid protein has at least about 70%, 75%, 80%, 85%, 90%, 95%, 96%, 97%, 98%, 99% or 100% sequence identity with SEQ ID NO: 5. Preferably amino acids at positions 588-602 of SEQ ID NO: 5 have at least 80% sequence identity with SEQ ID NO: 9. Preferably the rAAV virion comprising a modified capsid protein as defined herein further comprises an TNFα (TNF) promoter controlling the expression of a transgene, preferably a transgene as defined herein.

In preferred embodiments, the modified capsid protein comprises or consists of an amino acid sequence having SEQ ID NO: 5 (AAVrh10 A6). Preferably, the modified capsid protein has at least about 70%, 75%, 80%, 85%, 90%, 95%, 96%, 97%, 98%, 99% or 100% sequence identity with SEQ ID NO: 5. Preferably amino acids at positions 588-602 of SEQ ID NO: 5 have at least 80% sequence identity with SEQ ID NO: 9. Preferably the rAAV virion comprising a modified capsid protein as defined herein further comprises a (basic) FGF (FGF2) promoter controlling the expression of a transgene, preferably a transgene as defined herein.

In preferred embodiments, the modified capsid protein comprises or consists of an amino acid sequence having SEQ ID NO: 6 (AAVrh10 A2). Preferably, the modified capsid protein has at least about 70%, 75%, 80%, 85%, 90%, 95%, 96%, 97%, 98%, 99% or 100% sequence identity with SEQ ID NO: 6. Preferably amino acids at positions 588-602 of SEQ ID NO: 6 have at least 80% sequence identity with SEQ ID NO: 8. Preferably the rAAV virion comprising a modified capsid protein as defined herein further comprises an inducible promoter controlling the expression of a transgene, preferably a transgene as defined herein.

In preferred embodiments, the modified capsid protein comprises or consists of an amino acid sequence having SEQ ID NO: 6 (AAVrh10 A2). Preferably, the modified capsid protein has at least about 70%, 75%, 80%, 85%, 90%, 95%, 96%, 97%, 98%, 99% or 100% sequence identity with SEQ ID NO: 6. Preferably amino acids at positions 588-602 of SEQ ID NO: 6 have at least 80% sequence identity with SEQ ID NO: 8. Preferably the rAAV virion comprising a modified capsid protein as defined herein further comprises a promoter which confers expression in cells of the joint, which promoter controls the expression of a transgene, preferably a transgene as defined herein. Preferably, the promoter which confers expression in cells of the joint, is a promoter that confers expression of cells in the arthritic joint. A preferred promoter confers expression in at least one of connective tissue cells, synovial cells, sub-synovial cells, intimal macrophages, FLS, cartilage cells, chondrocytes, chondroblasts, adipocytes, osteoclasts and T-cells, preferably the promoter confers expression in cells of the FLS.

In preferred embodiments, the modified capsid protein comprises or consists of an amino acid sequence having SEQ ID NO: 6 (AAVrh10 A2). Preferably, the modified capsid protein has at least about 70%, 75%, 80%, 85%, 90%, 95%, 96%, 97%, 98%, 99% or 100% sequence identity with SEQ ID NO: 6. Preferably amino acids at positions 588-602 of SEQ ID NO: 6 have at least 80% sequence identity with SEQ ID NO: 8. Preferably the rAAV virion comprising a modified capsid protein as defined herein further comprises a SV40 promoter controlling the expression of a transgene, preferably a transgene as defined herein.

In preferred embodiments, the modified capsid protein comprises or consists of an amino acid sequence having SEQ ID NO: 6 (AAVrh10 A2). Preferably, the modified capsid protein has at least about 70%, 75%, 80%, 85%, 90%, 95%, 96%, 97%, 98%, 99% or 100% sequence identity with SEQ ID NO: 6. Preferably amino acids at positions 588-602 of SEQ ID NO: 6 have at least 80% sequence identity with SEQ ID NO: 8. Preferably the rAAV virion comprising a modified capsid protein as defined herein further comprises a CAG (cytomegalovirus early enhancer/chicken β-actin) promoter controlling the expression of a transgene, preferably a transgene as defined herein.

In preferred embodiments, the modified capsid protein comprises or consists of an amino acid sequence having SEQ ID NO: 6 (AAVrh10 A2). Preferably, the modified capsid protein has at least about 70%, 75%, 80%, 85%, 90%, 95%, 96%, 97%, 98%, 99% or 100% sequence identity with SEQ ID NO: 6. Preferably amino acids at positions 588-602 of SEQ ID NO: 6 have at least 80% sequence identity with SEQ ID NO: 8. Preferably the rAAV virion comprising a modified capsid protein as defined herein further comprises a liver-specific promoter controlling the expression of a transgene, preferably a transgene as defined herein. Preferably, the liver specific-promoter is a human alpha-1 antitrypsin (hAAT) promoter.

In preferred embodiments, the modified capsid protein comprises or consists of an amino acid sequence having SEQ ID NO: 6 (AAVrh10 A2). Preferably, the modified capsid protein has at least about 70%, 75%, 80%, 85%, 90%, 95%, 96%, 97%, 98%, 99% or 100% sequence identity with SEQ ID NO: 6. Preferably amino acids at positions 588-602 of SEQ ID NO: 6 have at least 80% sequence identity with SEQ ID NO: 8. Preferably the rAAV virion comprising a modified capsid protein as defined herein further comprises a liver-specific promoter controlling the expression of a transgene, preferably a transgene as defined herein. Preferably, the liver specific-promoter is a TBG (thyroxine-binding globulin) promoter.

In preferred embodiments, the modified capsid protein comprises or consists of an amino acid sequence having SEQ ID NO: 6 (AAVrh10 A2). Preferably, the modified capsid protein has at least about 70%, 75%, 80%, 85%, 90%, 95%, 96%, 97%, 98%, 99% or 100% sequence identity with SEQ ID NO: 6. Preferably amino acids at positions 588-602 of SEQ ID NO: 6 have at least 80% sequence identity with SEQ ID NO: 8. Preferably the rAAV virion comprising a modified capsid protein as defined herein further comprises an NFκB responsive (inducible) promoter controlling the expression of a transgene, preferably a transgene as defined herein. Preferably, the NFκB responsive (inducible) promoter is an NFκB responsive (inducible) minimal CMV promoter. Preferably, the NFκB responsive (inducible) CMV promoter is a promoter as described in Khoury et al. 2007, J Gene Med, 9:596-604.

In preferred embodiments, the modified capsid protein comprises or consists of an amino acid sequence having SEQ ID NO: 6 (AAVrh10 A2). Preferably, the modified capsid protein has at least about 70%, 75%, 80%, 85%, 90%, 95%, 96%, 97%, 98%, 99% or 100% sequence identity with SEQ ID NO: 6. Preferably amino acids at positions 588-602 of SEQ ID NO: 6 have at least 80% sequence identity with SEQ ID NO: 8. Preferably the rAAV virion comprising a modified capsid protein as defined herein further comprises a promoter of an inflammatory modulator controlling the expression of a transgene, preferably a transgene as defined herein. Preferably the promoter is a promoter of a pro-inflammatory cytokine gene. Preferably the promoter of a pro-inflammatory cytokine gene is a minimized promoter of a pro-inflammatory cytokine gene.

In preferred embodiments, the modified capsid protein comprises or consists of an amino acid sequence having SEQ ID NO: 6 (AAVrh10 A2). Preferably, the modified capsid protein has at least about 70%, 75%, 80%, 85%, 90%, 95%, 96%, 97%, 98%, 99% or 100% sequence identity with SEQ ID NO: 6. Preferably amino acids at positions 588-602 of SEQ ID NO: 6 have at least 80% sequence identity with SEQ ID NO: 8. Preferably the rAAV virion comprising a modified capsid protein as defined herein further comprises an IL-6 (HGF) promoter controlling the expression of a transgene, preferably a transgene as defined herein.

In preferred embodiments, the modified capsid protein comprises or consists of an amino acid sequence having SEQ ID NO: 6 (AAVrh10 A2). Preferably, the modified capsid protein has at least about 70%, 75%, 80%, 85%, 90%, 95%, 96%, 97%, 98%, 99% or 100% sequence identity with SEQ ID NO: 6. Preferably amino acids at positions 588-602 of SEQ ID NO: 6 have at least 80% sequence identity with SEQ ID NO: 8. Preferably the rAAV virion comprising a modified capsid protein as defined herein further comprises an CXCL10 promoter controlling the expression of a transgene, preferably a transgene as defined herein.

In preferred embodiments, the modified capsid protein comprises or consists of an amino acid sequence having SEQ ID NO: 6 (AAVrh10 A2). Preferably, the modified capsid protein has at least about 70%, 75%, 80%, 85%, 90%, 95%, 96%, 97%, 98%, 99% or 100% sequence identity with SEQ ID NO: 6. Preferably amino acids at positions 588-602 of SEQ ID NO: 6 have at least 80% sequence identity with SEQ ID NO: 8. Preferably the rAAV virion comprising a modified capsid protein as defined herein further comprises an MMP2 promoter controlling the expression of a transgene, preferably a transgene as defined herein.

In preferred embodiments, the modified capsid protein comprises or consists of an amino acid sequence having SEQ ID NO: 6 (AAVrh10 A2). Preferably, the modified capsid protein has at least about 70%, 75%, 80%, 85%, 90%, 95%, 96%, 97%, 98%, 99% or 100% sequence identity with SEQ ID NO: 6. Preferably amino acids at positions 588-602 of SEQ ID NO: 6 have at least 80% sequence identity with SEQ ID NO: 8. Preferably the rAAV virion comprising a modified capsid protein as defined herein further comprises an MMP13 promoter controlling the expression of a transgene, preferably a transgene as defined herein.

In preferred embodiments, the modified capsid protein comprises or consists of an amino acid sequence having SEQ ID NO: 6 (AAVrh10 A2). Preferably, the modified capsid protein has at least about 70%, 75%, 80%, 85%, 90%, 95%, 96%, 97%, 98%, 99% or 100% sequence identity with SEQ ID NO: 6. Preferably amino acids at positions 588-602 of SEQ ID NO: 6 have at least 80% sequence identity with SEQ ID NO: 8. Preferably the rAAV virion comprising a modified capsid protein as defined herein further comprises an ADAMDEC1 promoter controlling the expression of a transgene, preferably a transgene as defined herein.

In preferred embodiments, the modified capsid protein comprises or consists of an amino acid sequence having SEQ ID NO: 6 (AAVrh10 A2). Preferably, the modified capsid protein has at least about 70%, 75%, 80%, 85%, 90%, 95%, 96%, 97%, 98%, 99% or 100% sequence identity with SEQ ID NO: 6. Preferably amino acids at positions 588-602 of SEQ ID NO: 6 have at least 80% sequence identity with SEQ ID NO: 8. Preferably the rAAV virion comprising a modified capsid protein as defined herein further comprises an MMP12 promoter controlling the expression of a transgene, preferably a transgene as defined herein.

In preferred embodiments, the modified capsid protein comprises or consists of an amino acid sequence having SEQ ID NO: 6 (AAVrh10 A2). Preferably, the modified capsid protein has at least about 70%, 75%, 80%, 85%, 90%, 95%, 96%, 97%, 98%, 99% or 100% sequence identity with SEQ ID NO: 6. Preferably amino acids at positions 588-602 of SEQ ID NO: 6 have at least 80% sequence identity with SEQ ID NO: 8. Preferably the rAAV virion comprising a modified capsid protein as defined herein further comprises an ADAMTS5 promoter controlling the expression of a transgene, preferably a transgene as defined herein.

In preferred embodiments, the modified capsid protein comprises or consists of an amino acid sequence having SEQ ID NO: 6 (AAVrh10 A2). Preferably, the modified capsid protein has at least about 70%, 75%, 80%, 85%, 90%, 95%, 96%, 97%, 98%, 99% or 100% sequence identity with SEQ ID NO: 6. Preferably amino acids at positions 588-602 of SEQ ID NO: 6 have at least 80% sequence identity with SEQ ID NO: 8. Preferably the rAAV virion comprising a modified capsid protein as defined herein further comprises an TNFα (TNF) promoter controlling the expression of a transgene, preferably a transgene as defined herein.

In preferred embodiments, the modified capsid protein comprises or consists of an amino acid sequence having SEQ ID NO: 6 (AAVrh10 A2). Preferably, the modified capsid protein has at least about 70%, 75%, 80%, 85%, 90%, 95%, 96%, 97%, 98%, 99% or 100% sequence identity with SEQ ID NO: 6. Preferably amino acids at positions 588-602 of SEQ ID NO: 6 have at least 80% sequence identity with SEQ ID NO: 8. Preferably the rAAV virion comprising a modified capsid protein as defined herein further comprises a (basic) FGF (FGF2) promoter controlling the expression of a transgene, preferably a transgene as defined herein.

In preferred embodiments, the modified capsid protein comprises or consists of an amino acid sequence having SEQ ID NO: 7 (AAV-DJ-QR-P2). Preferably, the modified capsid protein has at least about 70%, 75%, 80%, 85%, 90%, 95%, 96%, 97%, 98%, 99% or 100% sequence identity with SEQ ID NO: 7. Preferably amino acids at positions 587-604 of SEQ ID NO: 7 have at least 80% sequence identity with SEQ ID NO: 12. Preferably the rAAV virion comprising a modified capsid protein as defined herein further comprises an inducible promoter controlling the expression of a transgene, preferably a transgene as defined herein.

In preferred embodiments, the modified capsid protein comprises or consists of an amino acid sequence having SEQ ID NO: 7 (AAV-DJ-QR-P2). Preferably, the modified capsid protein has at least about 70%, 75%, 80%, 85%, 90%, 95%, 96%, 97%, 98%, 99% or 100% sequence identity with SEQ ID NO: 7. Preferably amino acids at positions 587-604 of SEQ ID NO: 7 have at least 80% sequence identity with SEQ ID NO: 12. Preferably the rAAV virion comprising a modified capsid protein as defined herein further comprises a promoter which confers expression in cells of the joint, which promoter controls the expression of a transgene, preferably a transgene as defined herein. Preferably, the promoter which confers expression in cells of the joint, is a promoter that confers expression of cells in the arthritic joint. A preferred promoter confers expression in at least one of connective tissue cells, synovial cells, sub-synovial cells, intimal macrophages, FLS, cartilage cells, chondrocytes, chondroblasts, adipocytes, osteoclasts and T-cells, preferably the promoter confers expression in cells of the FLS.

In preferred embodiments, the modified capsid protein comprises or consists of an amino acid sequence having SEQ ID NO: 7 (AAV-DJ-QR-P2). Preferably, the modified capsid protein has at least about 70%, 75%, 80%, 85%, 90%, 95%, 96%, 97%, 98%, 99% or 100% sequence identity with SEQ ID NO: 7. Preferably amino acids at positions 587-604 of SEQ ID NO: 7 have at least 80% sequence identity with SEQ ID NO: 12. Preferably the rAAV virion comprising a modified capsid protein as defined herein further comprises a SV40 promoter controlling the expression of a transgene, preferably a transgene as defined herein.

In preferred embodiments, the modified capsid protein comprises or consists of an amino acid sequence having SEQ ID NO: 7 (AAV-DJ-QR-P2). Preferably, the modified capsid protein has at least about 70%, 75%, 80%, 85%, 90%, 95%, 96%, 97%, 98%, 99% or 100% sequence identity with SEQ ID NO: 7. Preferably amino acids at positions 587-604 of SEQ ID NO: 7 have at least 80% sequence identity with SEQ ID NO: 12. Preferably the rAAV virion comprising a modified capsid protein as defined herein further comprises a CAG (cytomegalovirus early enhancer/chicken B-actin) promoter controlling the expression of a transgene, preferably a transgene as defined herein.

In preferred embodiments, the modified capsid protein comprises or consists of an amino acid sequence having SEQ ID NO: 7 (AAV-DJ-QR-P2). Preferably, the modified capsid protein has at least about 70%, 75%, 80%, 85%, 90%, 95%, 96%, 97%, 98%, 99% or 100% sequence identity with SEQ ID NO: 7. Preferably amino acids at positions 587-604 of SEQ ID NO: 7 have at least 80% sequence identity with SEQ ID NO: 12. Preferably the rAAV virion comprising a modified capsid protein as defined herein further comprises a liver-specific promoter controlling the expression of a transgene, preferably a transgene as defined herein. Preferably, the liver specific-promoter is a human alpha-1 antitrypsin (hAAT) promoter.

In preferred embodiments, the modified capsid protein comprises or consists of an amino acid sequence having SEQ ID NO: 7 (AAV-DJ-QR-P2). Preferably, the modified capsid protein has at least about 70%, 75%, 80%, 85%, 90%, 95%, 96%, 97%, 98%, 99% or 100% sequence identity with SEQ ID NO: 7. Preferably amino acids at positions 587-604 of SEQ ID NO: 7 have at least 80% sequence identity with SEQ ID NO: 12. Preferably the rAAV virion comprising a modified capsid protein as defined herein further comprises a liver-specific promoter controlling the expression of a transgene, preferably a transgene as defined herein. Preferably, the liver specific-promoter is a TBG (thyroxine-binding globulin) promoter.

In preferred embodiments, the modified capsid protein comprises or consists of an amino acid sequence having SEQ ID NO: 7 (AAV-DJ-QR-P2). Preferably, the modified capsid protein has at least about 70%, 75%, 80%, 85%, 90%, 95%, 96%, 97%, 98%, 99% or 100% sequence identity with SEQ ID NO: 7. Preferably amino acids at positions 587-604 of SEQ ID NO: 7 have at least 80% sequence identity with SEQ ID NO: 12. Preferably the rAAV virion comprising a modified capsid protein as defined herein further comprises an NFκB responsive (inducible) promoter controlling the expression of a transgene, preferably a transgene as defined herein. Preferably, the NFκB responsive (inducible) promoter is an NFκB responsive (inducible) minimal CMV promoter. Preferably, the NFκB responsive (inducible) CMV promoter is a promoter as described in Khoury et al. 2007, J Gene Med, 9:596-604.

In preferred embodiments, the modified capsid protein comprises or consists of an amino acid sequence having SEQ ID NO: 7 (AAV-DJ-QR-P2). Preferably, the modified capsid protein has at least about 70%, 75%, 80%, 85%, 90%, 95%, 96%, 97%, 98%, 99% or 100% sequence identity with SEQ ID NO: 7. Preferably amino acids at positions 587-604 of SEQ ID NO: 7 have at least 80% sequence identity with SEQ ID NO: 12. Preferably the rAAV virion comprising a modified capsid protein as defined herein further comprises a promoter of an inflammatory modulator controlling the expression of a transgene, preferably a transgene as defined herein. Preferably the promoter is a promoter of a pro-inflammatory cytokine gene. Preferably the promoter of a pro-inflammatory cytokine gene is a minimized promoter of a pro-inflammatory cytokine gene.

In preferred embodiments, the modified capsid protein comprises or consists of an amino acid sequence having SEQ ID NO: 7 (AAV-DJ-QR-P2). Preferably, the modified capsid protein has at least about 70%, 75%, 80%, 85%, 90%, 95%, 96%, 97%, 98%, 99% or 100% sequence identity with SEQ ID NO: 7. Preferably amino acids at positions 587-604 of SEQ ID NO: 7 have at least 80% sequence identity with SEQ ID NO: 12. Preferably the rAAV virion comprising a modified capsid protein as defined herein further comprises an IL-6 (HGF) promoter controlling the expression of a transgene, preferably a transgene as defined herein.

In preferred embodiments, the modified capsid protein comprises or consists of an amino acid sequence having SEQ ID NO: 7 (AAV-DJ-QR-P2). Preferably, the modified capsid protein has at least about 70%, 75%, 80%, 85%, 90%, 95%, 96%, 97%, 98%, 99% or 100% sequence identity with SEQ ID NO: 7. Preferably amino acids at positions 587-604 of SEQ ID NO: 7 have at least 80% sequence identity with SEQ ID NO: 12. Preferably the rAAV virion comprising a modified capsid protein as defined herein further comprises an CXCL10 promoter controlling the expression of a transgene, preferably a transgene as defined herein.

In preferred embodiments, the modified capsid protein comprises or consists of an amino acid sequence having SEQ ID NO: 7 (AAV-DJ-QR-P2). Preferably, the modified capsid protein has at least about 70%, 75%, 80%, 85%, 90%, 95%, 96%, 97%, 98%, 99% or 100% sequence identity with SEQ ID NO: 7. Preferably amino acids at positions 587-604 of SEQ ID NO: 7 have at least 80% sequence identity with SEQ ID NO: 12. Preferably the rAAV virion comprising a modified capsid protein as defined herein further comprises an MMP2 promoter controlling the expression of a transgene, preferably a transgene as defined herein.

In preferred embodiments, the modified capsid protein comprises or consists of an amino acid sequence having SEQ ID NO: 7 (AAV-DJ-QR-P2). Preferably, the modified capsid protein has at least about 70%, 75%, 80%, 85%, 90%, 95%, 96%, 97%, 98%, 99% or 100% sequence identity with SEQ ID NO: 7. Preferably amino acids at positions 587-604 of SEQ ID NO: 7 have at least 80% sequence identity with SEQ ID NO: 12. Preferably the rAAV virion comprising a modified capsid protein as defined herein further comprises an MMP13 promoter controlling the expression of a transgene, preferably a transgene as defined herein.

In preferred embodiments, the modified capsid protein comprises or consists of an amino acid sequence having SEQ ID NO: 7 (AAV-DJ-QR-P2). Preferably, the modified capsid protein has at least about 70%, 75%, 80%, 85%, 90%, 95%, 96%, 97%, 98%, 99% or 100% sequence identity with SEQ ID NO: 7. Preferably amino acids at positions 587-604 of SEQ ID NO: 7 have at least 80% sequence identity with SEQ ID NO: 12. Preferably the rAAV virion comprising a modified capsid protein as defined herein further comprises an ADAMDEC1 promoter controlling the expression of a transgene, preferably a transgene as defined herein.

In preferred embodiments, the modified capsid protein comprises or consists of an amino acid sequence having SEQ ID NO: 7 (AAV-DJ-QR-P2). Preferably, the modified capsid protein has at least about 70%, 75%, 80%, 85%, 90%, 95%, 96%, 97%, 98%, 99% or 100% sequence identity with SEQ ID NO: 7. Preferably amino acids at positions 587-604 of SEQ ID NO: 7 have at least 80% sequence identity with SEQ ID NO: 12. Preferably the rAAV virion comprising a modified capsid protein as defined herein further comprises an MMP12 promoter controlling the expression of a transgene, preferably a transgene as defined herein.

In preferred embodiments, the modified capsid protein comprises or consists of an amino acid sequence having SEQ ID NO: 7 (AAV-DJ-QR-P2). Preferably, the modified capsid protein has at least about 70%, 75%, 80%, 85%, 90%, 95%, 96%, 97%, 98%, 99% or 100% sequence identity with SEQ ID NO: 7. Preferably amino acids at positions 587-604 of SEQ ID NO: 7 have at least 80% sequence identity with SEQ ID NO: 12. Preferably the rAAV virion comprising a modified capsid protein as defined herein further comprises an ADAMTS5 promoter controlling the expression of a transgene, preferably a transgene as defined herein.

In preferred embodiments, the modified capsid protein comprises or consists of an amino acid sequence having SEQ ID NO: 7 (AAV-DJ-QR-P2). Preferably, the modified capsid protein has at least about 70%, 75%, 80%, 85%, 90%, 95%, 96%, 97%, 98%, 99% or 100% sequence identity with SEQ ID NO: 7. Preferably amino acids at positions 587-604 of SEQ ID NO: 7 have at least 80% sequence identity with SEQ ID NO: 12. Preferably the rAAV virion comprising a modified capsid protein as defined herein further comprises an TNFα (TNF) promoter controlling the expression of a transgene, preferably a transgene as defined herein.

In preferred embodiments, the modified capsid protein comprises or consists of an amino acid sequence having SEQ ID NO: 7 (AAV-DJ-QR-P2). Preferably, the modified capsid protein has at least about 70%, 75%, 80%, 85%, 90%, 95%, 96%, 97%, 98%, 99% or 100% sequence identity with SEQ ID NO: 7. Preferably amino acids at positions 587-604 of SEQ ID NO: 7 have at least 80% sequence identity with SEQ ID NO: 12. Preferably the rAAV virion comprising a modified capsid protein as defined herein further comprises a (basic) FGF (FGF2) promoter controlling the expression of a transgene, preferably a transgene as defined herein.

In a second aspect, the present invention relates to an rAAV composition for use in treating, preventing or suppressing symptoms associated with an arthritic disease, wherein the rAAV composition comprises an rAAV virion of the invention and a pharmaceutically acceptable carrier, diluant, solubilizer, filler, preservative and/or excipient, preferably a pharmaceutically acceptable carrier. Such pharmaceutically acceptable carrier, diluents, solubilizer, filler, preservative and/or excipient may for instance be found in Remington: The Science and Practice of Pharmacy, 20th Edition. Baltimore, MD: Lippincott Williams & Wilkins, 2000. Any suitable pharmaceutically acceptable carrier, diluant, solubilizer, filler, preservative and/or excipient can be used in the present compositions (See e.g., Remington: The Science and Practice of Pharmacy, Alfonso R. Gennaro (Editor) Mack Publishing Company, April 1997). Preferred pharmaceutical forms would be in combination with sterile saline, dextrose solution, or buffered solution, or other pharmaceutically acceptable sterile fluids. Alternatively, a solid carrier may be used such as, for example, microcarrier beads.

Pharmaceutical compositions are typically sterile and stable under the conditions of manufacture and storage. Pharmaceutical compositions may be formulated as a solution, microemulsion, liposome, or other ordered structure suitable to accommodate high drug concentration. The carrier may be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. The parvoviral virion may be administered as a bolus or in a controlled release formulation, for example in a composition which includes a slow release polymer or other carriers that will protect the compound against rapid release, including implants and microencapsulated delivery systems. Biodegradable, biocompatible polymers may for example be used, such as ethylene vinyl acetate, polyanhydrides, polyglycolic acid, collagen, polyorthoesters, polylactic acid and polylactic, polyglycolic copolymers (PLG). As used herein, "pharmaceutically acceptable carrier" or "excipient" preferably includes any and all solvents, dispersion media, coatings, antibacterial and antifungal agents, isotonic and absorption delaying agents, and the like that are physiologically compatible. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated.

It may be advantageous to formulate parenteral compositions in dosage unit form for ease of administration and uniformity of dosage. "Dosage unit form" as used herein refers to physically discrete units suited as unitary dosages for subjects to be treated; each unit containing a predetermined quantity of active compound calculated to produce the desired therapeutic effect in association with the required pharmaceutical carrier. The specification for the dosage unit forms of the invention may be dictated by the unique characteristics of the active compound and the particular therapeutic effect to be achieved, and by the limitations inherent in the art of compounding such an active compound for the treatment of a condition in individuals.

Supplementary active compounds can also be incorporated into the pharmaceutical compositions of the invention. Guidance on co-administration of additional therapeutics may for example be found in the Compendium of Pharmaceutical and Specialties (CPS) of the Canadian Pharmacists Association.

In an embodiment, the rAAV composition further comprises empty particles (i.e., capsid-only particles, thus not comprising an rAAV genome). Therefore, alternatively, or in combination with another embodiment, in a further embodiment of the present invention, the rAAV composition of the invention further comprises an empty capsid in a ratio of empty capsid to rAAV virion of at least 1:1, more preferably at least 5:1, even more preferably at least 10:1. The rAAV composition can comprise the rAAV virion as defined above and an empty capsid, such as for example defined in WO 2016/055437, which is herein incorporated by reference, and as described in Aalbers et al. (2017) Hum. Gene Ther. 28 (2): 168-178. The empty capsid can be of the same serotype or of a different serotype as compared to the rAAV-transgene vector of the composition of the invention. Preferably, the empty capsid is of the same serotype as the rAAV virion. Within such rAAV composition, the empty capsid and the capsid of the rAAV virion can comprise a modified capsid protein of the invention, preferably the same type of modified capsid proteins. However, also encompassed is an rAAV composition wherein the empty capsids have a different serotype or are differently modified capsid proteins as compared to the modified capsid proteins of the rAAV virion. Further encompassed is an rAAV composition wherein the empty capsids have a mixture of serotypes, such as, but not limited to, a mixture of AAV2 and AAV5 capsids. The inventors report an increasing effect of transgene expression in joints after intraarticular administration of rAAV-virions admixed with a significant amount of empty capsids. Preferably in the rAAV-virion and the empty capsid are present within the composition in a ratio of empty capsid to rAAV-virion of at least 1:1, 2:1, 3:1, 4:1, 5:1, 10:1, 15:1, 20:1, 50:1, 100:1, or 1000:1, preferably at least 5:1 (i.e. an amount of empty capsids that is at least 5 times the amount of rAAV-transgene vectors). Preferably, said composition comprises rAAV-virion and empty capsid in a ratio of empty capsid to rAAV-transgene vector of at most 10000:1, 5000:1, 4000:1, 3000:1, 2000:1, 1000:1, 500:1, 400:1, 300:1, 200:1, 100:1, 90:1, 80:1, 70:1, 60:1, 50:1, 40:1, 30:1, 20:1, 15:1, 10:1 or 5:1, preferably at most 1000:1. Preferably said composition comprises rAAV-virion and empty capsids in a ratio of empty capsid to rAAV-virion of between 1:1 to 100:1, 2:1 to 100:1, 5:1 to 100:1, 1:1 to 20:1, 2:1 to 20:1 or preferably between 5:1 to 20:1.

Provided herein above is an embodiment wherein the rAAV-virion and the empty capsids are present in a single composition. Also encompassed within the present invention is an alternative embodiment wherein the rAAV-virion and the empty capsids are present in (at least two or more) separate, distinct compositions. In this alternative embodiment, the rAAV-virion and the empty capsids can be administered separately in time (e.g., sequentially) and/or localization, wherein localization is to be understood as the site of administration. Furthermore, the rAAV-virion and the empty capsids can be administered simultaneously, e.g., at substantially the same timing, optionally at a separate location.

In a third aspect, the present invention relates to an rAAV composition and an immunosuppressant for use in treating or preventing an arthritic disease or for use in treating or preventing symptoms associated with an arthritic disease, wherein the rAAV composition is as defined above and wherein the treatment or prevention comprises the administration of the rAAV composition and the administration of the immunosuppressant to an individual. WO 2016/055437, herein incorporated by reference, discloses an increasing effect of an immunosuppressant on AAV transgene expression when subjects were treated with both immunosuppressants and rAAV-virions. Furthermore, WO 2016/055437 discloses a surprising synergistic effect of the immunosuppressant together with empty vectors on rAAV transgene expression. In one embodiment, the immunosuppressant is applied separately from the rAAV composition, separate meaning separate in location and/or time. In such an embodiment, the immunosuppressant and the rAAV composition may be present in separate and distinct compositions. The immunosuppressant, the rAAV-virion and optionally the empty vectors may even each be present in a separate, distinct composition. In another embodiment, the immunosuppressant and the rAAV composition may be present in a single composition. In a further embodiment, the rAAV-virion and the immunosuppressant are present in a single composition, and preferably this composition is used in treatment together with a separate composition comprising the empty capsid. In an even further embodiment, the immunosuppressant and the empty capsid are present in a single composition, and preferably this composition is used in treatment together with a separate composition comprising the rAAV-virion. Therefore, the invention also provides for a composition comprising an empty capsid and an immunosuppressant as defined herein, for a composition comprising an rAAV-virion and an immunosuppressant as defined herein, and for a composition comprising an rAAV composition and an immunosuppressant as defined herein.

Preferably, an immunosuppressant for use in the present invention is an innate immune cell inhibitor, preferably a macrophage inhibitor. An innate immune cell is defined herein as a neutrophil, macrophage, monocyte, eosinophil, basophil, or dendritic cell, that has the potential to participate in the inflammatory response to a foreign substance. An innate immune cell inhibitor is herein defined as an agent that results in a decrease in innate immune cell activity and/or innate immune cell number. A macrophage inhibitor is defined herein as an agent that results in a decrease in macrophage activity and/or macrophage number. A "macrophage" is understood herein as an innate immune cell that engulfs and digests cellular debris, foreign substances, microbes, and cancer cells in a process called phagocytosis. Preferably, the innate immune cell or macrophage inhibitor of the invention, results in a decrease of at least 1, 2, 5, 10, 15, 20, 25, 30, 35, 45, 55, 65, 75, 85, 95% or preferably of 100% of the number or activity of innate immune cells or macrophages as compared to the initial number or activity of innate immune cells or macrophages before treatment. Innate immune cell or macrophage activity and/or number can be detected by any suitable assay known by the person skilled in the art, such as, but not limited to, MTT (3-(4,5-dimethylthiazol-2-yl)2,5-diphenyl tetrazolium bromide) colorimetric assay for testing macrophage cytotoxic activity in vitro as described by Ferrari et al. (Journal of Immunological Methods, 131 (1990) 165-172), by measurement of cytokine levels (e.g., CCL2, TNF), by histological and histochemical detection methods, for instance, by CD68 labeling or by in vivo magnetic resonance imaging (MRI) detection of superparamagnetic iron oxide (SPIO) uptake by macrophages, preferably after intravenous administration of SPIO as reviewed by Yi-Xiang J. Wang (Quant. Imaging Med Surg (2011) 1:35-40). The detection can either be in vitro or in vivo. Preferably, in vivo detection is in an animal model, preferably a rat or murine model.

Preferably, the immunosuppressant is a glucocorticoid and/or a bisphosphonate, preferably a liposomal bisphosphonate. Particular non-limiting examples of glucocortocoids are cortisol, cortisone, prednisone, prednisolone, methylprednisolone, dexamethasone, betamethasone, triamcinolone, beclometasone, fludrocortisone acetate, deoxycorticosterone acetate and aldosteron. Preferably, the immunosuppressant is triamcinolone. Particular non-limiting examples of bisphosphonates are etidronate, clodronte, tiludronate, pamidronate, neridronate, olpadronate, alendronate, ibandronate, risedronate and zoledronate. Preferably, the bisphosphonate is a liposome-encapsulated bisphosphonate or liposomal bisphosphonate, preferably liposomal clodronate. Preferably, the glucocorticoid is not dexamethasone. It is to be understood that the inflammatory or macrophage inhibitor of the invention is not limited to a glucocorticoids and/or a bisphosphonate. For instance, the inflammatory or macrophage inhibitor of the invention can also be an inflammatory or macrophage-depleting antibody such as an anti-F4/80 antibody. Preferably, such antibody is a human or humanized antibody. Further relevant immunosuppressants to be used in the present invention are cytostatic drugs (e.g. alkylating agents and/or antimetabolites such as methotrexate), drugs that modify the purinergic signaling pathway (e.g. methotrexate, adenosine analogs, adenosine receptor antagonists or agonists), non-steroidal anti-inflammatory drugs (NSAIDS, e.g. ibuprofen, diclofenac, meloxicam, naproxen, acetylsalicylic acid), biologicals such as TNF blockers (e.g. infliximab, etanercept, adalimumab, certolizumab, golimumab), IL-6 blockers (e.g. tocilizumab), IL-2 blockers (e.g. basiliximab, daclizumab), IL-1B blockers (e.g. anakinra, rilonacept, canakinumab) IL-17 (secukinumab, brodalumab, ixekinumab), anti-IL-12/IL-23 (ustekinumab), a PDE4-inhibitor (apremilast) muromonab, abatacept, and/or rituximab, and/or other compounds such hydroxychloroquine, chloroquine, leflunomide, sulfasalazine, azathioprine, cyclophosphamide, cyclosporine, gold salt, mTOR inhibitors (e.g. rapamycin/sirolimus, everolimus) and penicillamine.

Preferably, the rAAV composition and/or composition comprising empty capsids and/or the composition comprising the immunosuppressant further comprises a pharmaceutically acceptable carrier, diluents, solubilizer, filler, preservative and/or excipient as defined elsewhere herein.

Preferably, gene therapy according to the present invention further comprises the administration of an immunosuppressant as defined herein, either present within the rAAV composition, or comprised within a separate, distinct composition, i.e. separate and distinct from the rAAV composition. At administration, the rAAV composition and/or empty capsids and/or immunosuppressant of the invention is delivered to an individual, a cell, tissue or organ of said individual, preferably an individual suffering from a condition or disease as defined herein. Preferably, the rAAV composition and the immunosuppressant are administered simultaneously. Simultaneous administration is to be understood herein as administration at more or less the same time, preferably no longer separated than 15 min, 30 min, 1 hour, 2 hours, 3 hours, 12 hours or 24 hours in time, preferably no longer separated than 15 min in time. In another embodiment, the rAAV composition and the immunosuppressant are administered sequentially, wherein preferably the immunosuppressant is administered prior to the rAAV composition. Preferably, the immunosuppressant is administered at least 1 hour, 3 hours, 12 hours, 24 hours, 2 days, 4 days or 1 week before administration of the rAAV composition. In case the rAAV-virions and the empty capsids are present in separate compositions, the immunosuppressant may be administered simultaneously or within at least 15 min, 1 hour, 2 hours, 3 hours, 1 day, 2 days or 1 week prior to the empty capsids and the empty capsids in turn are administered simultaneously or within at least 15 min, 1 hour, 2 hours, 3 hours, 1 day, 2 days or 3 days prior to the rAAV-virion.

Within the embodiments defined herein, the immunosuppressant may be administered repeatedly, i.e. prior to and/or simultaneously with the rAAV composition. As indicated herein above, preferably the rAAV composition comprises a significant amount of empty capsids. Furthermore, the invention encompasses the administration of both rAAV-transgene vectors and empty capsids in separate, distinct compositions, which may be administered simultaneously or sequentially in a method or use of the invention. If comprised in separate compositions, the rAAV-transgene vectors and empty capsids are preferably administered simultaneously. In a further embodiment, the empty capsids are administered at most 3 days, 2 days, 1 day, 24 hours, 12 hours, 3 hours, 2 hours, 1 hour, 30 min, 15 min or 5 min, preferably at most 24 hours, prior to rAAV-transgene vector administration. Furthermore, if comprised in separate compositions, the rAAV-transgene vectors and empty capsids are preferably administered at the same site.

The immunosuppressant dose depends on the type of immunosuppressant. Effective dosages are known by the skilled person. A preferred therapeutic effective dosage of triamcinolone is indicated above. A preferred therapeutic effective dosage of liposomal clodronate is preferably a therapeutic effective dose as known by the skilled person, e.g. preferably 80-320 mg/dose intraarticular, more preferably 160 mg/dose intraarticular (Barrera et al. 2000, Arthritis & Rheumatism Vol 43 (9), p1951-1959).

Generally, a joint disorder is termed an arthropathy, and when involving inflammation of one or more joints the disorder is termed an arthritis. Most joint disorders involve arthritis, however, joint damage caused by external physical trauma is typically not termed arthritis. The term "arthritic disease" as used herein, also referred to as "arthritis", is herein defined as a form of joint disorder that involves inflammation of one or more joints. Currently, it is estimated that there are over a hundred different forms of arthritis. The arthritic disease is herein understood as referring to "joint pain" or "joint disease". In a preferred embodiment, the arthritic disease is selected from the group consisting of Adult-onset Still's disease, ankylosing spondylitis, arthritis, back pain, Behçet's disease, blunt trauma, bursitis, calcium pyrophosphate deposition disease (CPPD), carpal tunnel syndrome, chondromalacia patella, chronic fatigue syndrome, complex regional pain syndrome, cryopyrin-associated periodic syndromes (CAPS), degenerative disc disease, developmental-dysplasia of hip, Ehlers-Danlos, familial mediterranean fever, fibromyalgia, fifth disease, giant cell arteritis, gout, hemochromatosis, infectious arthritis, inflammatory arthritis, inflammatory bowel disease, joint replacement, juvenile arthritis, juvenile dermatomyositis (JD), juvenile idiopathic arthritis (JIA), juvenile rheumatoid arthritis, juvenile scleroderma, Kawasaki disease, lupus, lupus in children & teens, Lyme disease, mixed connective tissue disease, myositis (inc. polymyositis, dermatomyositis), osteoarthritis (OA), osteoporosis, pagets, palindromic rheumatism, patellofemoral pain syndrome, pediatric rheumatic diseases, pediatric SLE, polymyalgia rheumatica, pseudogout, psoriatic arthritis, Raynaud's phenomenon, reactive arthritis, reflex sympathetic dystrophy, Reiter's syndrome, rheumatic fever, rheumatism, rheumatoid arthritis, scleroderma, septic arthritis, Sjogren's disease, spinal stenosis, spondyloarthritis, Still's disease, systemic juvenile idiopathic arthritis, systemic lupus erythematosus, systemic lupus erythematosus in children & teens, systemic sclerosis, temporal arteritis, tendinitis, vasculitis and Wegener's granulomatosis. In a further preferred embodiment the arthritic disease is selected from the group consisting of rheumatoid arthritis (RA), juvenile rheumatoid arthritis, osteoarthritis (OA), gout, pseudogout, spondyloarthritis (SpA), psoriatic arthritis, ankylosing spondylitis, septic arthritis, arthritis, juvenile idiopathic arthritis, blunt trauma, joint replacement and Still's disease. In a more preferred embodiment, the arthritic disease is a joint disorder that involves inflammation of one or more joints. Preferably, the arthritic disease is selected from the group consisting of rheumatoid arthritis (RA), juvenile rheumatoid arthritis, osteoarthritis (OA), gout, pseudogout, spondyloarthritis (SpA), psoriatic arthritis, ankylosing spondylitis, septic arthritis, arthritis, juvenile idiopathic arthritis and Still's disease.

Alternatively, or in combination with another embodiment, in a further preferred embodiment of the present invention, the rAAV virion or the rAAV composition is administered systemically and/or locally. An rAAV composition and/or empty capsids and/or an immunosuppressant of the invention may be directly or indirectly administrated using suitable means known in the art. Methods and uses of the invention include delivery and administration of the rAAV composition and/or empty vector and/or immunosuppressant systemically, regionally or locally, or by any route, for example, by injection, infusion, orally (e.g., ingestion or inhalation), or topically (e.g., transdermally). Exemplary administration and delivery routes include intravenous (i.v.), intraarticular, intraperitoneal (i.p.), intraarterial, intramuscular, parenteral, subcutaneous, intrapleural, topical, dermal, intradermal, transdermal, parenterally, e.g. transmucosal, intracranial, intraspinal, oral (alimentary), mucosal, respiration, intranasal, intubation, intrapulmonary, intrapulmonary instillation, buccal, sublingual, intravascular, intrathecal, intracavity, iontophoretic, intraocular, ophthalmic, optical, intraglandular, intraorgan, intralymphatic. Improvements in means for providing an individual or a cell, tissue, organ of said individual with an rAAV composition and/or empty capsids and/or an immunosuppressant of the invention, are anticipated considering the progress that has already been achieved thus far. Such future improvements may of course be incorporated to achieve the mentioned effect of the invention. When administering an rAAV composition and/or empty capsids and/or an immunosuppressant of the invention, it is preferred that such combination and/or composition is dissolved in a solution that is compatible with the delivery method. For intravenous, subcutaneous, intramuscular, intrathecal, intraarticular and/or intraventricular administration it is preferred that the solution is a physiological salt solution. In case an immunosuppressant is present within the rAAV composition of the invention, the immunosuppressant is administered at the same site as the rAAV composition, i.e. preferably locally as indicated above. In the embodiment wherein the immunosuppressant is comprised within a separate composition distinct from the rAAV composition, the immunosuppressant may be administered systemically, preferably intramuscularly or intravenously. The rAAV composition may also be administered locally, preferably at a site of the body comprising substantive numbers of macrophages as defined herein, and the immunosuppressant is administered systemically, preferably intramuscularly or intravenously. Also encompassed in the invention is an embodiment wherein the immunosuppressant and the rAAV composition, even though present in distinct compositions, are administered at the same site, preferably locally, more preferably intraarticularly. As further indicated herein, administration of such distinct compositions may be either simultaneously or sequentially. In a preferred embodiment of the present invention, at least one of the rAAV composition and the immunosuppressant is administered locally. More preferably, the local administration is intraarticular administration. "Intraarticular injection" (also known as "joint injection" or "intraarticular injection") is herein defined as injection or infusion into the joint. Intraarticular injection is typically used for administration of an anti-inflammatory agent into a joint affected by inflammation.

In a further aspect, the present invention relates to an rAAV composition comprising an rAAV virion of the invention and a pharmaceutically acceptable carrier, diluant, solubilizer, filler, preservative and/or excipient, preferably a pharmaceutically acceptable carrier as defined herein. In a preferred embodiment, the composition further comprises empty capsids as herein defined and/or an immunosuppressant as herein defined.

In a further aspect, the present invention relates to a method for treating, preventing, or suppressing symptoms associated with an arthritic disease, wherein the method comprises the step of intraarticular administration of a medicament comprising an effective amount of an rAAV virion as defined herein or of an rAAV composition as defined above.

A "therapeutically effective amount" refers to an amount effective, at dosages and for periods of time necessary, to achieve the desired therapeutic result. A therapeutically effective amount of a nucleic acid, nucleic acid construct, rAAV virion or pharmaceutical composition may vary according to factors such as the disease state, age, sex, and weight of the subject to be treated, and the ability of the nucleic acid, nucleic acid construct, rAAV virion or pharmaceutical composition to elicit a desired response in the subject. Dosage regimens may be adjusted to provide the optimum therapeutic response. A therapeutically effective amount is also typically one in which any toxic or detrimental effects of the nucleic acid, nucleic acid construct, rAAV virion or pharmaceutical composition are outweighed by the therapeutically beneficial effects. A "prophylactically effective amount" refers to an amount effective, at dosages and for periods of time necessary, to achieve the desired prophylactic result, such as preventing or inhibiting various conditions. A prophylactic dose may be used in subjects prior to or at an earlier stage of disease, and a prophylactically effective amount may be more or less than a therapeutically effective amount in some cases. The dosage to be administered may depend to a large extent on the condition and size of the subject being treated as well as the therapeutic formulation, frequency of treatment and the route of administration. Regimens for continuing therapy, including dose, formulation, and frequency may be guided by the initial response and clinical judgment.

The term "subject" or "patient" is used interchangeably herein and refers to an animal, including the human species, that is treatable with the compositions and/or rAAV of the present invention. Accordingly, the term "subject" or "patient" includes, but is not limited to, human, non-human primate such as chimpanzees, and other apes and monkey species, or any mammal such as dog, cat, horse, sheep, pig, cow etc. In a preferred embodiment of the present invention, the subject treated with an rAAV according to the present invention is a mammal, more preferably a human, dog, cat or horse, most preferably a human.

In this document and in its claims, the verb "to comprise" and its conjugations are used in their non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

The word "approximately" or "about" when used in association with a numerical value (approximately 10, about 10) preferably means that the value may be the given value of 10 more or less 10% of the value.

All patent and literature references cited in the present specification are hereby incorporated by reference in their entirety.

The following examples are offered for illustrative purposes only, and are not intended to limit the scope of the present invention in any way.

DESCRIPTION OF THE FIGURES

The present invention will be discussed in more detail below, with reference to the attached drawings:

FIGS. 1, 1B, 1C, 1D, and 1E: Screening of capsid serotypes on HEK293T and FLS cells. Crude lysate containing 7 mutant capsid serotypes (plus AAV5) expressing yellow fluorescent protein (YFP) were used to transduce HEK293T cells or 3 different FLS cell lines (each from a different RA patient). After 72 hours (HEK293T) or 6 days (FLS), cells were assayed for percentage of cells expressing YFP by FLOW cytometry. FIG. 1B shows the % of YFP-expressing cells in 3 different FLS cell lines; FIG. 1C shows the mean fluorescent intensity (MFI) in HEK293T cells; FIG. 1D shows MFI in 3 different FLS cell lines (all cells); FIG. 1E shows MFI in 3 different FLS cell lines (only positive population). The sample legend is depicted in Table 2.

FIG. 2A shows FLS 1 at MOI 20K; FIG. 2B shows FLS 1 at MOI 100K; FIG. 2C shows FLS 2 at MOI 20K; FIG. 2D shows FLS 2 at MOI 100K; FIG. 2E shows FLS 3 at MOI 20K; and FIG. 2F shows FLS 3 at MOI 100K. Open bars show luciferase (RLU) and filled bars show "fold increase" over AAV5. In a different experiment, three additional FLS cell lines from RA patients were transduced with AAV (7 mutant serotypes or AAV5) expressing luciferase: BB4308 (FLS 4), BX 1592 (FLS 5), BB4426 (FLS 6) using 2 MOIs (10K or 100K rAAV particles per cell). FIG. 2G shows FLS 4 at MOI 10K; FIG. 2H shows FLS 4 at MOI 100K; FIG. 2I shows FLS 5 at MOI 10K; FIG. 2J shows FLS 5 at MOI 100K; FIG. 2K shows FLS 6 at MOI 10K; and FIG. 2L shows FLS 3 at MOI 100K.

Figure 1A:
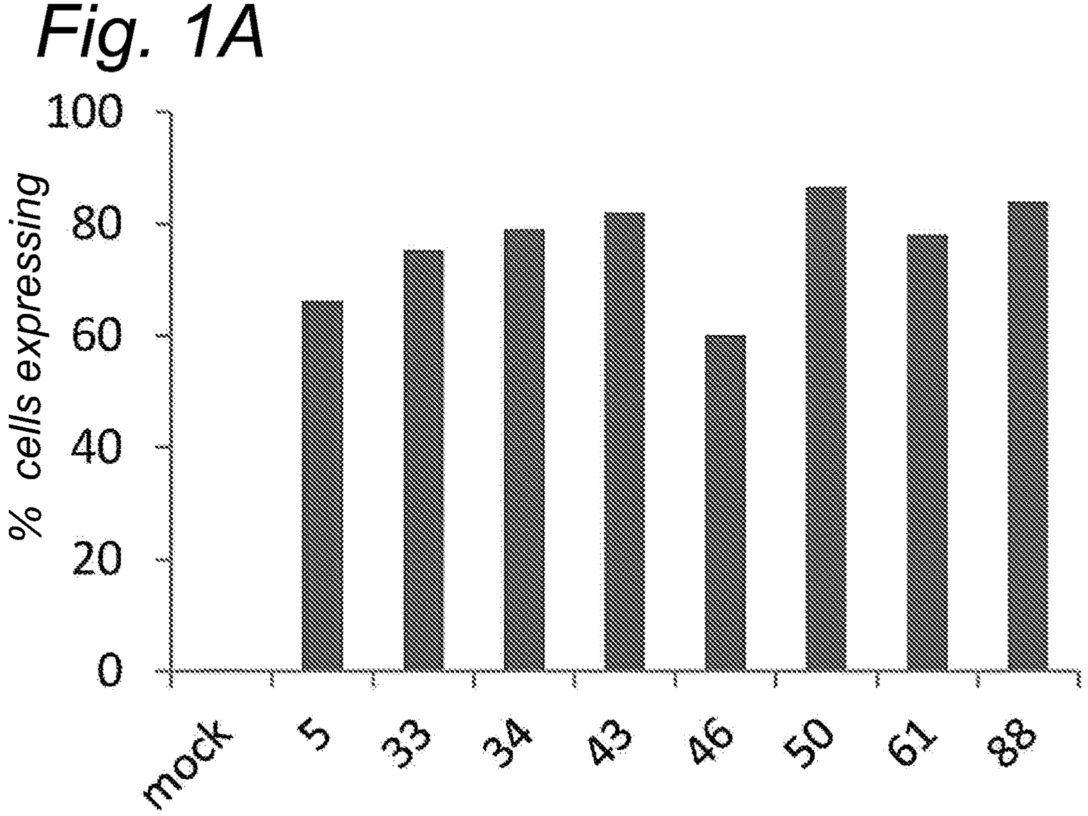
FIG. 1A shows % of HEK293T cells expressing YFP.
Figure 1B:
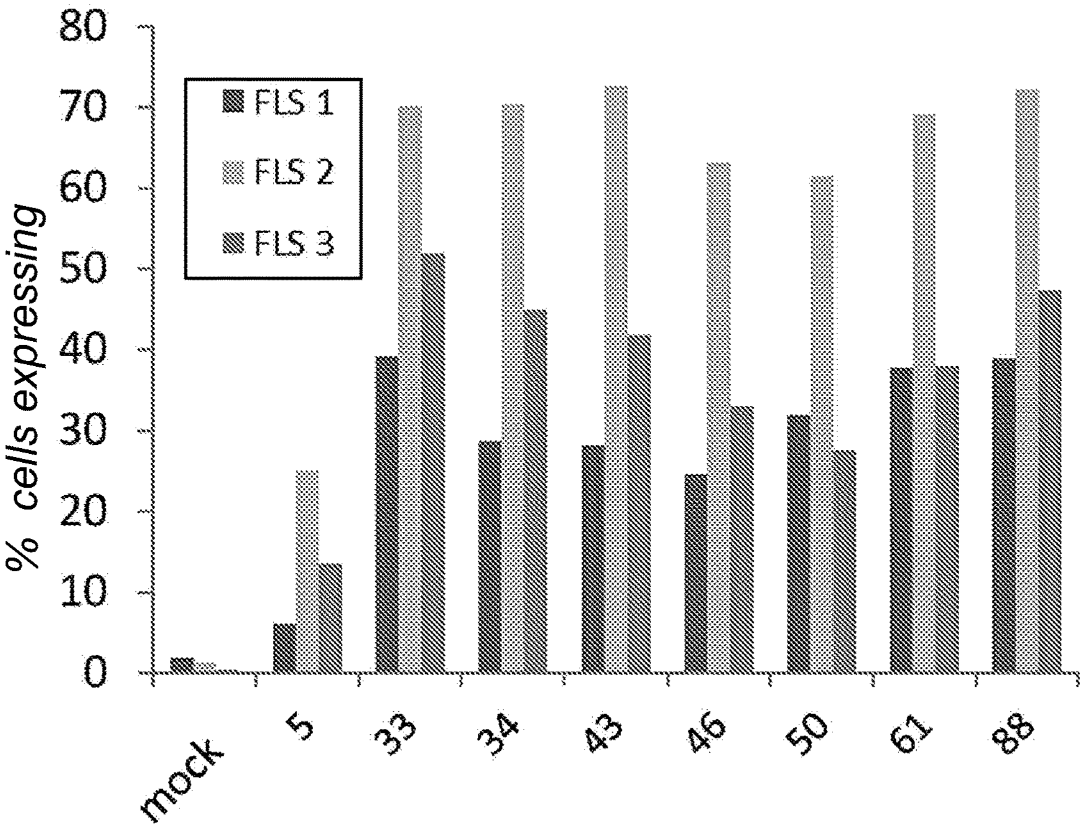
Figure 1C:
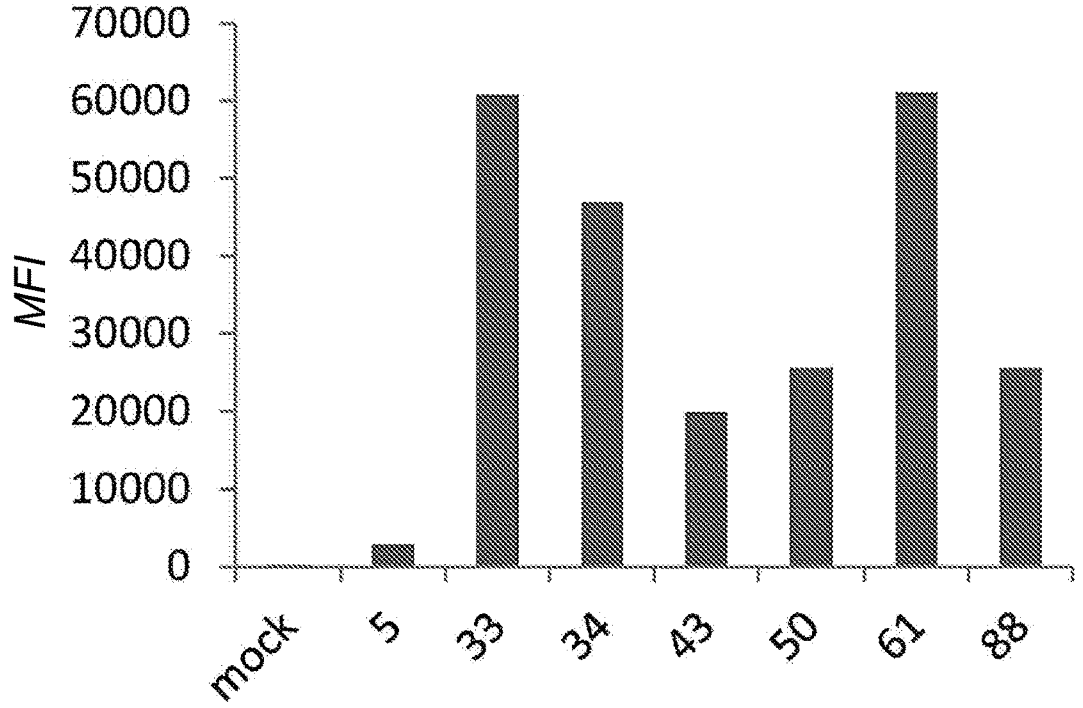
Figure 1D:
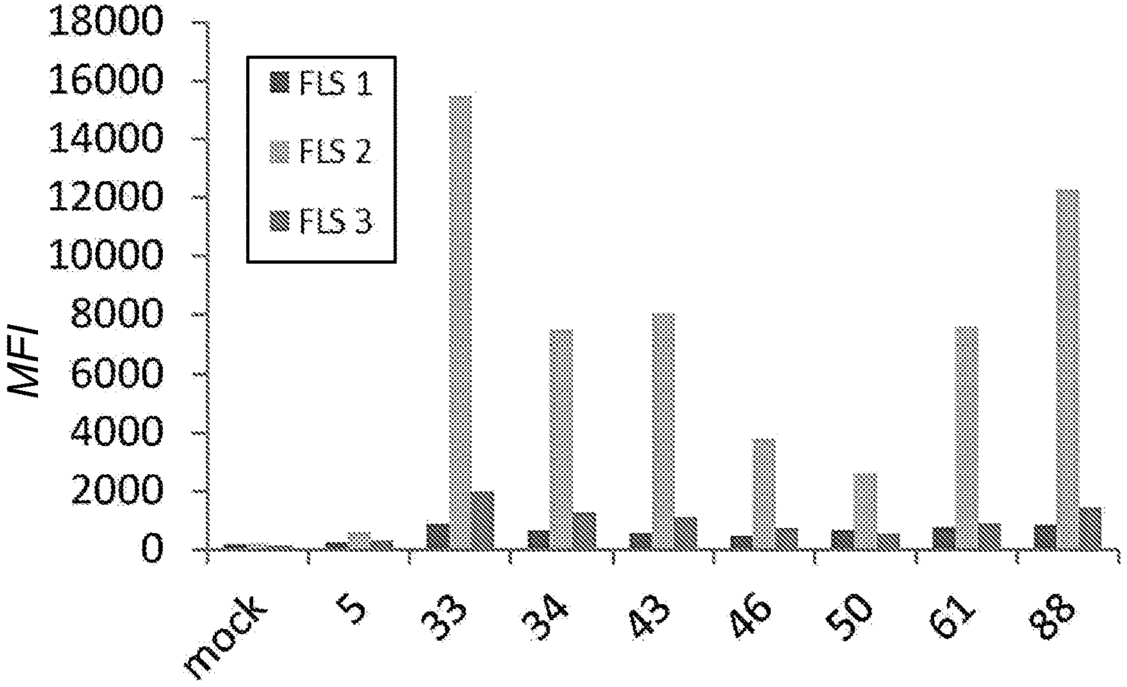
Figure 1E:
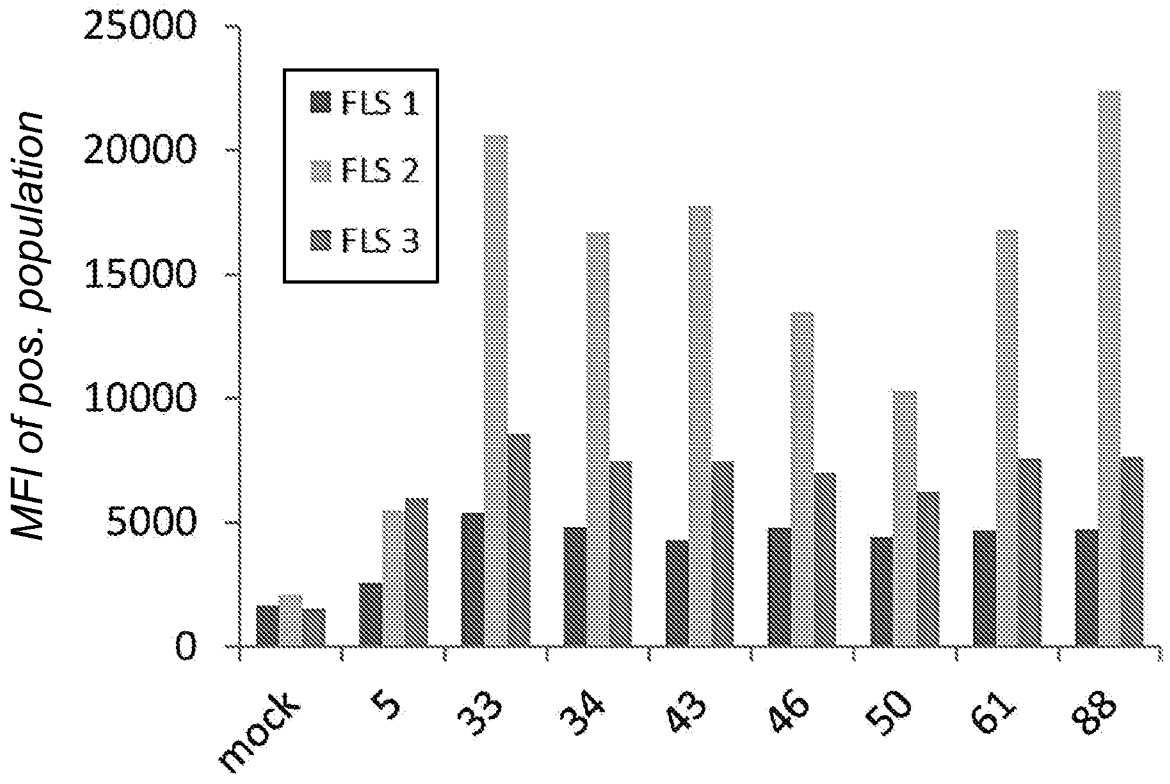
Figure 2B:
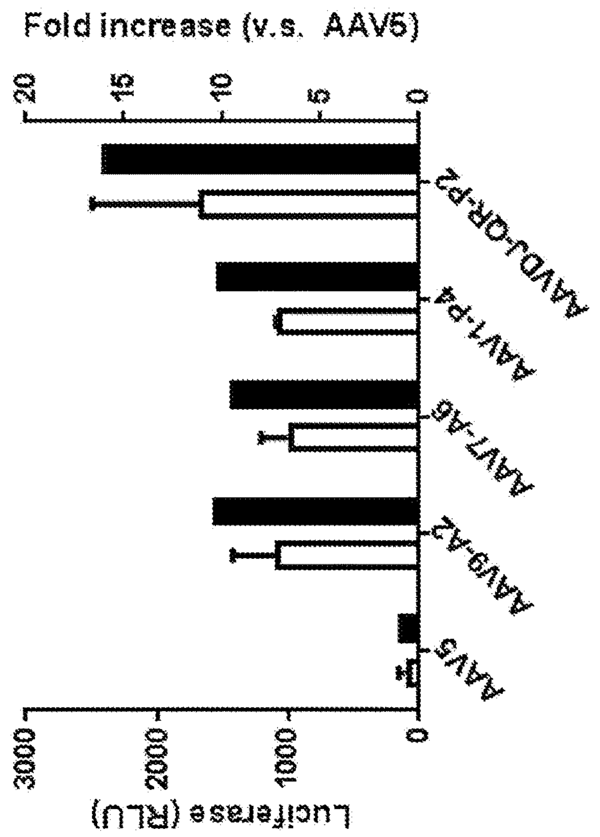
FIGS. 2A, 2B, 2C, 2D, 2E, 2F, 2G, 2H, 2I, 2J, 2K, 2L, and 2M: Capsid mutants show increased luciferase expression vs wt-AAV5 in FLS cells. Purified AAV (4 mutant serotypes or AAV5) expressing YFP-Luc fusion protein were used to transduce three different FLS cell lines from different RA patients: BB5498 (FLS 1), BB5540 (FLS 2) and BB7144 (FLS 3) using two MOIs (20000 or 100000 rAAV particles per cell). After 4 days, cells were lysed and luciferase expression was measured. Data is presented as absolute luciferase expression levels (RLU; white bars) or fold increase over AAV5 (black bars).
Figure 2A:
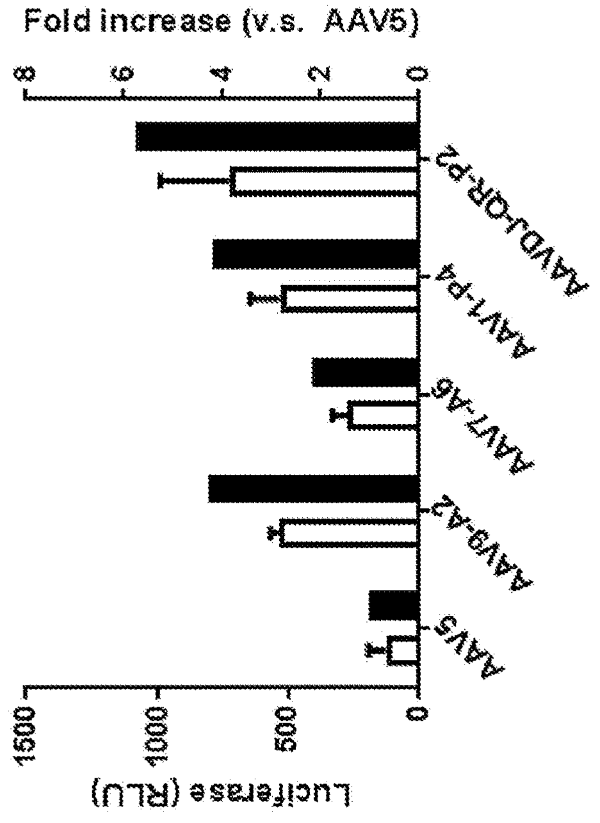
Figure 2D:
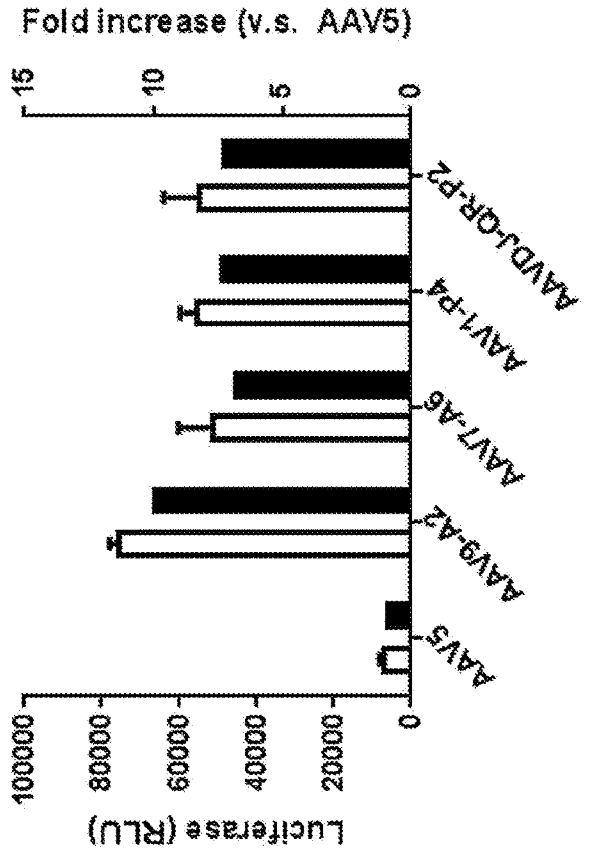
Figure 2C:
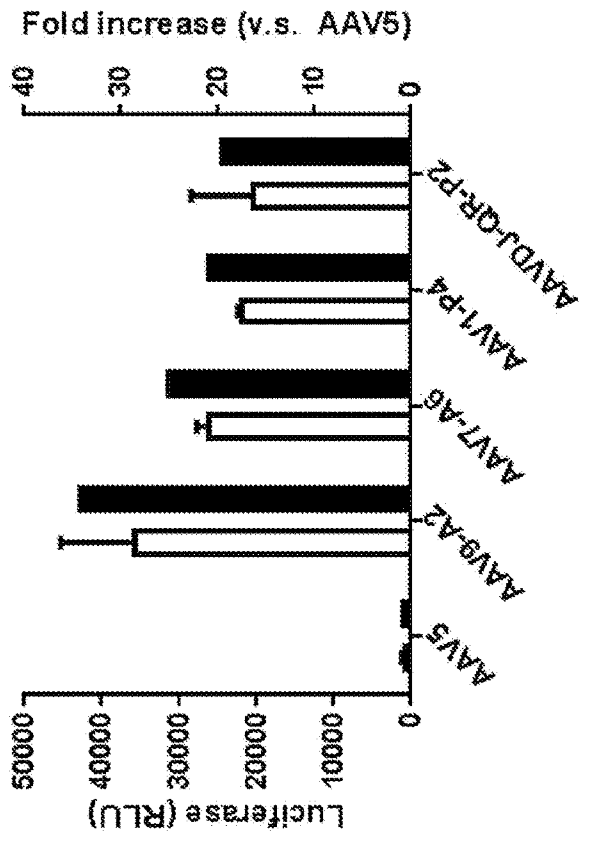
Figure 2F:
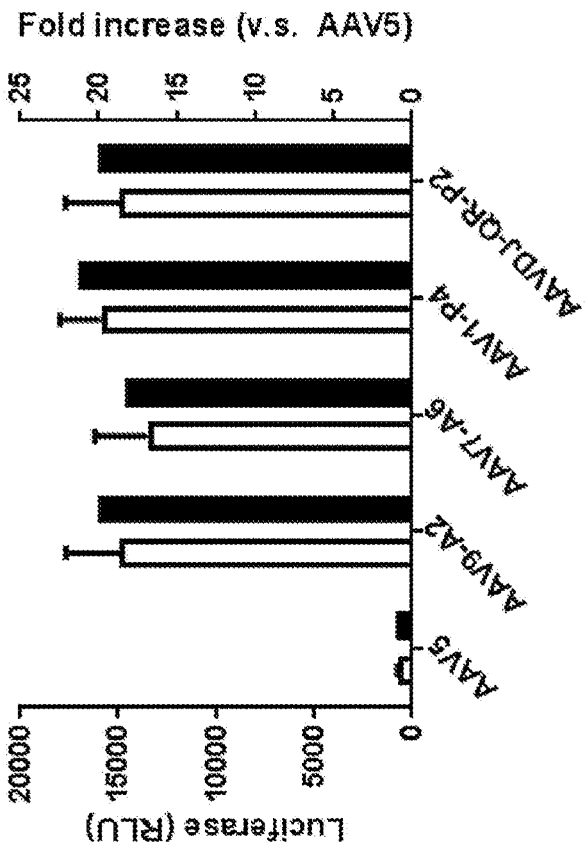
Figure 2E:
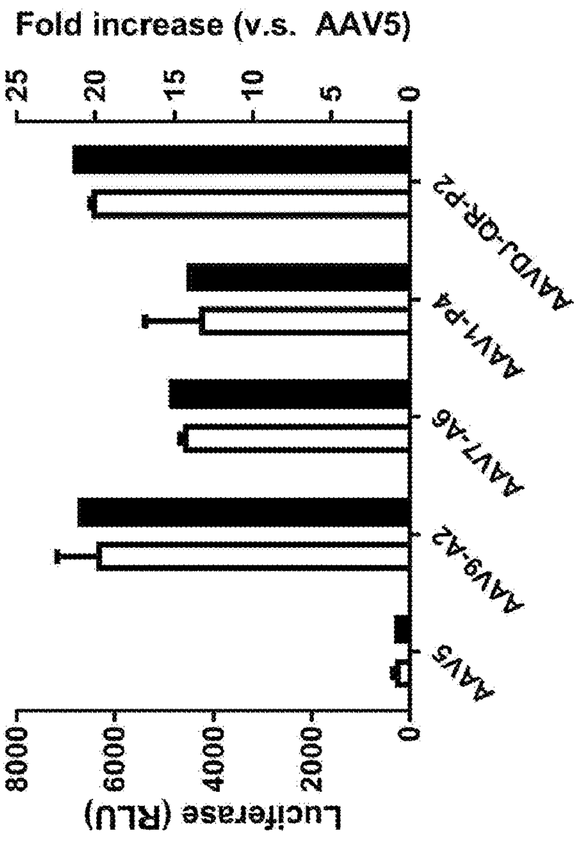
Figure 2H:
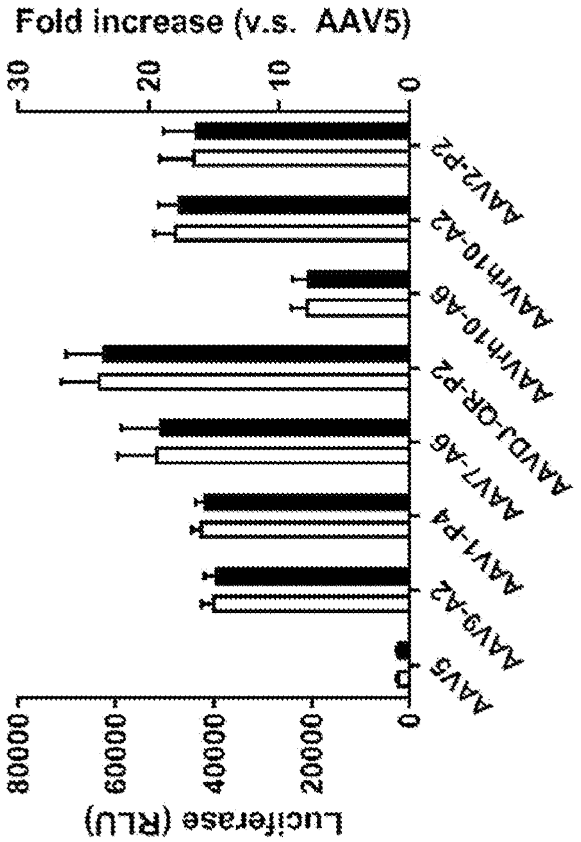
Figure 2G:
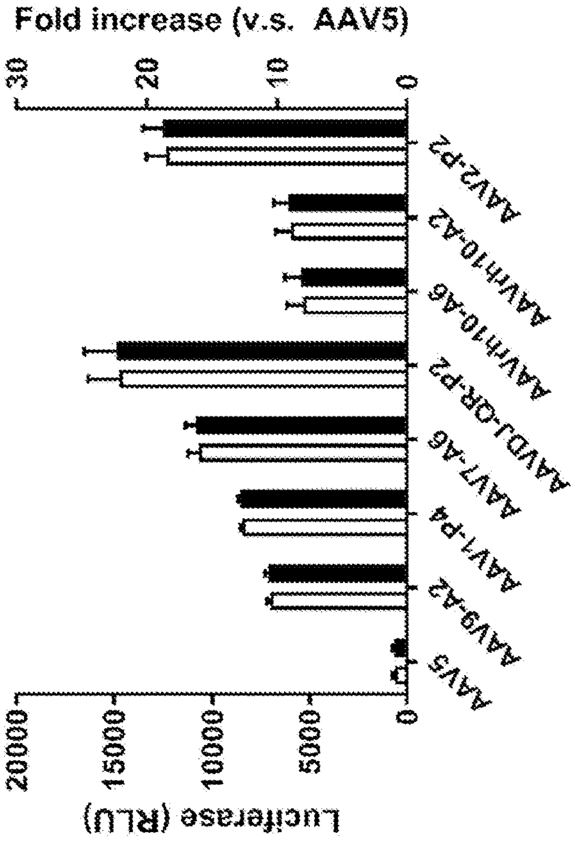
Figure 2J:
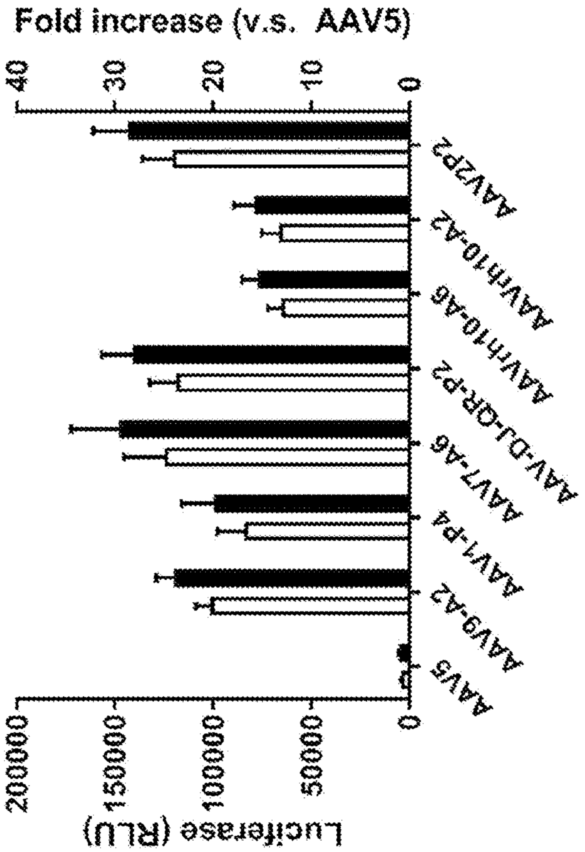
Figure 2I:
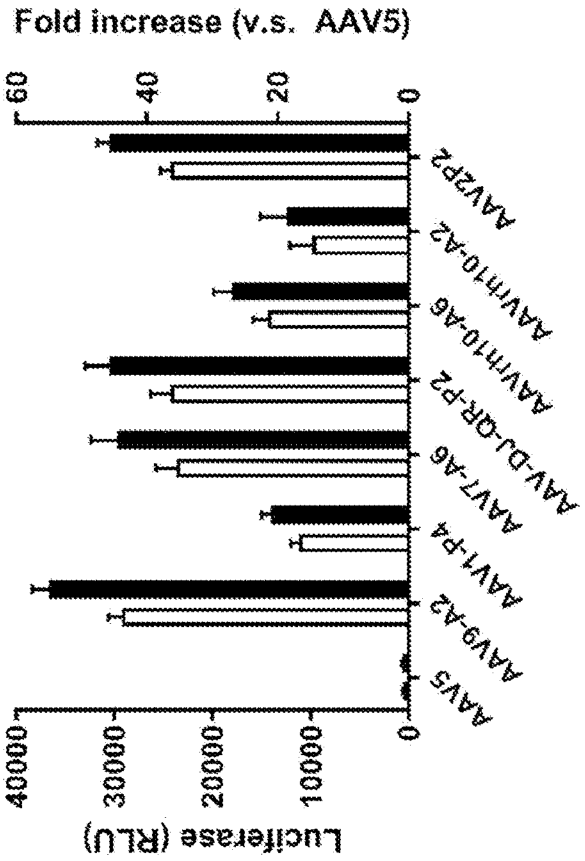
Figure 2L:
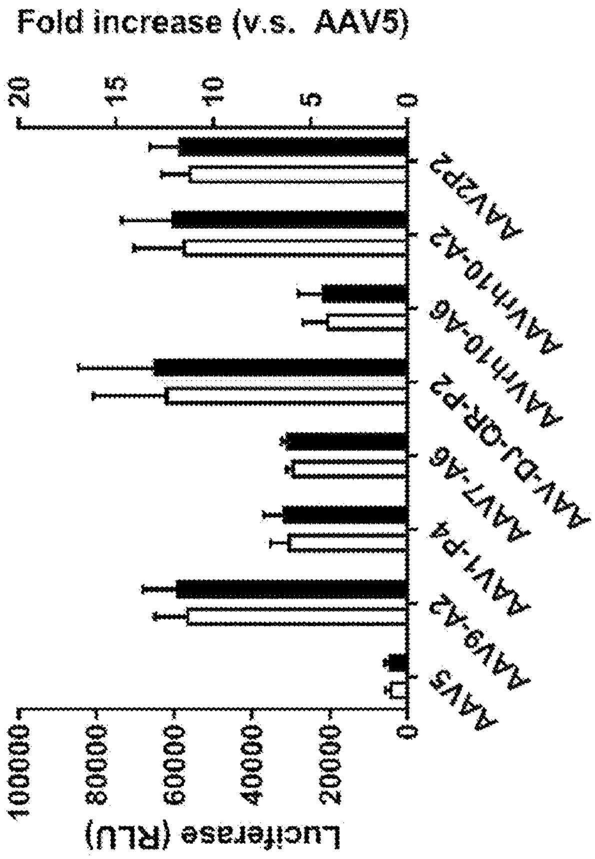
Figure 2K:
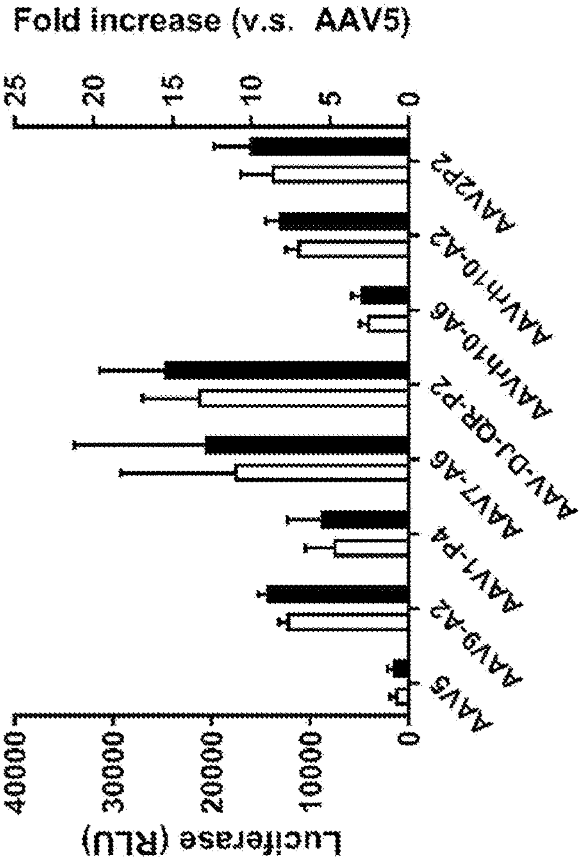
Figure 2M:
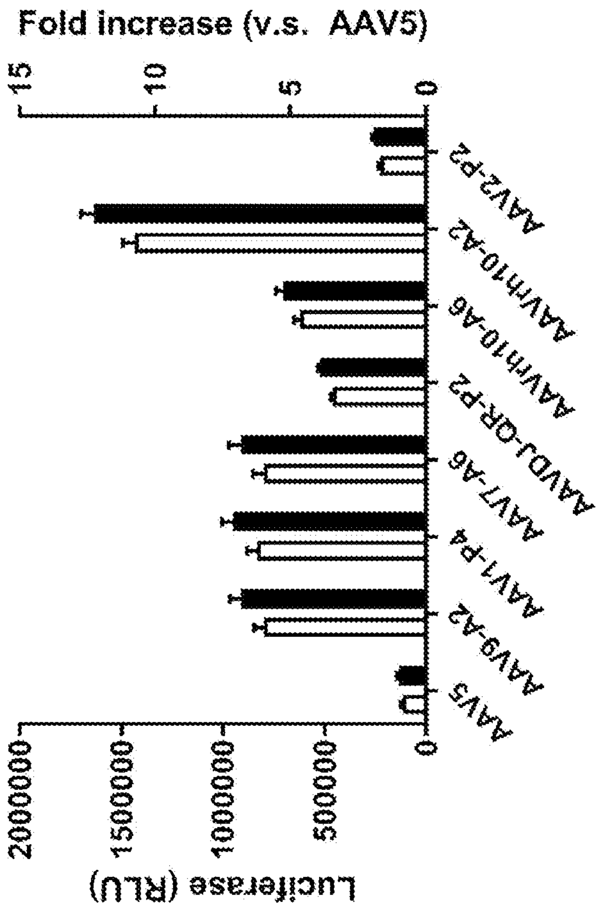

Transduction efficacy of the 7 mutant serotypes or AAV5 (MOI 100K) was also evaluated in HEK293T cells (FIG. 2M). Open bars show luciferase expression (RLU) and filled bars show "fold increase" over AAV5.

Figure 3A:
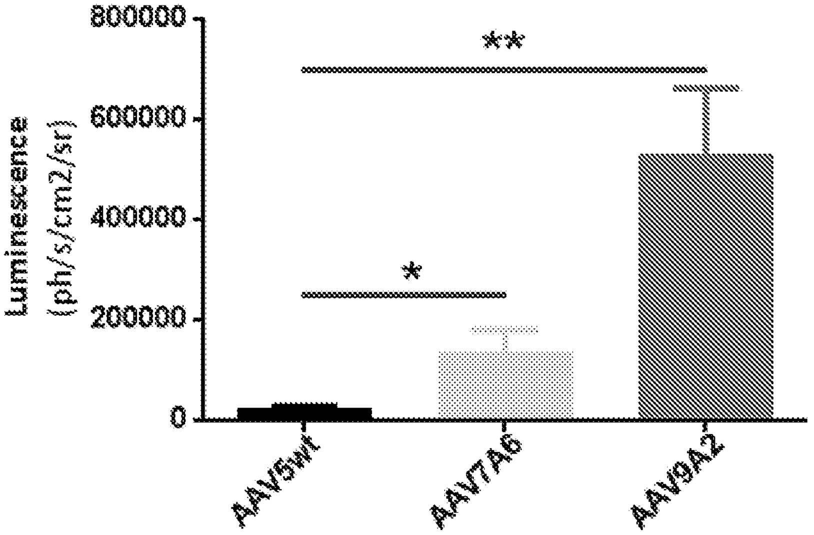
Figure 3B:
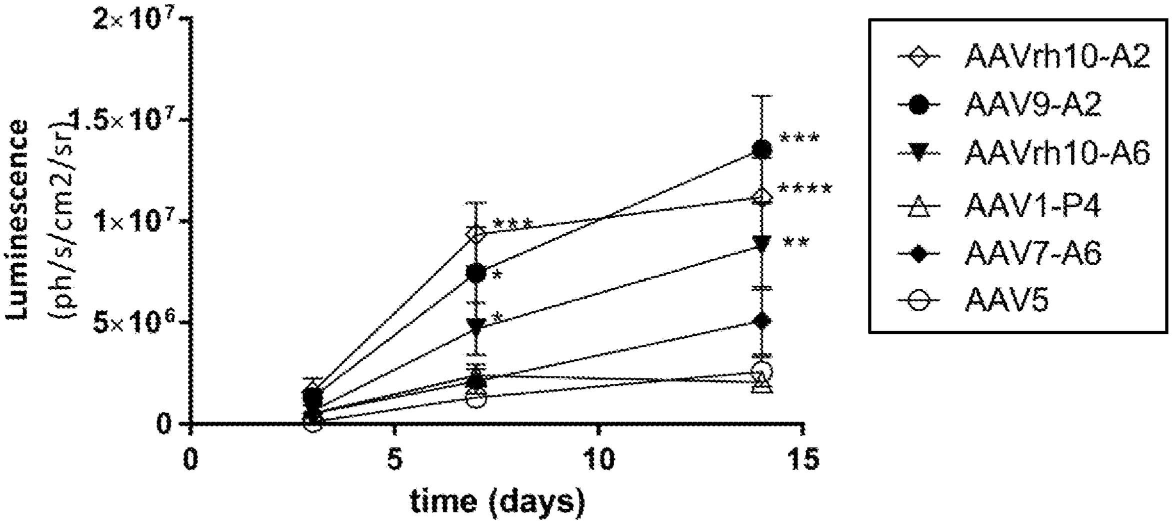

FIG. 3A: Capsid mutants exhibit increased gene expression in vivo. Two capsid mutants (AAV9-A2 and AAV7-A6) were compared with wtAAV5 using the air pouch synovium model. Luciferase-expressing vector was administered on day 0 following air pouch formation and luciferase expression was measured by live animal imaging (IVIS) on day 3 following transduction. Data shown is the luminescence (photon/second/square centimeter m2/steradian) in air pouch in mean+SEM. FIG. 3B: In a second experiment, 5 selected capsid mutants (AAV1-P4, AAV7-A6, AAV9-A2, AAVrh10-A2, AAVrh10-A6) and wtAAV5 were injected into the knee joints of mice. A luciferase expressing vector was injected on day 0 and expression was measured by live imaging (IVIS) at indicated time points after administration. Data shown is the luminescence (photon/second/square centimeter m2/steradian) (left panel) in mean+SEM. P<0.05, *P<0.01, **P<0.00001 vs. wtAAV5 at day 14. FIG. 3**C: Fold increase vs. wtAAV5.

Figures 3C, 4:
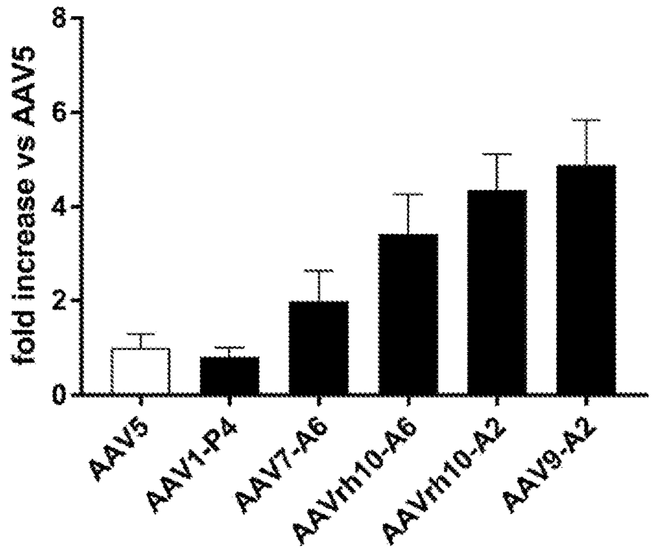

FIG. 4: CLUSTAL format alignment by MAFFT FFT-NS-I (v7.215). Below the alignment is a key denoting a conserved residue (*); and a non-conservative mutation( ). Sequences from top to bottom: SEQ ID NO:11; SEQ ID NO:8; SEQ ID NO:8; SEQ ID NO:20; SEQ ID NO:9; SEQ ID NO: 9; SEQ ID NO:21; SEQ ID NO:22; SEQ ID NO:10; SEQ ID NO:12.

FIG. 5: CLUSTAL multiple sequence alignment by MUSCLE (3.8). Below the alignment is a key denoting a conserved residue (*); a conservative mutation (:); a semi-conservative mutation (·); and a non-conservative mutation ( ). Sequences from top to bottom: SEQ ID NO:21; SEQ ID NO: 10; SEQ ID NO:22; SEQ ID NO: 12; SEQ ID NO:11; SEQ ID NO:8; SEQ ID NO:8; SEQ ID NO: 20; SEQ ID NO:9; SEQ ID NO:9.

FIG. 6: CLUSTAL format alignment of inserts P4, A2, A6, P2 and QR-P2 (SEQ ID NO'S: 8-12) by MAFFT FFT-NS-I (v7.215). Below the alignment is a key denoting a conserved residue (*); and a non-conservative mutation ( ). Sequences from top to bottom: SEQ ID NO:11; SEQ ID NO: 8; SEQ ID NO: 9; SEQ ID NO: 10; SEQ ID NO:12.

Figures 7, 8:
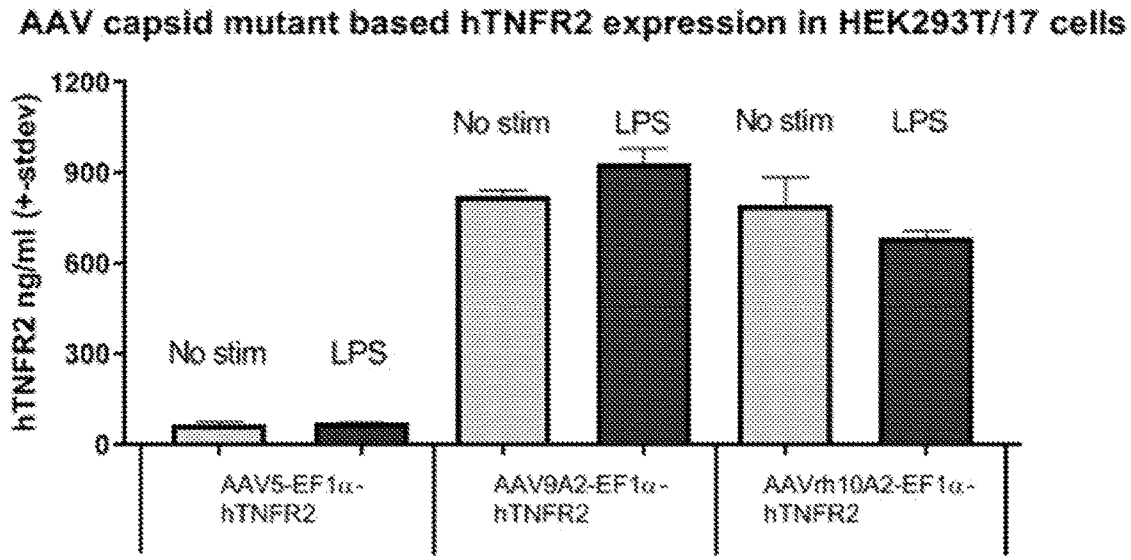

FIG. 7: CLUSTAL multiple sequence alignment of inserts P4, A2, A6, P2 and QR-P2 (SEQ ID NO's: 8-12) by MUSCLE (3.8). Below the alignment is a key denoting a conserved residue (*); and a non-conservative mutation ( ). Sequences from top to bottom: SEQ ID NO:10; SEQ ID NO: 12; SEQ ID NO:11; SEQ ID NO:8; SEQ ID NO:9.

FIG. 8: hTNFR2 expression levels in supernatant of EF1α-hTNFR-IgG1 AAV capsid mutants transduced HEK293T/17 cells.

SEQUENCE LISTING

Table 1 provides an explanation of the sequence references in correlation with the SEQ ID No's.

TABLE 1

Explanation of sequence references

| SEQ ID NO: | serotype | Modified capsid/insert/wild-type |
|---|---|---|
| 1 | AAV1 | Modified capsid |
| 2 | AAV2 | Modified capsid |
| 3 | AAV7 | Modified capsid |
| 4 | AAV9 | Modified capsid |
| 5 | AAVrh10 | Modified capsid |
| 6 | AAVrh10 | Modified capsid |
| 7 | AAV DJ-QR | Modified capsid |
| 8 | Insert A2 | Insert |
| 9 | Insert A6 | Insert |
| 10 | Insert P2 | Insert |
| 11 | Insert P4 | Insert |
| 12 | Insert QR-P2 | Insert |
| 13 | AAV1 | Wild-type capsid |
| 14 | AAV2 | Wild-type capsid |
| 15 | AAV7 | Wild-type capsid |
| 16 | AAV9 | Wild-type capsid |
| 17 | AAVrh10 | Wild-type capsid |
| 18 | AAV DJ-QR | Synthetic capsid |
| 19 | AAV5 | Wild-type capsid |

EXAMPLES

Example 1

Initial Screening of Capsid Library

1.1. Materials and Methods 96-well plates spotted (and subsequently dried) with crude lysate containing AAV from 91 different AAV capsid serotypes were obtained from Dirk Grimm and Kathleen Borner at the University of Heidelberg. Each vector encoded a YFP transgene driven by a CMV promoter. As FLS are the primary target cells in the joint, an AAV capsid mutant library was screened for serotypes that show increased expression in human FLS isolated from joints of rheumatoid arthritis patients (RA-FLS) (as described in van de Sande M G et al., (2011) Ann Rheum Dis 70:423-427). RA-FLS were plated (2500/well, 37° C./5% $CO_2$) directly onto the spotted plates (DMEM-GlutaMAX-I (Gibco, ref. 31966-021), 10% FBS (heat inactivated (HI) Bovine Serum Gold, Gibco, ref A15-151), 10 mM HEPES (Gibco, ref. 15630-056), 50 μg/ml gentamycin (Gibco, ref. 15710-049), 100 U/ml penicillin/100 μg/ml streptomycin (Sigma-Aldrich, ref. P0781) and all wells were visualized for YFP expression by fluorescence microscopy after 6 days.

1.2. Results

Transduction efficacy of capsid mutants vs. WT-AAV5 in FLS from RA patients.

In screening of the 91 capsid mutants, while the overall expression levels were low, the present inventors identified 7 different serotypes that showed higher expression than wtAAV5: AAV9-A2, AAV7-A6, AAV1-P4, AAVDJ-QR-P2, AAVrh10-A6, AAVrh10-A2 and AAV2-P2 (amino acid sequences SEQ ID NO: 1-7; wtAAV5 SEQ ID NO: 19).

Crude lysates of all 7 vectors were used in an in vitro transduction assay in 3 different patient FLS cell lines and in HEK293T cells (example 2).

TABLE 2

Sample legend for FIG. 1

| Sample | Capsid serotype | Insert/modified sequence | insert | Position in VP1 | SEQ ID NO: |
|---|---|---|---|---|---|
| 5 | 5 | none | none | — | 19 |
| 61 | AAV1 | GQSGNDVRSANAQAA (SEQ ID NO: 11) | P4 | 588-602 | 1 |
| 33 | AAV9 | GQRGNYSRGVDAQAA (SEQ ID NO: 8) | A2 | 586-600 | 4 |
| 34 | AAVrh10 | GQRGNYSRGVDAQAA (SEQ ID NO: 8) | A2 | 588-602 | 6 |
| 50 | AAV2 | QGQSGCDCRGDCFCA(QAA) (without QAA: SEQ ID NO: 21; with QAA: SEQ ID NO: 10) | P2 | 585-602 | 2 |
| 88 | AAV-DJ-QR | QGQRGCDCRGDCFCA(QAA) (without QAA: SEQ ID NO: 22; with QAA: SEQ ID NO: 12) | QR-P2 | 587-604 | 7 |

TABLE 2-continued

| Sample legend for FIG. 1 | | | | | |
|---|---|---|---|---|---|
| Sample | Capsid serotype | Insert/modified sequence | insert | Position in VP1 | SEQ ID NO: |
| 43 | AAV7 | GQRGNEARVREAQAA (SEQ ID NO: 9) | A6 | 587-601 | 3 |
| 46 | AAVrh10 | GQRGNEARVREAQAA (SEQ ID NO: 9) | A6 | 588-602 | 5 |

Example 2

Expression of Crude Lysates of 7 Selected Mutants 2.1. Materials and Methods

AAV Production

Details on the production of the crude AAV lysates can be found in Grosse et al. (J. Virol, 2017, doi: 10.1128/JVI.01198-17).

Aliquots of crude lysate for each of the selected 7 capsid mutants (plus wtAAV5 as a control) were used to transduce cells (HEK293T or 3 different FLS cell lines isolated from RA patients) and YFP expression was measured by flow cytometry 3 (HEK293T)—5 days (FLS) following transduction. In detail, HEK293T were seeded in a 96-well plate (Greiner Bio-One, ref. 655180) at 45000 cells per well. RA-FLS were seeded in a 96-well plate at 2500 cells per well. After overnight incubation, the cell supernatants were replaced with 40 μl DMEM-glutaMAX-I (Gibco 31966-021) containing 0.001% pluronic F68 solution (Sigma P5556). The virus lysates were added in duplo, 10 μl per well. After 4 hours, doxorubicin (final concentration 0.4 μM) (Sigma D1515) (Doxorubicin improves AAV transduction efficiency) in DMEM-glutaMAX-I containing FBS (heat inactivated (HI) Bovine Serum Gold, Gibco, ref A15-151), final concentration 1%) was added to the wells (50 μl per well). The day after, the medium of FLS was removed and DMEM-glutaMAX-I (10% FBS (heat inactivated (HI) Bovine Serum Gold, Gibco, ref A15-151), 10 mM HEPES (Gibco, ref. 15630), 50 μg/ml gentamycin (Gibco ref. 15710-049), 100 U/ml penicillin/100 μg/ml streptomycin (Sigma-Aldrich, ref. P0781)) was added (200 μl per well). The medium of HEK293T cells was not changed. Three (HEK293T cells) or 6 days (FLS) after transduction cells were trypsinized using 0.5% Trypsin/EDTA (Gibco ref. 15400-054) in PBS (Gibco, ref. 10010) and analyzed for YFP expression by FLOW cytometry (FACSCanto II, BD Biosciences). Both percentage of expressing cells and mean fluorescence intensity (MFI) for all cells was determined.

2.2. Results

Crude lysates of all 7 vectors were used in an in vitro transduction assay in 3 different patient FLS cell lines and in HEK293T cells. Cells were assayed for the percentage of cells expressing YFP by fluorescence microscopy (data not shown) or FLOW cytometry (FIG. 1 panels A-E). While there was some variability between cell types, all mutant capsids gave higher expression in both, FLS and HEK293T cells than AAV5-WT (FIG. 1). Table 2 provides the sample legend for FIG. 1. Based on these results, four capsid mutants were selected for further investigation (see example 3).

Example 3

In Vitro Testing of Capsid Variants in HEK293T and FLS 3.1 Materials and Methods 3.1.1 Four of the mutant capsid proteins, AAV9-A2, AAV7-A6, AAV1-P4, and AAVDJ-QR-P2, were further investigated. Purified vector (Iodixanol gradient) expressing a YFP-Luciferase fusion protein (to allow for visualization (YFP) as well as quantification by luciferase assay) was generated. Three different primary FLS lines isolated from rheumatoid arthritis patients (as described in van de Sande M G et al., (2011) Ann Rheum Dis 70:423-427) were transduced with each serotype at 2 vector doses (MOI 20,000 or 100,000) and after 4 days, cells were harvested and gene expression was quantified by luciferase assay (Promega Luciferase assay Kit).

In detail, RA-FLS were plated at 2500 cell/well in a 96-well plate (Greiner Bio-One, ref. 655207) in medium (DMEM-GlutaMAX (Gibco ref. 31966-021), 10% FBS (heat inactivated (HI) Bovine Serum Gold, ref A15-151), 10 mM HEPES (Gibco ref. 15630-056), 50 μg/ml gentamycin (Gibco, ref 15710-049), 100 u/ml penicillin/100 μg/ml streptomycin (Sigma-Aldrich Merck ref. P0781). After 48 h, medium was removed and virus (in DMEM-Glutamax containing 0.001% Pluronic-68 (Sigma, ref. p5556)) was added at an MOI of 20,000 or 100,000. After 4 h, medium containing Doxorubicin (Sigma, ref. D1515, final concentration 0.4 μM) and FBS (final concentration 1%) was added.

24 h later, medium was replaced with DMEM-GlutaMAX, (10% FBS, 10 mM HEPES, 50 μg/ml gentamycin, 100 u/ml penicillin, 100 μg/ml streptomycin). Four days post-transduction, cells were washed 1× with 100 μl PBS (Gibco, ref. 10010) and luciferase activity was determined using the ONE Glo™ luciferase assay system (Promega, ref. E6110): 100 μl Lysis buffer was added and cells were placed on a shaker for 10', 900 rpm at RT. Subsequently, 20 μl lysate was transferred to a white 96-well plate, 80 μl substrate (was added for 3' (dark) and luciferase activity was determined on a luminometer (1 sec/well, synergy HT, Biotek).

3.1.2. In a similar experiment, three additional FLS cell lines isolated from rheumatoid arthritis patients were transduced with AAV5 and 7 capsid mutants from a different AAV preparation than described in 3.1.1 (AAV9-A2, AAV1-P4, AAV7-A6, AAVDJ-QR-P2, AAVrh10-A6, AAVrh10-A2, AAV2-P2) containing a luciferase gene (MOI 10,000 and 100,000). The number of empty particles differed between the AAV preparations. To exclude a possible effect on transduction efficacy, empty capsid correction was done by adding AAV5 empty particles to equalize the percentage of empty particles per preparation.

3.1.3. The 7 capsid mutants from the same preparation as described in 3.1.2 were also tested in HEK293T cells. In detail, HEK293T were seeded in a 96-well plate (Greiner Bio-One, ref. 655180) at 50000 cells per well. After overnight incubation, the cell supernatants were replaced with DMEM-glutaMAX-I (Gibco 31966-021) containing 0.001% pluronic F68 solution (Sigma P5556). The different vectors were added in duplo, at an MOI of 100,000. In this protocol, empty capsid correction was done as described for 3.1.2. After 4 hours, doxorubicin (final concentration 0.4 μM) (Sigma D1515) in DMEM-glutaMAX-I-containing FBS (heat inactivated (HI) Bovine Serum Gold, Gibco, ref A15-151), final concentration 1%, was added to the wells. Three days after transduction, cells were harvested and gene expression was quantified by luciferase assay (Promega Luciferase assay Kit) on a luminometer (BMG Labtech Fluostar Omega).

3.2. Results 3.2.1 In vitro transductions of three different FLS cell lines were performed using recombinant AAV comprising one of the 4 mutant capsids (as well as AAV5 as control, made in the identical manner) following the protocol described in 3.1.1. All 4 serotypes showed increased expression levels when compared with AAV5, ranging from 2-fold to 35-fold increases, depending on the serotype and cell line used (FIG. 2A-F).

3.2.2 In another series of experiments, in vitro transduction efficacy of 7 mutant capsids (as well as AAV5 control, made in the identical manner) was assessed in 3 FLS cell lines. All 7 serotypes showed increased luciferase expression levels when compared with AAV5, ranging from 6-fold to 55-fold increases depending on the serotype and cell line used (FIG. 2G-L)

3.2.3 A similar experiment was performed in HEK293T cells. Transduction with all 7 serotypes resulted in enhanced luciferase expression compared with wtAAV5, ranging from 2-fold to 12-fold increases (FIG. 2M).

Example 4

In Vivo Study in the Air Pouch Synovium Model 4.1. Materials and Methods

Animals

Female Balb/c mice (8-10 weeks old and weighing 20-25 g; (Harlan, Boxmeer, the Netherlands)) were housed in individual ventilated cages at the animal facility of the Academic Medical Center, Amsterdam. Food and water were available ad libitum. All animal experiments were performed according to the guidelines of the Animal Research Ethics Committee of the University of Amsterdam.

Air Pouch Synovium (APS) Model

Two serotypes, AAV9-A2 and AAV7-A6, were compared against wtAAV5. The air pouch synovium model was adapted from Edwards et al (1981; J Pathol 134:147-156). At day 0, 3 ml of air was injected subcutaneously into the dorsal skin of 7-9 week-old female Balb/cOlaHsd mice (Harlan) (day 0). Immediately following the formation of the air pouch, 1 ml of air was removed and 1 ml of AAV (2e10 vector genomes/mouse in PBS (Gibco, ref. 10010 containing 0.001% pluronic F68 (Sigma, ref. p5556) was added directly into the air pouch. Three days following transduction, gene expression was measured by in vivo animal imaging.

Imaging of Luciferase Expression

Luciferase expression was measured at day 3. It was initially planned to continue monitoring expression for up to 3 months following vector administration, however, a parvovirus infection of the animal facility resulted in the premature termination of all ongoing experiments. D-luciferin potassium-salt substrate (Caliper Life Sciences, Hopkinton, MA, USA) was injected intraperitoneally (150 mg/kg of body weight, in a volume of approximately 200 μl). Photon counts were acquired 10 min after substrate administration for 5 min using a cooled charge-coupled device (CCD) camera system (Photon Imager, Biospace Lab, Paris, France) and image processing and signal intensity quantification and analysis were performed using M3 Vision (Biospace Lab). The number of photons emitted per second per square centimeter per steradian was calculated as a measure of luciferase activity.

General Animal Conditions and Ethics Statement

Air pouch formation, vector administration and in vivo imaging were performed under isoflurane anaesthesia (3% isoflurane and oxygen). At the end of the experiments, animals were sacrificed by cardiac puncture under isoflurane anaesthesia, followed by cervical dislocation. The studies were reviewed and approved by the animal care and use committee of the University of Amsterdam and carried out in strict accordance with the recommendations in the Dutch Law on Animal Welfare (Dutch: "Wet op Dierproeven"). Animals were maintained under pathogen-free conditions in the animal facility of the University of Amsterdam.

4.2. Results

Based on these promising results, a preliminary in vivo study was performed using the air pouch synovium (APS) model, where two serotypes, AAV9-A2 and AAV7-A6, were compared against wtAAV5. Due to an unfortunate infection in the animal facility that necessitated the premature termination of this study, we were only able to obtain data from a single time point, day 3 post vector administration. At this time point it was clear that the capsid mutants were giving rise to increased gene expression when compared with AAV5, with AAV7-A6 showing ~6-fold increased expression and AAV9-A2~22-fold (FIG. 3A).

Example 5

In Vivo Study: Intra-Articular Injections in Healthy Animals 5.1. Material and Methods Animals Male DBA1/J mice (12 weeks old, Envigo) were housed in individual ventilated cages at the animal facility of the Academic Medical Center, Amsterdam. Food and water were available ad libitum. All animal experiments were performed after approval of the Central Commission Animal Experiments (CCD) and the Animal Research Ethics Committee of the University of Amsterdam, the Netherlands.

Expression Study

Five rAAV comprising capsid mutants, i.e., AAV9-A2, AAV1-P4, AAV7-A6, AAVrh10-A6 and AAVrh10-A2, were compared against wtAAV5. As capsid load may affect expression (Aalbers C J et al., Hum Gene Ther 2017; 28 (2): 168-178), rAAV preparations were corrected for the capsid load by adding wtAAV5 empty particles. Healthy mice (n=9 per group) received intra-articular injections of AAV vector carrying the luciferase gene in both knees ($7.5\times10^9$ viral genomes per knee). Gene expression was determined by in vivo imaging at several time points after vector administration.

Imaging of Luciferase Expression

Luciferase expression was determined at indicated time points (FIG. 3B). At each time point, D-luciferin potassium-salt substrate (Caliper Life Sciences, Hopkinton, MA, USA) was injected intraperitoneally (150 mg/kg of body weight, in a volume of approximately 200 μl). Photon counts were acquired 15 min after substrate administration for 5 min using a cooled charge-coupled device (CCD) camera system (Photon Imager, Biospace Lab, Paris, France). Image processing and signal intensity quantification and analysis were performed using M3 Vision (Biospace Lab). The number of photons emitted per second per square centimeter per steradian was calculated as a measure of luciferase activity.

General Animal Conditions and Ethics Statement

Vector administration and in vivo imaging were performed under isoflurane anaesthesia (4% isoflurane and oxygen). The studies were carried out in strict accordance with the recommendations in the Dutch Law on Animal Welfare (Dutch: "Wet op Dierproeven"). Animals were maintained under pathogen-free conditions in the animal facility of the University of Amsterdam.

5.2. Results

At the first time point, day 3, AAV-mediated expression in the knee is detected in all groups and increases in time (FIG. 3B). All capsid mutants except AAV1-P4 show increased expression vs. wtAAV5 with AAV9-A2 showing the highest expression (~5 fold increased vs. wtAAV5 at day 14) (FIG. 3C). Expression levels at day 14 from high to low: AAV9-A2>AAVrh10-A2>AAVrh10-A6>AAV7-A6>wtAAV5>AAV1-P4. On day 7, AAVrh10-A2, AAV9-A2 and AAVrh10-A6 show significantly increased expression vs. wtAAV5 (P<0.05, *P<0.01, **P<0.00001 vs. wtAAV5 at day 14. (FIG. 3**B).

Example 6

Determination of Neutralizing Antibody Titers Against Capsid Mutants in Human Sera

6.1 Material and Methods

HEK293T cells were plated in DMEM containing 9% FBS, 0.9% penicillin/streptomycin in 96-well clear-bottomed plates. Cells were allowed to rest for 24 hours (at 37° C., 5% $CO_2$) before transduction. Human serum samples (obtained from the French blood institute) where diluted as follows: neat undiluted serum-1:4-1:16-1:64-1:256-1:1,024 (neat serum means 1 volume of virus for 1 volume of serum). A pooled mouse plasma sample (from 10 DBA/1 mice, taken 42 days after intra-articular injection of an AAV5-vector) was serially diluted in FBS as follows: 1:10-1:50-1:250-1:6,250-1:31,250. A solution of human Intravenous Immunoglobulin (IVig, Sanquin, lot 15D30H4560A) was serially semi-log diluted from 1:10 down to 1:10,000. Samples and controls were incubated together with the appropriate capsid mutant or wtAAV5 vector for 30'±5 min. at 35-38° C. at an MOI of 2,500 (as determined previously). After 48±2 hours, luciferase reagent was added and luminescence emission was measured with the VictorX microplate reader. Transduction inhibition titers were determined as the highest dilution of serum still associated to a detectable neutralizing activity, i.e. a neutralizing activity >50%.

6.2 Results

As presented in Table 3, 70%-85% of the samples did not contain neutralizing antibodies against wtAAV5 or the 7 capsid mutants. Most of the samples shared reactivity against the seven capsid mutants, thus a serum sample having reactivity against the wild type AAV5 capsid also reacted against other capsids. In terms of the level of response, they were also comparable between capsid mutants. The number of samples that did not react (ND=not detected) is indicated for each capsid mutant. These data are only given as information as it is very difficult to compare titers with different vectors. Regarding the pooled mouse serum sample from intra-articular injected joints, it only reacted against the WT AAV5 capsid that was used to immunize the animals, whereas no response was observed against mutant capsids (Table 3). All capsid mutants and WT AAV5 were neutralized by IVIg (titers>100) (data not shown).

TABLE 3

For each serum sample as well as the pooled mouse plasma, the inhibitory titer is reported and corresponds to the highest dilution still associated to a detectable neutralizing activity.

| | AAV5 | AAV9A2 | AAV-DJ-QR-P2 | AAVrh10-A2 | AAV1-P4 | AAV2-P2 | AAV7-A6 | AAVrh10-A6 |
|---|---|---|---|---|---|---|---|---|
| sample 1 | ***256*** | ***256*** | ***256*** | ***256*** | ***>1024*** | ***256*** | ***>1024*** | ***>1024*** |
| sample 2 | ***4*** | ND | ND | ND | ND | ND | ND | ND |
| sample 3 | ND | ND | ND | ND | ND | ND | ND | ND |
| sample 4 | ND | ND | ND | ND | ND | ND | ND | ND |
| sample 5 | ND | ND | ND | ND | ND | ND | ND | ND |
| sample 6 | ND | ND | ND | ND | ND | ND | ND | ND |
| sample 7 | ***64*** | ***64*** | ***64*** | ***256*** | ***256*** | ***64*** | ***256*** | ***256*** |
| sample 8 | ***16*** | ***16*** | ***16*** | ***64*** | ***16*** | ***64*** | ***64*** | ***64*** |
| sample 9 | ND | ND | ND | ND | ND | ND | ND | ND |
| sample 10 | 4 | 4 | ***16*** | 4 | ***64*** | ***64*** | ***64*** | ***64*** |
| sample 11 | ND | ND | ND | ND | ND | ND | ND | ND |
| sample 12 | ND | ND | ND | ND | ND | 1 | ND | ND |
| sample 13 | ND | ND | ND | ND | ND | ND | ND | ND |
| sample 14 | ND | 1 | ND | ND | 4 | 1 | ND | 1 |
| sample 15 | ND | ND | ND | ND | ND | ND | ND | ND |
| sample 16 | 1 | 1 | 4 | 4 | 4 | ***16*** | 1 | 1 |
| sample 17 | ND | ND | ND | ND | ND | ND | ND | ND |

TABLE 3-continued

For each serum sample as well as the pooled mouse plasma, the inhibitory titer is reported and corresponds to the highest dilution still associated to a detectable neutralizing activity.

| | AAV5 | AAV9A2 | AAV-DJ-QR-P2 | AAVrh10-A2 | AAV1-P4 | AAV2-P2 | AAV7-A6 | AAVrh10-A6 |
|---|---|---|---|---|---|---|---|---|
| sample 18 | ND | ND | ND | ND | ND | ND | ND | ND |
| sample 19 | ND | ND | ND | ND | 4 | ND | ND | ND |
| sample 20 | 4 | ***256*** | ***64*** | 4 | ND | ***256*** | ***16*** | ***16*** |
| % negative samples | **85** | **80** | **75** | **85** | **80** | **70** | **75** | **75** |
| mouse plasma | 256 | ND | ND | ND | ND | ND | ND | ND |

Titers >8 are considered as seropositive.
Positive signals are highlighted in bold/italic.
ND = Not Detectable

Example 7

In Vitro Expression of AAV Capsid Mutants Containing the EF1α Promoter and hTNFR2-IgG1 Transgene in HEK293T/17 Cells.

Material and Methods

Three AAV vectors (AAV5 wt, AAV9A2, AAVrh10A2) (antibody based affinity and Cesium chloride gradient purified) expressing human TNFR2-IgG1 (etanercept) were generated and expression levels were assessed in HEK293T/17 cells. AAV5 wt is wild type AAV5, AAV9A2 comprises the modified capsid protein AAV9 A2 and AAVrh10A2 comprises the modified capsid protein AAVrh10 A2.

In detail, HEK293T/17 cells were seeded in a 48-well plate (Costar, ref #3548.) at 105,000 cells per well. After overnight incubation, the cell supernatants were replaced with DMEM glutaMAX-I (Gibco 31966-021) containing 0.001% pluronic F68 solution (Sigma P5556). The different vectors were added in duplicate, at an multiplicity of infection (MOI) of 100,000. After 4 hours, doxorubicin (final concentration 0.4 μM) (Sigma D1515) or doxorubicin (final concentration 0.4 μM), (Sigma D1515) in combination with LPS (final concentration 1 μg/ml) (Sigma, ref #L2880-10 mg) (LPS induces inflammation of the cells) in DMEM-glutaMAX-I-containing FBS (heat inactivated (HI)) Bovine Serum Gold, (Gibco, ref 10270-106), (final concentration 1%), was added to the wells. Three days after transduction the supernatant was harvested and hTNFR2-IgG1 levels in the supernatant were quantified by a soluble hTNFR2 DuoSet Elisa (R&D systems ref #DY726).

Results

Transduction with AAV9A2 and AAVrh10A2 resulted in enhanced hTNFR2 expression levels compared to wtAAV5, ranging from 9- to 13-fold increases in non-stimulated and LPS-stimulated cells. (FIG. 8).

CONCLUSION

Virions comprising the modified capsid protein AAV9A2 or AAVrh10A2 result in higher gene expression levels in HEK293/17 cells as compared to AAV5 wt virions.

The present invention has been described above with reference to a number of exemplary embodiments as shown in the drawings. Modifications and alternative implementations of some parts or elements are possible, and are included in the scope of protection as defined in the appended claims.

The invention claimed is:

1. A method of reducing inflammation at a joint in a subject with an arthritic disease, the method comprising administering to the subject a recombinant adeno-associated virus (rAAV) virion comprising a modified capsid protein and a nucleic acid sequence comprising a promoter operably linked to a gene encoding an IL-6 inhibitor, wherein:

the modified capsid protein comprises:

i) an amino acid sequence having at least 95% sequence identity with the amino acid sequence of SEQ ID NO: 1, wherein amino acids at positions 588-602 of the amino acid sequence of SEQ ID NO: 1 consist of the amino acid sequence of SEQ ID NO: 11, ii) an amino acid sequence having at least 95% sequence identity with the amino acid sequence of SEQ ID NO: 2, wherein amino acids at positions 585-599 of the amino acid sequence of SEQ ID NO: 2 consist of the amino acid sequence of SEQ ID NO: 10, iii) an amino acid sequence having at least 95% sequence identity with the amino acid sequence of SEQ ID NO: 3, wherein amino acids at positions 587-601 of the amino acid sequence of SEQ ID NO: 3 consist of the amino acid sequence of SEQ ID NO: 9, iv) an amino acid sequence having at least 95% sequence identity with the amino acid sequence of SEQ ID NO: 4, wherein amino acids at positions 586-600 of the amino acid sequence of SEQ ID NO: 4 consist of the amino acid sequence of SEQ ID NO: 8, v) an amino acid sequence having at least 95% sequence identity with the amino acid sequence of SEQ ID NO: 5, wherein amino acids at positions 588-602 of the amino acid sequence of SEQ ID NO: 5 consist of the amino acid sequence of SEQ ID NO: 9, vi) an amino acid sequence having at least 95% sequence identity with the amino acid sequence of SEQ ID NO: 6, wherein amino acids at positions 588-602 of the amino acid sequence of SEQ ID NO: 6 consist of the amino acid sequence of SEQ ID NO: 8, or vii) an amino acid sequence having at least 95% sequence identity with the amino acid sequence of SEQ ID NO: 7, wherein amino acids at positions 587-601 of the amino acid sequence of SEQ ID NO: 7 consist of the amino acid sequence of SEQ ID NO: 12;

sequence identity is calculated based on the full length of the modified capsid amino acid sequence;

the rAAV virion is administered via intra-articular administration; and the rAAV virion transfects fibroblast-like synoviocytes.

2. The method according to claim 1, wherein the IL-6 inhibitor is selected from the group consisting of an IL-6 receptor antagonist, a humanized anti-IL-6 monoclonal antibody, a chimeric anti-IL-6 monoclonal antibody, a humanized rabbit anti-IL-6 monoclonal antibody, and a soluble IL-6 receptor.

3. The method according to claim 2, wherein the IL-6 receptor antagonist is tocilizumab or sarilumab.

4. The method according to claim 2, wherein the humanized anti-IL-6 monoclonal antibody is olokizumab or sirukumab.

5. The method according to claim 2, wherein the chimeric anti-IL-6 monoclonal antibody is siltuximab.

6. The method according to claim 2, wherein the humanized rabbit anti-IL-6 monoclonal antibody is clazakizumab.

7. The method according to claim 1, wherein the promoter is a constitutive promoter or an inducible promoter.

8. The method according to claim 7, wherein the inducible promoter is an NFκB responsive promoter.

9. The method according to claim 8, wherein the NFκB responsive promoter is an NFκB responsive CMV promoter.

10. The method according to claim 9, wherein the NFκB responsive CMV promoter is an NFκB responsive minimal CMV promoter.

11. The method according to claim 1, wherein the modified capsid protein comprises or consists of an amino acid sequence selected from the group consisting of the amino acid sequences of SEQ ID NOs: 1-7.

12. The method according to claim 11, wherein the modified capsid protein comprises or consists of the amino acid sequence of SEQ ID NO: 4 or the amino acid sequence of SEQ ID NO: 6.

13. The method of claim 1, wherein the rAAV virion is provided in a pharmaceutical composition, wherein the pharmaceutical composition comprises the rAAV virion and a pharmaceutically acceptable carrier.

14. The method of claim 13, the method further comprising administering an immunosuppressant to the subject.

15. The method of claim 1, wherein the arthritic disease is selected from the group consisting of rheumatoid arthritis (RA), juvenile rheumatoid arthritis, osteoarthritis (OA), gout, pseudogout, spondyloarthritis (SpA), psoriatic arthritis, ankylosing spondylitis, septic arthritis, juvenile idiopathic arthritis, and Still's disease.

16. The method of claim 14, wherein the immunosuppressant is administered via local administration.

17. The method of claim 16, wherein the local administration is intra-articular administration.

* * * * *

SEQUENCE LISTING

```
<160> NUMBER OF SEQ ID NOS: 33

<210> SEQ ID NO 1
<211> LENGTH: 745
<212> TYPE: PRT
<213> ORGANISM: Artificial Sequence
<220> FEATURE:
<223> OTHER INFORMATION: Synthetic polypeptide - AAV1 with insert P4

<400> SEQUENCE: 1

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80
```

-continued

```
Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Glu Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495
```

```
Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Glu Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Phe Gln Ser Ser Gly Gln Ser Gly Asn
            580                 585                 590

Asp Val Arg Ser Ala Asn Ala Gln Ala Ala Gly Asp Val His Ala Met
        595                 600                 605

Gly Ala Leu Pro Gly Met Val Trp Gln Asp Arg Asp Val Tyr Leu Gln
    610                 615                 620

Gly Pro Ile Trp Ala Lys Ile Pro His Thr Asp Gly His Phe His Pro
625                 630                 635                 640

Ser Pro Leu Met Gly Gly Phe Gly Leu Lys Asn Pro Pro Pro Gln Ile
                645                 650                 655

Leu Ile Lys Asn Thr Pro Val Pro Ala Asn Pro Pro Ala Glu Phe Ser
            660                 665                 670

Ala Thr Lys Phe Ala Ser Phe Ile Thr Gln Tyr Ser Thr Gly Gln Val
        675                 680                 685

Ser Val Glu Ile Glu Trp Glu Leu Gln Lys Glu Asn Ser Lys Arg Trp
    690                 695                 700

Asn Pro Glu Val Gln Tyr Thr Ser Asn Tyr Ala Lys Ser Ala Asn Val
705                 710                 715                 720

Asp Phe Thr Val Asp Asn Asn Gly Leu Tyr Thr Glu Pro Arg Pro Ile
                725                 730                 735

Gly Thr Arg Tyr Leu Thr Arg Pro Leu
            740                 745


<210> SEQ ID NO 2
<211> LENGTH: 746
<212> TYPE: PRT
<213> ORGANISM: Artificial Sequence
<220> FEATURE:
<223> OTHER INFORMATION: Synthetic polypeptide - AAV2 with insert P2

<400> SEQUENCE: 2

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110
```

```
Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
    450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525
```

```
Asp Glu Glu Lys Phe Phe Pro Gln Ser Gly Val Leu Ile Phe Gly Lys
    530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Gln Gly Gln Ser Gly Cys Asp Cys
            580                 585                 590

Arg Gly Asp Cys Phe Cys Ala Gln Ala Ala Thr Ala Asp Val Asn Thr
        595                 600                 605

Gln Gly Val Leu Pro Gly Met Val Trp Gln Asp Arg Asp Val Tyr Leu
    610                 615                 620

Gln Gly Pro Ile Trp Ala Lys Ile Pro His Thr Asp Gly His Phe His
625                 630                 635                 640

Pro Ser Pro Leu Met Gly Gly Phe Gly Leu Lys His Pro Pro Pro Gln
                645                 650                 655

Ile Leu Ile Lys Asn Thr Pro Val Pro Ala Asn Pro Ser Thr Thr Phe
            660                 665                 670

Ser Ala Ala Lys Phe Ala Ser Phe Ile Thr Gln Tyr Ser Thr Gly Gln
        675                 680                 685

Val Ser Val Glu Ile Glu Trp Glu Leu Gln Lys Glu Asn Ser Lys Arg
    690                 695                 700

Trp Asn Pro Glu Ile Gln Tyr Thr Ser Asn Tyr Asn Lys Ser Val Asn
705                 710                 715                 720

Val Asp Phe Thr Val Asp Thr Asn Gly Val Tyr Ser Glu Pro Arg Pro
                725                 730                 735

Ile Gly Thr Arg Tyr Leu Thr Arg Asn Leu
            740                 745


<210> SEQ ID NO 3
<211> LENGTH: 746
<212> TYPE: PRT
<213> ORGANISM: Artificial Sequence
<220> FEATURE:
<223> OTHER INFORMATION: Synthetic polypeptide - AAV7 with insert A6

<400> SEQUENCE: 3

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Ala Lys Lys Arg
    130                 135                 140
```

```
Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Ser Val Gly Ser Gly Thr Val Ala Ala Gly Gly
        195                 200                 205

Gly Ala Pro Met Ala Asp Asn Asn Glu Gly Ala Asp Gly Val Gly Asn
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Glu Thr Ala Gly Ser Thr Asn Asp Asn
            260                 265                 270

Thr Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Lys Leu Arg Phe Lys Leu Phe Asn Ile
305                 310                 315                 320

Gln Val Lys Glu Val Thr Thr Asn Asp Gly Val Thr Thr Ile Ala Asn
                325                 330                 335

Asn Leu Thr Ser Thr Ile Gln Val Phe Ser Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Ile Pro Gln Tyr Gly Tyr Leu Thr Leu Asn Asn
    370                 375                 380

Gly Ser Gln Ser Val Gly Arg Ser Ser Phe Tyr Cys Leu Glu Tyr Phe
385                 390                 395                 400

Pro Ser Gln Met Leu Arg Thr Gly Asn Asn Phe Glu Phe Ser Tyr Ser
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ala
        435                 440                 445

Arg Thr Gln Ser Asn Pro Gly Gly Thr Ala Gly Asn Arg Glu Leu Gln
    450                 455                 460

Phe Tyr Gln Gly Gly Pro Ser Thr Met Ala Glu Gln Ala Lys Asn Trp
465                 470                 475                 480

Leu Pro Gly Pro Cys Phe Arg Gln Gln Arg Val Ser Lys Thr Leu Asp
                485                 490                 495

Gln Asn Asn Asn Ser Asn Phe Ala Trp Thr Gly Ala Thr Lys Tyr His
            500                 505                 510

Leu Asn Gly Arg Asn Ser Leu Val Asn Pro Gly Val Ala Met Ala Thr
        515                 520                 525

His Lys Asp Asp Glu Asp Arg Phe Phe Pro Ser Ser Gly Val Leu Ile
    530                 535                 540

Phe Gly Lys Thr Gly Ala Thr Asn Lys Thr Thr Leu Glu Asn Val Leu
545                 550                 555                 560
```

```
Met Thr Asn Glu Glu Glu Ile Arg Pro Thr Asn Pro Val Ala Thr Glu
                565                 570                 575

Glu Tyr Gly Ile Val Ser Ser Asn Leu Gln Gly Gln Arg Gly Asn Glu
            580                 585                 590

Ala Arg Val Arg Glu Ala Gln Ala Ala Gln Thr Gln Val Val Asn Asn
        595                 600                 605

Gln Gly Ala Leu Pro Gly Met Val Trp Gln Asn Arg Asp Val Tyr Leu
    610                 615                 620

Gln Gly Pro Ile Trp Ala Lys Ile Pro His Thr Asp Gly Asn Phe His
625                 630                 635                 640

Pro Ser Pro Leu Met Gly Gly Phe Gly Leu Lys His Pro Pro Pro Gln
                645                 650                 655

Ile Leu Ile Lys Asn Thr Pro Val Pro Ala Asn Pro Pro Glu Val Phe
            660                 665                 670

Thr Pro Ala Lys Phe Ala Ser Phe Ile Thr Gln Tyr Ser Thr Gly Gln
        675                 680                 685

Val Ser Val Glu Ile Glu Trp Glu Leu Gln Lys Glu Asn Ser Lys Arg
    690                 695                 700

Trp Asn Pro Glu Ile Gln Tyr Thr Ser Asn Phe Glu Lys Gln Thr Gly
705                 710                 715                 720

Val Asp Phe Ala Val Asp Ser Gln Gly Val Tyr Ser Glu Pro Arg Pro
                725                 730                 735

Ile Gly Thr Arg Tyr Leu Thr Arg Asn Leu
            740                 745
```

<210> SEQ ID NO 4
<211> LENGTH: 745
<212> TYPE: PRT
<213> ORGANISM: Artificial Sequence
<220> FEATURE:
<223> OTHER INFORMATION: Synthetic polypeptide - AAV9 with insert A2

<400> SEQUENCE: 4

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175
```

```
Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Gly Gln Arg Gly Asn Tyr Ser
            580                 585                 590
```

```
Arg Gly Val Asp Ala Gln Ala Ala Gln Thr Gly Trp Val Gln Asn Gln
        595                 600                 605

Gly Ile Leu Pro Gly Met Val Trp Gln Asp Arg Asp Val Tyr Leu Gln
    610                 615                 620

Gly Pro Ile Trp Ala Lys Ile Pro His Thr Asp Gly Asn Phe His Pro
625                 630                 635                 640

Ser Pro Leu Met Gly Gly Phe Gly Met Lys His Pro Pro Pro Gln Ile
                645                 650                 655

Leu Ile Lys Asn Thr Pro Val Pro Ala Asp Pro Pro Thr Ala Phe Asn
            660                 665                 670

Lys Asp Lys Leu Asn Ser Phe Ile Thr Gln Tyr Ser Thr Gly Gln Val
        675                 680                 685

Ser Val Glu Ile Glu Trp Glu Leu Gln Lys Glu Asn Ser Lys Arg Trp
    690                 695                 700

Asn Pro Glu Ile Gln Tyr Thr Ser Asn Tyr Tyr Lys Ser Asn Asn Val
705                 710                 715                 720

Glu Phe Ala Val Asn Thr Glu Gly Val Tyr Ser Glu Pro Arg Pro Ile
                725                 730                 735

Gly Thr Arg Tyr Leu Thr Arg Asn Leu
            740                 745


<210> SEQ ID NO 5
<211> LENGTH: 747
<212> TYPE: PRT
<213> ORGANISM: Artificial Sequence
<220> FEATURE:
<223> OTHER INFORMATION: Synthetic polypeptide - AAVrh10 with insert A6

<400> SEQUENCE: 5

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205
```

```
Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Ala Gly Thr Gln Gln Leu Leu
    450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
    530                 535                 540

Phe Gly Lys Gln Gly Ala Gly Lys Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gly Gln Arg Gly Asn
            580                 585                 590

Glu Ala Arg Val Arg Glu Ala Gln Ala Ala Ile Val Gly Ala Val Asn
        595                 600                 605

Ser Gln Gly Ala Leu Pro Gly Met Val Trp Gln Asn Arg Asp Val Tyr
    610                 615                 620
```

Leu Gln Gly Pro Ile Trp Ala Lys Ile Pro His Thr Asp Gly Asn Phe
625 630 635 640

His Pro Ser Pro Leu Met Gly Gly Phe Gly Leu Lys His Pro Pro Pro
645 650 655

Gln Ile Leu Ile Lys Asn Thr Pro Val Pro Ala Asp Pro Pro Thr Thr
660 665 670

Phe Ser Gln Ala Lys Leu Ala Ser Phe Ile Thr Gln Tyr Ser Thr Gly
675 680 685

Gln Val Ser Val Glu Ile Glu Trp Glu Leu Gln Lys Glu Asn Ser Lys
690 695 700

Arg Trp Asn Pro Glu Ile Gln Tyr Thr Ser Asn Tyr Tyr Lys Ser Thr
705 710 715 720

Asn Val Asp Phe Ala Val Asn Thr Asp Gly Thr Tyr Ser Glu Pro Arg
725 730 735

Pro Ile Gly Thr Arg Tyr Leu Thr Arg Asn Leu
740 745

<210> SEQ ID NO 6
<211> LENGTH: 747
<212> TYPE: PRT
<213> ORGANISM: Artificial Sequence
<220> FEATURE:
<223> OTHER INFORMATION: Synthetic polypeptide - AAVrh10 with insert A2

<400> SEQUENCE: 6

Met Ala Ala Asp Gly Tyr Leu Pro Asp Trp Leu Glu Asp Asn Leu Ser
1 5 10 15

Glu Gly Ile Arg Glu Trp Trp Asp Leu Lys Pro Gly Ala Pro Lys Pro
20 25 30

Lys Ala Asn Gln Gln Lys Gln Asp Asp Gly Arg Gly Leu Val Leu Pro
35 40 45

Gly Tyr Lys Tyr Leu Gly Pro Phe Asn Gly Leu Asp Lys Gly Glu Pro
50 55 60

Val Asn Ala Ala Asp Ala Ala Ala Leu Glu His Asp Lys Ala Tyr Asp
65 70 75 80

Gln Gln Leu Lys Ala Gly Asp Asn Pro Tyr Leu Arg Tyr Asn His Ala
85 90 95

Asp Ala Glu Phe Gln Glu Arg Leu Gln Glu Asp Thr Ser Phe Gly Gly
100 105 110

Asn Leu Gly Arg Ala Val Phe Gln Ala Lys Lys Arg Val Leu Glu Pro
115 120 125

Leu Gly Leu Val Glu Glu Gly Ala Lys Thr Ala Pro Gly Lys Lys Arg
130 135 140

Pro Val Glu Pro Ser Pro Gln Arg Ser Pro Asp Ser Ser Thr Gly Ile
145 150 155 160

Gly Lys Lys Gly Gln Gln Pro Ala Lys Lys Arg Leu Asn Phe Gly Gln
165 170 175

Thr Gly Asp Ser Glu Ser Val Pro Asp Pro Gln Pro Ile Gly Glu Pro
180 185 190

Pro Ala Gly Pro Ser Gly Leu Gly Ser Gly Thr Met Ala Ala Gly Gly
195 200 205

Gly Ala Pro Met Ala Asp Asn Asn Glu Gly Ala Asp Gly Val Gly Ser
210 215 220

Ser Ser Gly Asn Trp His Cys Asp Ser Thr Trp Leu Gly Asp Arg Val
225 230 235 240

```
Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Ala Gly Thr Gln Gln Leu Leu
    450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
    530                 535                 540

Phe Gly Lys Gln Gly Ala Gly Lys Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gly Gln Arg Gly Asn
            580                 585                 590

Tyr Ser Arg Gly Val Asp Ala Gln Ala Ala Ile Val Gly Ala Val Asn
        595                 600                 605

Ser Gln Gly Ala Leu Pro Gly Met Val Trp Gln Asn Arg Asp Val Tyr
    610                 615                 620

Leu Gln Gly Pro Ile Trp Ala Lys Ile Pro His Thr Asp Gly Asn Phe
625                 630                 635                 640

His Pro Ser Pro Leu Met Gly Gly Phe Gly Leu Lys His Pro Pro Pro
                645                 650                 655
```

```
Gln Ile Leu Ile Lys Asn Thr Pro Val Pro Ala Asp Pro Pro Thr Thr
            660                 665                 670

Phe Ser Gln Ala Lys Leu Ala Ser Phe Ile Thr Gln Tyr Ser Thr Gly
        675                 680                 685

Gln Val Ser Val Glu Ile Glu Trp Glu Leu Gln Lys Glu Asn Ser Lys
    690                 695                 700

Arg Trp Asn Pro Glu Ile Gln Tyr Thr Ser Asn Tyr Tyr Lys Ser Thr
705                 710                 715                 720

Asn Val Asp Phe Ala Val Asn Thr Asp Gly Thr Tyr Ser Glu Pro Arg
                725                 730                 735

Pro Ile Gly Thr Arg Tyr Leu Thr Arg Asn Leu
            740                 745


<210> SEQ ID NO 7
<211> LENGTH: 748
<212> TYPE: PRT
<213> ORGANISM: Artificial Sequence
<220> FEATURE:
<223> OTHER INFORMATION: Synthetic polypeptide - AAVDJ with insert QR-P2

<400> SEQUENCE: 7

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Ile Gly Glu Pro Pro
            180                 185                 190

Ala Ala Pro Ser Gly Val Gly Ser Leu Thr Met Ala Ala Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270
```

-continued

```
Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Ser Phe Lys Leu Phe Asn Ile
305                 310                 315                 320

Gln Val Lys Glu Val Thr Gln Asn Glu Gly Thr Lys Thr Ile Ala Asn
                325                 330                 335

Asn Leu Thr Ser Thr Ile Gln Val Phe Thr Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Ile Pro Gln Tyr Gly Tyr Leu Thr Leu Asn Asn
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Thr Tyr Thr
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Arg Thr Gln Thr Thr Gly Gly Thr Thr Asn Thr Gln Thr Leu Gly Phe
    450                 455                 460

Ser Gln Gly Gly Pro Asn Thr Met Ala Asn Gln Ala Lys Asn Trp Leu
465                 470                 475                 480

Pro Gly Pro Cys Tyr Arg Gln Gln Arg Val Ser Lys Thr Ser Ala Asp
                485                 490                 495

Asn Asn Asn Ser Glu Tyr Ser Trp Thr Gly Ala Thr Lys Tyr His Leu
            500                 505                 510

Asn Gly Arg Asp Ser Leu Val Asn Pro Gly Pro Ala Met Ala Ser His
        515                 520                 525

Lys Asp Asp Glu Glu Lys Phe Phe Pro Gln Ser Gly Val Leu Ile Phe
    530                 535                 540

Gly Lys Gln Gly Ser Glu Lys Thr Asn Val Asp Ile Glu Lys Val Met
545                 550                 555                 560

Ile Thr Asp Glu Glu Glu Ile Arg Thr Thr Asn Pro Val Ala Thr Glu
                565                 570                 575

Gln Tyr Gly Ser Val Ser Thr Asn Leu Gln Gln Gly Gln Arg Gly Cys
            580                 585                 590

Asp Cys Arg Gly Asp Cys Phe Cys Ala Gln Ala Ala Thr Ala Asp Val
        595                 600                 605

Asn Thr Gln Gly Val Leu Pro Gly Met Val Trp Gln Asp Arg Asp Val
    610                 615                 620

Tyr Leu Gln Gly Pro Ile Trp Ala Lys Ile Pro His Thr Asp Gly His
625                 630                 635                 640

Phe His Pro Ser Pro Leu Met Gly Gly Phe Gly Leu Lys His Pro Pro
                645                 650                 655

Pro Gln Ile Leu Ile Lys Asn Thr Pro Val Pro Ala Asp Pro Pro Thr
            660                 665                 670

Thr Phe Asn Gln Ser Lys Leu Asn Ser Phe Ile Thr Gln Tyr Ser Thr
        675                 680                 685
```

Gly Gln Val Ser Val Glu Ile Glu Trp Glu Leu Gln Lys Glu Asn Ser
690 695 700

Lys Arg Trp Asn Pro Glu Ile Gln Tyr Thr Ser Asn Tyr Tyr Lys Ser
705 710 715 720

Thr Ser Val Asp Phe Ala Val Asn Thr Glu Gly Val Tyr Ser Glu Pro
725 730 735

Arg Pro Ile Gly Thr Arg Tyr Leu Thr Arg Asn Leu
740 745

<210> SEQ ID NO 8
<211> LENGTH: 15
<212> TYPE: PRT
<213> ORGANISM: Artificial Sequence
<220> FEATURE:
<223> OTHER INFORMATION: Synthetic peptide - insert A2

<400> SEQUENCE: 8

Gly Gln Arg Gly Asn Tyr Ser Arg Gly Val Asp Ala Gln Ala Ala
1 5 10 15

<210> SEQ ID NO 9
<211> LENGTH: 15
<212> TYPE: PRT
<213> ORGANISM: Artificial Sequence
<220> FEATURE:
<223> OTHER INFORMATION: Synthetic peptide - insert A6

<400> SEQUENCE: 9

Gly Gln Arg Gly Asn Glu Ala Arg Val Arg Glu Ala Gln Ala Ala
1 5 10 15

<210> SEQ ID NO 10
<211> LENGTH: 18
<212> TYPE: PRT
<213> ORGANISM: Artificial Sequence
<220> FEATURE:
<223> OTHER INFORMATION: Synthetic peptide - insert P2

<400> SEQUENCE: 10

Gln Gly Gln Ser Gly Cys Asp Cys Arg Gly Asp Cys Phe Cys Ala Gln
1 5 10 15

Ala Ala

<210> SEQ ID NO 11
<211> LENGTH: 15
<212> TYPE: PRT
<213> ORGANISM: Artificial Sequence
<220> FEATURE:
<223> OTHER INFORMATION: Synthetic peptide - insert P4

<400> SEQUENCE: 11

Gly Gln Ser Gly Asn Asp Val Arg Ser Ala Asn Ala Gln Ala Ala
1 5 10 15

<210> SEQ ID NO 12
<211> LENGTH: 18
<212> TYPE: PRT
<213> ORGANISM: Artificial Sequence
<220> FEATURE:
<223> OTHER INFORMATION: Synthetic peptide - insert QR-P2

<400> SEQUENCE: 12

Gln Gly Gln Arg Gly Cys Asp Cys Arg Gly Asp Cys Phe Cys Ala Gln
1 5 10 15

Ala Ala

<210> SEQ ID NO 13
<211> LENGTH: 736
<212> TYPE: PRT
<213> ORGANISM: Adeno-associated virus 1

<400> SEQUENCE: 13

Met Ala Ala Asp Gly Tyr Leu Pro Asp Trp Leu Glu Asp Asn Leu Ser
1 5 10 15

Glu Gly Ile Arg Glu Trp Trp Asp Leu Lys Pro Gly Ala Pro Lys Pro
20 25 30

Lys Ala Asn Gln Gln Lys Gln Asp Asp Gly Arg Gly Leu Val Leu Pro
35 40 45

Gly Tyr Lys Tyr Leu Gly Pro Phe Asn Gly Leu Asp Lys Gly Glu Pro
50 55 60

Val Asn Ala Ala Asp Ala Ala Ala Leu Glu His Asp Lys Ala Tyr Asp
65 70 75 80

Gln Gln Leu Lys Ala Gly Asp Asn Pro Tyr Leu Arg Tyr Asn His Ala
85 90 95

Asp Ala Glu Phe Gln Glu Arg Leu Gln Glu Asp Thr Ser Phe Gly Gly
100 105 110

Asn Leu Gly Arg Ala Val Phe Gln Ala Lys Lys Arg Val Leu Glu Pro
115 120 125

Leu Gly Leu Val Glu Glu Gly Ala Lys Thr Ala Pro Gly Lys Lys Arg
130 135 140

Pro Val Glu Gln Ser Pro Gln Glu Pro Asp Ser Ser Ser Gly Ile Gly
145 150 155 160

Lys Thr Gly Gln Gln Pro Ala Lys Lys Arg Leu Asn Phe Gly Gln Thr
165 170 175

Gly Asp Ser Glu Ser Val Pro Asp Pro Gln Pro Leu Gly Glu Pro Pro
180 185 190

Ala Thr Pro Ala Ala Val Gly Pro Thr Thr Met Ala Ser Gly Gly Gly
195 200 205

Ala Pro Met Ala Asp Asn Asn Glu Gly Ala Asp Gly Val Gly Asn Ala
210 215 220

Ser Gly Asn Trp His Cys Asp Ser Thr Trp Leu Gly Asp Arg Val Ile
225 230 235 240

Thr Thr Ser Thr Arg Thr Trp Ala Leu Pro Thr Tyr Asn Asn His Leu
245 250 255

Tyr Lys Gln Ile Ser Ser Ala Ser Thr Gly Ala Ser Asn Asp Asn His
260 265 270

Tyr Phe Gly Tyr Ser Thr Pro Trp Gly Tyr Phe Asp Phe Asn Arg Phe
275 280 285

His Cys His Phe Ser Pro Arg Asp Trp Gln Arg Leu Ile Asn Asn Asn
290 295 300

Trp Gly Phe Arg Pro Lys Arg Leu Asn Phe Lys Leu Phe Asn Ile Gln
305 310 315 320

Val Lys Glu Val Thr Thr Asn Asp Gly Val Thr Thr Ile Ala Asn Asn
325 330 335

Leu Thr Ser Thr Val Gln Val Phe Ser Asp Ser Glu Tyr Gln Leu Pro
340 345 350

Tyr Val Leu Gly Ser Ala His Gln Gly Cys Leu Pro Pro Phe Pro Ala
355 360 365

```
Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Glu Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Glu Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Phe Gln Ser Ser Ser Thr Asp Pro Ala
            580                 585                 590

Thr Gly Asp Val His Ala Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys Asn Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735
```

<210> SEQ ID NO 14
<211> LENGTH: 735
<212> TYPE: PRT
<213> ORGANISM: Adeno-associated virus 2

<400> SEQUENCE: 14

```
Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400
```

```
Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
    450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735


<210> SEQ ID NO 15
<211> LENGTH: 737
<212> TYPE: PRT
<213> ORGANISM: Adeno-associated virus 7

<400> SEQUENCE: 15

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30
```

```
Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Ala Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Ser Val Gly Ser Gly Thr Val Ala Ala Gly Gly
        195                 200                 205

Gly Ala Pro Met Ala Asp Asn Asn Glu Gly Ala Asp Gly Val Gly Asn
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Glu Thr Ala Gly Ser Thr Asn Asp Asn
            260                 265                 270

Thr Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Lys Leu Arg Phe Lys Leu Phe Asn Ile
305                 310                 315                 320

Gln Val Lys Glu Val Thr Thr Asn Asp Gly Val Thr Thr Ile Ala Asn
                325                 330                 335

Asn Leu Thr Ser Thr Ile Gln Val Phe Ser Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Ile Pro Gln Tyr Gly Tyr Leu Thr Leu Asn Asn
    370                 375                 380

Gly Ser Gln Ser Val Gly Arg Ser Ser Phe Tyr Cys Leu Glu Tyr Phe
385                 390                 395                 400

Pro Ser Gln Met Leu Arg Thr Gly Asn Asn Phe Glu Phe Ser Tyr Ser
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ala
        435                 440                 445
```

Arg Thr Gln Ser Asn Pro Gly Gly Thr Ala Gly Asn Arg Glu Leu Gln
    450                 455                 460

Phe Tyr Gln Gly Gly Pro Ser Thr Met Ala Glu Gln Ala Lys Asn Trp
465                 470                 475                 480

Leu Pro Gly Pro Cys Phe Arg Gln Gln Arg Val Ser Lys Thr Leu Asp
                485                 490                 495

Gln Asn Asn Asn Ser Asn Phe Ala Trp Thr Gly Ala Thr Lys Tyr His
            500                 505                 510

Leu Asn Gly Arg Asn Ser Leu Val Asn Pro Gly Val Ala Met Ala Thr
        515                 520                 525

His Lys Asp Asp Glu Asp Arg Phe Phe Pro Ser Ser Gly Val Leu Ile
    530                 535                 540

Phe Gly Lys Thr Gly Ala Thr Asn Lys Thr Thr Leu Glu Asn Val Leu
545                 550                 555                 560

Met Thr Asn Glu Glu Glu Ile Arg Pro Thr Asn Pro Val Ala Thr Glu
                565                 570                 575

Glu Tyr Gly Ile Val Ser Ser Asn Leu Gln Ala Ala Asn Thr Ala Ala
            580                 585                 590

Gln Thr Gln Val Val Asn Asn Gln Gly Ala Leu Pro Gly Met Val Trp
        595                 600                 605

Gln Asn Arg Asp Val Tyr Leu Gln Gly Pro Ile Trp Ala Lys Ile Pro
    610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asn Pro Pro Glu Val Phe Thr Pro Ala Lys Phe Ala Ser Phe Ile
            660                 665                 670

Thr Gln Tyr Ser Thr Gly Gln Val Ser Val Glu Ile Glu Trp Glu Leu
        675                 680                 685

Gln Lys Glu Asn Ser Lys Arg Trp Asn Pro Glu Ile Gln Tyr Thr Ser
    690                 695                 700

Asn Phe Glu Lys Gln Thr Gly Val Asp Phe Ala Val Asp Ser Gln Gly
705                 710                 715                 720

Val Tyr Ser Glu Pro Arg Pro Ile Gly Thr Arg Tyr Leu Thr Arg Asn
                725                 730                 735

Leu

<210> SEQ ID NO 16
<211> LENGTH: 736
<212> TYPE: PRT
<213> ORGANISM: Adeno-associated virus 9

<400> SEQUENCE: 16

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

```
Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495
```

```
Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735


<210> SEQ ID NO 17
<211> LENGTH: 738
<212> TYPE: PRT
<213> ORGANISM: Adeno-associated virus rh10

<400> SEQUENCE: 17

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125
```

-continued

```
Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Ala Gly Thr Gln Gln Leu Leu
    450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
    530                 535                 540
```

Phe Gly Lys Gln Gly Ala Gly Lys Asp Asn Val Asp Tyr Ser Ser Val
545 550 555 560

Met Leu Thr Ser Glu Glu Glu Ile Lys Thr Thr Asn Pro Val Ala Thr
565 570 575

Glu Gln Tyr Gly Val Val Ala Asp Asn Leu Gln Gln Gln Asn Ala Ala
580 585 590

Pro Ile Val Gly Ala Val Asn Ser Gln Gly Ala Leu Pro Gly Met Val
595 600 605

Trp Gln Asn Arg Asp Val Tyr Leu Gln Gly Pro Ile Trp Ala Lys Ile
610 615 620

Pro His Thr Asp Gly Asn Phe His Pro Ser Pro Leu Met Gly Gly Phe
625 630 635 640

Gly Leu Lys His Pro Pro Pro Gln Ile Leu Ile Lys Asn Thr Pro Val
645 650 655

Pro Ala Asp Pro Pro Thr Thr Phe Ser Gln Ala Lys Leu Ala Ser Phe
660 665 670

Ile Thr Gln Tyr Ser Thr Gly Gln Val Ser Val Glu Ile Glu Trp Glu
675 680 685

Leu Gln Lys Glu Asn Ser Lys Arg Trp Asn Pro Glu Ile Gln Tyr Thr
690 695 700

Ser Asn Tyr Tyr Lys Ser Thr Asn Val Asp Phe Ala Val Asn Thr Asp
705 710 715 720

Gly Thr Tyr Ser Glu Pro Arg Pro Ile Gly Thr Arg Tyr Leu Thr Arg
725 730 735

Asn Leu

<210> SEQ ID NO 18
<211> LENGTH: 737
<212> TYPE: PRT
<213> ORGANISM: Artificial Sequence
<220> FEATURE:
<223> OTHER INFORMATION: Synthetic polypeptide - AAV DJ-QR

<400> SEQUENCE: 18

Met Ala Ala Asp Gly Tyr Leu Pro Asp Trp Leu Glu Asp Thr Leu Ser
1 5 10 15

Glu Gly Ile Arg Gln Trp Trp Lys Leu Lys Pro Gly Pro Pro Pro Pro
20 25 30

Lys Pro Ala Glu Arg His Lys Asp Asp Ser Arg Gly Leu Val Leu Pro
35 40 45

Gly Tyr Lys Tyr Leu Gly Pro Phe Asn Gly Leu Asp Lys Gly Glu Pro
50 55 60

Val Asn Glu Ala Asp Ala Ala Ala Leu Glu His Asp Lys Ala Tyr Asp
65 70 75 80

Arg Gln Leu Asp Ser Gly Asp Asn Pro Tyr Leu Lys Tyr Asn His Ala
85 90 95

Asp Ala Glu Phe Gln Glu Arg Leu Lys Glu Asp Thr Ser Phe Gly Gly
100 105 110

Asn Leu Gly Arg Ala Val Phe Gln Ala Lys Lys Arg Leu Leu Glu Pro
115 120 125

Leu Gly Leu Val Glu Glu Ala Ala Lys Thr Ala Pro Gly Lys Lys Arg
130 135 140

Pro Val Glu His Ser Pro Val Glu Pro Asp Ser Ser Ser Gly Thr Gly
145 150 155 160

```
Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Ile Gly Glu Pro Pro
            180                 185                 190

Ala Ala Pro Ser Gly Val Gly Ser Leu Thr Met Ala Ala Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Ser Phe Lys Leu Phe Asn Ile
305                 310                 315                 320

Gln Val Lys Glu Val Thr Gln Asn Glu Gly Thr Lys Thr Ile Ala Asn
                325                 330                 335

Asn Leu Thr Ser Thr Ile Gln Val Phe Thr Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Ile Pro Gln Tyr Gly Tyr Leu Thr Leu Asn Asn
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Thr Tyr Thr
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Arg Thr Gln Thr Thr Gly Gly Thr Thr Asn Thr Gln Thr Leu Gly Phe
    450                 455                 460

Ser Gln Gly Gly Pro Asn Thr Met Ala Asn Gln Ala Lys Asn Trp Leu
465                 470                 475                 480

Pro Gly Pro Cys Tyr Arg Gln Gln Arg Val Ser Lys Thr Ser Ala Asp
                485                 490                 495

Asn Asn Asn Ser Glu Tyr Ser Trp Thr Gly Ala Thr Lys Tyr His Leu
            500                 505                 510

Asn Gly Arg Asp Ser Leu Val Asn Pro Gly Pro Ala Met Ala Ser His
        515                 520                 525

Lys Asp Asp Glu Glu Lys Phe Phe Pro Gln Ser Gly Val Leu Ile Phe
    530                 535                 540

Gly Lys Gln Gly Ser Glu Lys Thr Asn Val Asp Ile Glu Lys Val Met
545                 550                 555                 560

Ile Thr Asp Glu Glu Glu Ile Arg Thr Thr Asn Pro Val Ala Thr Glu
                565                 570                 575
```

```
Gln Tyr Gly Ser Val Ser Thr Asn Leu Gln Arg Gly Asn Arg Gln Ala
            580                 585                 590

Ala Thr Ala Asp Val Asn Thr Gln Gly Val Leu Pro Gly Met Val Trp
        595                 600                 605

Gln Asp Arg Asp Val Tyr Leu Gln Gly Pro Ile Trp Ala Lys Ile Pro
    610                 615                 620

His Thr Asp Gly His Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asp Pro Pro Thr Thr Phe Asn Gln Ser Lys Leu Asn Ser Phe Ile
            660                 665                 670

Thr Gln Tyr Ser Thr Gly Gln Val Ser Val Glu Ile Glu Trp Glu Leu
        675                 680                 685

Gln Lys Glu Asn Ser Lys Arg Trp Asn Pro Glu Ile Gln Tyr Thr Ser
    690                 695                 700

Asn Tyr Tyr Lys Ser Thr Ser Val Asp Phe Ala Val Asn Thr Glu Gly
705                 710                 715                 720

Val Tyr Ser Glu Pro Arg Pro Ile Gly Thr Arg Tyr Leu Thr Arg Asn
                725                 730                 735

Leu


<210> SEQ ID NO 19
<211> LENGTH: 724
<212> TYPE: PRT
<213> ORGANISM: Adeno-associated virus 5

<400> SEQUENCE: 19

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Gly Pro Leu Gly Asp Asn Asn Gln Gly Ala
        195                 200                 205
```

-continued

```
Asp Gly Val Gly Asn Ala Ser Gly Asp Trp His Cys Asp Ser Thr Trp
    210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
        275                 280                 285

Arg Leu Ile Asn Asn Tyr Trp Gly Phe Arg Pro Arg Ser Leu Arg Val
    290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Glu Gly Cys
            340                 345                 350

Leu Pro Ala Phe Pro Pro Gln Val Phe Thr Leu Pro Gln Tyr Gly Tyr
        355                 360                 365

Ala Thr Leu Asn Arg Asp Asn Thr Glu Asn Pro Thr Glu Arg Ser Ser
    370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
                405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Asn Asn Thr Gly Gly Val Gln
        435                 440                 445

Phe Asn Lys Asn Leu Ala Gly Arg Tyr Ala Asn Thr Tyr Lys Asn Trp
    450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
            500                 505                 510

Asn Asn Leu Gln Gly Ser Asn Thr Tyr Ala Leu Glu Asn Thr Met Ile
        515                 520                 525

Phe Asn Ser Gln Pro Ala Asn Pro Gly Thr Thr Ala Thr Tyr Leu Glu
    530                 535                 540

Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
                565                 570                 575

Thr Thr Ala Pro Ala Thr Gly Thr Tyr Asn Leu Gln Glu Ile Val Pro
            580                 585                 590

Gly Ser Val Trp Met Glu Arg Asp Val Tyr Leu Gln Gly Pro Ile Trp
        595                 600                 605

Ala Lys Ile Pro Glu Thr Gly Ala His Phe His Pro Ser Pro Ala Met
    610                 615                 620
```

Gly Gly Phe Gly Leu Lys His Pro Pro Pro Met Met Leu Ile Lys Asn
625 630 635 640

Thr Pro Val Pro Gly Asn Ile Thr Ser Phe Ser Asp Val Pro Val Ser
645 650 655

Ser Phe Ile Thr Gln Tyr Ser Thr Gly Gln Val Thr Val Glu Met Glu
660 665 670

Trp Glu Leu Lys Lys Glu Asn Ser Lys Arg Trp Asn Pro Glu Ile Gln
675 680 685

Tyr Thr Asn Asn Tyr Asn Asp Pro Gln Phe Val Asp Phe Ala Pro Asp
690 695 700

Ser Thr Gly Glu Tyr Arg Thr Thr Arg Pro Ile Gly Thr Arg Tyr Leu
705 710 715 720

Thr Arg Pro Leu

<210> SEQ ID NO 20
<211> LENGTH: 13
<212> TYPE: PRT
<213> ORGANISM: Artificial Sequence
<220> FEATURE:
<223> OTHER INFORMATION: Synthetic peptide - insert AAV7A6

<400> SEQUENCE: 20

Gly Gln Arg Gly Asn Glu Ala Arg Val Arg Glu Ala Gln
1 5 10

<210> SEQ ID NO 21
<211> LENGTH: 15
<212> TYPE: PRT
<213> ORGANISM: Artificial Sequence
<220> FEATURE:
<223> OTHER INFORMATION: Synthetic peptide - insert AAV2P2

<400> SEQUENCE: 21

Gln Gly Gln Ser Gly Cys Asp Cys Arg Gly Asp Cys Phe Cys Ala
1 5 10 15

<210> SEQ ID NO 22
<211> LENGTH: 15
<212> TYPE: PRT
<213> ORGANISM: Artificial Sequence
<220> FEATURE:
<223> OTHER INFORMATION: Synthetic peptide - insert AAVDJQRP2

<400> SEQUENCE: 22

Gln Gly Gln Arg Gly Cys Asp Cys Arg Gly Asp Cys Phe Cys Ala
1 5 10 15

<210> SEQ ID NO 23
<211> LENGTH: 19
<212> TYPE: PRT
<213> ORGANISM: Artificial Sequence
<220> FEATURE:
<223> OTHER INFORMATION: Synthetic peptide - insert AAV2P2
<220> FEATURE:
<221> NAME/KEY: MOD_RES
<222> LOCATION: (1)..(1)
<223> OTHER INFORMATION: Any amino acid or absent
<220> FEATURE:
<221> NAME/KEY: MOD_RES
<222> LOCATION: (2)..(2)
<223> OTHER INFORMATION: Any amino acid or absent
<220> FEATURE:
<221> NAME/KEY: MOD_RES
<222> LOCATION: (5)..(5)
<223> OTHER INFORMATION: Any amino acid

```
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (14)..(14)
<223> OTHER INFORMATION: Any amino acid or absent
<220> FEATURE:
<221> NAME/KEY: MOD_RES
<222> LOCATION: (15)..(15)
<223> OTHER INFORMATION: Any amino acid or absent

<400> SEQUENCE: 23

Xaa Xaa Gly Gln Xaa Gly Xaa Xaa Xaa Arg Xaa Xaa Xaa Xaa Xaa Ala
1               5                   10                  15

Gln Ala Ala


<210> SEQ ID NO 24
<211> LENGTH: 19
<212> TYPE: PRT
<213> ORGANISM: Artificial Sequence
<220> FEATURE:
<223> OTHER INFORMATION: Synthetic peptide - alternative formula for
      sequence Z
<220> FEATURE:
<221> NAME/KEY: MOD_RES
<222> LOCATION: (1)..(1)
<223> OTHER INFORMATION: Q or absent
<220> FEATURE:
<221> NAME/KEY: MOD_RES
<222> LOCATION: (4)..(4)
<223> OTHER INFORMATION: S or R
<220> FEATURE:
<221> NAME/KEY: MOD_RES
<222> LOCATION: (6)..(6)
<223> OTHER INFORMATION: N or C
<220> FEATURE:
<221> NAME/KEY: MOD_RES
<222> LOCATION: (7)..(7)
<223> OTHER INFORMATION: D, Y or E
<220> FEATURE:
<221> NAME/KEY: MOD_RES
<222> LOCATION: (8)..(8)
<223> OTHER INFORMATION: C, V, S or A
<220> FEATURE:
<221> NAME/KEY: MOD_RES
<222> LOCATION: (10)..(10)
<223> OTHER INFORMATION: G, S or V
<220> FEATURE:
<221> NAME/KEY: MOD_RES
<222> LOCATION: (11)..(11)
<223> OTHER INFORMATION: A, V, R or absent
<220> FEATURE:
<221> NAME/KEY: MOD_RES
<222> LOCATION: (12)..(12)
```

<223> OTHER INFORMATION: D, N or E
<220> FEATURE:
<221> NAME/KEY: MOD_RES
<222> LOCATION: (13)..(13)
<223> OTHER INFORMATION: C or A
<220> FEATURE:
<221> NAME/KEY: MOD_RES
<222> LOCATION: (14)..(14)
<223> OTHER INFORMATION: F or Q
<220> FEATURE:
<221> NAME/KEY: MOD_RES
<222> LOCATION: (15)..(15)
<223> OTHER INFORMATION: C, A or absent
<220> FEATURE:
<221> NAME/KEY: MOD_RES
<222> LOCATION: (16)..(16)
<223> OTHER INFORMATION: A or absent
<220> FEATURE:
<221> NAME/KEY: MOD_RES
<222> LOCATION: (17)..(17)
<223> OTHER INFORMATION: Q or absent
<220> FEATURE:
<221> NAME/KEY: MOD_RES
<222> LOCATION: (18)..(18)
<223> OTHER INFORMATION: A or absent
<220> FEATURE:
<221> NAME/KEY: MOD_RES
<222> LOCATION: (19)..(19)
<223> OTHER INFORMATION: A or absent

<400> SEQUENCE: 24

Xaa Gly Gln Xaa Gly Xaa Xaa Xaa Arg Xaa Xaa Xaa Xaa Xaa Xaa Xaa
1               5                   10                  15

Xaa Xaa Xaa

<210> SEQ ID NO 25
<211> LENGTH: 18
<212> TYPE: PRT
<213> ORGANISM: Artificial Sequence
<220> FEATURE:
<223> OTHER INFORMATION: Synthetic peptide - alternative formula for
      sequence Z
<220> FEATURE:
<221> NAME/KEY: MOD_RES
<222> LOCATION: (1)..(1)
<223> OTHER INFORMATION: Q or absent
<220> FEATURE:
<221> NAME/KEY: MOD_RES
<222> LOCATION: (4)..(4)
<223> OTHER INFORMATION: S or R
<220> FEATURE:
<221> NAME/KEY: MOD_RES
<222> LOCATION: (6)..(6)
<223> OTHER INFORMATION: N or C
<220> FEATURE:
<221> NAME/KEY: MOD_RES
<222> LOCATION: (7)..(7)
<223> OTHER INFORMATION: D, Y or E
<220> FEATURE:
<221> NAME/KEY: MOD_RES
<222> LOCATION: (8)..(8)
<223> OTHER INFORMATION: C, V, S or A
<220> FEATURE:
<221> NAME/KEY: MOD_RES
<222> LOCATION: (10)..(10)
<223> OTHER INFORMATION: G, S or V
<220> FEATURE:
<221> NAME/KEY: MOD_RES
<222> LOCATION: (11)..(11)
<223> OTHER INFORMATION: D or absent
<220> FEATURE:
<221> NAME/KEY: MOD_RES
<222> LOCATION: (12)..(12)
<223> OTHER INFORMATION: C or absent
<220> FEATURE:
<221> NAME/KEY: MOD_RES

```
<222> LOCATION: (13)..(13)
<223> OTHER INFORMATION: A, V, R or F
<220> FEATURE:
<221> NAME/KEY: MOD_RES
<222> LOCATION: (14)..(14)
<223> OTHER INFORMATION: N, D, E or C
<220> FEATURE:
<221> NAME/KEY: MOD_RES
<222> LOCATION: (16)..(16)
<223> OTHER INFORMATION: Q or absent
<220> FEATURE:
<221> NAME/KEY: MOD_RES
<222> LOCATION: (17)..(17)
<223> OTHER INFORMATION: A or absent
<220> FEATURE:
<221> NAME/KEY: MOD_RES
<222> LOCATION: (18)..(18)
<223> OTHER INFORMATION: A or absent

<400> SEQUENCE: 25

Xaa Gly Gln Xaa Gly Xaa Xaa Xaa Arg Xaa Xaa Xaa Xaa Xaa Ala Xaa
1               5                   10                  15

Xaa Xaa


<210> SEQ ID NO 26
<211> LENGTH: 18
<212> TYPE: PRT
<213> ORGANISM: Artificial Sequence
<220> FEATURE:
<223> OTHER INFORMATION: Synthetic peptide - preferred embodiment of
      formula I
<220> FEATURE:
<221> NAME/KEY: MOD_RES
<222> LOCATION: (1)..(1)
<223> OTHER INFORMATION: Q or absent
<220> FEATURE:
<221> NAME/KEY: MOD_RES
<222> LOCATION: (4)..(4)
<223> OTHER INFORMATION: R or S
<220> FEATURE:
<221> NAME/KEY: MOD_RES
<222> LOCATION: (6)..(6)
<223> OTHER INFORMATION: C or N
<220> FEATURE:
<221> NAME/KEY: MOD_RES
<222> LOCATION: (7)..(7)
<223> OTHER INFORMATION: D, E or Y
<220> FEATURE:
<221> NAME/KEY: MOD_RES
<222> LOCATION: (8)..(8)
<223> OTHER INFORMATION: C, A, S or V
<220> FEATURE:
<221> NAME/KEY: MOD_RES
<222> LOCATION: (10)..(10)
<223> OTHER INFORMATION: G, V or S
<220> FEATURE:
<221> NAME/KEY: MOD_RES
<222> LOCATION: (11)..(11)
<223> OTHER INFORMATION: D or absent
<220> FEATURE:
<221> NAME/KEY: MOD_RES
<222> LOCATION: (12)..(12)
<223> OTHER INFORMATION: C or absent
<220> FEATURE:
<221> NAME/KEY: MOD_RES
<222> LOCATION: (13)..(13)
<223> OTHER INFORMATION: F, R, V or A
<220> FEATURE:
<221> NAME/KEY: MOD_RES
<222> LOCATION: (14)..(14)
<223> OTHER INFORMATION: C, D, N or E

<400> SEQUENCE: 26

Xaa Gly Gln Xaa Gly Xaa Xaa Xaa Arg Xaa Xaa Xaa Xaa Xaa Ala Gln
1               5                   10                  15
```

Ala Ala

<210> SEQ ID NO 27
<211> LENGTH: 85
<212> TYPE: PRT
<213> ORGANISM: Artificial Sequence
<220> FEATURE:
<223> OTHER INFORMATION: Synthetic polypeptide - formula II; general formula I (SEQ ID NO. 23) inserted
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (14)..(14)
<223> OTHER INFORMATION: Any amino acid
<220> FEATURE:
<221> NAME/KEY: MOD_RES
<222> LOCATION: (15)..(15)
<223> OTHER INFORMATION: Any amino acid
<220> FEATURE:
<221> NAME/KEY: MOD_RES
<222> LOCATION: (17)..(17)
<223> OTHER INFORMATION: Any amino acid
<220> FEATURE:
<221> NAME/KEY: MOD_RES
<222> LOCATION: (18)..(18)
<223> OTHER INFORMATION: Any amino acid
<220> FEATURE:
<221> NAME/KEY: MOD_RES
<222> LOCATION: (19)..(19)
<223> OTHER INFORMATION: Any amino acid
<220> FEATURE:
<221> NAME/KEY: MOD_RES
<222> LOCATION: (20)..(20)
<223> OTHER INFORMATION: Any amino acid
<220> FEATURE:
<221> NAME/KEY: MOD_RES
<222> LOCATION: (22)..(22)
<223> OTHER INFORMATION: Any amino acid
<220> FEATURE:
<221> NAME/KEY: MOD_RES
<222> LOCATION: (24)..(24)
<223> OTHER INFORMATION: Any amino acid or absent
<220> FEATURE:
<221> NAME/KEY: MOD_RES
<222> LOCATION: (25)..(25)
<223> OTHER INFORMATION: Any amino acid or absent
<220> FEATURE:
<221> NAME/KEY: MOD_RES
<222> LOCATION: (26)..(26)
<223> OTHER INFORMATION: Any amino acid or absent
<220> FEATURE:
<221> NAME/KEY: MOD_RES
<222> LOCATION: (27)..(27)
<223> OTHER INFORMATION: Any amino acid or absent
<220> FEATURE:
<221> NAME/KEY: MOD_RES
<222> LOCATION: (30)..(30)
<223> OTHER INFORMATION: Any amino acid
<220> FEATURE:
<221> NAME/KEY: MOD_RES
<222> LOCATION: (32)..(32)
<223> OTHER INFORMATION: Any amino acid
<220> FEATURE:
<221> NAME/KEY: MOD_RES
<222> LOCATION: (33)..(33)
<223> OTHER INFORMATION: Any amino acid
<220> FEATURE:
<221> NAME/KEY: MOD_RES
<222> LOCATION: (34)..(34)
<223> OTHER INFORMATION: Any amino acid
<220> FEATURE:
<221> NAME/KEY: MOD_RES
<222> LOCATION: (36)..(36)
<223> OTHER INFORMATION: Any amino acid
<220> FEATURE:
<221> NAME/KEY: MOD_RES
<222> LOCATION: (37)..(37)
<223> OTHER INFORMATION: Any amino acid
<220> FEATURE:
<221> NAME/KEY: MOD_RES
<222> LOCATION: (38)..(38)
<223> OTHER INFORMATION: Any amino acid
<220> FEATURE:
<221> NAME/KEY: MOD_RES
<222> LOCATION: (39)..(39)
<223> OTHER INFORMATION: Any amino acid or absent
<220> FEATURE:
<221> NAME/KEY: MOD_RES
<222> LOCATION: (40)..(40)
<223> OTHER INFORMATION: Any amino acid or absent
<220> FEATURE:
<221> NAME/KEY: MOD_RES
<222> LOCATION: (45)..(45)
<223> OTHER INFORMATION: Any amino acid
<220> FEATURE:
<221> NAME/KEY: MOD_RES
<222> LOCATION: (46)..(46)
<223> OTHER INFORMATION: Any amino acid
<220> FEATURE:
<221> NAME/KEY: MOD_RES
<222> LOCATION: (47)..(47)
<223> OTHER INFORMATION: Any amino acid
<220> FEATURE:
<221> NAME/KEY: MOD_RES
<222> LOCATION: (48)..(48)
<223> OTHER INFORMATION: Any amino acid
<220> FEATURE:
<221> NAME/KEY: MOD_RES
<222> LOCATION: (49)..(49)
<223> OTHER INFORMATION: Any amino acid
<220> FEATURE:
<221> NAME/KEY: MOD_RES
<222> LOCATION: (50)..(50)
<223> OTHER INFORMATION: Any amino acid or absent
<220> FEATURE:
<221> NAME/KEY: MOD_RES
<222> LOCATION: (51)..(51)
<223> OTHER INFORMATION: Any amino acid or absent
<220> FEATURE:
<221> NAME/KEY: MOD_RES
<222> LOCATION: (52)..(52)
<223> OTHER INFORMATION: Any amino acid or absent
<220> FEATURE:
<221> NAME/KEY: MOD_RES
<222> LOCATION: (53)..(53)
<223> OTHER INFORMATION: Any amino acid or absent
<220> FEATURE:
<221> NAME/KEY: MOD_RES
<222> LOCATION: (54)..(54)
<223> OTHER INFORMATION: Any amino acid or absent
<220> FEATURE:
<221> NAME/KEY: MOD_RES
<222> LOCATION: (55)..(55)
<223> OTHER INFORMATION: Any amino acid or absent
<220> FEATURE:
<221> NAME/KEY: MOD_RES
<222> LOCATION: (56)..(56)
<223> OTHER INFORMATION: Any amino acid or absent
<220> FEATURE:
<221> NAME/KEY: MOD_RES
<222> LOCATION: (57)..(57)

<223> OTHER INFORMATION: Any amino acid or absent
<220> FEATURE:
<221> NAME/KEY: MOD_RES
<222> LOCATION: (58)..(58)
<223> OTHER INFORMATION: Any amino acid or absent
<220> FEATURE:
<221> NAME/KEY: MOD_RES
<222> LOCATION: (59)..(59)
<223> OTHER INFORMATION: Any amino acid or absent
<220> FEATURE:
<221> NAME/KEY: MOD_RES
<222> LOCATION: (67)..(67)
<223> OTHER INFORMATION: Any amino acid

<400> SEQUENCE: 27

```
Glu Glu Glu Ile Xaa Xaa Xaa Xaa Pro Val Ala Thr Glu Xaa Xaa Gly
1               5                   10                  15

Xaa Xaa Xaa Xaa Asn Xaa Gln Xaa Xaa Xaa Xaa Gly Gln Xaa Gly Xaa
            20                  25                  30

Xaa Xaa Arg Xaa Xaa Xaa Xaa Xaa Ala Gln Ala Ala Xaa Xaa Xaa Xaa
        35                  40                  45

Xaa Xaa Xaa Xaa Xaa Xaa Xaa Xaa Xaa Xaa Xaa Leu Pro Gly Met Val
    50                  55                  60

Trp Gln Xaa Arg Asp Val Tyr Leu Gln Gly Pro Ile Trp Ala Lys Ile
65                  70                  75                  80

Pro His Thr Asp Gly
                85
```

<210> SEQ ID NO 28
<211> LENGTH: 1470
<212> TYPE: DNA
<213> ORGANISM: artificial sequence
<220> FEATURE:
<223> OTHER INFORMATION: etanercept

<400> SEQUENCE: 28

```
atggctcctg tcgccgtctg ggccgcactg gctgtcgggc tggaactgtg ggccgccgca     60

catgcactgc ccgctcaggt cgcattcacc ccatacgcac ctgagccagg aagcacatgc    120

aggctgagag agtactatga tcagaccgcc cagatgtgct gttccaagtg ctctcccggc    180

cagcacgcca aggtgttctg taccaagaca tccgacacag tgtgcgatag ctgtgaggac    240

tccacctaca cacagctgtg gaactgggtg cctgagtgcc tgagctgtgg ctcccggtgc    300

agctccgacc aggtggagac acaggcctgt acacgggagc agaatagaat ctgcacctgt    360

aggcctggct ggtattgcgc actgagcaag caggagggat gcaggctgtg cgcaccactg    420

aggaagtgta ggcctggatt cggagtggcc aggccaggca ccgagacaag cgatgtggtg    480

tgcaagccct gtgcccctgg caccttttcc aacaccacat ctagcacaga catctgccgc    540

ccccaccaga tctgtaacgt ggtggccatc cctggcaatg cctctatgga tgccgtgtgc    600

acctccacat ctccaacccg gagcatggca ccaggagcag tgcacctgcc acagcccgtg    660

agcacaagaa gccagcacac ccagccaaca ccagagccta gcaccgcacc aagcacatcc    720

ttcctgctgc caatgggacc atctccacct gcagagggaa gcaccggcga tgagcctaag    780

tcttgcgaca agacccacac atgcccacca tgtccagcac cagagctgct gggaggacct    840

tccgtgttcc tgtttcctcc aaagccaaag gataccctga tgatctcccg gacccctgag    900

gtgacatgcg tggtggtgga cgtgagccac gaggacccag aggtgaagtt taactggtac    960

gtggacggcg tggaggtgca caatgccaag accaagccca gggaggagca gtacaactcc   1020

acctatcgcg tggtgtctgt gctgacagtg ctgcaccagg actggctgaa cggcaaggag   1080
```

```
tataagtgca aggtgagcaa taaggccctg cctgccccaa tcgagaagac catctccaag   1140

gcaaagggac agcctaggga gccacaggtg tacacactgc cccccttccag agaggagatg   1200

accaagaacc aggtgtctct gacatgtctg gtgaagggct tctatccatc tgatatcgcc   1260

gtggagtggg agagcaatgg ccagcccgag aacaattaca agaccacacc acccgtgctg   1320

gactccgatg gctctttctt tctgtatagc aagctgaccg tggacaagtc caggtggcag   1380

cagggcaacg tgttcagctg cagcgtgatg cacgaagcac tgcacaatca ttacacccag   1440

aagtcactgt cactgtctcc agggaagtag                                     1470
```

```
<210> SEQ ID NO 29
<211> LENGTH: 489
<212> TYPE: PRT
<213> ORGANISM: artificial sequence
<220> FEATURE:
<223> OTHER INFORMATION: etanercept + signal peptide

<400> SEQUENCE: 29

Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
            20                  25                  30

Ala Pro Glu Pro Gly Ser Thr Cys Arg Leu Arg Glu Tyr Tyr Asp Gln
        35                  40                  45

Thr Ala Gln Met Cys Cys Ser Lys Cys Ser Pro Gly Gln His Ala Lys
    50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Met Asp Ala Val Cys Thr Ser Thr Ser Pro Thr Arg Ser
        195                 200                 205

Met Ala Pro Gly Ala Val His Leu Pro Gln Pro Val Ser Thr Arg Ser
    210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Pro Ala Glu Gly Ser Thr Gly
                245                 250                 255

Asp Glu Pro Lys Ser Cys Asp Lys Thr His Thr Cys Pro Pro Cys Pro
            260                 265                 270

Ala Pro Glu Leu Leu Gly Gly Pro Ser Val Phe Leu Phe Pro Pro Lys
        275                 280                 285
```

```
Pro Lys Asp Thr Leu Met Ile Ser Arg Thr Pro Glu Val Thr Cys Val
    290                 295                 300

Val Val Asp Val Ser His Glu Asp Pro Glu Val Lys Phe Asn Trp Tyr
305                 310                 315                 320

Val Asp Gly Val Glu Val His Asn Ala Lys Thr Lys Pro Arg Glu Glu
                325                 330                 335

Gln Tyr Asn Ser Thr Tyr Arg Val Val Ser Val Leu Thr Val Leu His
            340                 345                 350

Gln Asp Trp Leu Asn Gly Lys Glu Tyr Lys Cys Lys Val Ser Asn Lys
        355                 360                 365

Ala Leu Pro Ala Pro Ile Glu Lys Thr Ile Ser Lys Ala Lys Gly Gln
    370                 375                 380

Pro Arg Glu Pro Gln Val Tyr Thr Leu Pro Pro Ser Arg Glu Glu Met
385                 390                 395                 400

Thr Lys Asn Gln Val Ser Leu Thr Cys Leu Val Lys Gly Phe Tyr Pro
                405                 410                 415

Ser Asp Ile Ala Val Glu Trp Glu Ser Asn Gly Gln Pro Glu Asn Asn
            420                 425                 430

Tyr Lys Thr Thr Pro Pro Val Leu Asp Ser Asp Gly Ser Phe Phe Leu
        435                 440                 445

Tyr Ser Lys Leu Thr Val Asp Lys Ser Arg Trp Gln Gln Gly Asn Val
    450                 455                 460

Phe Ser Cys Ser Val Met His Glu Ala Leu His Asn His Tyr Thr Gln
465                 470                 475                 480

Lys Ser Leu Ser Leu Ser Pro Gly Lys
                485


<210> SEQ ID NO 30
<211> LENGTH: 467
<212> TYPE: PRT
<213> ORGANISM: artificial sequence
<220> FEATURE:
<223> OTHER INFORMATION: etanercept

<400> SEQUENCE: 30

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
    130                 135                 140

Gly Thr Phe Ser Asn Thr Thr Ser Ser Thr Asp Ile Cys Arg Pro His
145                 150                 155                 160
```

```
Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465
```

<210> SEQ ID NO 31
<211> LENGTH: 85
<212> TYPE: PRT
<213> ORGANISM: Artificial Sequence
<220> FEATURE:
<223> OTHER INFORMATION: Synthetic polypeptide - formula I; alternative sequence Z (SEQ ID NO. 24) inserted
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)

<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (14)..(14)
<223> OTHER INFORMATION: Any amino acid
<220> FEATURE:
<221> NAME/KEY: MOD_RES
<222> LOCATION: (15)..(15)
<223> OTHER INFORMATION: Any amino acid
<220> FEATURE:
<221> NAME/KEY: MOD_RES
<222> LOCATION: (17)..(17)
<223> OTHER INFORMATION: Any amino acid
<220> FEATURE:
<221> NAME/KEY: MOD_RES
<222> LOCATION: (18)..(18)
<223> OTHER INFORMATION: Any amino acid
<220> FEATURE:
<221> NAME/KEY: MOD_RES
<222> LOCATION: (19)..(19)
<223> OTHER INFORMATION: Any amino acid
<220> FEATURE:
<221> NAME/KEY: MOD_RES
<222> LOCATION: (20)..(20)
<223> OTHER INFORMATION: Any amino acid
<220> FEATURE:
<221> NAME/KEY: MOD_RES
<222> LOCATION: (22)..(22)
<223> OTHER INFORMATION: Any amino acid
<220> FEATURE:
<221> NAME/KEY: MOD_RES
<222> LOCATION: (24)..(24)
<223> OTHER INFORMATION: Any amino acid or absent
<220> FEATURE:
<221> NAME/KEY: MOD_RES
<222> LOCATION: (25)..(25)
<223> OTHER INFORMATION: Any amino acid or absent
<220> FEATURE:
<221> NAME/KEY: MOD_RES
<222> LOCATION: (26)..(26)
<223> OTHER INFORMATION: Q or absent
<220> FEATURE:
<221> NAME/KEY: MOD_RES
<222> LOCATION: (29)..(29)
<223> OTHER INFORMATION: S or R
<220> FEATURE:
<221> NAME/KEY: MOD_RES
<222> LOCATION: (31)..(31)
<223> OTHER INFORMATION: N or C
<220> FEATURE:
<221> NAME/KEY: MOD_RES
<222> LOCATION: (32)..(32)
<223> OTHER INFORMATION: D, Y or E
<220> FEATURE:
<221> NAME/KEY: MOD_RES
<222> LOCATION: (33)..(33)
<223> OTHER INFORMATION: C, V, S or A
<220> FEATURE:
<221> NAME/KEY: MOD_RES
<222> LOCATION: (35)..(35)
<223> OTHER INFORMATION: G, S or V
<220> FEATURE:
<221> NAME/KEY: MOD_RES
<222> LOCATION: (36)..(36)
<223> OTHER INFORMATION: A, V, R or absent
<220> FEATURE:
<221> NAME/KEY: MOD_RES
<222> LOCATION: (37)..(37)
<223> OTHER INFORMATION: D, N or E
<220> FEATURE:
<221> NAME/KEY: MOD_RES
<222> LOCATION: (38)..(38)
<223> OTHER INFORMATION: C or A
<220> FEATURE:
<221> NAME/KEY: MOD_RES
<222> LOCATION: (39)..(39)
<223> OTHER INFORMATION: F or Q
<220> FEATURE:
<221> NAME/KEY: MOD_RES
<222> LOCATION: (40)..(40)
<223> OTHER INFORMATION: C, A or absent
<220> FEATURE:
<221> NAME/KEY: MOD_RES
<222> LOCATION: (41)..(41)
<223> OTHER INFORMATION: A or absent
<220> FEATURE:
<221> NAME/KEY: MOD_RES
<222> LOCATION: (42)..(42)
<223> OTHER INFORMATION: Q or absent
<220> FEATURE:
<221> NAME/KEY: MOD_RES
<222> LOCATION: (43)..(43)
<223> OTHER INFORMATION: A or absent
<220> FEATURE:
<221> NAME/KEY: MOD_RES
<222> LOCATION: (44)..(44)
<223> OTHER INFORMATION: A or absent
<220> FEATURE:
<221> NAME/KEY: MOD_RES
<222> LOCATION: (45)..(45)
<223> OTHER INFORMATION: Any amino acid
<220> FEATURE:
<221> NAME/KEY: MOD_RES
<222> LOCATION: (46)..(46)
<223> OTHER INFORMATION: Any amino acid
<220> FEATURE:
<221> NAME/KEY: MOD_RES
<222> LOCATION: (47)..(47)
<223> OTHER INFORMATION: Any amino acid
<220> FEATURE:
<221> NAME/KEY: MOD_RES
<222> LOCATION: (48)..(48)
<223> OTHER INFORMATION: Any amino acid
<220> FEATURE:
<221> NAME/KEY: MOD_RES
<222> LOCATION: (49)..(49)
<223> OTHER INFORMATION: Any amino acid
<220> FEATURE:
<221> NAME/KEY: MOD_RES
<222> LOCATION: (50)..(50)
<223> OTHER INFORMATION: Any amino acid or absent
<220> FEATURE:
<221> NAME/KEY: MOD_RES
<222> LOCATION: (51)..(51)
<223> OTHER INFORMATION: Any amino acid or absent
<220> FEATURE:
<221> NAME/KEY: MOD_RES
<222> LOCATION: (52)..(52)
<223> OTHER INFORMATION: Any amino acid or absent
<220> FEATURE:
<221> NAME/KEY: MOD_RES
<222> LOCATION: (53)..(53)
<223> OTHER INFORMATION: Any amino acid or absent
<220> FEATURE:
<221> NAME/KEY: MOD_RES
<222> LOCATION: (54)..(54)
<223> OTHER INFORMATION: Any amino acid or absent
<220> FEATURE:
<221> NAME/KEY: MOD_RES
<222> LOCATION: (55)..(55)
<223> OTHER INFORMATION: Any amino acid or absent
<220> FEATURE:
<221> NAME/KEY: MOD_RES
<222> LOCATION: (56)..(56)
<223> OTHER INFORMATION: Any amino acid or absent
<220> FEATURE:
<221> NAME/KEY: MOD_RES
<222> LOCATION: (57)..(57)
<223> OTHER INFORMATION: Any amino acid or absent
<220> FEATURE:
<221> NAME/KEY: MOD_RES
<222> LOCATION: (58)..(58)
<223> OTHER INFORMATION: Any amino acid or absent
<220> FEATURE:

<221> NAME/KEY: MOD_RES
<222> LOCATION: (59)..(59)
<223> OTHER INFORMATION: Any amino acid or absent
<220> FEATURE:
<221> NAME/KEY: MOD_RES
<222> LOCATION: (67)..(67)
<223> OTHER INFORMATION: Any amino acid

<400> SEQUENCE: 31

```
Glu Glu Glu Ile Xaa Xaa Xaa Xaa Pro Val Ala Thr Glu Xaa Xaa Gly
1               5                   10                  15

Xaa Xaa Xaa Xaa Asn Xaa Gln Xaa Xaa Xaa Gly Gln Xaa Gly Xaa Xaa
            20                  25                  30

Xaa Arg Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Leu Pro Gly Met Val
    50                  55                  60

Trp Gln Xaa Arg Asp Val Tyr Leu Gln Gly Pro Ile Trp Ala Lys Ile
65                  70                  75                  80

Pro His Thr Asp Gly
                85
```

<210> SEQ ID NO 32
<211> LENGTH: 84
<212> TYPE: PRT
<213> ORGANISM: Artificial Sequence
<220> FEATURE:
<223> OTHER INFORMATION: Synthetic polypeptide - formula II; alternative sequence Z (SEQ ID NO. 25) inserted
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (14)..(14)
<223> OTHER INFORMATION: Any amino acid
<220> FEATURE:
<221> NAME/KEY: MOD_RES
<222> LOCATION: (15)..(15)
<223> OTHER INFORMATION: Any amino acid
<220> FEATURE:
<221> NAME/KEY: MOD_RES
<222> LOCATION: (17)..(17)
<223> OTHER INFORMATION: Any amino acid
<220> FEATURE:
<221> NAME/KEY: MOD_RES
<222> LOCATION: (18)..(18)
<223> OTHER INFORMATION: Any amino acid
<220> FEATURE:
<221> NAME/KEY: MOD_RES
<222> LOCATION: (19)..(19)
<223> OTHER INFORMATION: Any amino acid
<220> FEATURE:
<221> NAME/KEY: MOD_RES
<222> LOCATION: (20)..(20)
<223> OTHER INFORMATION: Any amino acid
<220> FEATURE:
<221> NAME/KEY: MOD_RES
<222> LOCATION: (22)..(22)

<223> OTHER INFORMATION: Any amino acid
<220> FEATURE:
<221> NAME/KEY: MOD_RES
<222> LOCATION: (24)..(24)
<223> OTHER INFORMATION: Any amino acid or absent
<220> FEATURE:
<221> NAME/KEY: MOD_RES
<222> LOCATION: (25)..(25)
<223> OTHER INFORMATION: Any amino acid or absent
<220> FEATURE:
<221> NAME/KEY: MOD_RES
<222> LOCATION: (26)..(26)
<223> OTHER INFORMATION: Q or absent
<220> FEATURE:
<221> NAME/KEY: MOD_RES
<222> LOCATION: (29)..(29)
<223> OTHER INFORMATION: S or R
<220> FEATURE:
<221> NAME/KEY: MOD_RES
<222> LOCATION: (31)..(31)
<223> OTHER INFORMATION: N or C
<220> FEATURE:
<221> NAME/KEY: MOD_RES
<222> LOCATION: (32)..(32)
<223> OTHER INFORMATION: D, Y or E
<220> FEATURE:
<221> NAME/KEY: MOD_RES
<222> LOCATION: (33)..(33)
<223> OTHER INFORMATION: C, V, S or A
<220> FEATURE:
<221> NAME/KEY: MOD_RES
<222> LOCATION: (35)..(35)
<223> OTHER INFORMATION: G, S, or V
<220> FEATURE:
<221> NAME/KEY: MOD_RES
<222> LOCATION: (36)..(36)
<223> OTHER INFORMATION: D or absent
<220> FEATURE:
<221> NAME/KEY: MOD_RES
<222> LOCATION: (37)..(37)
<223> OTHER INFORMATION: C or absent
<220> FEATURE:
<221> NAME/KEY: MOD_RES
<222> LOCATION: (38)..(38)
<223> OTHER INFORMATION: A, V, R or F
<220> FEATURE:
<221> NAME/KEY: MOD_RES
<222> LOCATION: (39)..(39)
<223> OTHER INFORMATION: N, D, E or C
<220> FEATURE:
<221> NAME/KEY: MOD_RES
<222> LOCATION: (41)..(41)
<223> OTHER INFORMATION: Q or absent
<220> FEATURE:
<221> NAME/KEY: MOD_RES
<222> LOCATION: (42)..(42)
<223> OTHER INFORMATION: A or absent
<220> FEATURE:
<221> NAME/KEY: MOD_RES
<222> LOCATION: (43)..(43)
<223> OTHER INFORMATION: A or absent
<220> FEATURE:
<221> NAME/KEY: MOD_RES
<222> LOCATION: (44)..(44)
<223> OTHER INFORMATION: Any amino acid
<220> FEATURE:
<221> NAME/KEY: MOD_RES
<222> LOCATION: (45)..(45)
<223> OTHER INFORMATION: Any amino acid
<220> FEATURE:
<221> NAME/KEY: MOD_RES
<222> LOCATION: (46)..(46)
<223> OTHER INFORMATION: Any amino acid
<220> FEATURE:
<221> NAME/KEY: MOD_RES
<222> LOCATION: (47)..(47)
<223> OTHER INFORMATION: Any amino acid
<220> FEATURE:
<221> NAME/KEY: MOD_RES
<222> LOCATION: (48)..(48)
<223> OTHER INFORMATION: Any amino acid
<220> FEATURE:
<221> NAME/KEY: MOD_RES
<222> LOCATION: (49)..(49)
<223> OTHER INFORMATION: Any amino acid or absent
<220> FEATURE:
<221> NAME/KEY: MOD_RES
<222> LOCATION: (50)..(50)
<223> OTHER INFORMATION: Any amino acid or absent
<220> FEATURE:
<221> NAME/KEY: MOD_RES
<222> LOCATION: (51)..(51)
<223> OTHER INFORMATION: Any amino acid or absent
<220> FEATURE:
<221> NAME/KEY: MOD_RES
<222> LOCATION: (52)..(52)
<223> OTHER INFORMATION: Any amino acid or absent
<220> FEATURE:
<221> NAME/KEY: MOD_RES
<222> LOCATION: (53)..(53)
<223> OTHER INFORMATION: Any amino acid or absent
<220> FEATURE:
<221> NAME/KEY: MOD_RES
<222> LOCATION: (54)..(54)
<223> OTHER INFORMATION: Any amino acid or absent
<220> FEATURE:
<221> NAME/KEY: MOD_RES
<222> LOCATION: (55)..(55)
<223> OTHER INFORMATION: Any amino acid or absent
<220> FEATURE:
<221> NAME/KEY: MOD_RES
<222> LOCATION: (56)..(56)
<223> OTHER INFORMATION: Any amino acid or absent
<220> FEATURE:
<221> NAME/KEY: MOD_RES
<222> LOCATION: (57)..(57)
<223> OTHER INFORMATION: Any amino acid or absent
<220> FEATURE:
<221> NAME/KEY: MOD_RES
<222> LOCATION: (58)..(58)
<223> OTHER INFORMATION: Any amino acid or absent
<220> FEATURE:
<221> NAME/KEY: MOD_RES
<222> LOCATION: (66)..(66)
<223> OTHER INFORMATION: Any amino acid

<400> SEQUENCE: 32

Glu Glu Glu Ile Xaa Xaa Xaa Xaa Pro Val Ala Thr Glu Xaa Xaa Gly
1 5 10 15

Xaa Xaa Xaa Xaa Asn Xaa Gln Xaa Xaa Xaa Gly Gln Xaa Gly Xaa Xaa
20 25 30

Xaa Arg Xaa Xaa Xaa Xaa Xaa Ala Xaa Xaa Xaa Xaa Xaa Xaa Xaa Xaa
35 40 45

Xaa Xaa Xaa Xaa Xaa Xaa Xaa Xaa Xaa Xaa Leu Pro Gly Met Val Trp
50 55 60

Gln Xaa Arg Asp Val Tyr Leu Gln Gly Pro Ile Trp Ala Lys Ile Pro
65 70 75 80

His Thr Asp Gly

<210> SEQ ID NO 33
<211> LENGTH: 84
<212> TYPE: PRT
<213> ORGANISM: Artificial Sequence
<220> FEATURE:
<223> OTHER INFORMATION: Synthetic polypeptide - formula II; preferred embodiment of formula I (SEQ ID NO. 26) inserted
<220> FEATURE:
<221> NAME/KEY: MOD_RES
<222> LOCATION: (5)..(5)
<223> OTHER INFORMATION: Any amino acid
<220> FEATURE:

<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (14)..(14)
<223> OTHER INFORMATION: Any amino acid
<220> FEATURE:
<221> NAME/KEY: MOD_RES
<222> LOCATION: (15)..(15)
<223> OTHER INFORMATION: Any amino acid
<220> FEATURE:
<221> NAME/KEY: MOD_RES
<222> LOCATION: (17)..(17)
<223> OTHER INFORMATION: Any amino acid
<220> FEATURE:
<221> NAME/KEY: MOD_RES
<222> LOCATION: (18)..(18)
<223> OTHER INFORMATION: Any amino acid
<220> FEATURE:
<221> NAME/KEY: MOD_RES
<222> LOCATION: (19)..(19)
<223> OTHER INFORMATION: Any amino acid
<220> FEATURE:
<221> NAME/KEY: MOD_RES
<222> LOCATION: (20)..(20)
<223> OTHER INFORMATION: Any amino acid
<220> FEATURE:
<221> NAME/KEY: MOD_RES
<222> LOCATION: (22)..(22)
<223> OTHER INFORMATION: Any amino acid
<220> FEATURE:
<221> NAME/KEY: MOD_RES
<222> LOCATION: (24)..(24)
<223> OTHER INFORMATION: Any amino acid or absent
<220> FEATURE:
<221> NAME/KEY: MOD_RES
<222> LOCATION: (25)..(25)
<223> OTHER INFORMATION: Any amino acid or absent
<220> FEATURE:
<221> NAME/KEY: MOD_RES
<222> LOCATION: (26)..(26)
<223> OTHER INFORMATION: Q or absent
<220> FEATURE:
<221> NAME/KEY: MOD_RES
<222> LOCATION: (29)..(29)
<223> OTHER INFORMATION: S or R
<220> FEATURE:
<221> NAME/KEY: MOD_RES
<222> LOCATION: (31)..(31)
<223> OTHER INFORMATION: N or C
<220> FEATURE:
<221> NAME/KEY: MOD_RES
<222> LOCATION: (32)..(32)
<223> OTHER INFORMATION: D, Y or E
<220> FEATURE:
<221> NAME/KEY: MOD_RES
<222> LOCATION: (33)..(33)
<223> OTHER INFORMATION: C, V, S or A
<220> FEATURE:
<221> NAME/KEY: MOD_RES
<222> LOCATION: (35)..(35)
<223> OTHER INFORMATION: G, S or V
<220> FEATURE:
<221> NAME/KEY: MOD_RES
<222> LOCATION: (36)..(36)
<223> OTHER INFORMATION: D or absent
<220> FEATURE:
<221> NAME/KEY: MOD_RES
<222> LOCATION: (37)..(37)
<223> OTHER INFORMATION: C or absent
<220> FEATURE:
<221> NAME/KEY: MOD_RES
<222> LOCATION: (38)..(38)
<223> OTHER INFORMATION: F, R, V or A
<220> FEATURE:
<221> NAME/KEY: MOD_RES
<222> LOCATION: (39)..(39)
<223> OTHER INFORMATION: C, D, N or E
<220> FEATURE:
<221> NAME/KEY: MOD_RES
<222> LOCATION: (44)..(44)
<223> OTHER INFORMATION: Any amino acid
<220> FEATURE:
<221> NAME/KEY: MOD_RES
<222> LOCATION: (45)..(45)
<223> OTHER INFORMATION: Any amino acid
<220> FEATURE:
<221> NAME/KEY: MOD_RES
<222> LOCATION: (46)..(46)
<223> OTHER INFORMATION: Any amino acid
<220> FEATURE:
<221> NAME/KEY: MOD_RES
<222> LOCATION: (47)..(47)
<223> OTHER INFORMATION: Any amino acid
<220> FEATURE:
<221> NAME/KEY: MOD_RES
<222> LOCATION: (48)..(48)
<223> OTHER INFORMATION: Any amino acid
<220> FEATURE:
<221> NAME/KEY: MOD_RES
<222> LOCATION: (49)..(49)
<223> OTHER INFORMATION: Any amino acid or absent
<220> FEATURE:
<221> NAME/KEY: MOD_RES
<222> LOCATION: (50)..(50)
<223> OTHER INFORMATION: Any amino acid or absent
<220> FEATURE:
<221> NAME/KEY: MOD_RES
<222> LOCATION: (51)..(51)
<223> OTHER INFORMATION: Any amino acid or absent
<220> FEATURE:
<221> NAME/KEY: MOD_RES
<222> LOCATION: (52)..(52)
<223> OTHER INFORMATION: Any amino acid or absent
<220> FEATURE:
<221> NAME/KEY: MOD_RES
<222> LOCATION: (53)..(53)
<223> OTHER INFORMATION: Any amino acid or absent
<220> FEATURE:
<221> NAME/KEY: MOD_RES
<222> LOCATION: (54)..(54)
<223> OTHER INFORMATION: Any amino acid or absent
<220> FEATURE:
<221> NAME/KEY: MOD_RES
<222> LOCATION: (55)..(55)
<223> OTHER INFORMATION: Any amino acid or absent
<220> FEATURE:
<221> NAME/KEY: MOD_RES
<222> LOCATION: (56)..(56)
<223> OTHER INFORMATION: Any amino acid or absent
<220> FEATURE:
<221> NAME/KEY: MOD_RES
<222> LOCATION: (57)..(57)
<223> OTHER INFORMATION: Any amino acid or absent
<220> FEATURE:
<221> NAME/KEY: MOD_RES
<222> LOCATION: (58)..(58)
<223> OTHER INFORMATION: Any amino acid or absent
<220> FEATURE:
<221> NAME/KEY: MOD_RES
<222> LOCATION: (66)..(66)
<223> OTHER INFORMATION: Any amino acid

<400> SEQUENCE: 33

Glu Glu Glu Ile Xaa Xaa Xaa Xaa Pro Val Ala Thr Glu Xaa Xaa Gly
1               5                   10                  15

-continued

```
Xaa Xaa Xaa Xaa Asn Xaa Gln Xaa Xaa Xaa Gly Gln Xaa Gly Xaa Xaa
            20                  25                  30

Xaa Arg Xaa Xaa Xaa Xaa Xaa Ala Gln Ala Ala Xaa Xaa Xaa Xaa Xaa
        35                  40                  45

Xaa Xaa Xaa Xaa Xaa Xaa Xaa Xaa Xaa Xaa Leu Pro Gly Met Val Trp
    50                  55                  60

Gln Xaa Arg Asp Val Tyr Leu Gln Gly Pro Ile Trp Ala Lys Ile Pro
65                  70                  75                  80

His Thr Asp Gly
```